(12) United States Patent
Rogers et al.

(10) Patent No.: US 12,144,579 B2
(45) Date of Patent: Nov. 19, 2024

(54) WIRELESS SKIN SENSOR WITH METHODS AND USES

(71) Applicant: NORTHWESTERN UNIVERSITY, Evanston, IL (US)

(72) Inventors: John A. Rogers, Wilmette, IL (US); Shuai Xu, Evanston, IL (US); Yajing Li, Evanston, IL (US); Philipp Gutruf, Evanston, IL (US); Surabhi R. Madhvapathy, Evanston, IL (US); Siddharth Krishnan, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 17/043,161

(22) PCT Filed: Mar. 29, 2019

(86) PCT No.: PCT/US2019/025031
§ 371 (c)(1),
(2) Date: Sep. 29, 2020

(87) PCT Pub. No.: WO2019/191703
PCT Pub. Date: Oct. 3, 2019

(65) Prior Publication Data
US 2021/0022609 A1 Jan. 28, 2021

Related U.S. Application Data

(60) Provisional application No. 62/650,826, filed on Mar. 30, 2018, provisional application No. 62/696,685, (Continued)

(51) Int. Cl.
*A61B 5/00* (2006.01)
*A61B 5/01* (2006.01)

(52) U.S. Cl.
CPC ............ *A61B 5/0008* (2013.01); *A61B 5/01* (2013.01); *A61B 5/442* (2013.01); *A61B 5/443* (2013.01);
(Continued)

(58) Field of Classification Search
CPC ......... A61B 5/0008; A61B 5/01; A61B 5/442; A61B 5/443; A61B 5/445;
(Continued)

(56) References Cited

U.S. PATENT DOCUMENTS 9,612,140 B2 4/2017 Mazzeo et al.
10,791,992 B1 * 10/2020 Desai ..................... A61B 5/68
(Continued)

FOREIGN PATENT DOCUMENTS

JP 2003528400 A 9/2003
JP 2005094185 A 4/2005
(Continued)

OTHER PUBLICATIONS

USPTO (ISR/US), "International Search Report for PCT/US2019/025031", US, Jun. 17, 2019.
(Continued)

*Primary Examiner* — Daniel L Cerioni
(74) *Attorney, Agent, or Firm* — Locke Lord LLP; Tim Tingkang Xia, Esq.

(57) ABSTRACT

Provided are wireless electronic devices for thermally interfacing with a biological tissue. The device may have a flexible substrate; a thermal actuator supported by said flexible substrate configured to provide a thermal input to said biological tissue; a temperature sensor supported by said flexible substrate configured to measure a temperature to determine thermal conductivity of said biological tissue; and a wireless electronic system in electronic communication with said thermal actuator and said temperature sensor,
(Continued)

wherein said wireless electronic system is configured to provide two-way communication with an external controller. Also provided are related methods of using the electronic devices, including for cosmetic, beauty, or medical applications.

26 Claims, 66 Drawing Sheets

Related U.S. Application Data filed on Jul. 11, 2018, provisional application No. 62/791,390, filed on Jan. 11, 2019.

(52) U.S. Cl.
CPC ...... *A61B 5/445* (2013.01); *A61B 2562/0271* (2013.01); *A61B 2562/164* (2013.01); *A61B 2562/227* (2013.01)

(58) Field of Classification Search
CPC ...... A61B 2562/0271; A61B 2562/164; A61B 2562/227
See application file for complete search history.

(56) References Cited

U.S. PATENT DOCUMENTS

| | | | |
|---|---|---|---|
| 2005/0109102 A1* | 5/2005 | Liu | G01F 1/6845 73/204.27 |
| 2005/0223721 A1* | 10/2005 | Kirby | F25D 23/062 62/157 |
| 2008/0091121 A1 | 4/2008 | Sun et al. | |
| 2008/0275319 A1 | 11/2008 | Van Gogh et al. | |
| 2010/0237060 A1* | 9/2010 | Novikov | H05B 1/0272 219/490 |
| 2010/0238636 A1 | 9/2010 | Mascaro et al. | |
| 2011/0021930 A1* | 1/2011 | Mazzeo | G01D 11/30 600/485 |
| 2012/0165759 A1* | 6/2012 | Rogers | A61B 5/6883 604/264 |
| 2013/0041235 A1 | 2/2013 | Rogers et al. | |
| 2013/0333094 A1* | 12/2013 | Rogers | A61N 1/0476 2/161.7 |
| 2015/0380355 A1* | 12/2015 | Rogers | H01L 29/78603 257/773 |
| 2016/0120468 A1* | 5/2016 | Mathew | A61B 5/01 600/301 |
| 2016/0220184 A1* | 8/2016 | Manion | G01F 13/008 |
| 2017/0347891 A1 | 12/2017 | Rogers et al. | |
| 2018/0014734 A1 | 1/2018 | Rogers et al. | |
| 2019/0369728 A1* | 12/2019 | Rogers | H04W 4/80 |

FOREIGN PATENT DOCUMENTS

| | | |
|---|---|---|
| JP | 2007175487 A | 7/2007 |
| JP | 2008075975 A | 4/2008 |
| JP | 2013517053 A | 5/2013 |
| JP | 2016106187 A | 6/2016 |
| JP | 2016174671 A | 10/2016 |
| JP | 2017080421 A | 5/2017 |
| JP | 2017532079 A | 11/2017 |
| WO | 2016025438 A1 | 2/2016 |
| WO | 2016054348 A1 | 4/2016 |
| WO | 2016196675 A1 | 12/2016 |
| WO | 2017055229 A1 | 4/2017 |
| WO | 2018000104 A1 | 1/2018 |

OTHER PUBLICATIONS

A Wearable Hydration Sensor with Conformal Nanowire Electrodes. Adv. Healthcare Mater. 2017, 1601159.
Xian Huang, Woon-Hong Yeo, Yuhao Liu, John A. Rogers. Epidermal Differential Impedance Sensor for Conformal Skin Hydration Monitoring. Biointerphases (2012) (7:52).
Flexible and Stretchable 3ω Sensors for Thermal Characterization of Human Skin. Advanced Functional Materials (2017), 27(26): 1701282.
S Krishnan, Y Shi, RC Webb, Y Ma, P Bastien, KE Crawford, A Wang, . . . JA Rogers. Multimodal epidermal devices for hydration monitoring. Microsystems and Nanoengineering 3 (17014).
RC Webb, S Krishnan, JA Rogers. Ultrathin, Skin-Like Devices for Precise, Continuous Thermal Property Mapping of Human Skin and Soft Tissues. Stretchable Bioelectronics for Medical Devices and Systems, 117-132. 2016.
J. Kottner, A. Lichterfeld, U. Blume-Peytavi, British Journal of Dermatology 2013, 169, 528.
M. N. Sawka, S. J. Montain, W. A. Latzka, Comp Biochem Physiol A Mol Integr Physiol 2001, 128, 679.
L. S. Jutte, M. A. Merrick, C. D. Ingersoll, J. E. Edwards, Arch Phys Med Rehabil 2001, 82, 845.
P. V. Pople, K. K. Singh, Int J Pharm 2012, 434, 70.
P. Clarys, R. Clijsen, J. Taeymans, A. O. Barel, Skin Res Technol 2012, 18, 316.
E. Alanen, J. Nuutinen, K. Nicklen, T. Lahtinen, J. Monkkonen, Skin Res Technol 2004, 10, 32.
J. E. Tooke, J. Ostergren, B. Fagrell, Int J Microcirc Clin Exp 1983, 2, 277.
M. Vogt, H. Ermert, IEEE Trans Ultrason Ferroelectr Freq Control 2005, 52, 375.
F. Mirrashed, J. C. Sharp, Skin Res Technol 2004, 10, 149.
J. Welzel, C. Reinhardt, E. Lankenau, C. Winter, H. H. Wolff, British Journal of Dermatology 2004, 150, 220.
A. B. Raff, D. Kroshinsky, JAMA 2016, 316, 325.
Q. Weng, A. B. Raff, J. M. Cohen, et al., JAMA Dermatology 2017, 153, 141.
T. Someya, Y. Kato, T. Sekitani, S. Iba, Y. Noguchi, Y. Murase, H. Kawaguchi, T. Sakurai, Proc Natl Acad Sci U S A 2005, 102, 12321.
K. R. Holmes, Thermal Properties, http://users.ece.utexas.edu/~valvano/research/Thermal.pdf, accessed: May 10, 2017.
Y. Lee, K. Hwang, Surgical and Radiologic Anatomy 2002, 24, 183.
O. Akkus, M. Kizilgul, Evaluation of Skin and Subcutaneous Adipose Tissue Thickness for Optimal Insulin Injection, 2012.
Dupont, Dupont Kapton Summary of Properties, http://www.dupont.com/kapton/general/H-38479-4.pdf, accessed: Feb. 5, 2017.
J. W. Valvano, J. R. Cochran, K. R. Diller, Int J Thermophys 1985, 6, 301.
R. Ghadially, L. Halkier-Sorensen, P. M. Elias, J Am Acad Dermatol 1992, 26, 387.
A. V. Rawlings, D. A. Canestrari, B. Dobkowski, Dermatol Ther 2004, 17 Suppl 1, 49.
R. L. Rietschel, J Invest Dermatol 1978, 70, 152.
K. Hwang, D. J. Kim, S. H. Hwang, Journal of Craniofacial Surgery 2006, 17, 54.
E. Yalcin, M. Akyuz, B. Onder, H. Unalan, I. Degirmenci, Journal of Spinal Cord Medicine 2013, 36, 225.
S. E. Gustafsson, Review of Scientific Instruments 1991, 62, 797.
M. N. Zaiac, A. Walker, Clin. Dermatol. 2013, 31, 627.
K. N. Shah, A. I. Rubin, Curr. Probl. Pediatr. Adolesc. Health Care 2012, 42, 204.
R. S. Fawcett, S. Linford, D. L. Stulberg, Am. Fam. Physician 2004, 69, 1417.
M. Cutolo, C. Pizzorni, M. E. Secchi, A. Sulli, Best Pract. Res. Clin. Rheumatol. 2008, 22, 1093.
L. Thomas, E. G. Zook, E. Haneke, J.-L. Drapé, R. Baran, J. F. Kreusch, In Baran & Dawber's Diseases of the Nails and their Management; Wiley-Blackwell, 2012; pp. 637-743.
C. Grover, S. Bansal, Indian Dermatol. Online J. 2018, 9, 3.
T. E. Rohrer, B. Leslie, D. J. Grande, J. Dermatol. Surg. Oncol. 1994, 20, 19.
R. H. Rice, Y. Xia, R. J. Alvarado, B. S. Phinney, J. Proteome Res. 2010, 9, 6752.
S. Yaemsiri, N. Hou, M. M. Slining, K. He, J. Eur. Acad. Dermatol. Venereol. JEADV 2010, 24, 420.

(56) References Cited

OTHER PUBLICATIONS

S. Amendola, G. Bovesecchi, P. Coppa, G. Marrocco, In 2016 IEEE International Symposium on Antennas and Propagation (APSURSI); 2016; pp. 461-462.
M. Johnson, S. Shuster, Br. J. Dermatol. 1994, 130, 195.
J. B. Hamilton, H. Terada, G. E. Mestler, J. Gerontol. 1955, 10, 401.
U. Wollina, M. Berger, K. Karte, Skin Res. Technol. 2001, 7, 60.
D. T. Dias, A. Steimacher, A. C. Bento, A. M. Neto, M. L. Baesso, Photochem. Photobiol. 2007, 83, 1144.
T. E. Cooper, G. J. Trezek, Aerosp. Med. 1971, 42, 24.
T. A. Balasubramaniam, H. F. Bowman, J. Biomech. Eng. 1977, 99, 148.
A. Chanmugam, A. Bhargava, C. Herman, Int. Mech. Eng. Congr. Expo. Proc. Int. Mech. Eng. Congr. Expo. Int. Mech. Eng. Congr. Expo. 2012, 2012, 717.
A. M. Stoll, J. Invest. Dermatol. 1977, 69, 328.
A. Sizov, D. Cederkrantz, L. Salmi, A. Rosén, L. Jacobson, S. E. Gustafsson, M. Gustavsson, Rev. Sci. Instrum. 2016, 87, 74901.
Thermal Conductivity: Theory, Properties, and Applications; Tritt, T. M., Ed.; Physics of Solids and Liquids; Springer US, 2004.
A. R. Moritz, F. C. Henriques, Am. J. Pathol. 1947, 23, 695.
J. P. Bull, J. C. Lawrence, Fire Mater. 1979, 3, 100.
T. H. Benzinger, A. W. Pratt, C. Kitzinger, Proc. Natl. Acad. Sci. U. S. A. 1961, 47, 730.
R. Refinetti, Exp. Physiol. 2003, 88, 423.
A. Dittmar, T. Pauchard, G. Delhomme, E. Vernet-Maury, Sens. Actuators B Chem. 1992, 7, 327.
M. Salcman, E. Moriyama, H. J. Elsner, H. Rossman, R. A. Gettleman, G. Neuberth, G. Corradino, J. Neurosurg. 1989, 70, 592.
J. Grayson, J. Physiol. 1952, 118, 54.
R. K. Jain, F. H. Grantham, P. M. Gullino, J. Natl. Cancer Inst. 1979, 62, 927.
J. Bangsbo, Y. Hellsten, Acta Physiol. Scand. 1998, 162, 305.
H. Barcroft, O. G. Edholm, J. Physiol. 1943, 102, 5.
Marieb, Elaine; Katja Hoehn (2007). Human Anatomy & Physiology (7th ed.). Pearson Benjamin Cummings. p. 142.
Martini & Nath: "Fundamentals of Anatomy & Physiology" 8th Edition, pp. 158, Pearson Education, 2009.
Kim, D.H.; Lu, N.S.; Ma, R.; Kim, Y.-S.; Kim, R.-H.; Wang, S.; Wu, J.; Won, S. M.; Tao, H.; Islam, A.; Yu, K.-J.; Kim, T.-I.; Chowdhury, R.; Ying, M.; Xu, L.; Li, M.; Chung, H.-J.; Keum, H.; McCormick, M.; Liu, P.; Zhang, Y.-W.; Omenetto, F.G.; Huang, Y.; Coleman, T.; Rogers, J. A. Epidermal Electronics. Science 2011, 333, 838-843.
Wang, S.D.; Li, M.; Wu, J.; Kim, D.-H.; Lu, N.; Su, Y.; Kang, Z.; Huang, Y.; Rogers, J. A. Mechanics of Epidermal Electronics. J. Appl. Mech. 2012, 3, 031022.
Rogers, J. A.; Someya, T.; Huang, Y. Materials and Mechanics for Stretchable Electronics. Science 2010, 327, 1603-1607.
Zhang, Y.; Huang, Y.; Rogers, J. A. Mechanics of Stretchable Batteries and Supercapacitors. Curr. Opin. Solid. St. M. 2015, 19, 190-199.
Zhang, Y.; Fu, H.; Su, Y.; Xu, S.; Cheng, H.; Fan, J. .: Hwang, K.-C.; Rogers, J. A.; Huang, Y. Mechanics of Ultra-Stretchable Self-Similar Serpentine Interconnects. Acta Mater. 2013, 61, 7816-7827.
Zhang, Y.; Wang, S.; Li, X.; Fan, J. A.; Xu, S.; Song, Y. M.; Choi, K.-J.; Yeo, W.-H.; Lee, W.; Nazaar, S. N.; Lu, B.; Yin, L.; Hwang, K.-C.; Rogers, J. A.; Huang, Y. Experimental and Theoretical Studies of Serpentine Microstructures Bonded to Prestrained Elastomers for Stretchable Electronics. Adv. Func. Mater. 2014, 24, 2028-2037.
Guo, C. F.; Liu, Q.; Wang, G.; Wang, Y.; Shi, Z.; Sou, Z.; Chu, C. W.; Ren, Z. Fatigue-Free, Superstretchable, Transparent, and Biocompatible Metal Electrodes. P. Natl. Acad. Sci. USA. 2015, 112, 12332-12337.
Kim, D. H.; Ahn, J. H.; Won, M. C.; Kim, H.-S.; Kim, T.-H.; Song, J.; Huang, Y. Y.; Liu, Z.; Lu, C.; Rogers, J. A. Stretchable and Foldable Silicon Integrated Circuits. Science 2008, 320, 507-511. .
White, M.S.; Kaltenbrunner, M.; Gtowacki, E. D.; Gutnichenko, K.; Kettlegruber, G.; Graz, I.; Aazou, S.; Ulbricht, C.; Egbe, D. A.; Miron, M. C.; Major, Z.; Scharber, M. C.; Sekitani, T.; Someya, T.; Seigfried, B.; Sariciftci, N. S. "Ultrathin, highly flexible and stretchable PLEDs" Nat. Photonics, 2013, 7, 811-816.
Melzer, M.; Kaltenbrunner, M.; Makarov, D.; Karnaushenko, D.; Karnaushenko, D.; (Sekitani, T.; Someya, T.; Schmidt, O. G. Imperceptible Magnetoelectronics. Nat. Commun. 2015, 6, 6050.
Bauer, S.; Bauer-Gogonea, S.; Graz, I.; Kaltenbrunner, M.; Keplinger, C.; Schwodiauer, R. 25th Anniversary Article: A Soft Future: From Robots and Sensor Skin to Energy Harvesters. 2014, 1, 149-161.
Benight, S. J.; Wang, C.; Tok, J. B. H.; Bao, Z. Stretchable and Self-Healing Polymers Jand Devices for Electronic Skin. Prog. Polym. Sci. 2013, 12, 1961-1977.
Hammock, M. L.; Chortos, A.; Tee, B. C.-K.; Tok, J. B.-H.; Bao, Z. 25th Anniversary Article: The Evolution of Electronic Skin (E-Skin): A Brief History, Design Considerations, and Recent Progress. Adv. Mater. 2013, 42, 5997-6038.
Klinker, L; Lee, S.; Work, J.; Wright, J.; Ma, Y.; Ptaszek, L.; Webb, R. C.; Liu, C.; Sheth, N.; Mansour, M.; Rogers, J. A.; Huang, Y.; Chen, H.; Ghaffari, R. Balloon Catheters with Integrated Stretchable Electronics for Electrical Stimulation, Ablation and Blood Flow Monitoring. Extreme Mechanics Lett. 2015, 3, 45-54.
Hattori, Y.; Falgout, L.; Lee, W.; Jung, S. Y.; Poon, E.; Lee, J. W.; Na, I.; Geisler, A.; Sadhwani, D.; Zhang, Y.; Su, Y.; Wang, X.; Liu, Z.; Xia, J.; Cheng, H.; Webb, R. C.; Bonifas, A. P.; Won, P.; Jeong, J. W.; Jang, K. I.; Song, Y. M.; Nardone, B.; Nodzenski, M.; Fan, J. A.; Huang, Y.; West, D. P.; Paller, A. S.; Alam, M.; Yeo, W. H.; Rogers, J. A. Multifunctional Skin-Like Electronics for Quantitative, Clinical Monitoring of Cutaneous Wound Healing. Adv. Health. Mater. 3, 2014, 1597-1607.
Zhang, Y.; Webb, R. C.; Luo, H.; Xue, Y.; Kurniawan, J.; Cho, N. H.; Krishnan, S.; Li, Y.; Huang, Y.; Rogers, J. A. Theoretical and Experimental Studies of Epidermal Heat Flux Sensors for Measurements of Core Body Temperature. Adv. Health. Mater. 2016, 5, 119-127.
Koh, A.; Gutcrog, S. R.; Meyers, J. D.; Lu, C.; Webb, R. C.; Shin, G.; Li, Y.; Kang, S. K.; Huang, Y.; Efimov, I. R.; Rogers, J. A. Ultrathin Injectable Sensors of Temperature, Thermal Conductivity, Heath Capacity for Cardiac Ablation Monitoring. Adv. Health. Mater. 2016, 5, 373-381.
Gao, L.; Zhang, Y.; Malyarchuk, V.; Jia, L.; Jang, K. I.; Webb, R. C.; Fu, H.; Shi, Y.; Zhou, G.; Shi, L.; Shah, D.; Huang, X.; Xu, B.; Yu, C.; Huang, Y.; Rogers, J. A. Epidermal Photonic Devices for Quantitative Imaging of Temperature and Thermal Transport Characteristics of the Skin. Nature Commun. 2014, 5, 4938.
Webb, R. C.; Pielak, R. M.; Bastien, P.; Ayers, J.; Niittynen, J.; Kurniawan, J.; Manco, M.; Lin, A.; Cho, N. H.; Malyrchuk, V.; Balooch, G.; Rogers, J. A. Thermal Transport Characteristics of Human Skin Measured in Vivo using Ultrathin Conformal Arrays of Thermal Sensors and Actuators. PLoS One 2015, 10, e0118131.
Webb, R. C.; Ma, Y.; Krishnan, S.; Li, Y.; Yoon, S.; Guo, X.; Feng, X.; Shi, Y.; Seidel, M.; Cho, N. H.; Kirniawan, J.; Ahad, J.; Sheth, N.; Kim, J.; Taylor, J. G.; Darlington, T.; Chang, K.; Huang, W.; Ayers, J.; Gruebele, A.; Pielak, R. M.; Slepian, M. J.; Huang, Y.; Gorbach, A. M.; Rogers, J. A. Epidermal Devices for Noninvasive, Precise, and Continuous Mapping of Macrovascular and Microvascular Blood Fow. Science Adv. 2015, 1, e1500701.
Bian, J.; Song, J.; Webb, R. C.; Bonifas, A. P.; Rogers, J. A.; Huang, Y. Thermal Analysis of Ultrathin, Compliant Sensors for Characterization of the Human Skin. RSC Adv. 2014, 4, 5694-5697.
Webb, R. C.; Bonifas, A. P.; Behnaz, A.; et al. Ultrathin Conformal Devices for Precise and Continuous Thermal Characterization of Human Skin. Nature Mater. 2013, 12, 938-944.
Wilkin, J. K. Oral Thermal-Induced Flushing in Erythematotelangiectatic Rosacea. J. Investigative Dermatology, 1981, 76, 15-18.
Mosby's Medical Dictionary (9th Ed.). St. Louis, Missouri: Elsevier. 2013, ISBN 978-0-323-08541-0.
ABAQUS Analysis User's Manual 2014, V6.14.
Mit.edu/~6.777/matprops/polyimide.htm (accessed Dec. 4, 2017).
Carslaw, H. S.; Jaeger, J. C. (1959) Conduction of Heat in Solids. Oxford,: Clarendon Press. 510 p.p.
Cohen, M. L. Measurement of the Thermal Properties of Human Skin. A Review. J. Invest. Dermatol. 1977, 69, 333-338.

(56) References Cited

OTHER PUBLICATIONS

I. Benedek and M.M. Feldstein (Eds), Handbook of Pressure Sensitive Adhesives and Products, Taylor and Francis Group, Boca Raton 2009.
Tucker, G., Development and application of time-temperature integrators to thermal food processing, Ph.D. thesis, University of Birmingham 2008.
http://www.aetnaplastics.com/site_media/media/documents/acrylite_ff_material_data_sheet.pdf. accessed Feb. 25, 2018.
Fundamentals of Heat and Mass Transfer (1st ed.). PHI Learning Pvt. Ltd., 2010. ISBN 8120340310.
WHO child growth standards: length/height-for-age, weight-for-age, weight-for-length, weight-for-height and body mass index-for-age: methods and development. ISBN92-4-154693-X.
Hohendorff B, Weidermann C, Burkhart JK, Rommens PM, Prommersberger KJ, Konerding MA. Lengths, Girths, and Diameters of Children's Fingers from 3 to 10 years of age. Ann Anat. 3, 2010, 156-161.
http://ctherm.com/files/C-Therm_TCi_Thermal_Conductivity_-_2016.pdf. Accessed Feb. 15, 2018.
Van de Staak, W. J. B.; Brakker, A. J. M.; de Rijke-Herweijer, H. E.; Measurements of the Thermal Conductivity of the Skin as an Indication of Skin Blood Flow. J. Invest. Dermatol. 1968, 5, 149-154.
Fitzpatrick, T. B. The Validity and Practicality of Sun-Reactive Skin Types I through IV. Arch. Dermatol. 1988, 124, 869-871.
https://www.makeitfrom.com/material-properties/Low-Density-Polyethylene-LDPE.
https://krayden.com/sylgard-184/. accessed Feb. 25, 2018.
Erickson, D.; Sinton, D.; Li, D. Joule Heating and Heat Transfer in Poly(dimethylsiloxane) Microfluidic Systems. Lab Chip 2003, 3, 141-149.
Andersson, S. P. Pressure and vol. Dependence of Thermal Conductivity and Isothermal Bulk Modulus up to 1 GPa for Poly(isobutylene). J. Polym. Sci. B Polym. Phys. 1998, 36, 1781-1792.
Springer Handbook of Condensed Matter and Materials Data. Martienssen, W.; (Warlimont, H. Springer-Verlag Berlin Heidelberg. 2005, 488 pp. ISBN: 978-3-540-30437-1.
https://www.makeitfrom.com/material-properties/Polymethylmethacrylate-PMMAAcrylic. Accessed Feb. 25, 2018.
Dow Corning Sylgard 170 Silicone Elastomer Product Information. Accessed Feb. 25, 2018.
http://www.abgrp.co.uk/downloads/abg-datasheets/ldpe.pdf. accessed Feb. 25, 2018.
http://www.professionalplastics.com/professional plastics/thermalpropertiesofplasticmaterials. pdf. accessed Feb. 25, 2018.
JPO, "First Office Action for JP Application No. 2021-502734", Japan, Dec. 13, 2021.
JPO, "Second Office Action for JP Application No. 2021-502734", Japan, Jul. 11, 2022.

* cited by examiner a
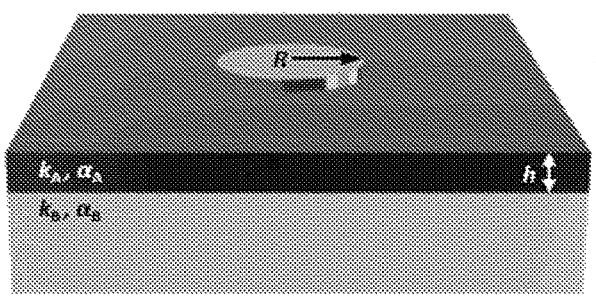
b
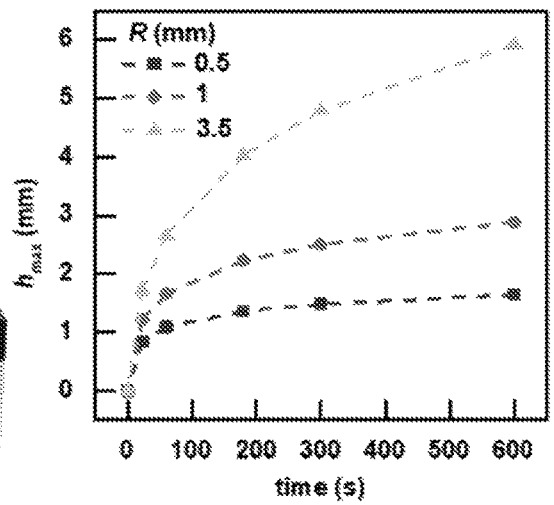
FIG. 9A
FIG. 9B
c
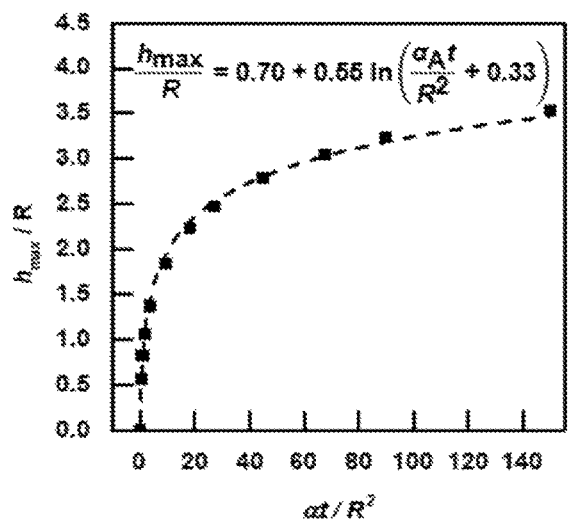
d
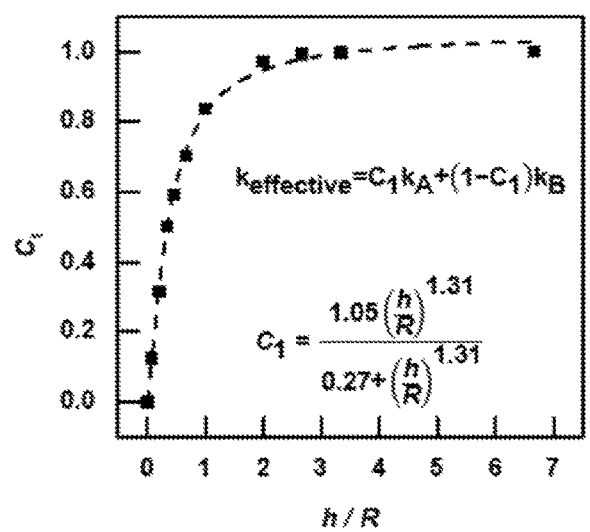
FIG. 9C
FIG. 9D

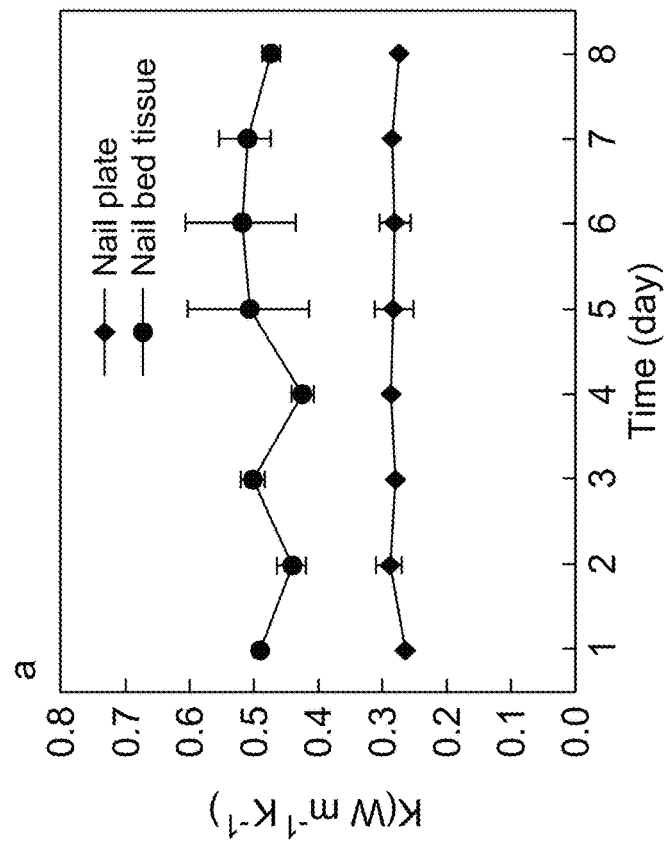
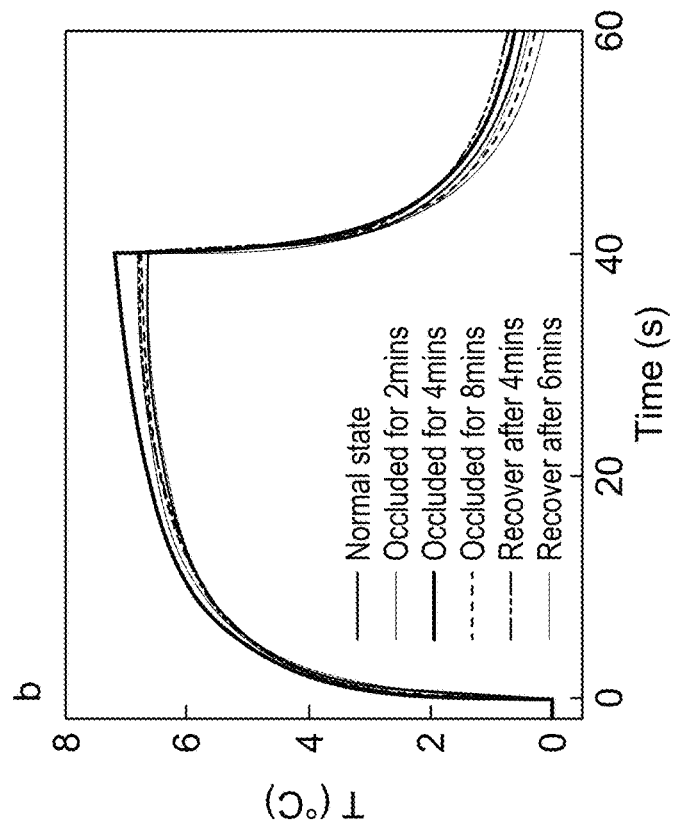
FIG. 12B
FIG. 12A

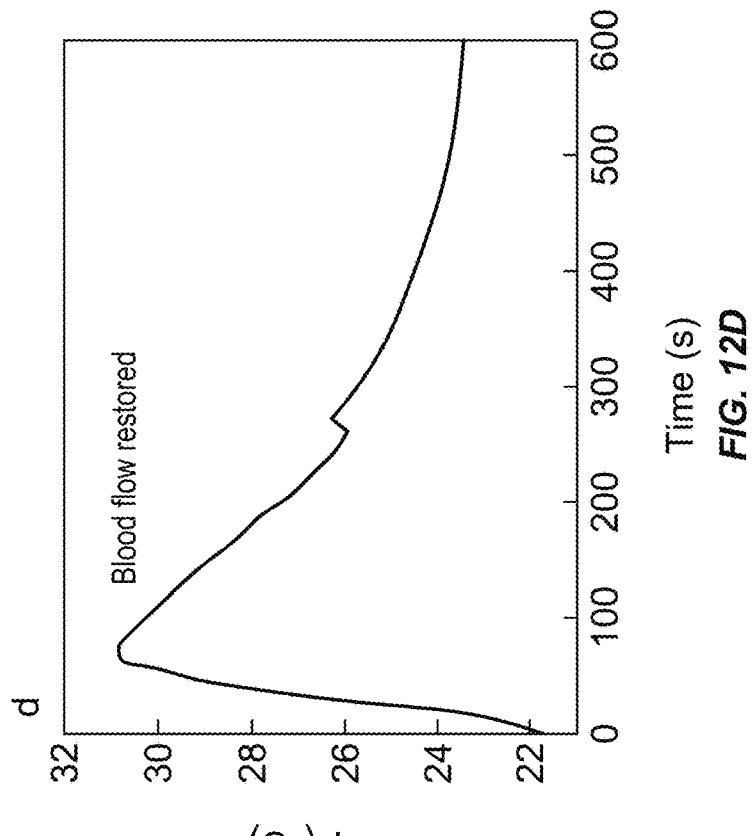
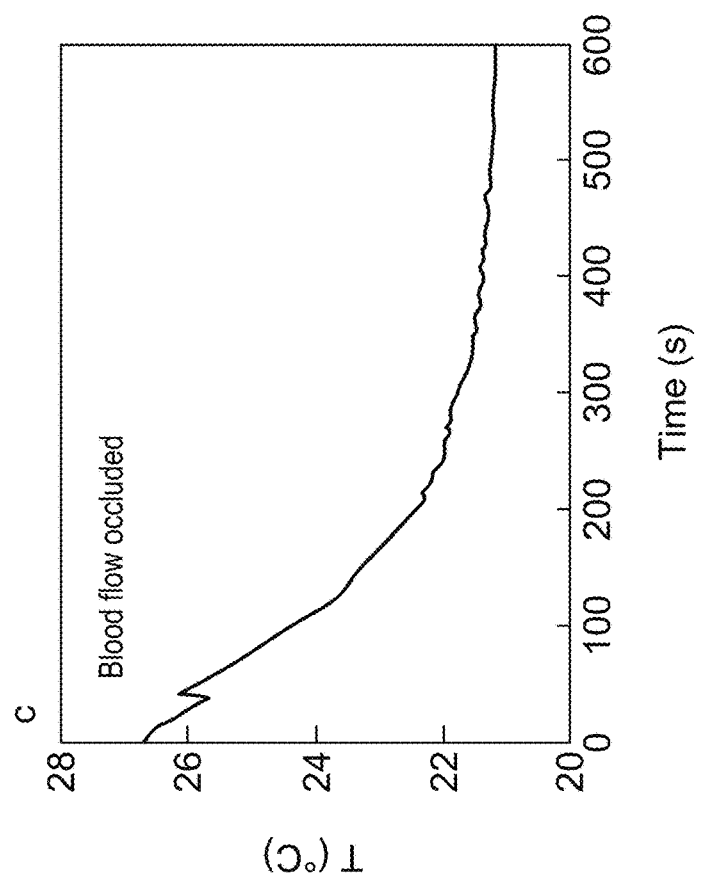
FIG. 12D
FIG. 12C

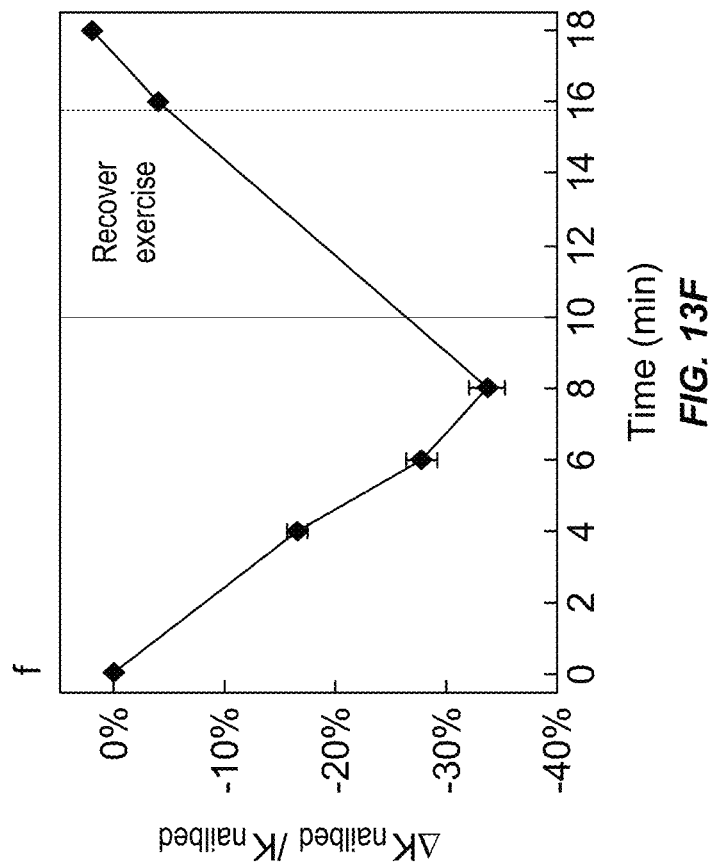
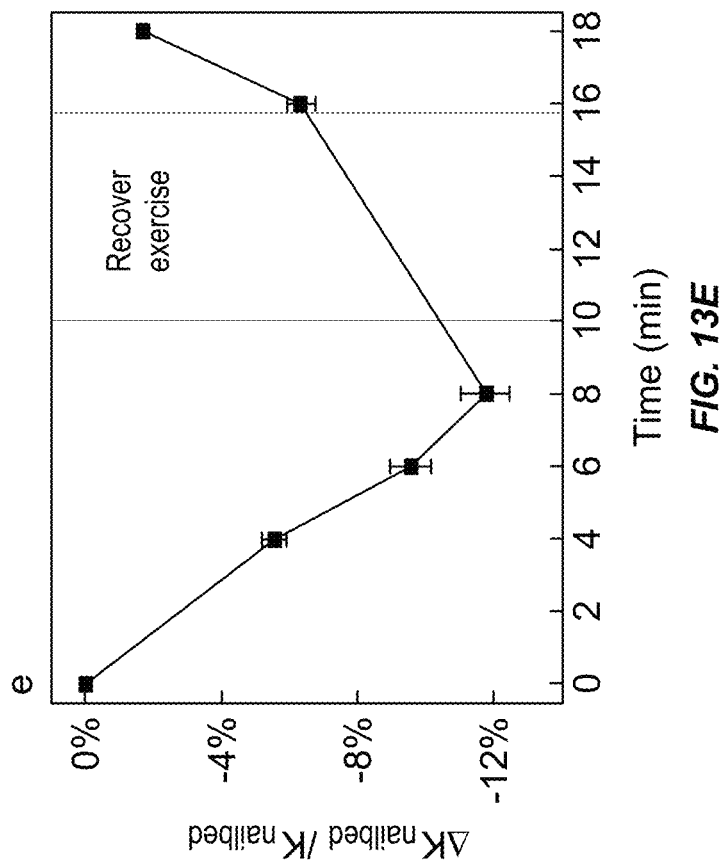
FIG. 13E
FIG. 13F

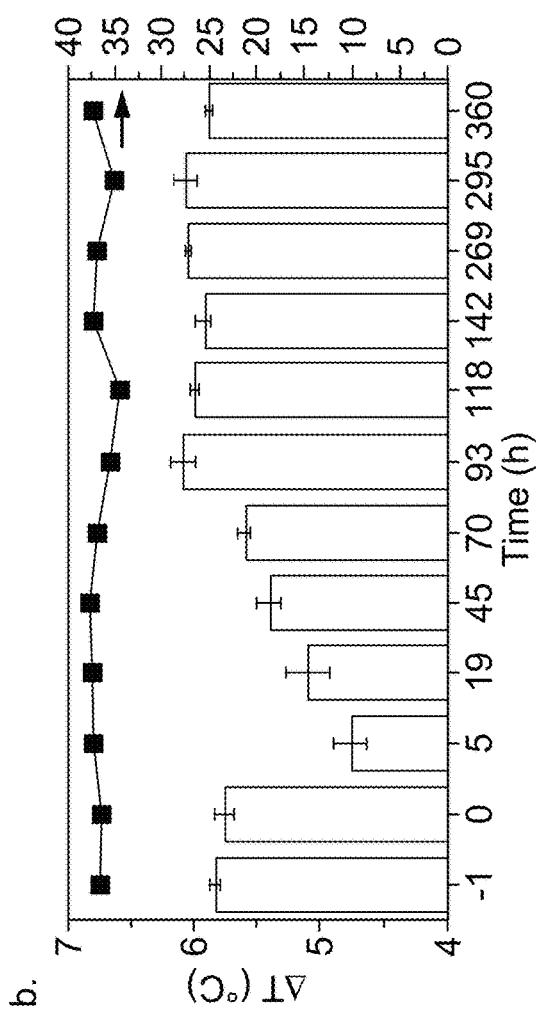
FIG. 14A
FIG. 14B
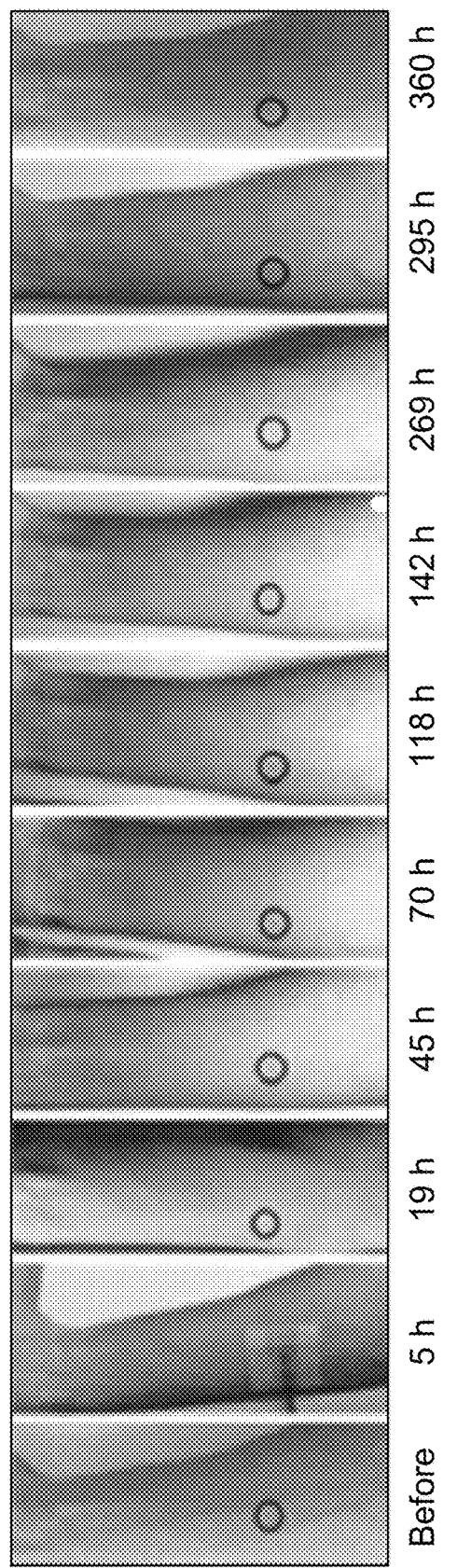
FIG. 14C

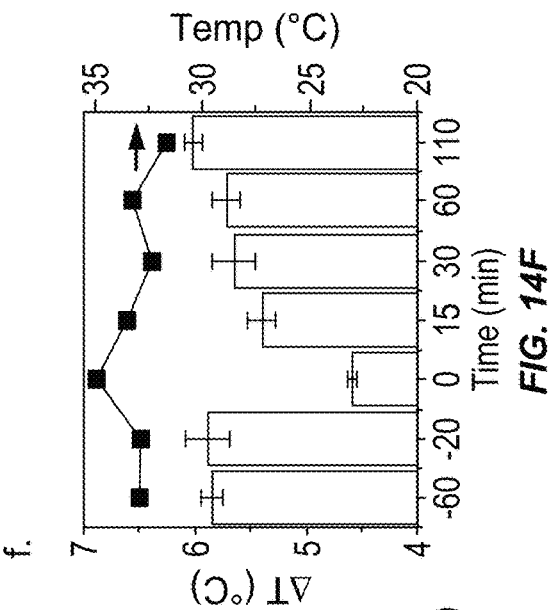
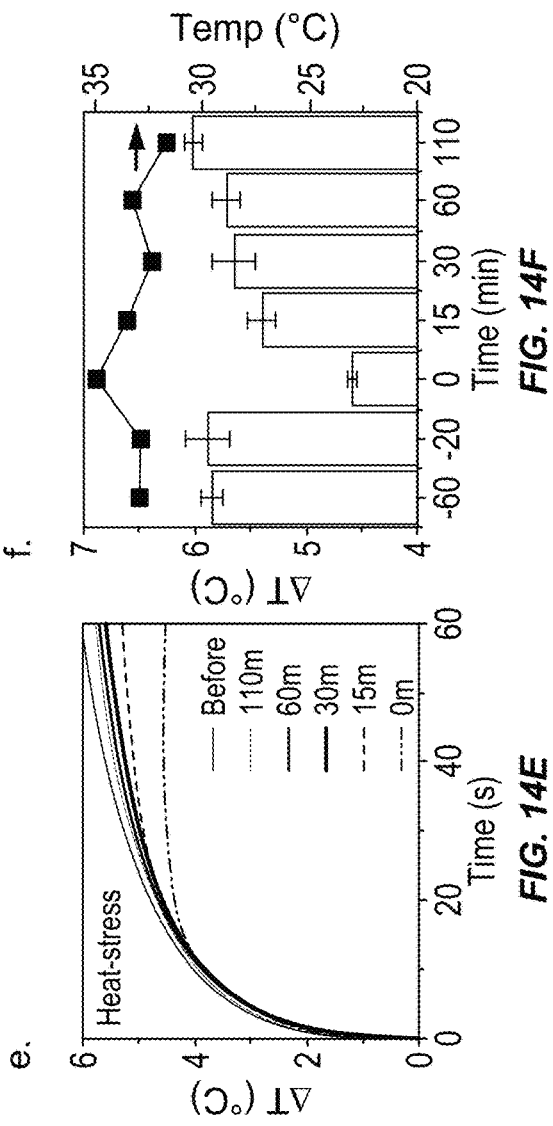
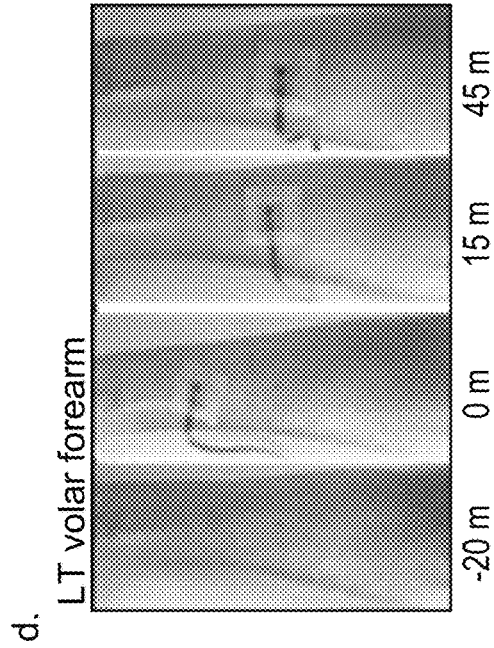
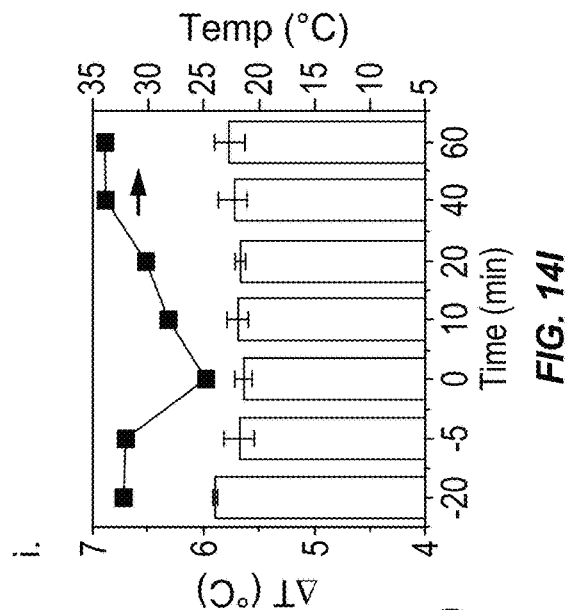
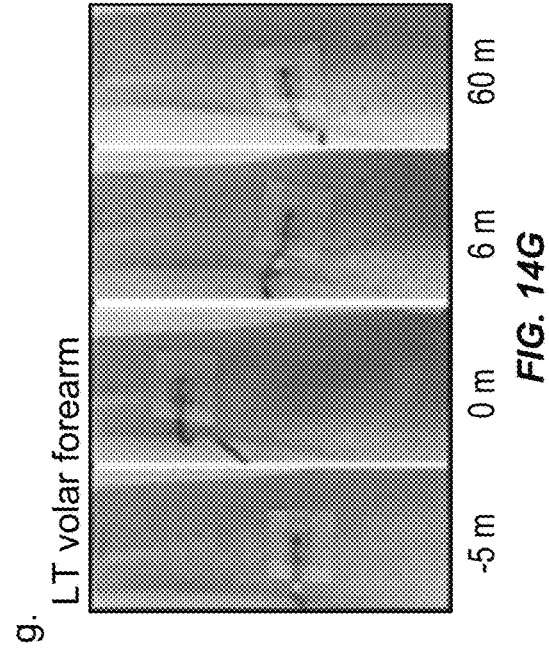
FIG. 14D
FIG. 14E
FIG. 14F
FIG. 14G
FIG. 14H
FIG. 14I

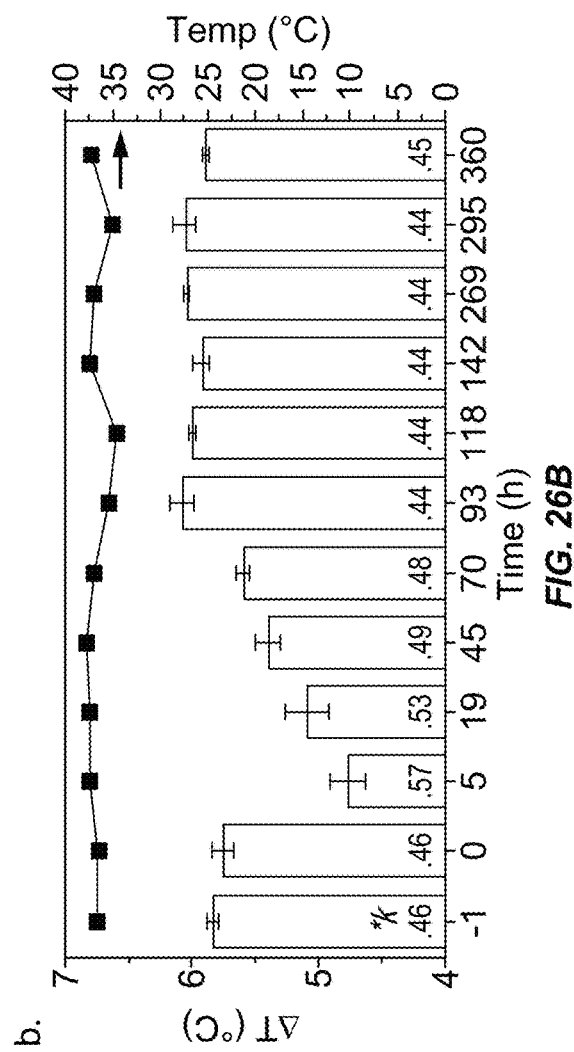
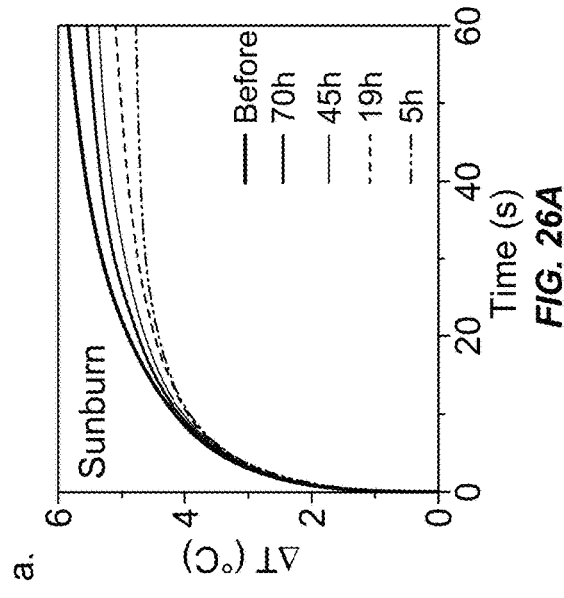
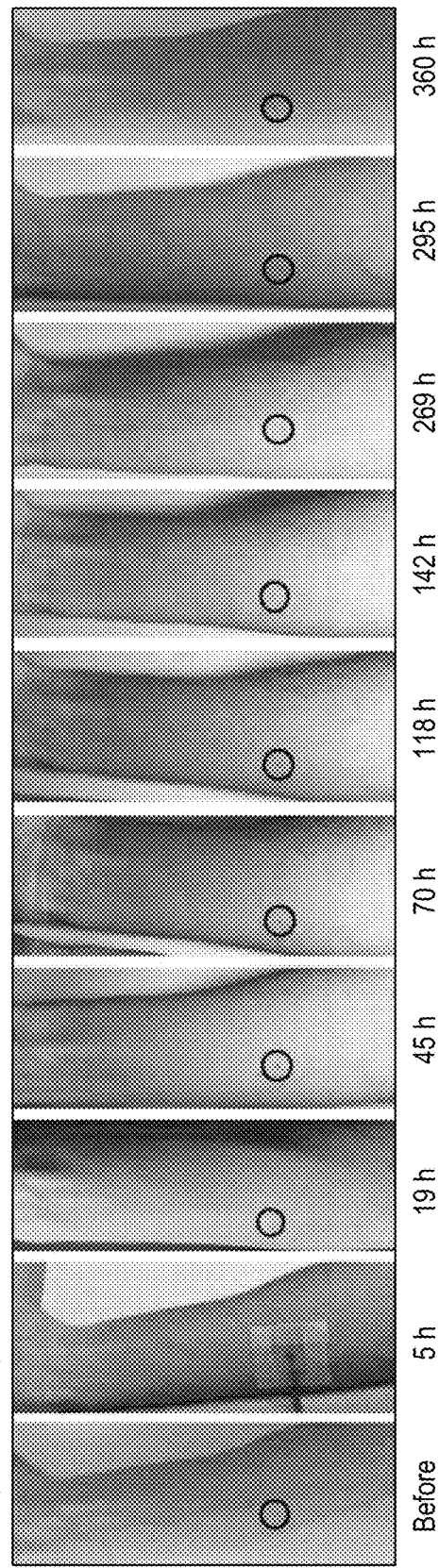
FIG. 26A
FIG. 26B
FIG. 26C

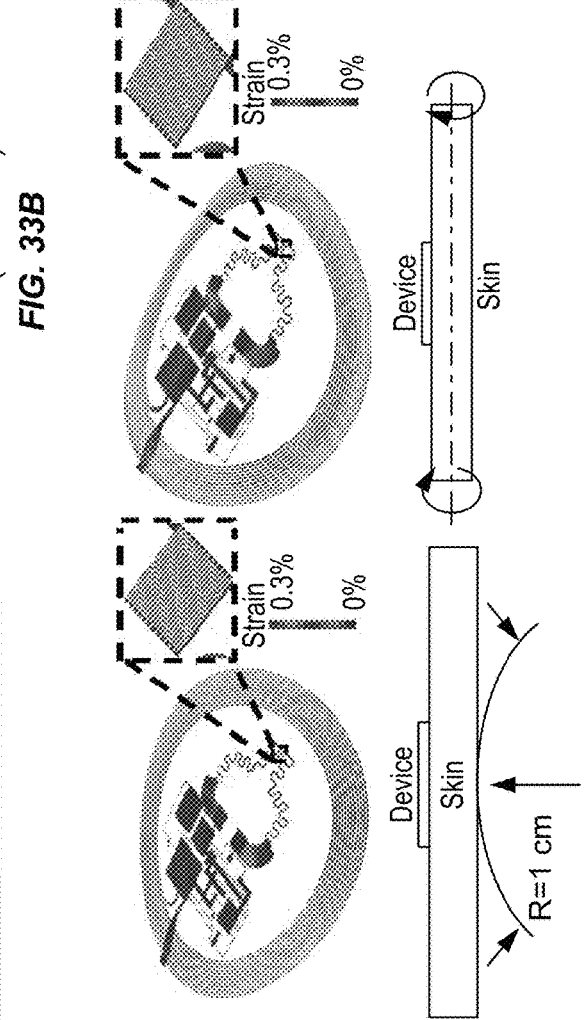
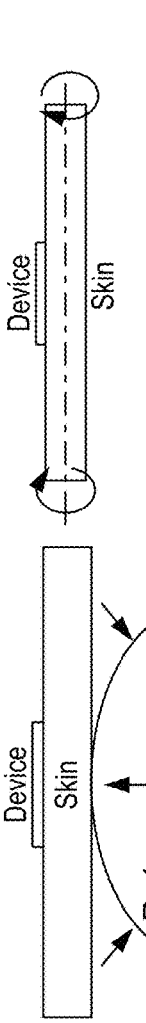
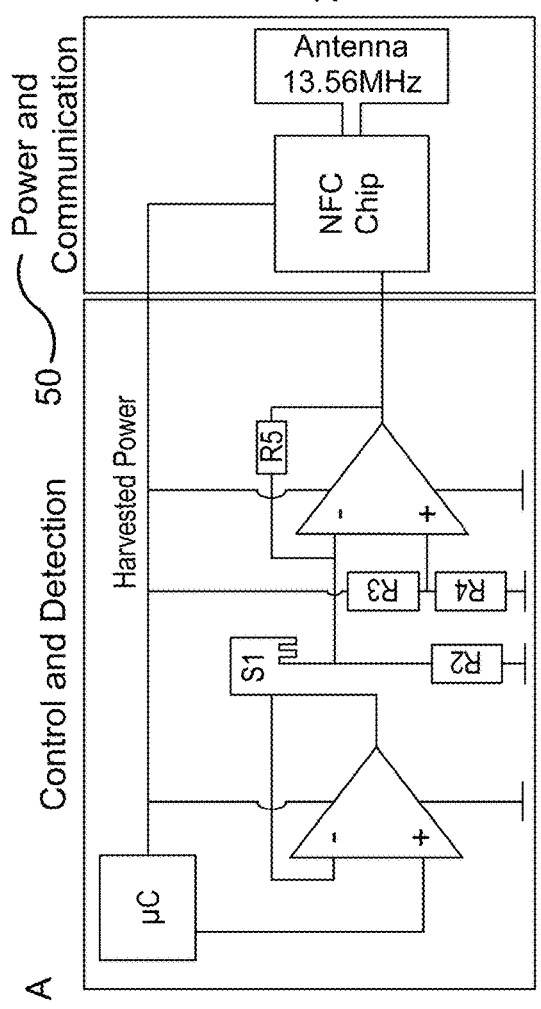
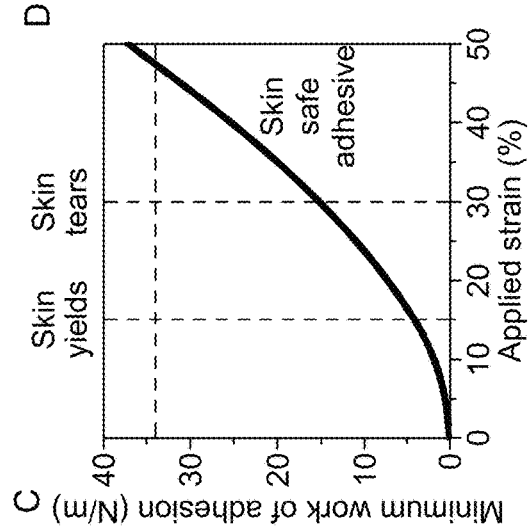
FIG. 33A
FIG. 33B
FIG. 33C
FIG. 33D

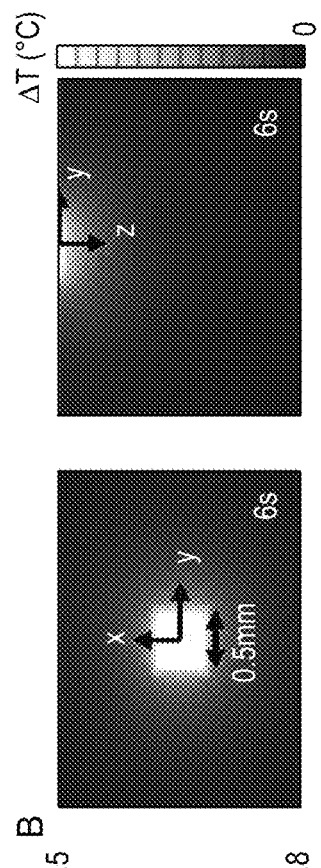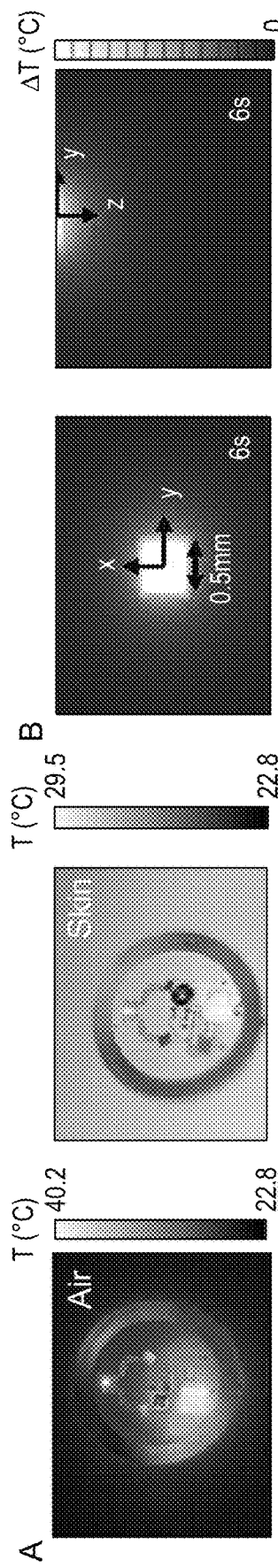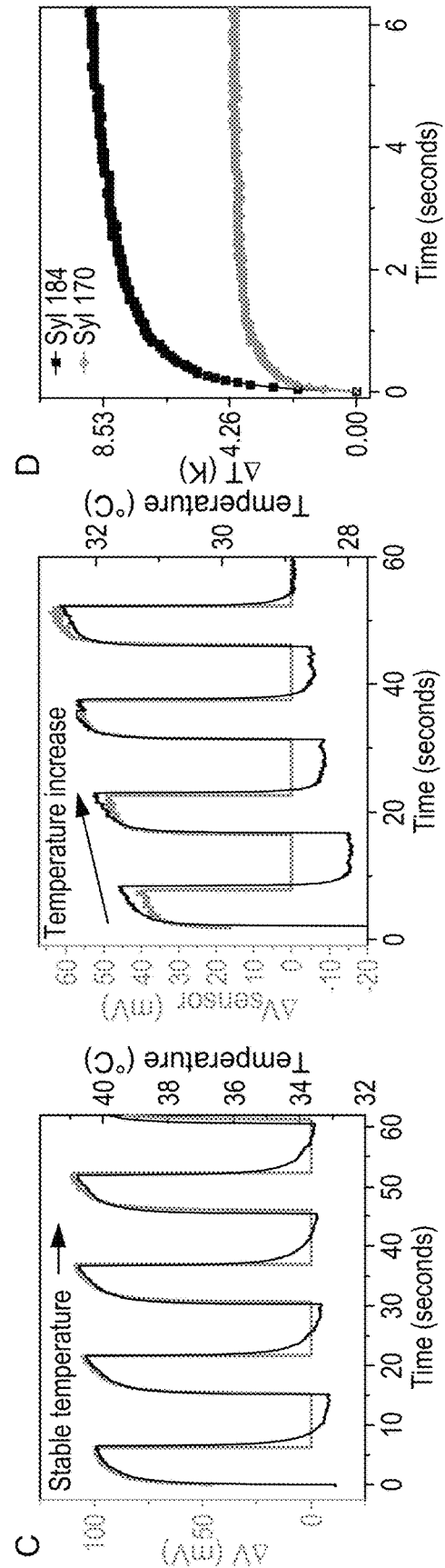
FIG. 34A
FIG. 34B
FIG. 34C
FIG. 34D

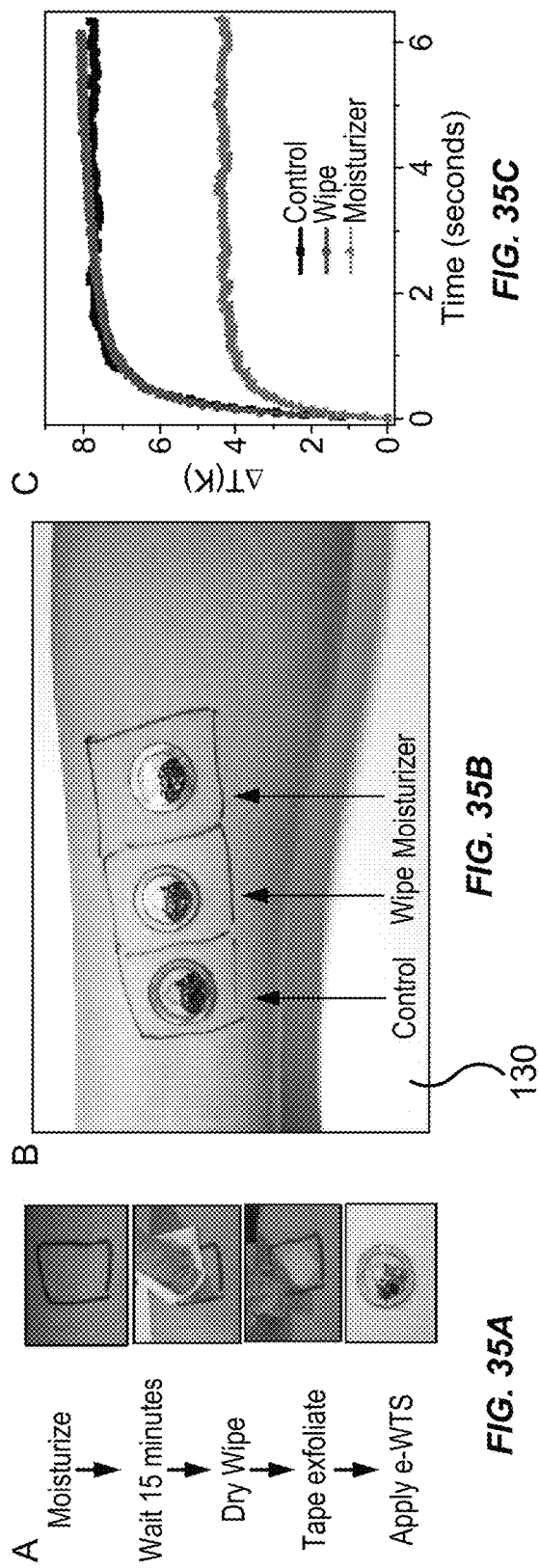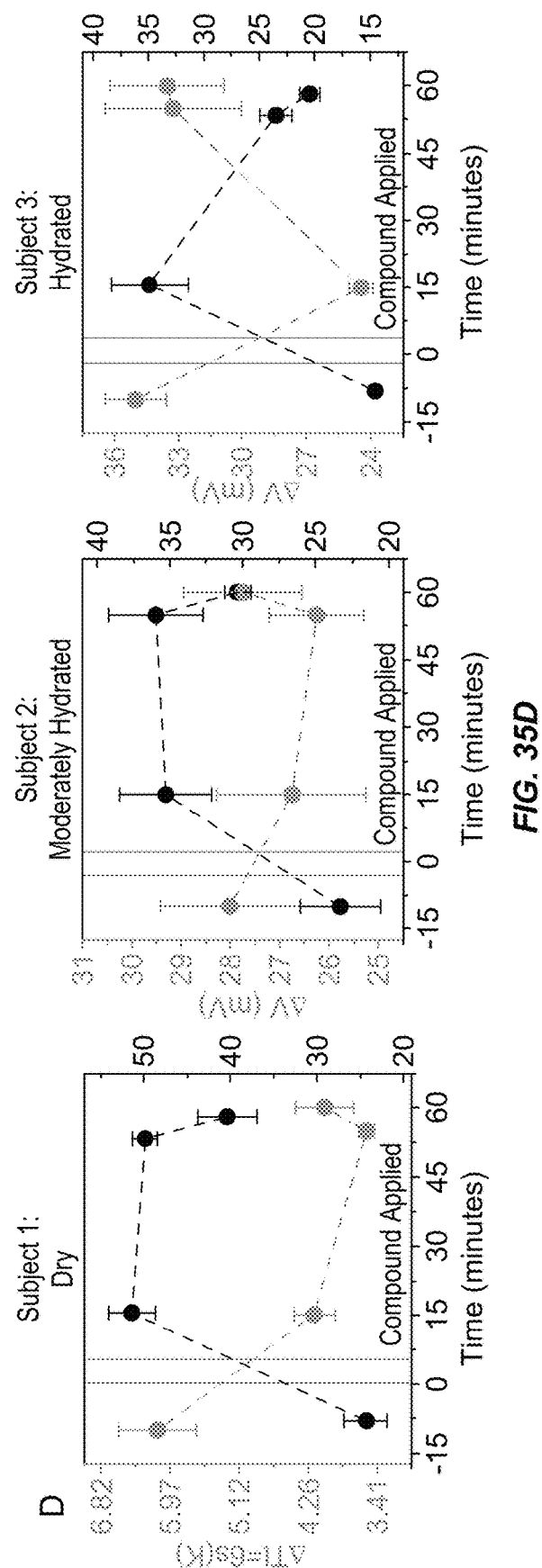
FIG. 35A
FIG. 35B
FIG. 35C
FIG. 35D

| Top layer/bottom layer materials | Thermal conductivity of top layer [W m$^{-1}$ K$^{-1}$] | Thermal conductivity of bottom layer [W m$^{-1}$ K$^{-1}$] |
| --- | --- | --- |
| Ecoflex/Ecoflex | 0.22±0.01 | 0.22±0.01 |
| Ecoflex/Sylgard 567 | 0.23±0.01 | 0.29±0.01 |
| Ecoflex/Sylgard 170 | 0.21±0.01 | 0.42±0.02 |
| Ecoflex/Sylgard 164 | 0.23±0.01 | 0.66±0.01 |
| Sylgard 567/Ecoflex | 0.32±0.01 | 0.21±0.02 |
| Sylgard 567/Sylgard 567 | 0.30±0.01 | 0.30±0.02 |
| Sylgard 567/Sylgard 170 | 0.30±0.01 | 0.46±0.02 |
| Sylgard 567/Sylgard 164 | 0.31±0.01 | 0.67±0.01 |

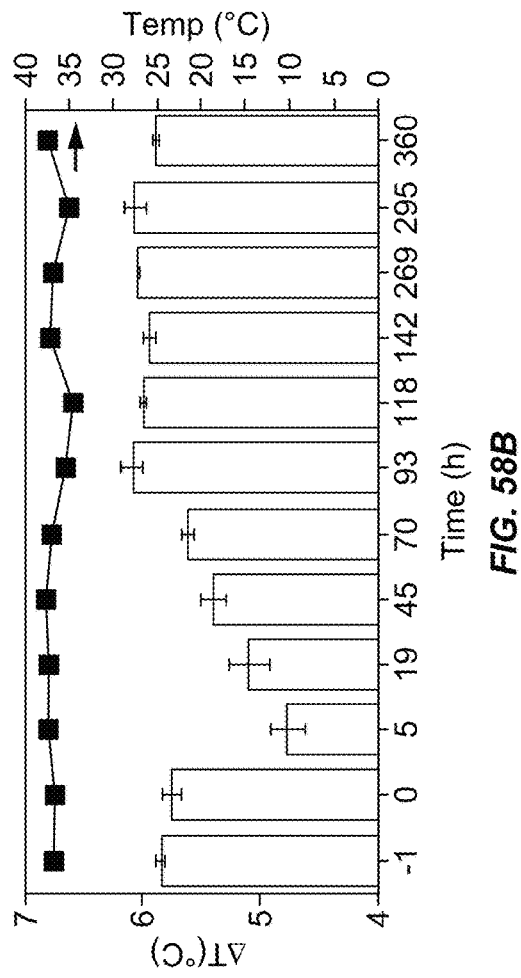
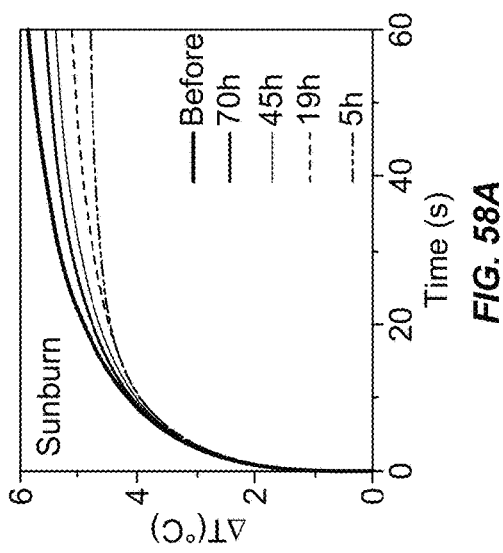
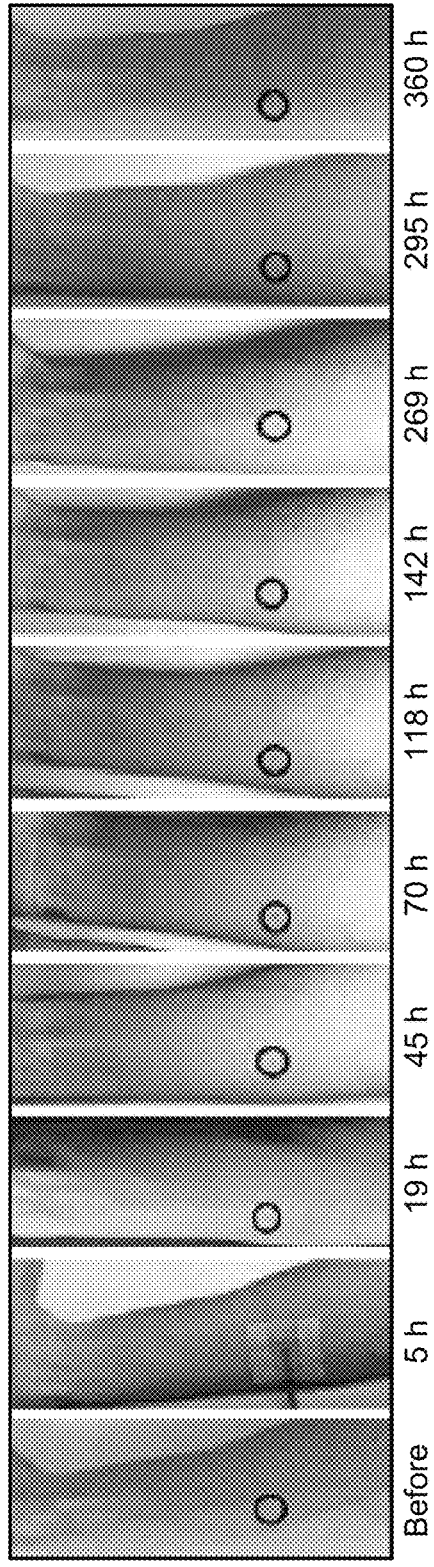
FIG. 58A
FIG. 58B
FIG. 58C

WIRELESS SKIN SENSOR WITH METHODS AND USES

CROSS-REFERENCE TO RELATED APPLICATIONS

This application claims the benefit of and priority to U.S. Provisional Patent Application Nos. 62/650,826 filed Mar. 30, 2018, 62/791,390, filed Jan. 11, 2019, and 62/696,685 filed Jul. 11, 2018 each of which are specifically incorporated by reference in their entirety to the extent not inconsistent herewith.

BACKGROUND

Wearable electronics are a class of systems with potential to broadly impact a range of technologies, industries and consumer products. Advances in wearable systems are driven, in part, by development of new materials and device architectures providing for new functionalities implemented using device form factors compatible with the body. Wearable consumer products are available, for example, that exploit small and portable electronic and/or photonic systems provided in body mounted form factors, such as systems building off of conventional body worn devices such as eye glasses, wrist bands, foot ware, etc. New device platforms are also under development to extend the range of wearable technology applications that incorporate advanced functionality in spatially complaint form factors compatible with low power operation, wireless communication and novel integration schemes for interfacing with the body. (See, e.g., Kim et al., Annu. Rev. Biomed. Eng. 2012.14; 113-128; Windmiller, et al., Electroanalysis; 2013, 25, 1, 29-46; Zeng et al., Adv. Mater., 2014, 26, 5310-5336; Ahn et al., J Phys. D: Appl. Phys., 2012, 45, 103001).

Tissue mounted systems represents one class of wearable systems supporting diverse applications in healthcare, sensing, motion recognition and communication. Recent advances in epidermal electronics, for example, provide a class of skin-mounted electronic systems provided in physical formats enabling mechanically robust and physically intimate contact with the skin. Certain classes of epidermal electronic systems have been developed, for example, combining high performance stretchable and/or ultrathin functional materials with soft elastic substrates implemented in device geometries useful for establishing and maintaining conformal contact with the soft, curvilinear and time varying surface of the skin. (See, e.g., US Pat. Pub. 2013/0041235; W.-H. Yeo et. al., "Multifunctional Epidermal Electronics Printed Directly Onto the Skin," Advanced Materials 25, 2773-2778 (2013); PCT Pub. Nos. WO 2016/025438; WO 2016/054348; WO 2016/196675).

Skin is the largest organ of the human body and it provides one of the most diverse sets of functions. The outermost layer, the stratum corneum (SC), serves as a protective barrier and the first defense against physical, chemical and biological damage. The skin also receives and processes multiple sensory stimuli, such as touch, pain and temperature, and aids in the control of body temperature and the flow of fluids in and out of the body. These processes are highly regulated by nervous and circulatory systems, but also depend directly and indirectly on thermal characteristics of the skin and, therefore, hydration status. Not only is the skin of such functional importance that makes monitoring and maintenance of the skin important, but there is a large market around skin beauty, including cosmetics.

Important to the adoption of the emerging class of epidermal electronic systems in practical situations is the continued development of devices that are robust and wireless to thereby support a wide range of applications, including for personal healthcare assessment and clinical medicine, such as in the cosmetics/beauty and/or clinical dermatology fields. Particularly needed is the ability to reliably measure various physical properties of skin, in a manner that does not limit a user's range of motion, lifestyle and that is not necessarily limited to a clinical setting.

BRIEF SUMMARY

The invention addresses the need to reliably measure various physical properties of skin, in a manner that does not limit a user's range of motion, lifestyle and that is not necessarily limited to a clinical setting, by specially configured electronic devices that are wireless and conformable to the underlying tissue. The ability to wirelessly wear the devices in a manner that is comfortable and unobtrusive to the user provides a number of functional benefits. For example, important biological tissue parameters may be obtained, even for a user outside of a controlled medical setting. Those parameters may be communicated at a distance for evaluation in real-time, or at a later time, such as by the user or a third party, such as a medical caregiver, friend or family member. The devices and methods are also compatible with a more active intervention, ranging from a warning provided to the user to an automated response, such as application of a hydrating compound, sun block compound, or any other response depending on the application of interest.

Although the devices and methods provided herein are compatible with a range of applications, one relevant application relates to the sensor output that can be used to guide patient behavior and support skin moisturization. This is applicable to numerous skin conditions as well as general skin health. There are numerous conditions where personalized measurements of skin hydration is important. This includes skin problems characterized by skin barrier dysfunction such as atopic dermatitis, inherited disorders for cornification, or asteatotic eczema. For general skin wellness, particularly in dry or cold environments, a measure of personalized skin hydration can improve skin moisturization.

A list of representative embodiments, include any one or more of:

1. A wireless electronic device for thermally interfacing with a biological tissue comprising: a flexible substrate; a thermal actuator supported by said flexible substrate configured to provide a thermal input to said biological tissue; a temperature sensor supported by said flexible substrate configured to measure a temperature to determine thermal conductivity of said biological tissue; and a wireless electronic system in electronic communication with said thermal actuator and said temperature sensor, wherein said wireless electronic system is configured to provide two-way communication with an external controller.

2. The wireless electronic device of embodiment 1, wherein said external controller is configured to determine a tissue parameter based on said thermal conductivity.

3. The wireless electronic device of any of the above embodiments, wherein the thermal input corresponds to a temperature increase of said thermal actuator.

4. The wireless electronic device of any of the above embodiments, configured for long-term interfacing with the biological tissue for a time period that is greater than or equal to 1 day.

5. The wireless electronic device of embodiment 4, configured to provide a periodically continuous measure of thermal conductivity over a time period that is greater than or equal to 10 minutes.

6. The wireless electronic device of any of the above embodiments, wherein the biological tissue comprises skin and the wireless electronic device is an epidermal electronic device that is configured to conformally mount to the skin or a material disposed thereon.

7. The wireless electronic device of any of the above embodiments, wherein the biological tissue corresponds to a finger or a toe-nail.

8. The wireless electronic device of any of the above embodiments that is configured for implantation in a living animal, wherein the biological tissue comprises an internal organ or a subcutaneous tissue.

9. The wireless electronic device of any of the above embodiments, wherein the biological tissue is a transplanted tissue, including a transplanted organ.

10. The wireless electronic device of any of the above embodiments, wherein said thermal conductivity is used to calculate a tissue parameter that is one or more of tissue hydration, inflammation state, tissue oxygenation, tissue perfusion, blood flow, or tissue healing, tissue damage, or tissue health.

11. The wireless electronic device of embodiment 10, wherein the tissue parameter is associated with a sunburn parameter.

12. The wireless electronic device of embodiment 10, wherein the tissue parameter is personalized for an individual user.

13. The wireless electronic device of any of the above embodiments, configured to contact a moisturizer product, wherein the temperature sensor measures a temperature change in the moisturizer product to determine a moisturizer water content.

14. The wireless electronic device of embodiment 13, wherein the moisturizer product is positioned on a skin surface.

15. The wireless electronic device of any of the above embodiments, for personalized use by an individual user for skin hydration monitoring, evaluation, and treatment thereof.

16. The wireless electronic device of embodiment 15, that obtains a baseline skin hydration value and determines deviation from the baseline skin hydration value indicative of worsening dry skin.

17. The wireless electronic device of embodiment 15, further comprising a haptic feedback element to warn the user of a low tissue hydration condition.

18. The wireless electronic device of any of the above embodiments, wherein the temperature sensor measures a temperature change of the biological tissue comprising skin to evaluate excess skin water loss and low skin hydration.

19. The wireless electronic device of embodiment 18, wherein the excess skin water loss is associated with atopic dermatitis or eczema.

20. The wireless electronic device of any of the above embodiments, configured for use in detecting a dermatological risk condition.

21. The wireless electronic device of any of the above embodiments, wherein a temperature change of the biological tissue indicates an inflammation condition or edema.

22. The wireless electronic device of any of the above embodiments, used to detect an early sunburn damage condition to skin.

23. The wireless electronic device of any of the above embodiments, wherein said actuator and said sensor comprise a resistive wire, whose resistance varies with temperature.

24. The wireless electronic device of any of the above embodiments, wherein said sensor corresponds to said actuator.

25. The wireless electronic device of embodiment 24, wherein said sensor and actuator are formed from an electrically resistive wire whose resistance varies with temperature to measure temperature and that delivers thermal power to the biological tissue by Joule heating.

26. The wireless electronic device of any of embodiments 1-22, wherein said actuator and said sensor are formed from distinct resistive wires and separated from each other by a separation distance.

27. The wireless electronic device of any of the above embodiments, comprising a plurality of temperature sensors and/or a plurality of thermal actuators.

28. The wireless electronic device of any of the above embodiments, wherein said wireless electronic system is configured to power said wireless electronic device from said external controller.

29. The wireless electronic device of any of the above embodiments, further comprising a battery to at least partially power said wireless electronic device.

30. The wireless electronic device of any of the above embodiments, wherein the thermal conductivity is determined at a selected depth from a surface of said biological tissue, ranging to a maximum depth of 8 mm.

31. The wireless electronic device of any of the embodiments, further comprising:
  a. a first and a second active region, wherein each region comprises an electrically conductive wire that serves as the temperature sensor and the thermal actuator; optionally, the active regions may be described in terms of a geometry, such as a spiral disk, square, rectangular, or any other geometry where the wire density may be high (e.g., minimal separation distance between adjacent coils) of
  b. a first contact pad and a first electrically conductive ribbon that electrically connects the first contact pad to the first active region;
  c. a second contact pad and a second electrically conductive ribbon that electrically connects the second contact pad to the second active region;
  d. an encapsulation layer that fluidically isolates said first and second active regions; and
  e. wherein said flexible substrate supports said first and second contact pads.

32. The wireless electronic device of any of the above embodiments, further comprising a serpentine electrical interconnect that electrically connects the temperature sensor and thermal actuator a contact pad supported by the flexible substrate.

33. The wireless electronic device of any of the above embodiments, configured to conformally mount to a nail surface, wherein the tissue parameter is a nail bed parameter selected from one or more of: nail plate alteration, nail matrix alteration, hyponychium alteration, proximal nail fold alteration, lateral nail fold composition or nail bed alteration.

34. The wireless electronic device of embodiment 33, wherein the thermal input is provided to a nail bed underlying the nail.

35. The wireless device of any of the above embodiments, selected to measure a thermal property from one or more of: a low penetration depth for a superficial skin layer hydration parameter; an intermediate penetration depth for a blood flow parameter; a high penetration depth for deep dermis and subcutaneous fat tissue for an infection parameter.

36. The wireless electronic device of any of the above embodiments, wherein the thermal actuator and temperature sensor are formed from serpentine metal wires that are less than 50 µm wide and less than 1 µm thick.

37. The wireless electronic device of embodiment 36, wherein the serpentine metal wires are Cr/Au wires.

38. The wireless electronic device of any of the above embodiments, further comprising an encapsulating layer of PI with a thickness less than 10 µm.

39. The wireless electronic device of any of the above embodiments, wherein the flexible substrate comprises silicone having a thickness less than 200 µm.

40. The wireless electronic device of any of the above embodiments, comprising one or more physical parameters selected from the group consisting of:
   a. a substrate layer thickness less than 200 µm thick;
   b. an actuator thickness less than or equal to 20 µm;
   c. a sensor thickness less than or equal to 20 µm;
   d. a barrier layer thickness less than or equal to 30 µm;
   e. a sensor area less than or equal to 25 mm$^2$;
   f. an actuator area less than or equal to 25 mm$^2$;
   g. an effective Young's modulus of less than or equal to 1 MPa;
   h. a total device footprint less than or equal to 1 cm$^2$;
   i. an effective bending stiffness selected from the range of 0.1 nN·m to 1 N·m.

41. The wireless electronic device of any of the above embodiments, having a continuous measurement of thermal conductivity for a time period that is greater than or equal to 10 minutes.

42. The wireless electronic device of any of the above embodiments, that is disposable.

43. The wireless electronic device of any of the above embodiments that is a multifunctional device, further comprising an additional sensor for measuring one or more additional tissue parameters selected from the group consisting of temperature at a unique location, ambient electromagnetic radiation (including UV radiation), position, a skin modulus, and color.

44. The wireless electronic device of embodiments 43, wherein the additional sensor is one or more of an optical sensor such as a photodetector, ambient electromagnetic radiation sensor, an accelerometer, a piezoelectric device to measure a skin modulus, an impedance sensor, a motion sensor, or a vibration sensor.

45. The wireless electronic device of any of the above embodiments, further comprising an external controller.

46. The wireless electronic device of embodiment 45, wherein the external controller is a portable electronic device, including a smart phone, tablet, or computer.

47. The wireless electronic device of embodiment 45, wherein the external controller electronically records a time course of tissue thermal conductivity.

48. A method of determining a tissue parameter, the method comprising the steps of:
   providing any of the wireless electronic devices of the above embodiments;
   interfacing the wireless electronic device with a biological tissue;
   wirelessly actuating the thermal actuator from an external controller to thereby increase a temperature of the biological tissue;
   measuring a change in temperature of the biological tissue over time with the temperature sensor; and calculating a thermal conductivity of the biological tissue, thereby determining a tissue parameter of the biological tissue.

49. The method of embodiment 48, further comprising the step of evaluating the tissue parameter and for an adverse tissue parameter, taking a therapeutic action to improve the adverse tissue parameter.

50. The method of embodiment 49, wherein the tissue parameter comprises hydration or UV damage of skin, and the therapeutic action is application of a moisturizer or a sun-block.

51. The method of any of embodiments 48-50, wherein the interfacing step comprises conformally contacting the wireless electronic device with an exposed surface of the tissue.

52. The method of any of embodiments 48-51, further comprising the step of wirelessly powering the wireless electronic device with an external controller.

53. The method of any of the above embodiments used to determine a hydration state, blood flow state, inflammation state, or a sunburn state of the biological tissue.

54. The method of any of the above embodiments, further comprising the step of:
   a. alerting a user to an adverse skin condition.

55. The method of embodiment 54, wherein the alerting step comprises:
   a. a haptic signal; or
   b. an alert by the external controller.

56. The method of any of the above embodiments, further comprising the step of:
   a. establishing a baseline tissue parameter for a user, thereby providing individualized use of the device tailored to a user.

57. The method of any of the above embodiments, further comprising the step of exerting a force on biological tissue that is skin to determine skin softness or elasticity.

58. A method of measuring thermal conductivity of a biological tissue comprising: thermally interfacing the device of claim 1 with a biological tissue; and actuating the thermal actuator and measuring thermal conductivity of a biological tissue.

59. The method of embodiment 58, wherein the thermal conductivity reflects a skin tissue parameter associated with a cosmetic or a medical application.

60. A device for performing any of the above method embodiments.

Any of the devices and methods described herein may further comprise one or more components useful for the application of interest. Examples include, but are not limited to, amplifiers, strain gauges, temperature sensors, wireless power coils, solar cells, inductive coils, high frequency inductors, high frequency capacitors, high frequency oscillators, high frequency antennae, multiplex circuits, electrocardiography sensors, electromyography sensors, electroencephalography sensors, electrophysiological sensors, thermistors, transistors, diodes, resistors, capacitive sensors, light emitting diodes, superstrate, embedding layers, encapsulating layers, planarizing layers or any combinations of these.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE SEVERAL VIEWS OF THE DRAWING(S)

FIG. 1 illustrates a device cross-section including the layered components. The thermal sensor/actuator is connected to underlying circuitry enabling wireless power transfer, sensing, and data communication with a near-field-communication (NFC) reader. Further details are provided of the underlying electronics and circuitry.

FIG. 2 describes the performance of the wireless sensor to measure skin temperature compared to a gold-standard infrared camera. Furthermore, the sensor exhibits superb linearity.

FIG. 3 describes the ability of the wireless thermal sensor to quantify the differing water content of a glycerol/water mixture. With decreasing levels of water content, the sensor clearly outputs a linear difference in temperature change.

FIG. 4 demonstrates the wireless sensor in active sensing mode. A mild amount of heat (imperceptible) is applied to the skin to obtain the measurement. In a simple test, the sensor clearly distinguishes skin that before and after moisturization.

FIG. 5 shows the difference in skin hydration measurements with moisturizer products of varying amounts of water. In this example petrolatum, a moisturizer product with nearly 0 water content. This product exhibits the greatest change in skin hydration. Aquaphor, another occlusive type of moisturizer, exhibits the next highest skin hydration improvement. Creams, lotion, and gels all have decreasing levels of hydration potential. This demonstration was performed on a single subject's forearm.

FIG. 6 shows that the decay of moisturizer duration and efficacy over time on human skin. The cream, which has a greater hydrating effect, has a longer durable response in hydrating the skin compared to lotion.

FIG. 7 demonstrates a novel clinical metric "skin hydration factor" enabled by the sensor. The grey bar shows the skin 15 minutes after having a moisturizer product applied and then repeated 1 hour later. This demonstrates the ability for the moisturizer to increase skin hydration specific to an individual. Larger scale population studies on multiple individuals can be used to create an average "skin hydration factor" reflective of an individual moisturizer product's ability to hydrate the skin. This would be useful for consumers attempting to distinguish moisturizer performance based by skin hydration improvement.

FIG. 8 shows the sensor directly placed overlying a moisturizer product. The sensor is able to quantify varying levels of hydration based on the content of the moisturizer product itself. This may serve as a useful sensor for cosmetics manufacturers to verify the water content of their products.

FIGS. 9A-D summarizes of the essential features that define the depth sensitivity of measurements using epidermal thermal depth sensors (e-TDS). FIG. 9A Schematic illustration of the bilayer system used for FIG. 9B FEA calculations of $h_{max}$ as a function of t for different R and FIG. 9C scaling law for critical depth as a function of R and t. The equation is a numerical fit (represented by the dotted line) with adjusted R-squared error=0.996 FIG. 9D Scaling law for constant $C_1$ as a function of h/R to determine $k_{effective}$. The equation is a numerical fit of the calculations (shown as a dotted line) with adjusted R-squared error=0.997.

FIG. 10 illustrates the effect of petrolatum (Vaseline®, Unilever®), an occlusive moisturizer, on skin hydration analyzed using two sensors with depth sensitivity to skin and fat respectively. Measurements involve three subjects evaluated before, and 15 minutes after application of ~5 mg/cm² of petrolatum to the forearm. In all cases, k extracted from e-TDS 1 increases by 15-25%, while the value extracted from e-TDS 2 remains nearly unchanged. These results suggest modulation of the properties only of superficial tissue, the stratum corneum (~100 μm). The finding that $k_{petroatum}$=0.19 W m$^{-1}$K$^{-1}$ indicates that the e-TDS does not measure a change due to the thermal properties of petrolatum, but rather an increase in $k_{effective}$ by prevention of transepidermal water loss (TEWL), consistent with previous studies using conventional devices for measuring TEWL.

Figures 13A, 13B:
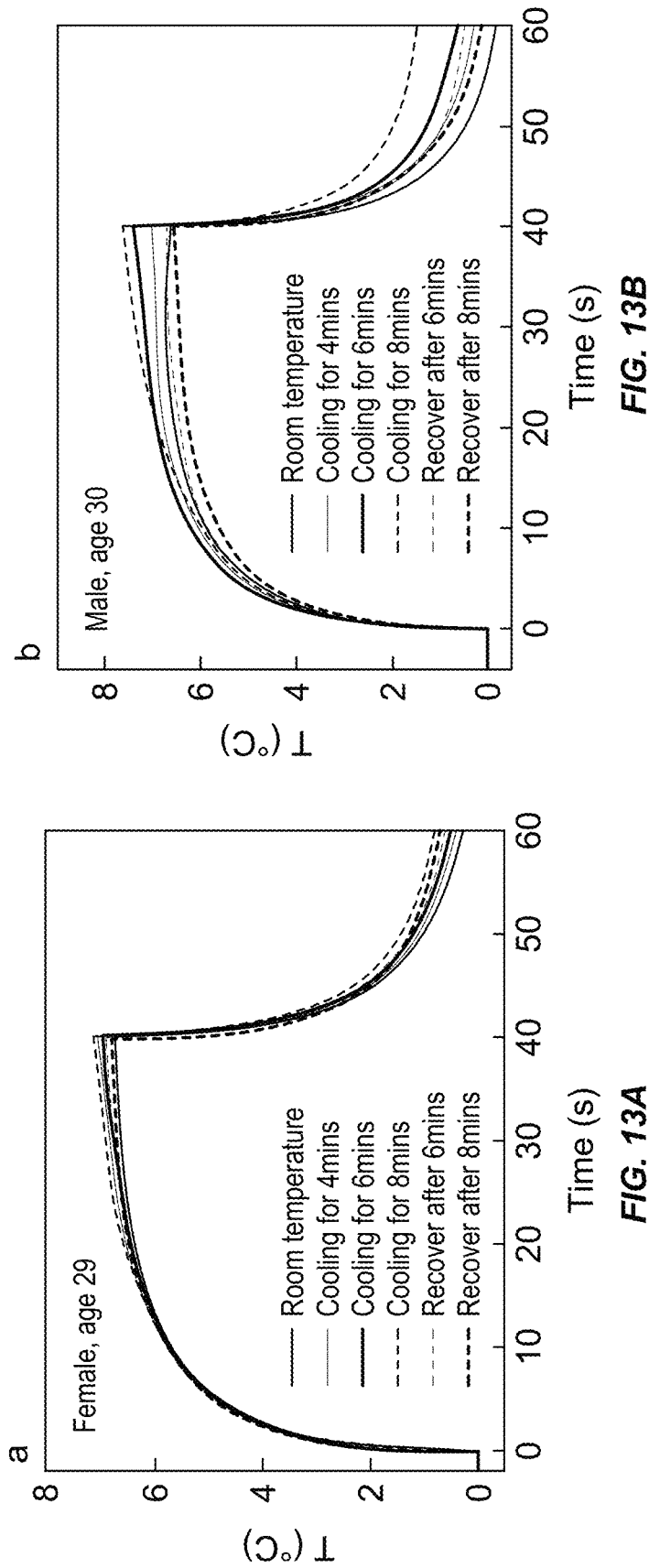
Figure 13D:
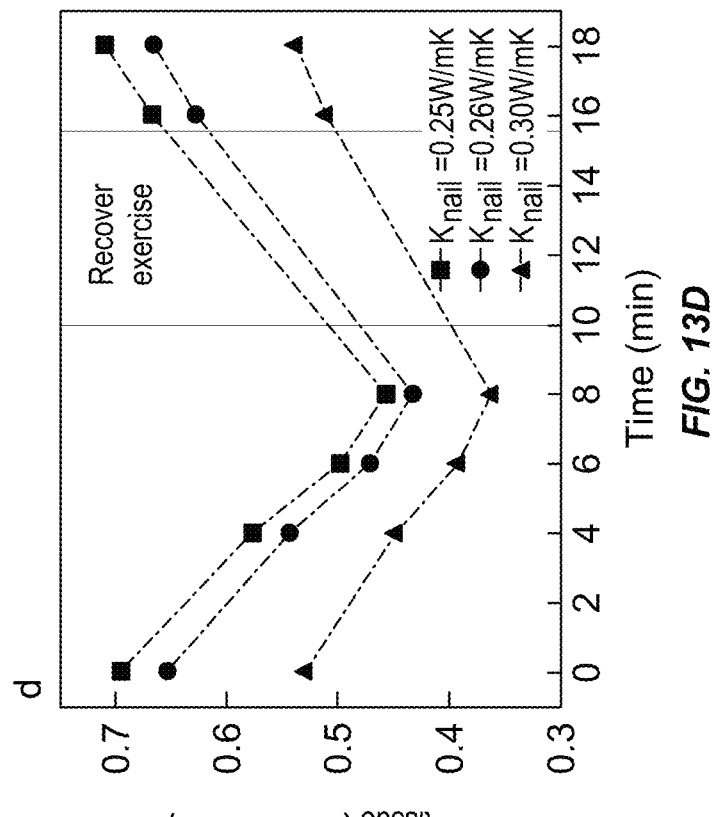
Figure 13C:
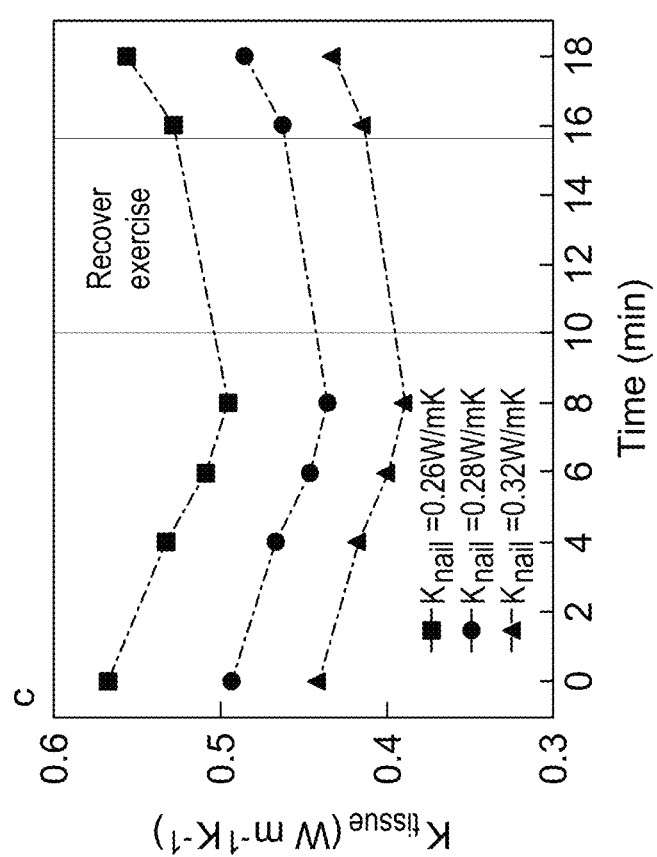

FIG. 13 provides an illustration of the use of the nail bed thermal sensor to detect changes in thermal conductivity related to cooling and re-heating.

FIG. 14 demonstrates the ability of the thermal sensor to track the healing of the skin related to a sunburn—this sensor enables a repeatable, quantifiable measure of sunburn recovery that tracks well with skin erythema resolution. Similarly, heat and cold stresses can be measured as well.

Figure 15:
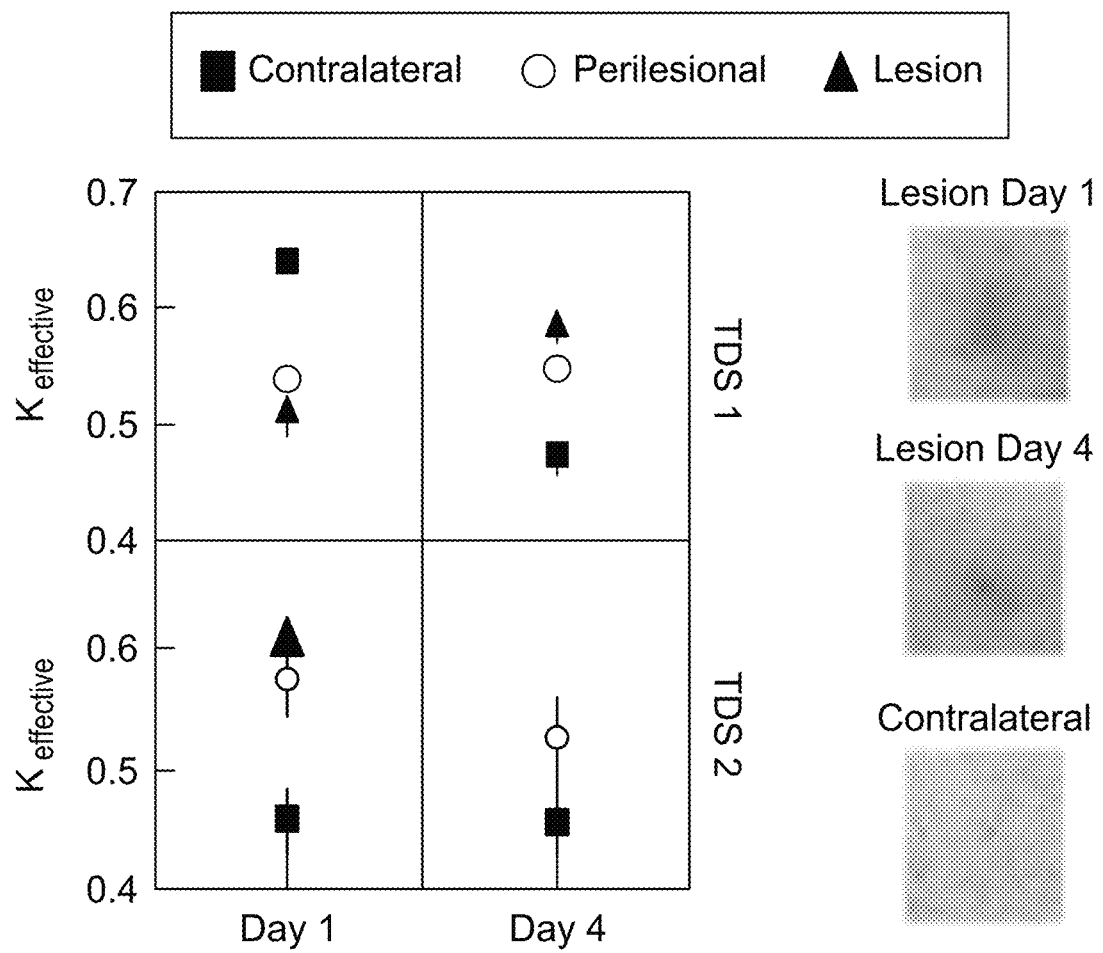

FIG. 15 is an illustration of the sensor being able to track healing of a lesion on the skin affected by cellulitis. The sensor can provide a thermal conductivity measurement of the both the superficial skin and deeper skin (dermis and subcutaneous fat). The values derived can be used for both diagnostic confirmation and to track healing.

Figure 16:
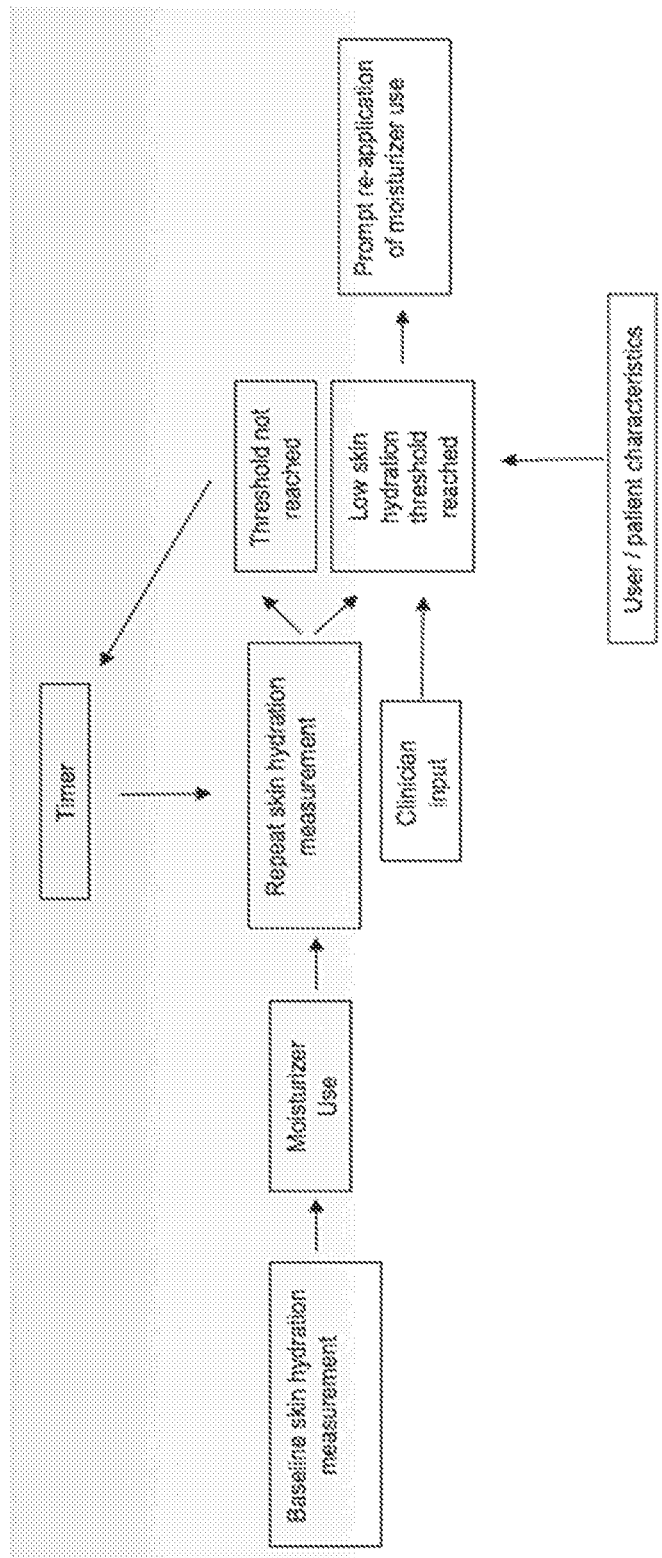

FIG. 16 provides an example in which a baseline skin hydration is taken. Moisturizer use can then be applied. Based on a set elapse of time, a repeat measurement can either indicate significant moisture loss or no significant moisture loss of the skin. If a threshold is met, the user is notified to moisturizer.

Figure 17:
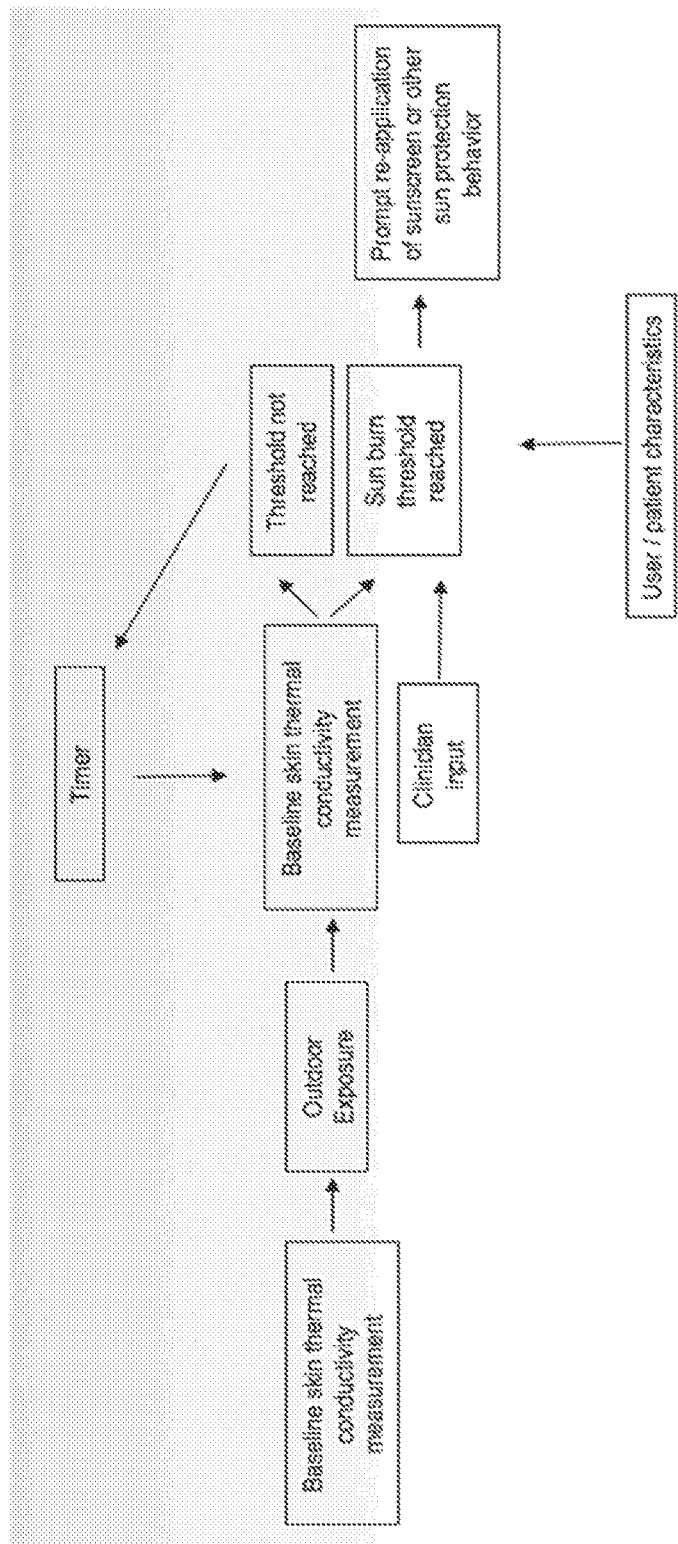

FIG. 17 provides an example in which a skin hydration measure can be replaced with a skin sunburn measure to interrogate whether the sensor detects local skin inflammation indicative of a sunburn. A threshold can then be used to warn the user to engage in sun protection behaviors such as shade shaking or use of sunscreen.

Figure 18:
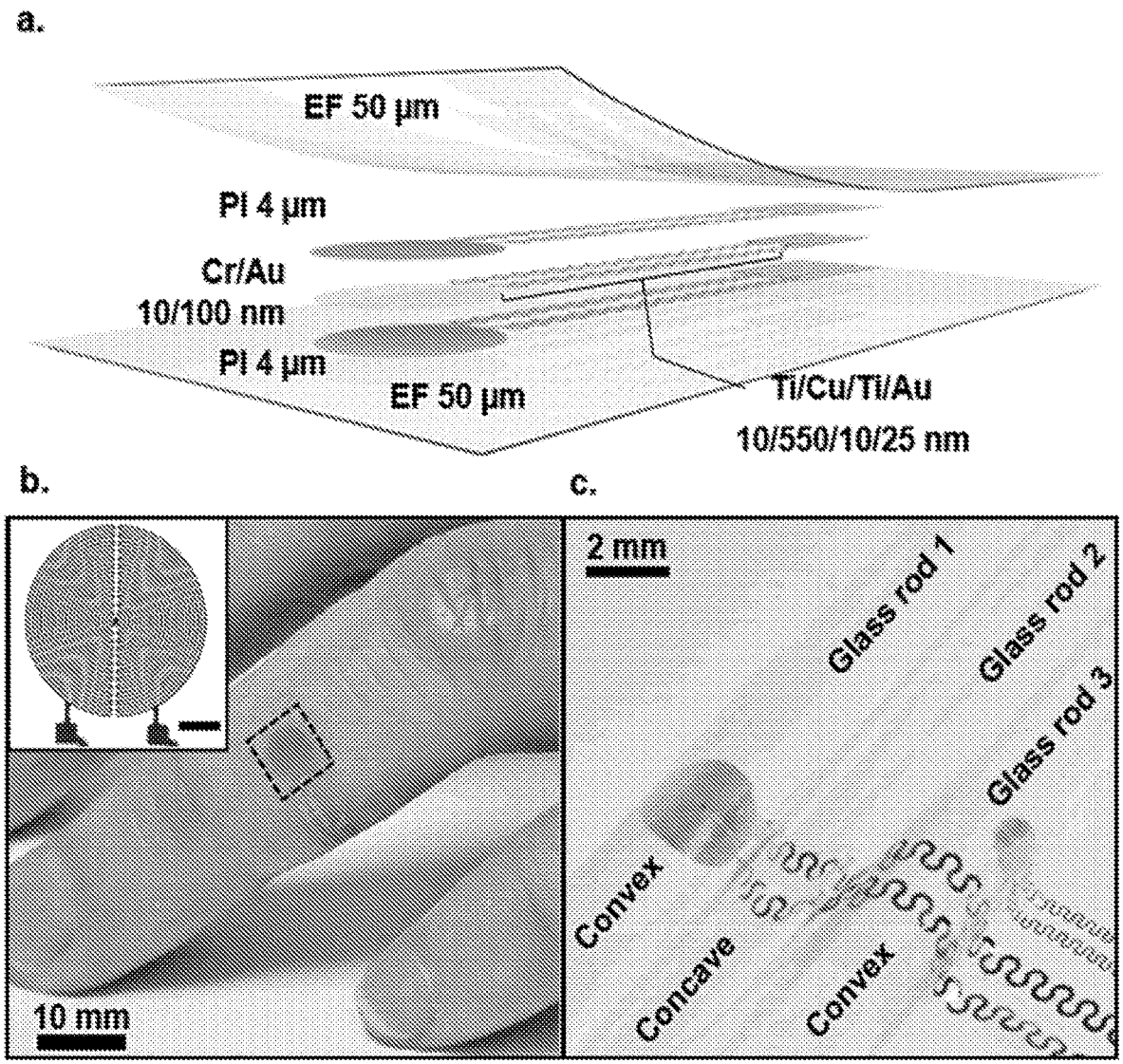

FIG. 18: Device components and validation. (a) Schematic illustration of the resistive sensor device layers. (b) Digital image of resistive sensor device laminated on the ring finger of Subject's left hand. Inset: Optical microscope image of actuator/sensor demonstrating the pattern of the resistive wire (scale bar 250 μm). (c) Optical image of two devices with different actuator/sensor sizes threaded between a series of three transparent glass rods such that the device is draped over the two outmost rods and positioned under the middle most rod.

Figure 19:
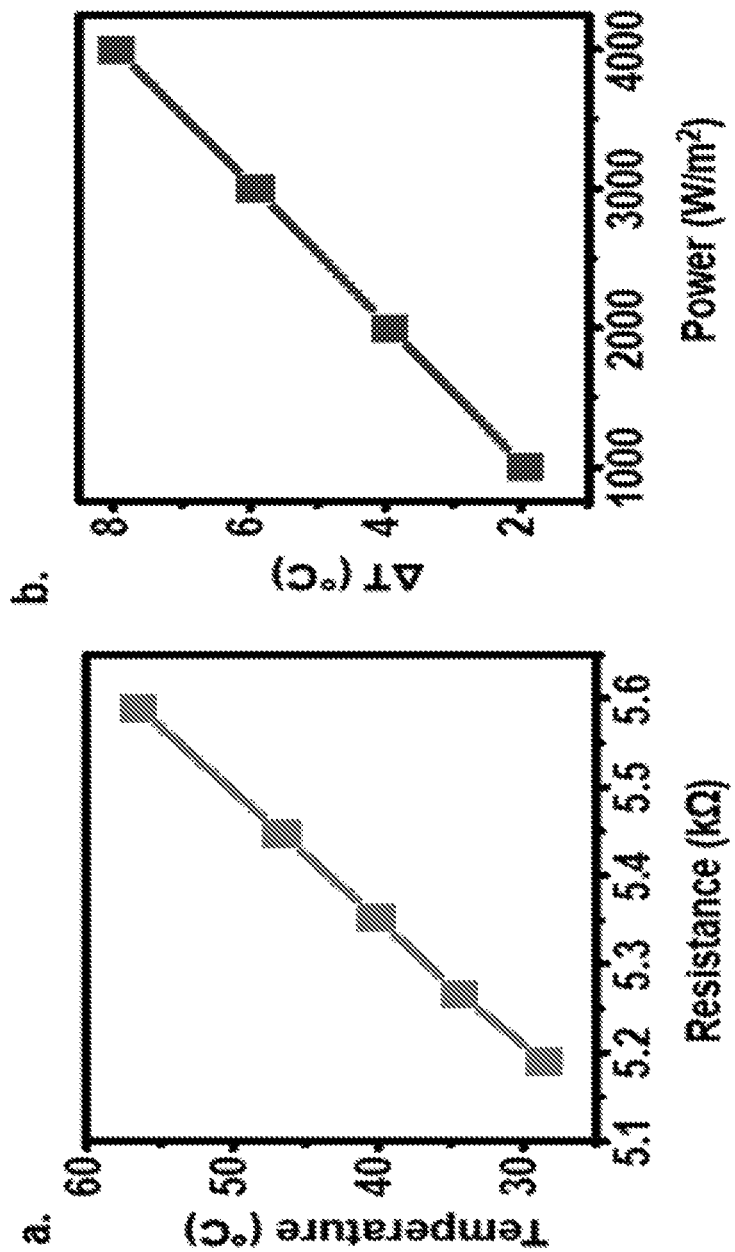

FIG. 19: (a) Representative plot of the linear relationship between temperature and resistance for a given device. (b) Representative plot of the linear relationship between the change in temperature as a function of power density of four separate measurements after identical transient heating times.

Figure 20:
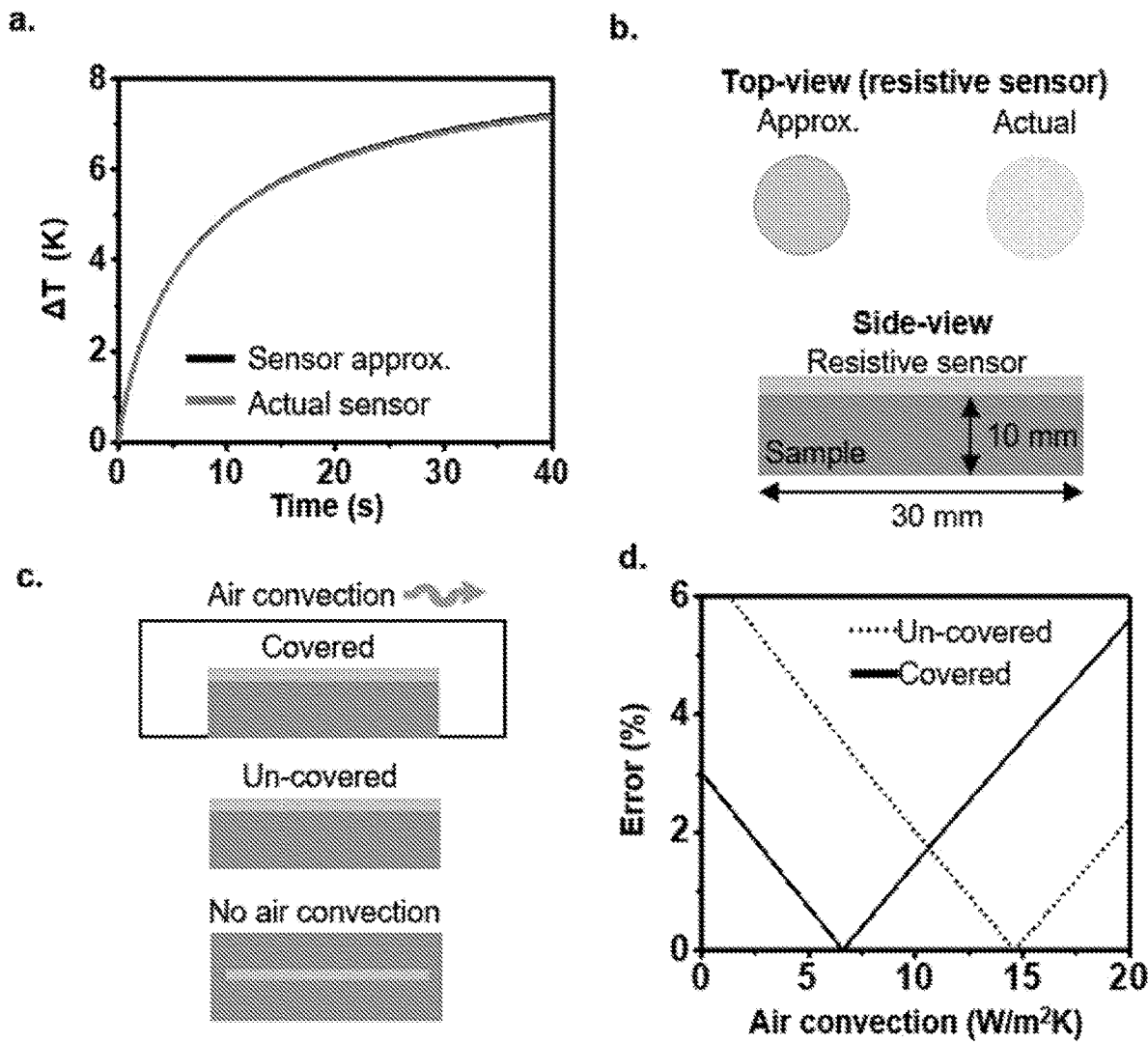

FIG. 20: Determination of the air convection coefficient. (a) Simulated plot of the change in temperature as a function of time (s) showing good agreement between FEA that considers the actual sensor shape (red line) vs. a sensor shape approximated as a circle (black line). (b) A top-view illustration of the actual (left) and approximated (right) sensor shapes, and a side-view illustration of a sensor atop a sample (bottom). (c) Illustrations showing the experimental set-ups for validation of air convection approximations. (d) Plot of simulated error % as a function of air convection (W/m²K) for both 'covered' (black line; 6 W/m²/K) and 'un-covered' (dotted line; 15 W/m²K) interpreted from experiment data-sets.

Figure 21:
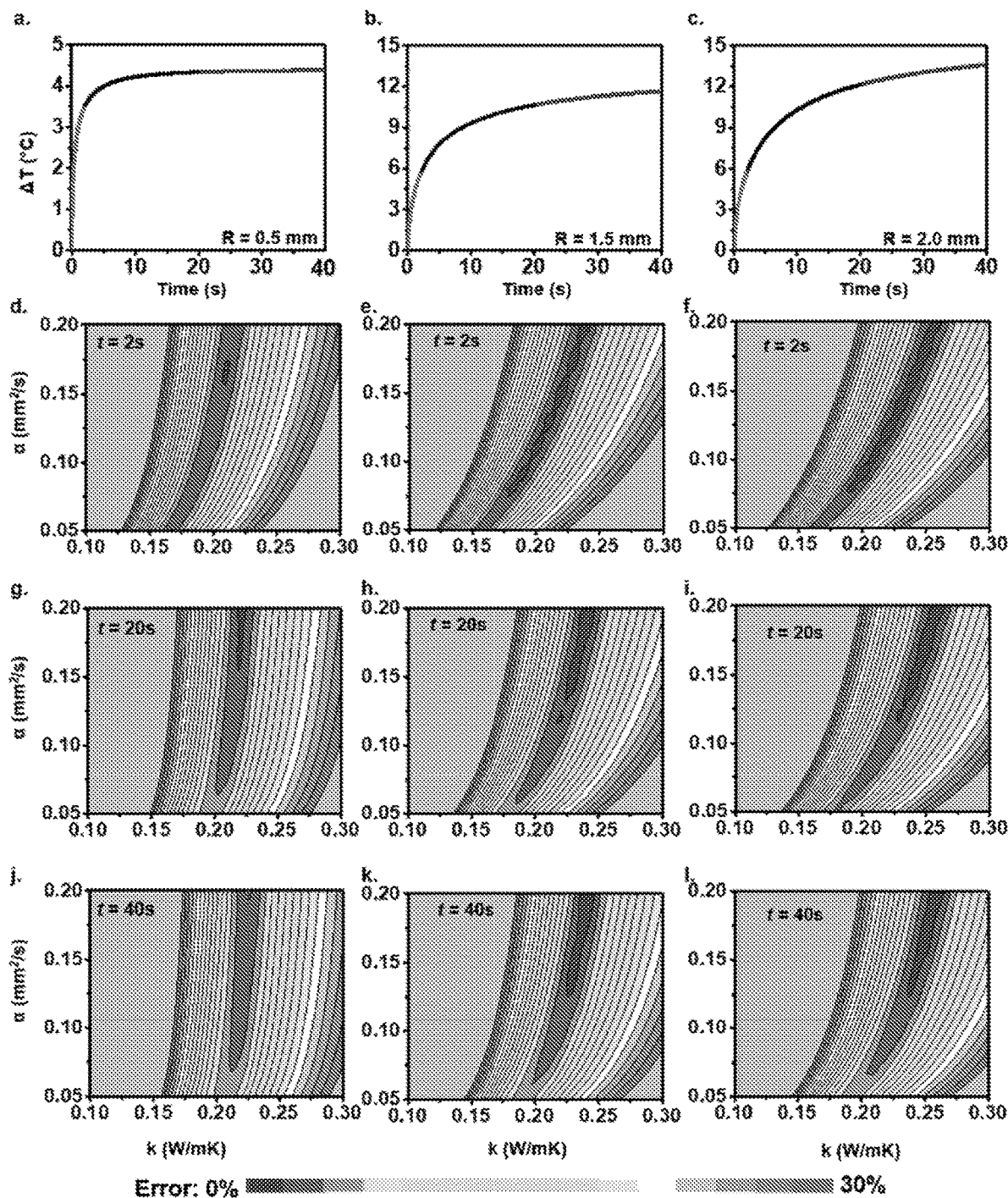

FIG. 21: Comparison of different heater sizes. (a-c) Plots of the change in temperature ($\Delta T$; ° C.) as a function of transient heating time (s) at intervals of 2 s (red line), 20 s (black line), and 40 s (blue line) overlaid as an example of the high degree of reproducibility across measurement of a static surface for radius, R=0.5 mm (a), R=1.5 mm (b), and R=2.0 mm (c). (d-1) 2D error surface plots of thermal diffusivity (a; mm²/s) vs. thermal conductivity (k; W/mK) over transient heating times of 2 s, 20 s and 40 s and heater radii R=0.5 mm ((d), (g), and (j), respectively), R=1.5 mm ((e), (h), and (k), respectively), and R=2.0 mm ((f), (i), and (1), respectively). Measurements were collected while laminated on a silicone substrate (Ecoflex, 10 mm thick, 60 mm diameter, cured at 70° C.×24 hours) at a power density of 3 mW/mm².

Figure 22:
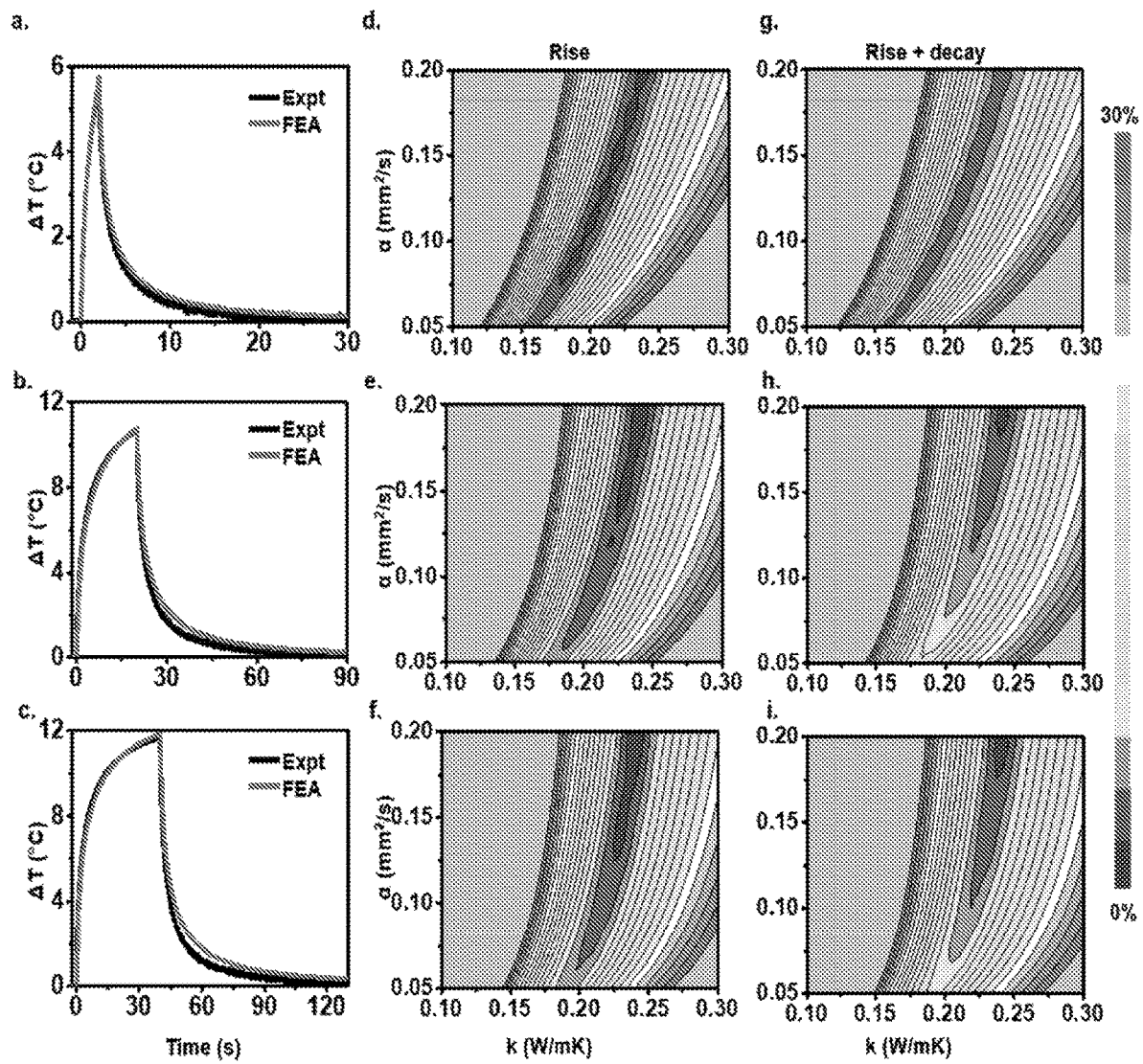

FIG. 22: Comparison of transient heating time and temperature decay. (a), (b) and (c) are representative plots of the change in temperature as a function of transient heating time (s) with FEA fit (red curve) of experimental data collection (black curve) at 2 s, 20 s and 40 s intervals, respectively). The plots are accompanied by corresponding 2-dimensional (2D) error surfaces spanning a range of thermal diffusivity (0.05 mm²/s-0.20 mm²/s) and thermal conductivity (0.10 W/mK-0.30 W/mK), which encompass only the rise (from $\Delta T_{min}$ to $\Delta T_{max}$) at a specified transient heating time of 2 s, 20 s or 40 s ((d), (e), and (f), respectively) or the complete rise (over 2 s, 20 s or 40 s) and temperature decay post transient heating (over 30 s, 90 s or 130 s), ((g), (h), and (i), respectively). Measurements were collected while laminated on a silicone substrate (Ecoflex, 10 mm thick, 60 mm diameter, cured at 70° C.×24 hours) at a power density of 3 mW/mm², using a heater with a radius of 1.5 mm.

Figure 23:
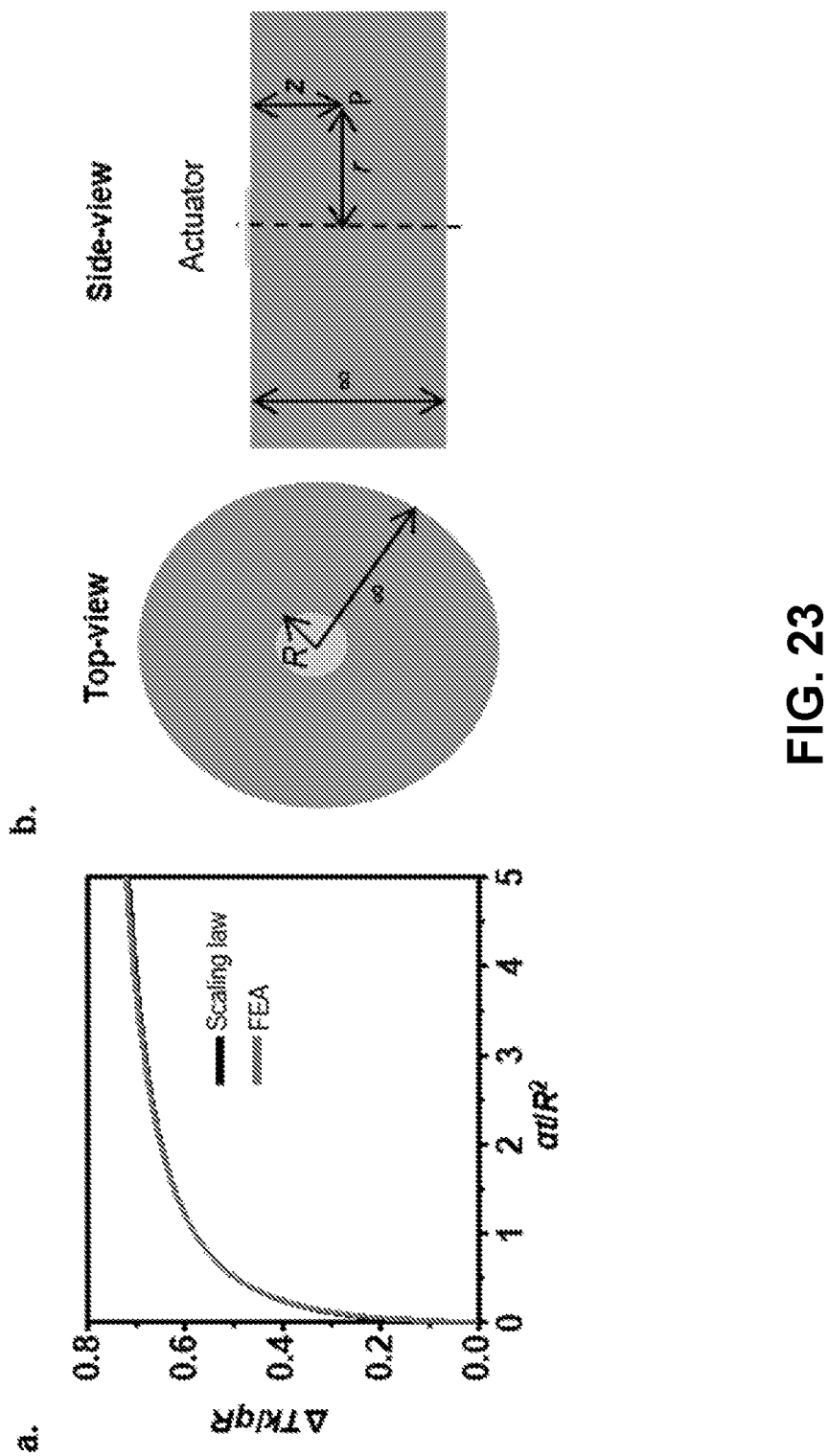

FIG. 23: Comparison between scaling law and FEA. (a) Normalized time versus temperature curves obtained by the scaling law and FEA. (b) Schematic representation (left: top-view, right side-view) of the scaling law and FEA model.

Figure 24:
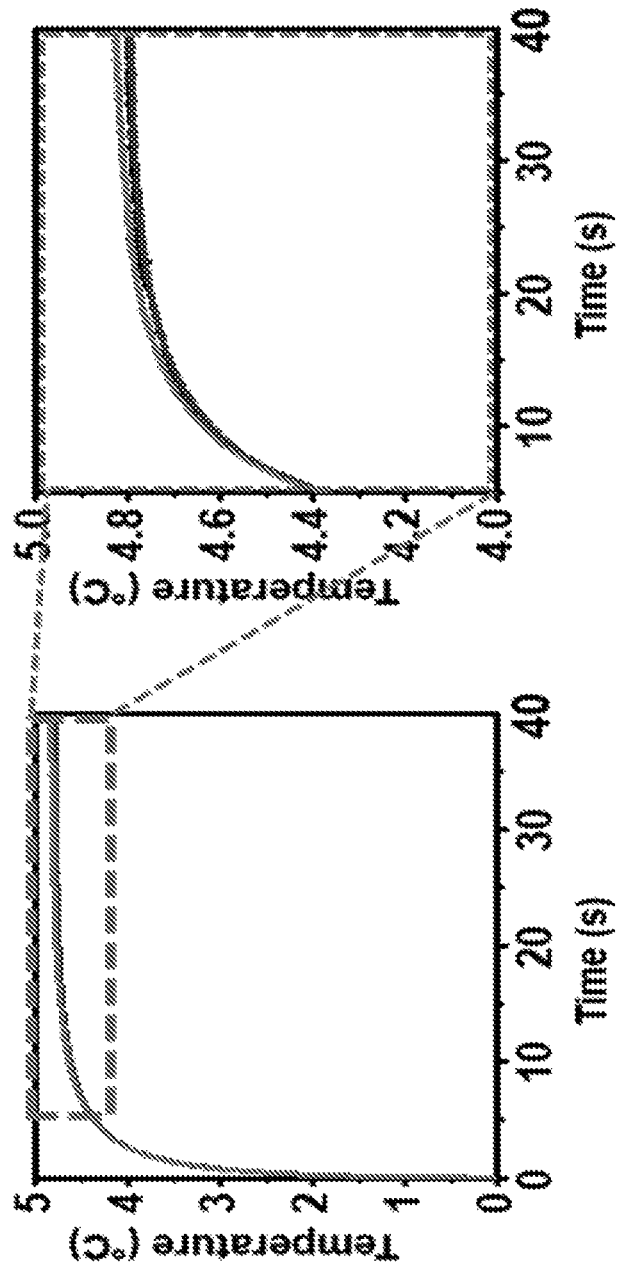

FIG. 24: Experimental Reproducibility. Representative temperature vs. time plots show repeated experimental measurements on S184 at 3 mW/mm² using a resistive sensor with R=0.5 mm and number of samples, n=3.

Figure 25:
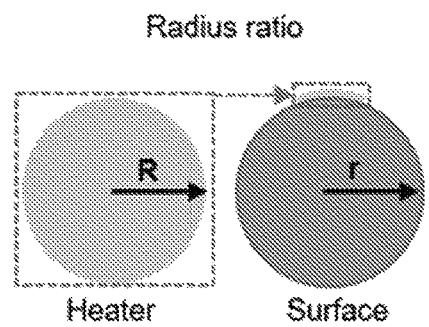
Figure 25:
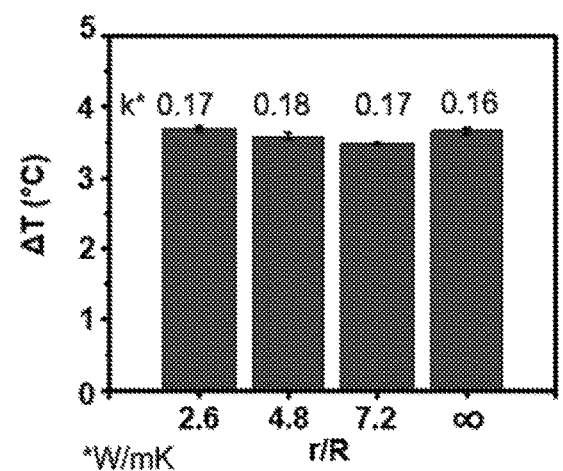
Figure 25:
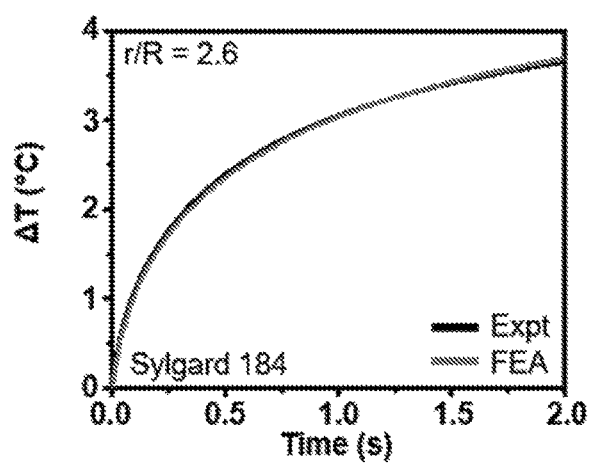
Figure 25:
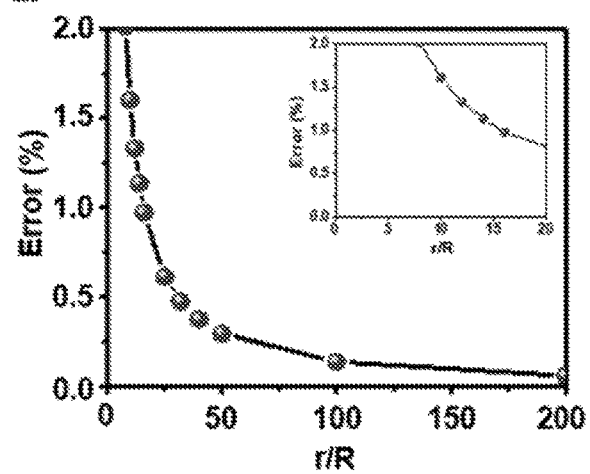
Figure 26D:
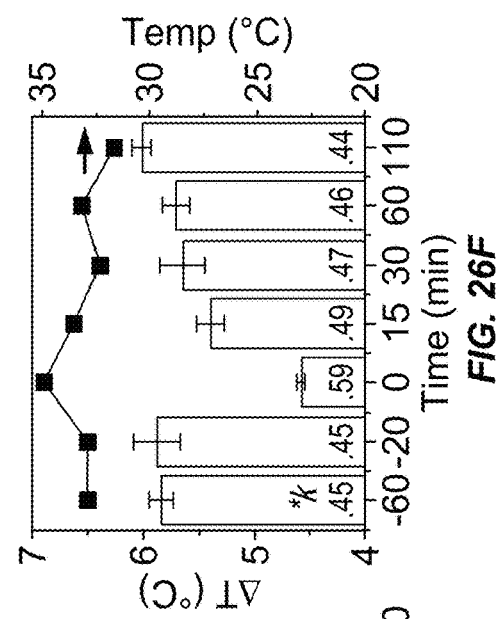
Figure 26E:
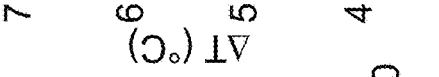
Figure 26F:
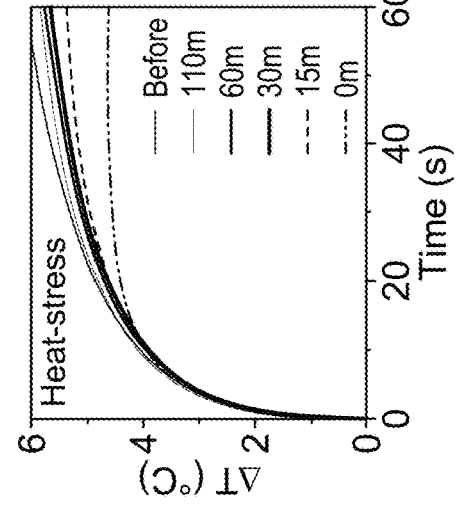
Figure 26G:
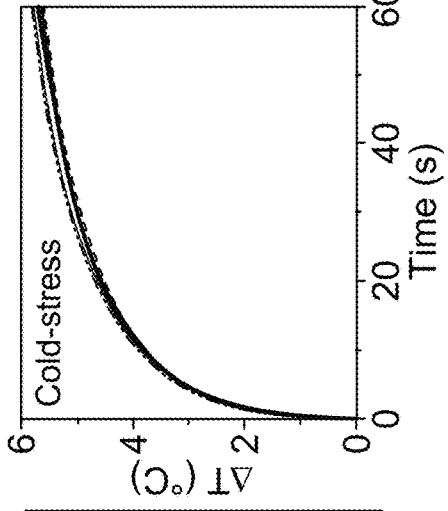
Figure 26H:
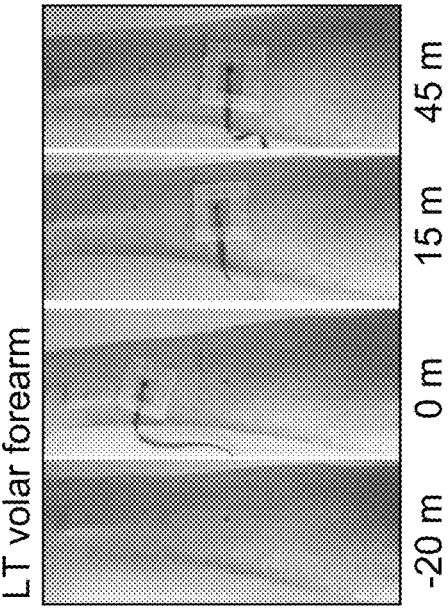
Figure 26I:
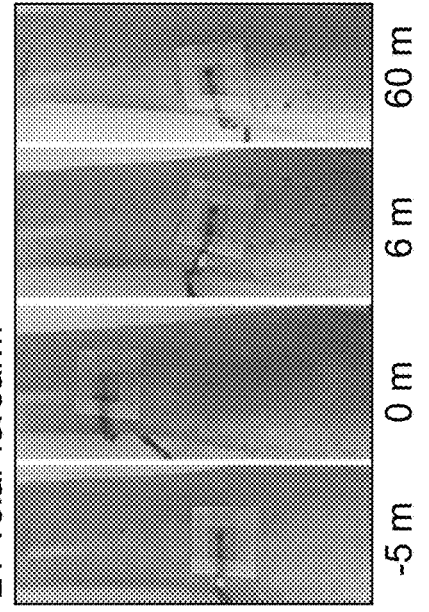

FIG. 25: Thermal conductivity measurements on curved surfaces. (a) Schematic representation of heater radius (R) compared to the radius (r) of the surface under study. (b) Plot of the change in temperature after 2 s of transient heating with heater radius R=0.5 mm on a series of curved silicone substrates (r/R=2.6, 4.7, 7.2, and ∞). Values above each column represent the average thermal conductivity of each silicone surface (W/mK). (c) Representative example of fit between experimental result (r/R=5.2; black curve) compared to FEA (red curve) over a 2 s period of transient heating. (d) Plot of the error % observed as a function of r/R. The inset is an expanded view of the plot between r/R=0 to r/R=20.

FIG. 26: Monitoring erythema. (a) Plot of $\Delta T$ (° C.) as a function of transient heating time collected from the right volar aspect of the forearm prior to sunburn induced erythema, and at four-time intervals post erythema: 5 h, 19 h, 45 h, and 70 h. (b) Plot of $\Delta T$ (° C.) as a function of transient heating time intervals over the course of 360 h post erythema. The black data points represent the temperature recorded from the resistive device prior to transient heating, and the values in white represent k calculated based on the scaling law. (c) Digital images of the right volar aspect of the forearm at time intervals from just prior to erythema through 360 h post erythema. (d) Digital images of the left volar aspect of the forearm at time intervals from just prior to erythema (via heat-stress) through 110 m post erythema. (e) Plot of $\Delta T$ (° C.) as a function of transient heating time on the left volar aspect of the forearm prior to erythema induced via 20 min of heat-stress, and at five-time intervals: 0 min, 15 min, 30 min, 60 min, and 110 min post heating. (f) Plot of $\Delta T$ (° C.) as a function of transient heating time over the course of 170 min (at 60 min and 20 min prior to heating and up to 110 min post heating. The black data points represent the temperature recorded from the resistive device prior to transient heating, and the values in white represent k calculated based on the scaling law. (g) Digital images of the left volar aspect of the forearm at time intervals from just prior to erythema (via cold-stress) through 60 min post erythema. Images were taken immediately before the time thermal measurements were collected. Erythema via cold-stress was induced through 20 min of incubation with a frozen icepack. (h) Plot of $\Delta T$ (° C.) as a function of transient heating time on the left volar forearm prior to erythema induced via 20 min of cooling, and at five-time intervals: 0 min, 15 min, 30 min, 40 min, and 60 min post cooling. (i) Plot of $\Delta T$ (° C.) as a function of transient heating time over the course of 80 min (at 20 min and 5 min prior to heating and up to 60 min post cold-stress). The black data points represent the temperature recorded from the resistive device prior to transient heating, and the values in white represent k calculated based on the scaling law. All images were taken immediately prior to the time of thermal measurement. All measurements were collected using a resistive sensor device with radius R=2.0 mm and power density of 2.0 mW/mm² with 60 s thermal actuation intervals. Error bars throughout are based on at least 4 separate measurements collected within a 4 min time window.

Figure 27:
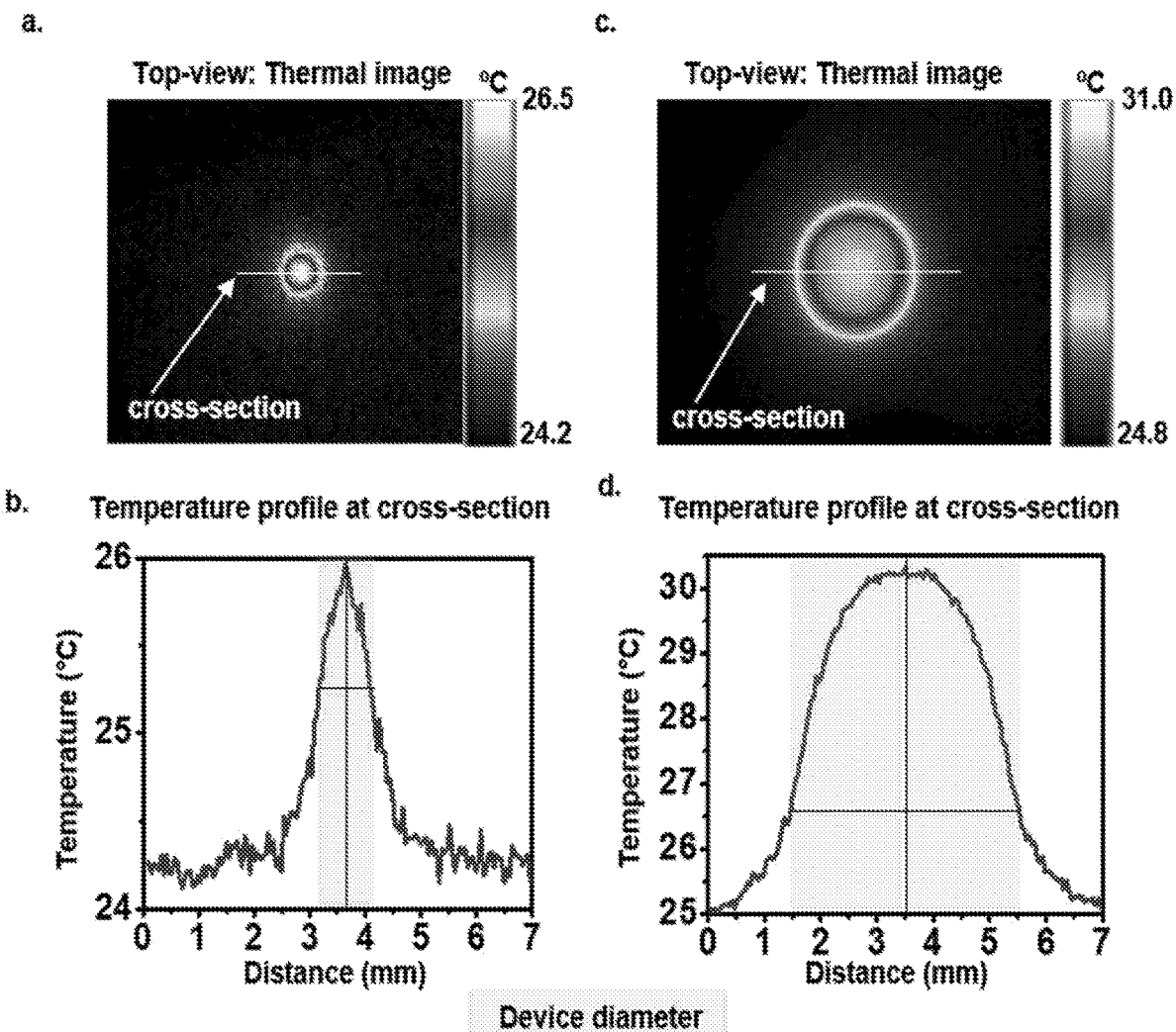

FIG. 27: Thermal profile (IR). (a) IR image of the top of a resistive sensor (R=0.5 mm) after 5 s of actuation at 2 mW/mm² on LDPE. (b) Cross-section view of the image from (a) plotted as temperature (° C.) vs. distance (mm). (c) IR image of the top of a resistive sensor (R=2.0 mm) after 5 s of actuation at 2 mW/mm² on LDPE. (d) Cross-section view of the image from (c) plotted as temperature (° C.) vs. distance (mm).

Figure 28:
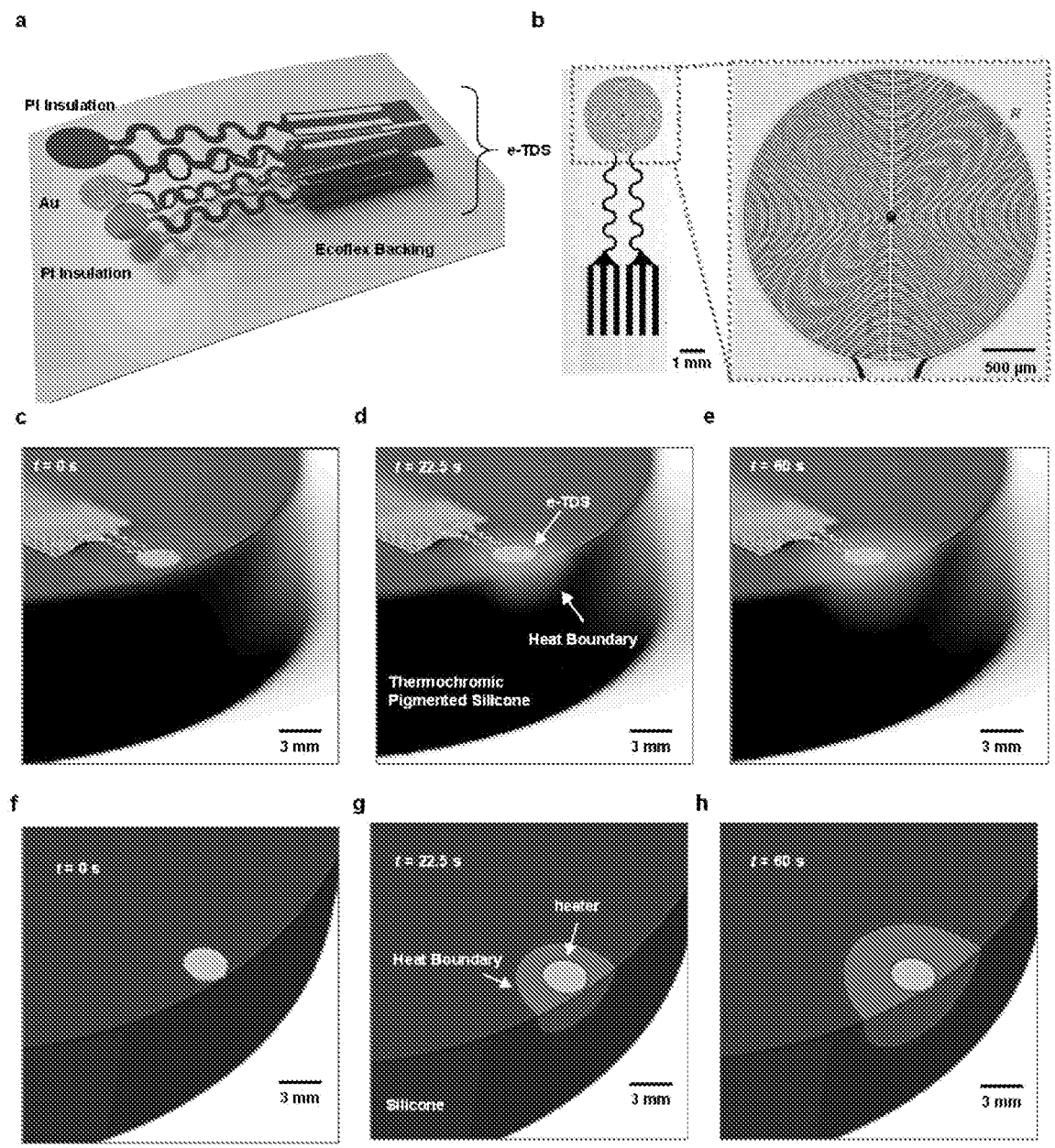

FIG. 28: Principle of operation of epidermal thermal depth sensors (e-TDS). (a) Illustration of the layers of a representative e-TDS (b) Optical image and magnified view of an e-TDS with a coil of radius R. (c) Image of an e-TDS printed onto silicone (Ecoflex) mixed with a thermochromic pigment that turns from black to pink for temperatures above 25° C. Image is taken at ambient temperature T=22° C., before the heater is turned On (t=0 s). Image of same sensor as in panel (b) for an applied power density of q=10 mW mm⁻² at (d) t=22.5 s and (e) t=60 s. (f) Cross-sectional view of FEA results for an e-TDS with R=1.5 mm, and an applied power density of q=10 mW mm⁻² at t=0 s, (g) t=22.5 s and (h) t=60 s. The red shaded region indicates the area of silicone that is at T>25° C.

Figure 29:
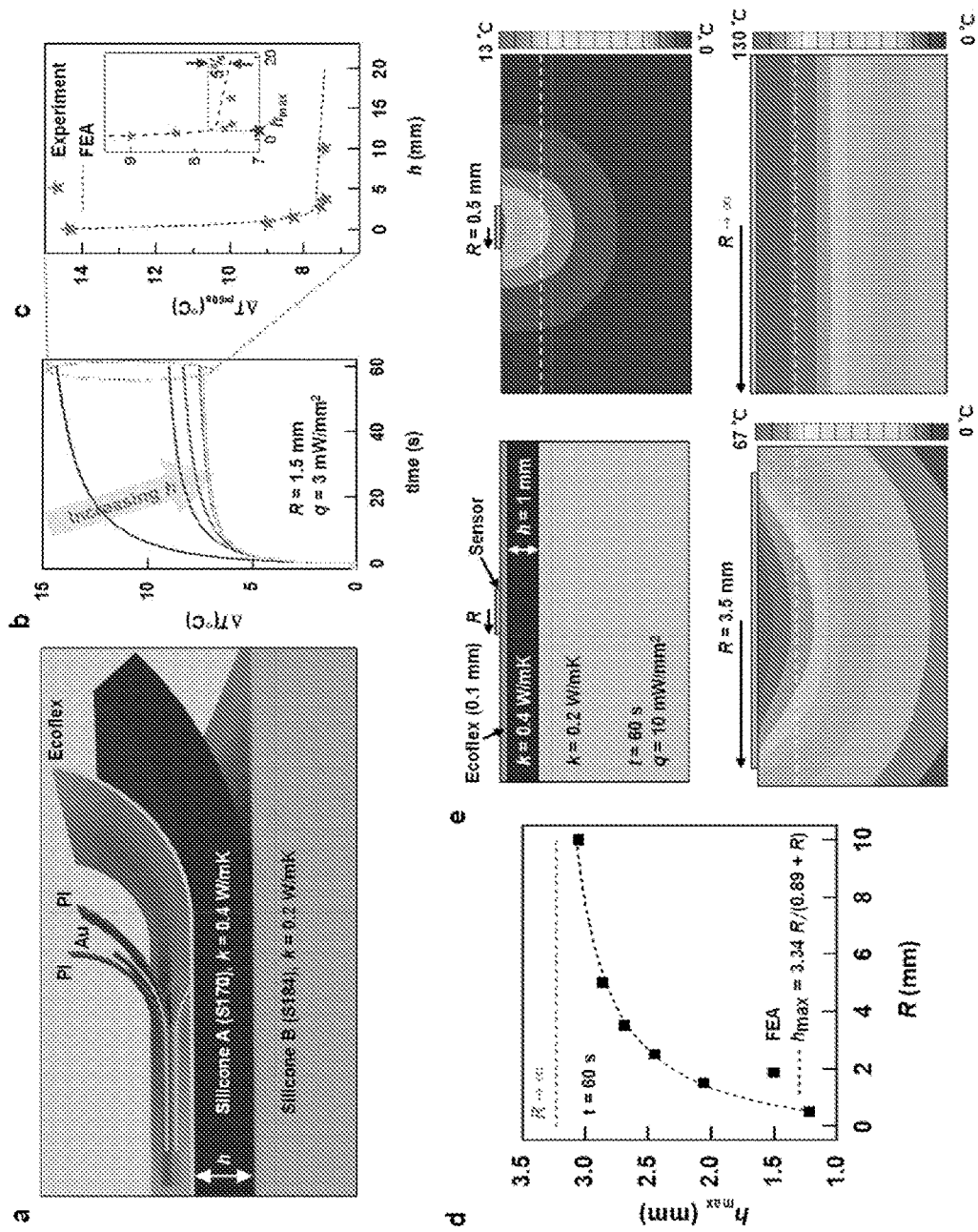

FIG. 29: Dependence of depth sensitivity ($h_{max}$) on radius of the e-TDS. (a) Schematic illustration of an e-TDS mounted on a bilayer silicone sample designed to characterize the depth sensitivity of the measurement. (b) Change in temperature ($\Delta T$) as a function of time for an e-TDS with R=1.5 mm and q=3 mW mm$^{-2}$. Thickness of the silicone A layer (h) increases in the direction indicated by the arrow (c) $\Delta T$ at t=60s as a function of h. The procedure to calculate the 5% threshold for depth sensitivity ($h_{max}$), is described in the inset of panel (c) (d) $h_{max}$ as a function of R determined from FEA simulations. The red dotted line represents the limiting value of $h_{max}$ for an infinitely large e-TDS at a measurement time of 60 s. The dotted line represents an analytical fit of the FEA calculations with adjusted R-squared error=0.998. (e) Cross-sectional schematic image showing the parameters used for the FEA simulations, and the corresponding temperature contour maps for t=60 s measurement time and q=10 mW mm$^{-2}$, for varying R.

Figure 30:
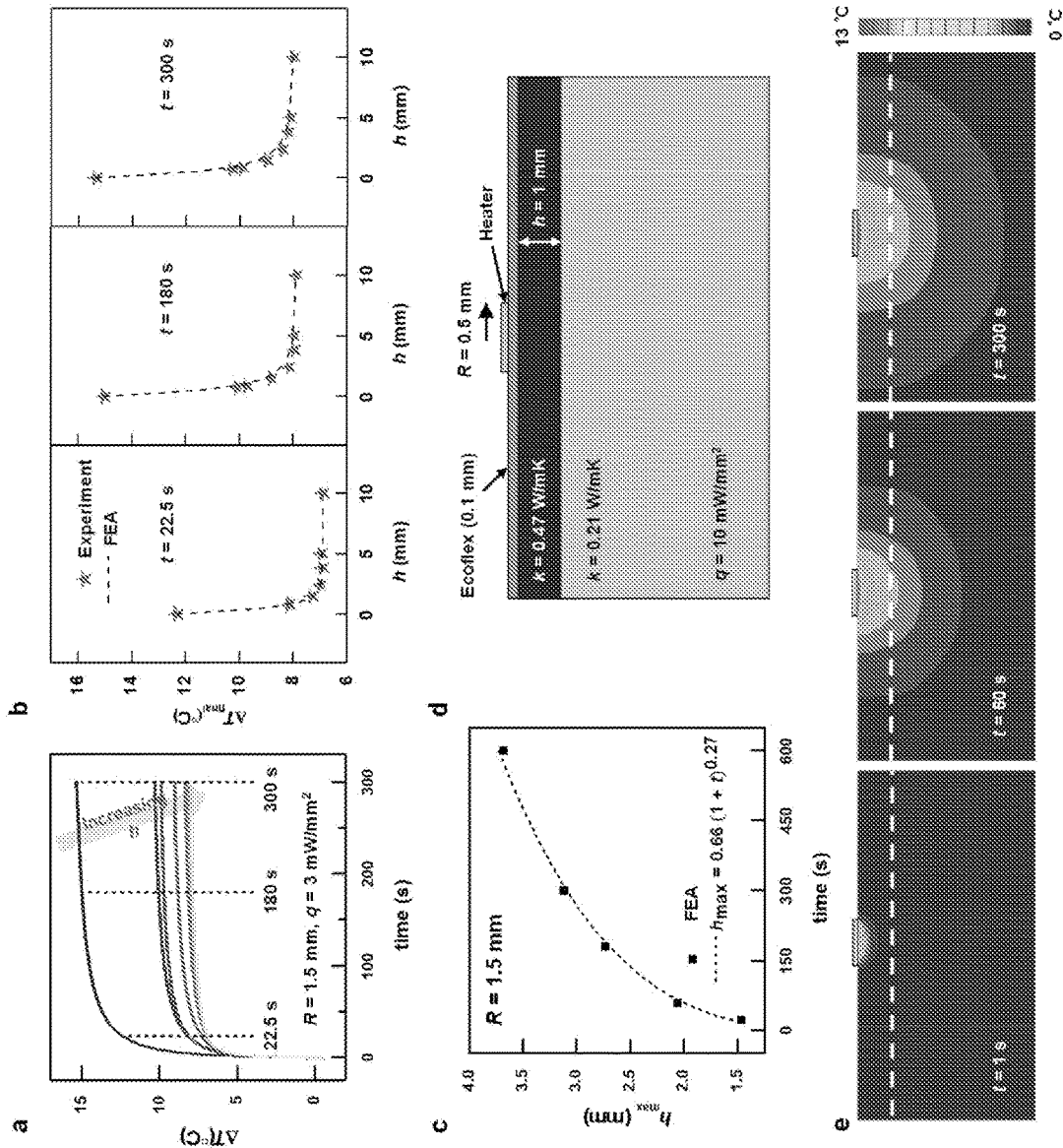

FIG. 30: Dependence of the depth sensitivity on the measurement time. (a) $\Delta T$ as a function of time for an e-TDS with R=1.5 mm and q=3 mW mm$^{-2}$. (b) $\Delta T$ at t=22.5 s, 180 s, and 300 s as a function of h extracted from panel (a). (c) $h_{max}$ as a function of measurement time for an e-TDS with a R=1.5 mm. The dashed line represents an analytical fit of the FEA calculations with adjusted R-squared error=0.994. (d) Cross-sectional schematic image showing the parameters used for FEA simulations. (e) Corresponding cross-sectional temperature contour maps for R=0.5 mm and q=10 mW mm$^{-2}$ at measurement times of t=1 s, 60 s, and 300 s.

Figure 31:
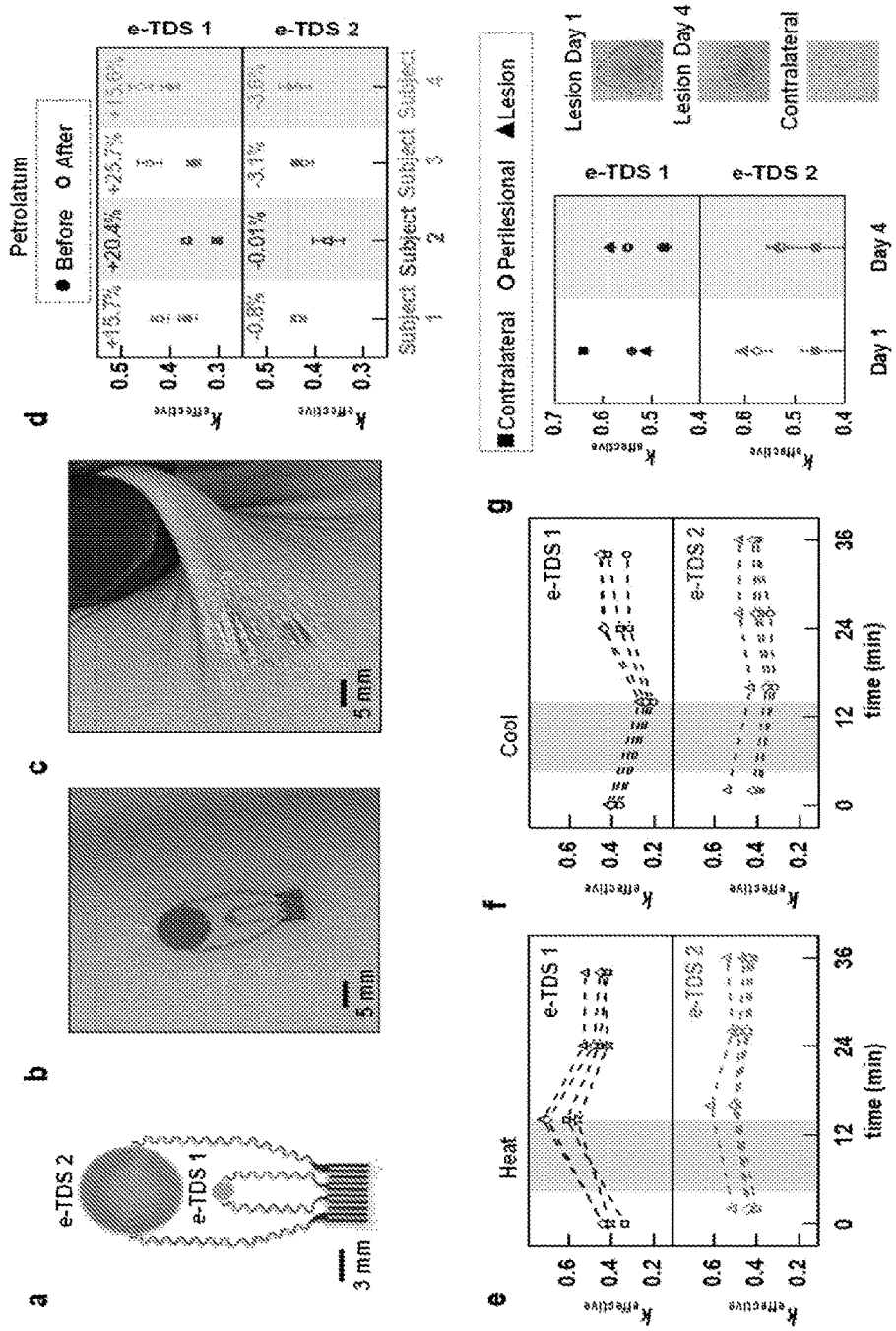

FIG. 31: Experiments on human skin. (a) Optical image of a dual e-TDS system with device radii $R_1$=0.75 mm, and $R_2$=3.5 mm. Image of such a system mounted on (b) relaxed and (c) stretched human skin demonstrating flexibility and conformity. (d) Measurement of skin thermal conductivity ($k_{effective}$ (W m$^{-1}$K$^{-1}$)) before (closed symbol) and fifteen minutes after (open symbol) application of petrolatum for four different subjects with $q_1$=3 mW mm$^{-2}$ and $q_2$=1 mW mm$^{-2}$ for t=60 s. Percentage change in $k_{effective}$ after application of petrolatum are noted above the symbols. (e) $k_{effective}$ (W m$^{-1}$K$^{-1}$) (t=60 s, $q_1$=3 mW mm$^{-2}$ and $q_2$=1 mW mm$^{-2}$) for e-TDS 1 and 2 before and 10 minutes after the application of heat using a hot pack on the front of the human arm for four different subjects (denoted by different symbols). The heating period is shaded in red. (f) $k_{effective}$ (W m$^{-1}$K$^{-1}$) (t=60 s, $q_1$=3 mW mm$^{-2}$ and $q_2$=1 mW mm$^{-2}$) for e-TDS 1 and 2 before and 10 minutes after cooling the skin on the front of the arm using a cold pack for four different subjects (denoted by different symbols). Cooling period is shaded in blue. (g) Measurement of $k_{effective}$ (W m$^{-1}$ K$^{-1}$) taken 4 days apart (t=60s, $q_1$=5 mW mm$^{-2}$ and $q_2$=1 mW mm$^{-2}$) on a cellulitis lesion, the perilesional area, and contralateral leg using the double-heater e-TDS along with corresponding images. Measurements of cellulitis were taken on one subject. The lesion on Day 1 and Day 4 is outlined in red.

Figure 32:
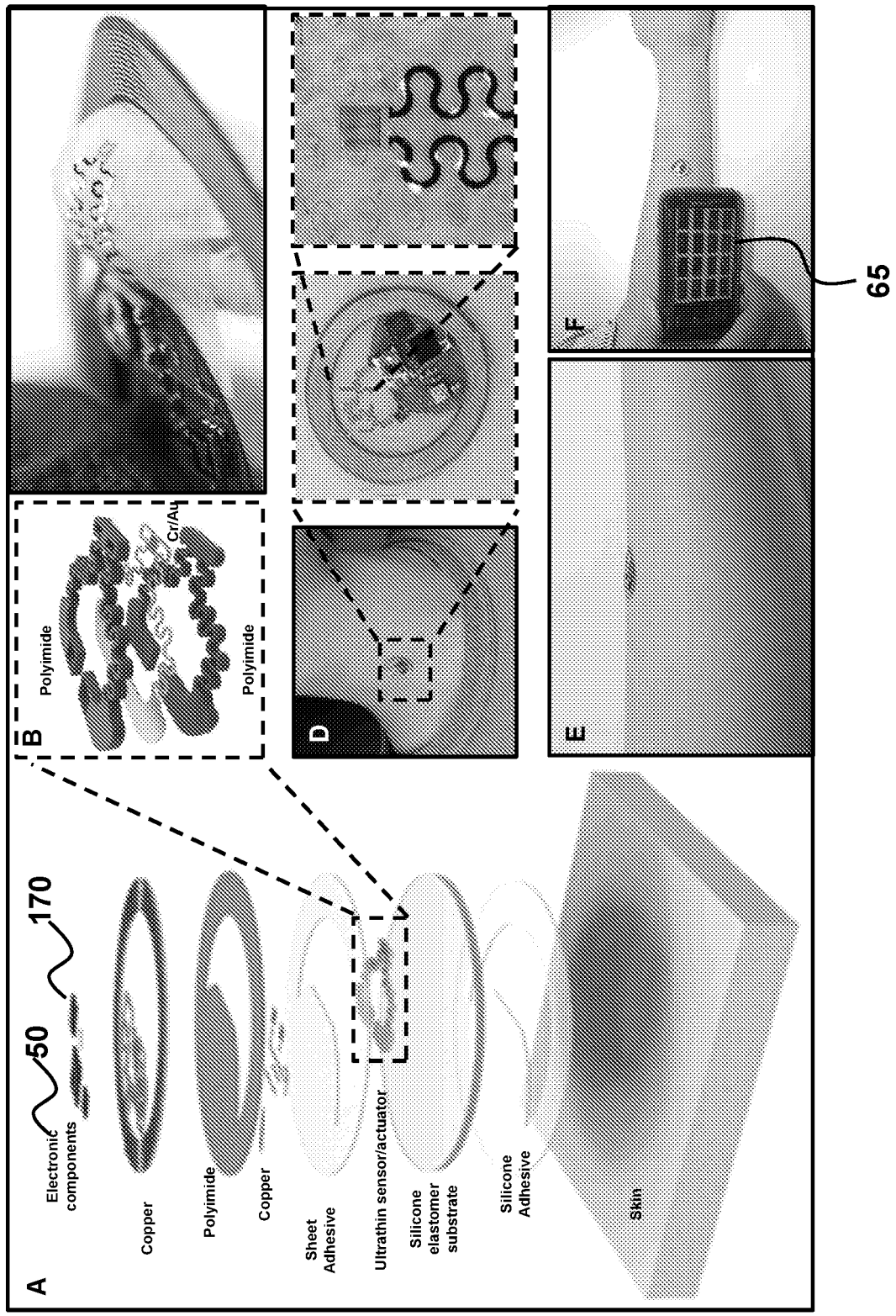
Figure 34E:
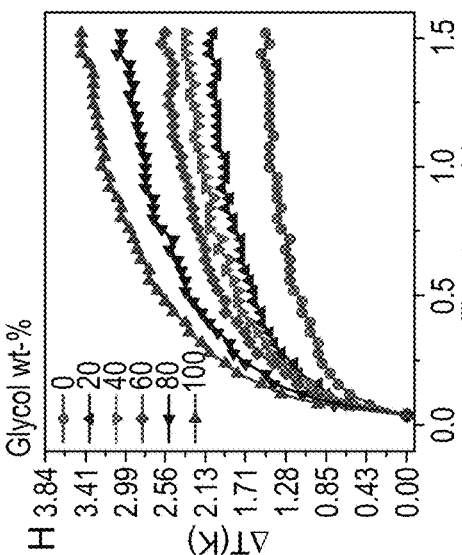
Figure 34F:
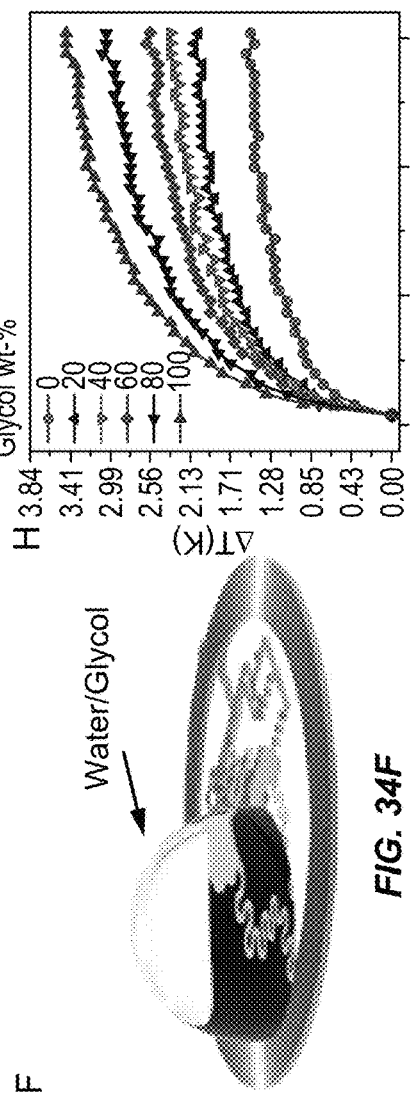
Figure 34H:
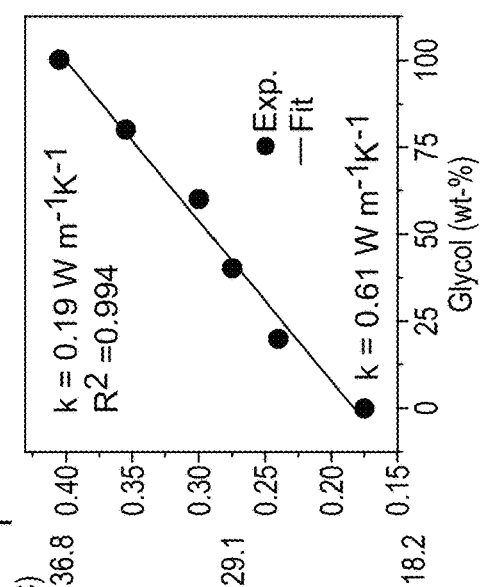
Figure 34G:
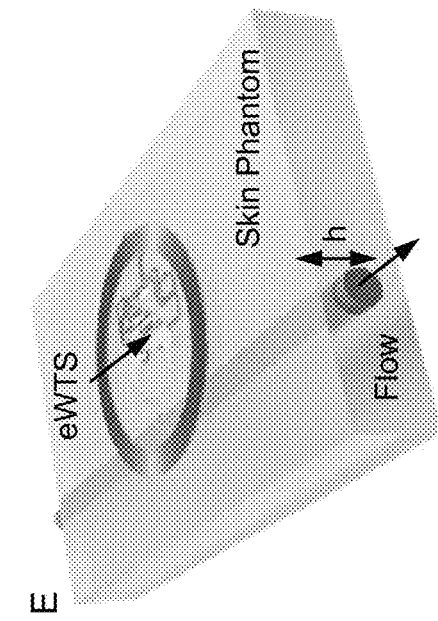
Figure 34I:
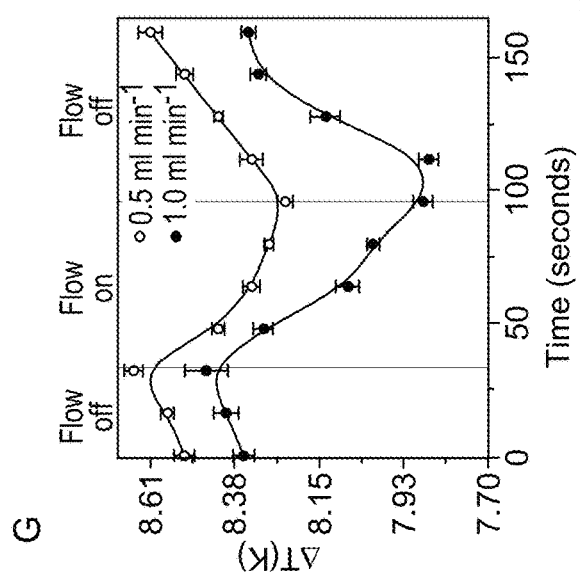

FIG. 32: Device construction. A. Exploded view schematic of epidermal wireless thermal sensor (eWTS). B. Exploded view schematic of ultrathin, soft, thermal sensing/actuating element. C. Optical image of sensor held with tweezer. D. Optical image of skin mounted sensor, illustrating constituent components. E. Side-view image of sensor on human arm. F. Simulated smartphone readout using NFC protocols.

FIG. 33: Electrical and thermal characterization. A. Schematic of epidermal wireless thermal sensor (eWTS) circuit, showing components responsible for sensing, control and wireless power harvesting and data transmission. B. Wirelessly recorded sensor output, during sequential actuation at a frequency of and 33% duty cycle, showing measured voltage change due to thermal actuation E. Computed curve of minimum work of adhesion between eWTS and skin as a function of applied, uniaxial strain, showing yield and fracture points of skin, and adhesion offered by the sensor. F. Strain distribution in eWTS during bending (left) and twisting (right) showing nearly 0% strain at receiver coil and resistive sensing/actuating element.

FIG. 34: Wireless, in vitro measurements on biological phantom systems. A. IR thermographs of eWTS in air (left) and on skin (right). B. 3D-FEA computed top-view (left) and side-view (right) heat maps showing temperature distribution into skin 6s after actuation at 7.9 mW. C. Wirelessly measured raw voltage during actuation, overlaid with simultaneously acquired IR data for stable temperature (left) and drifting temperature (right). D. Calibrated, wirelessly acquired transient temperature rise on two commercially elastomers with different thermal properties. E. Schematic illustration (top) and measured transient temperature rise 6s after actuation (bottom) on a benchtop flow system mimicking near-surface blood vessels and catheters, at two flow rates, showing the effect of convective cooling in the presence of flow. F. Schematic illustration of eWTS with droplet of glycol/DI $H_2O$ mixture. G. IR image showing cold droplet on sensing/actuating element. H. Transient temperature rise for different ratios of DI $H_2O$ and glycol by wt-%, showing different thermal response. I. Measured temperature increase 2s after actuating, overlaid with linear fit.

Figure 35E:
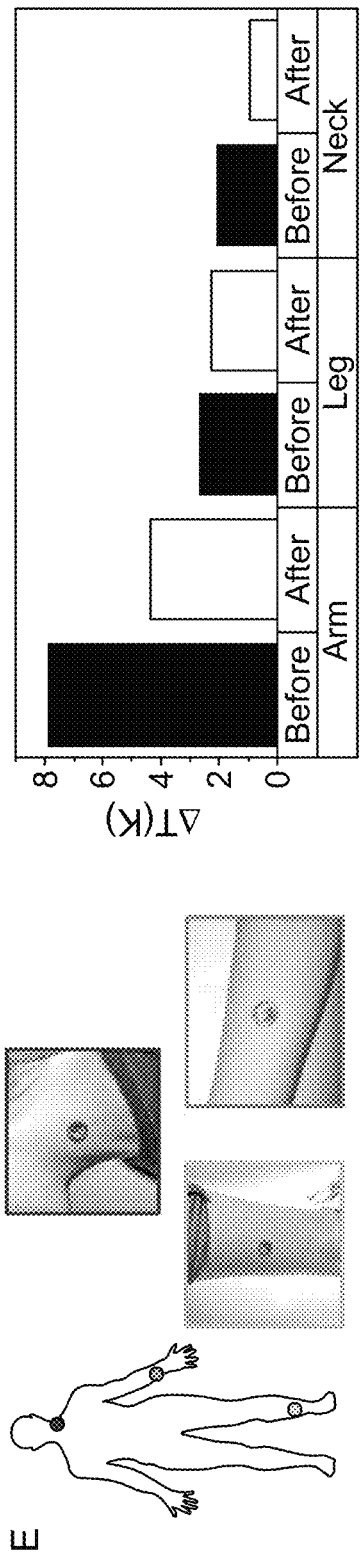
Figure 35F:
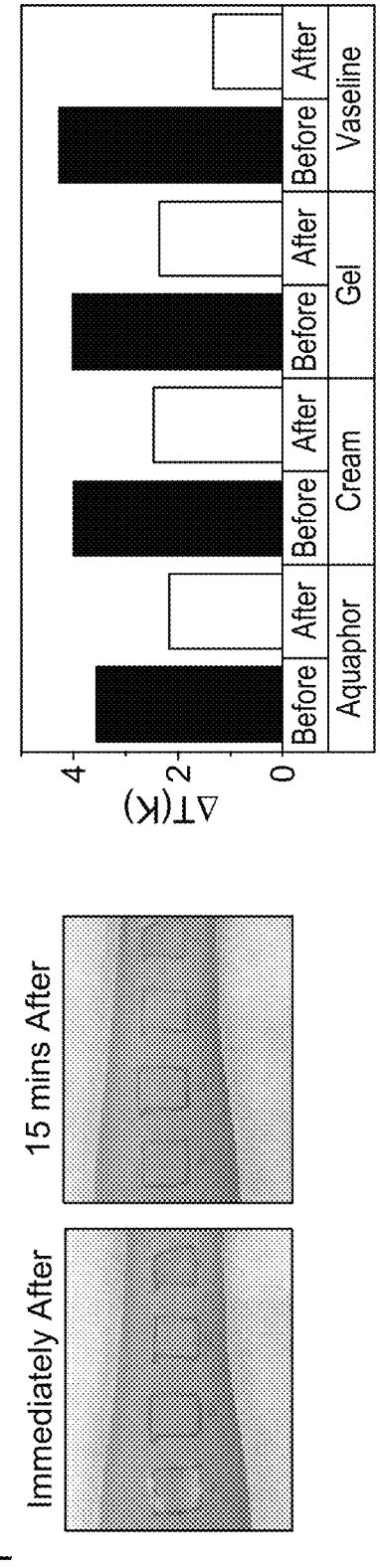

FIG. 35: Wireless, in vivo skin hydration measurements. A. Schematic illustration and optical images of protocol for topical compound experiments. B. Optical image of multiple sensors on subject's arm, that are sequentially read out using the same electronics, each on locations with a different treatment. C. Data recorded sequentially from the three locations shown in B. D. Time series measurements with eWTS and corneometer on three subjects with varying hydration levels before and after the application of a topical moisturizing compound. E. Schematic illustration of different body locations for topical moisturizer (Vaseline) application (left) and measured transient temperature rise before and after application of moisturizer. F. Optical image of subject's arm immediately after application of 4 different topical compounds, Aquaphor, Cream, Gel and Vaseline (left) and 15 minutes later, after dry-wiping and tape exfoliation (right). Transient temperature response before (black) and 15 minutes after (red) application of each of these compounds. The 'after' measurements are performed after dry-wiping and tape-exfoliation.

Figure 36:
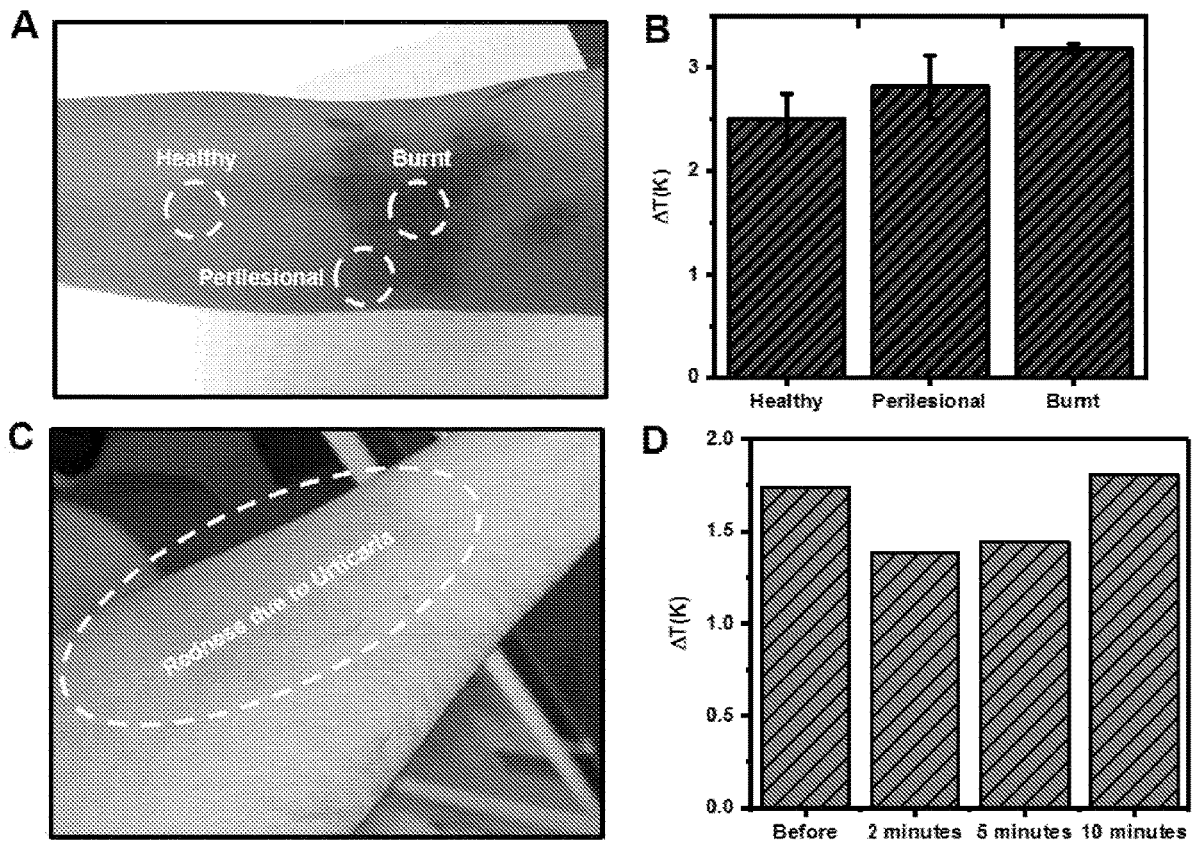

FIG. 36: In vivo detection of changes in the thermal properties of skin due to trauma. A. Optical image of subject's arm, 3 days after suffering burns, showing burnt, healthy and perilesional locations. B. Measured temperature increase 6s after actuation at each of these three locations. C. Optical image of subject's arm 2 minutes after dermatographic urticaria, showing inflammation and redness. D. Measured temperature increase 6s after actuation before, 2 minutes after, 5 minutes after and 10 minutes after urticaria.

Figure 37A:
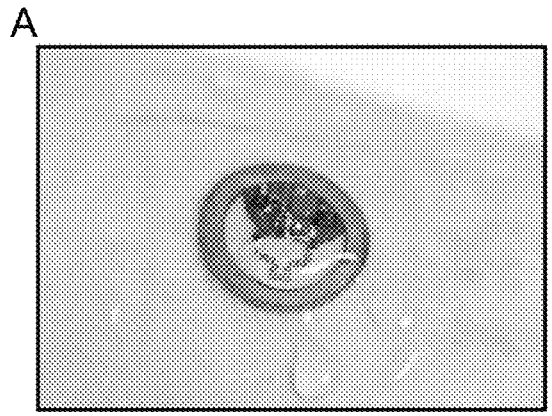
Figure 37B:
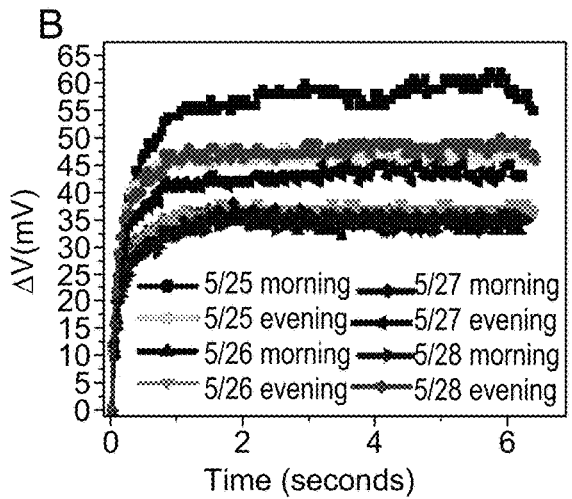
Figure 37D:
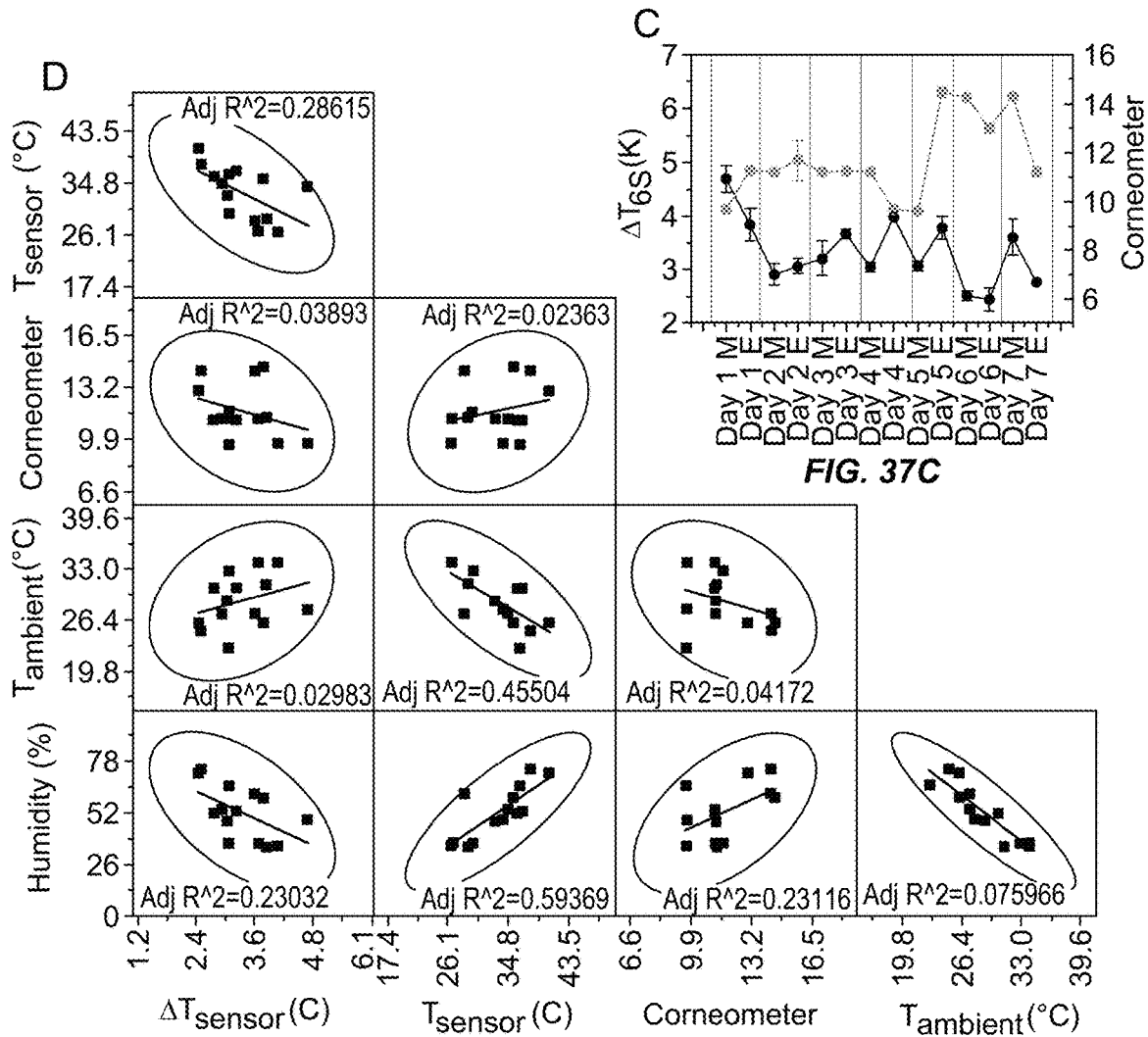

FIG. 37: In vivo detection of changes in the thermal properties of skin due to trauma. A. Optical image of wet eWTS, simulating shower conditions. Water does not affect the electronics. B. Transient temperature rise over 7 days, showing stable operation. C. Measured temperature rise after 6s over 7 days, as compared to corneometer measurement over adjacent skin location. D. Scatteplot matrix showing correlations between measured sensor temperature rise, starting temperature, corneometer measurement and ambient conditions as measured by weather logs for humidity and temperature at the times of the measurement for Evanston, IL during the period of the study.

Figure 38:
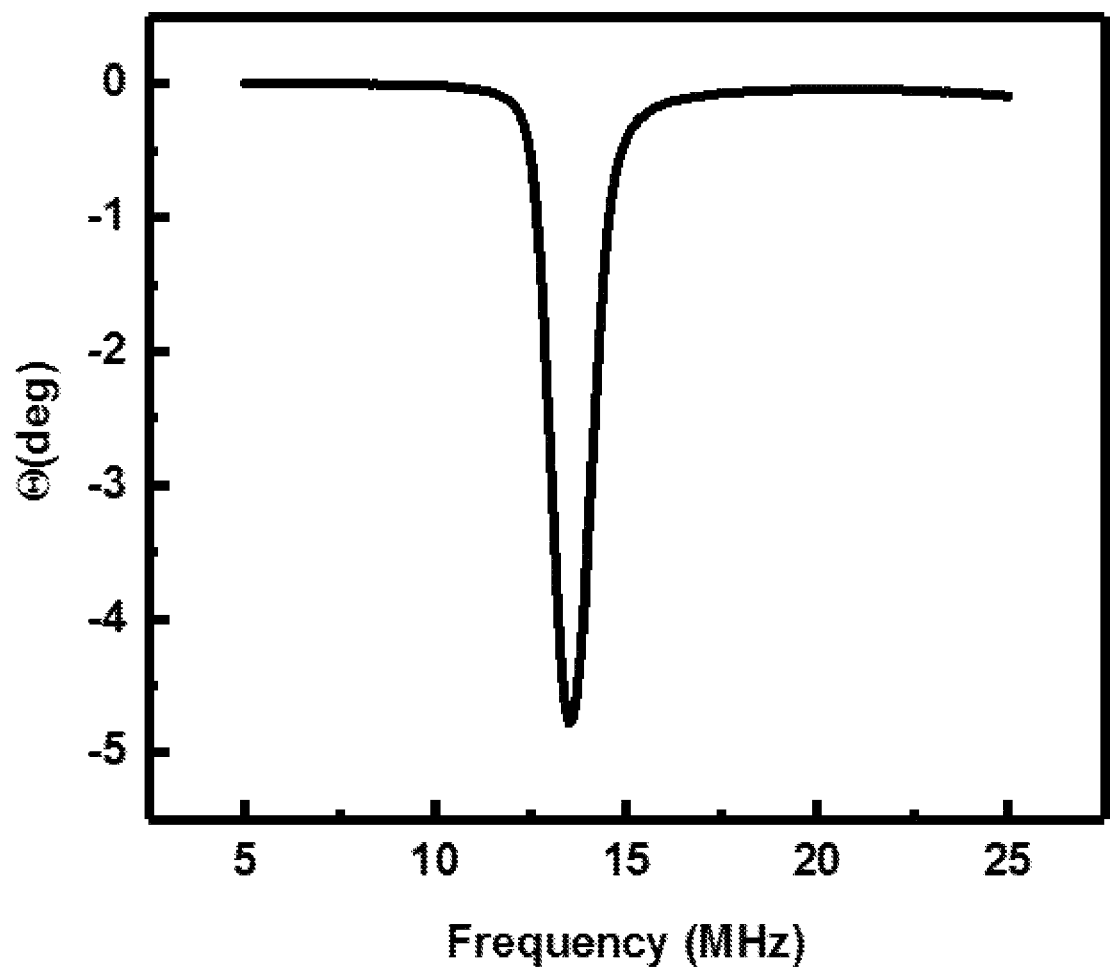

FIG. 38: Quality factor analysis.

Figure 39:
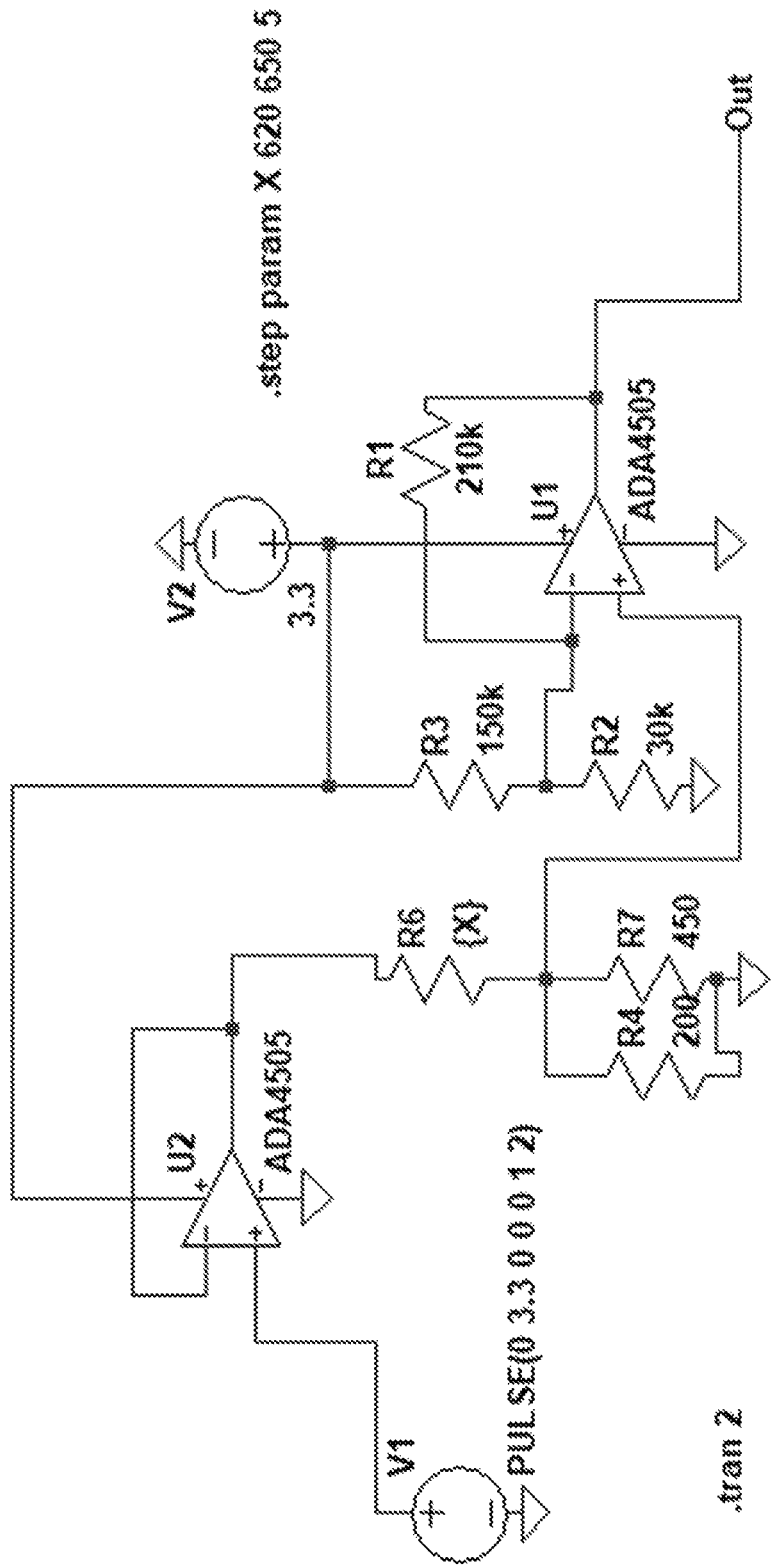

FIG. 39: LTSpice simulation of sensor response.

Figure 40:
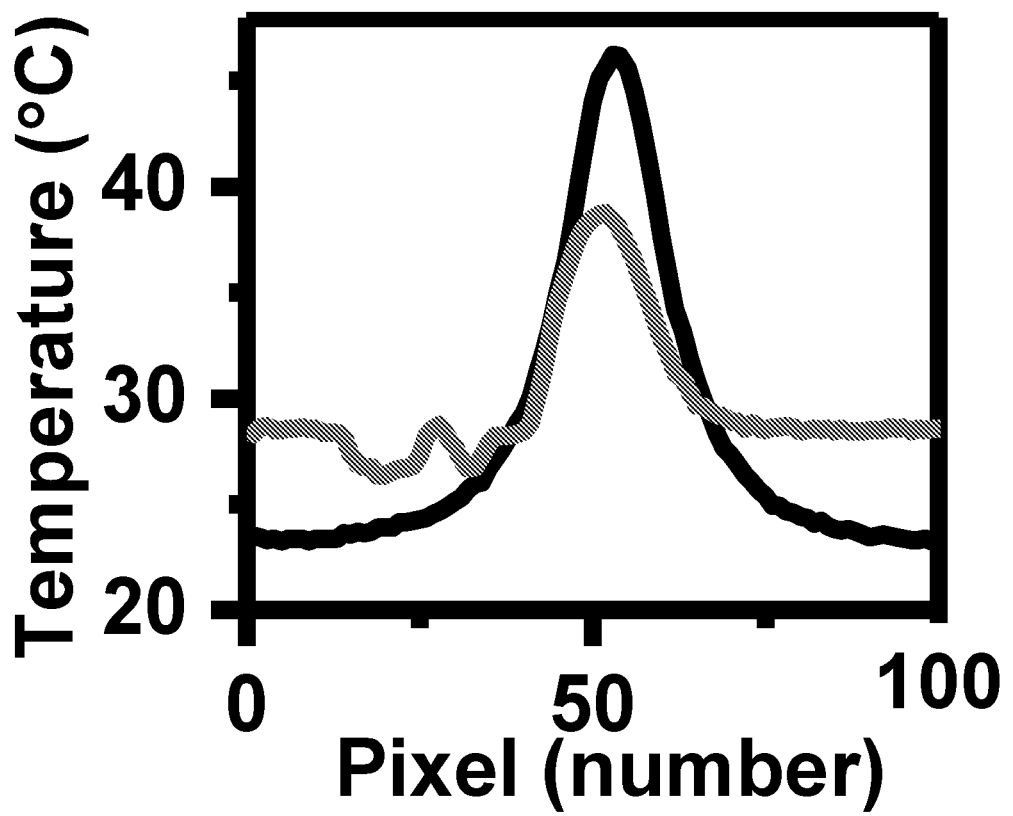

FIG. 40: IR Temperature profile around sensor in air and skin.

Figure 41:
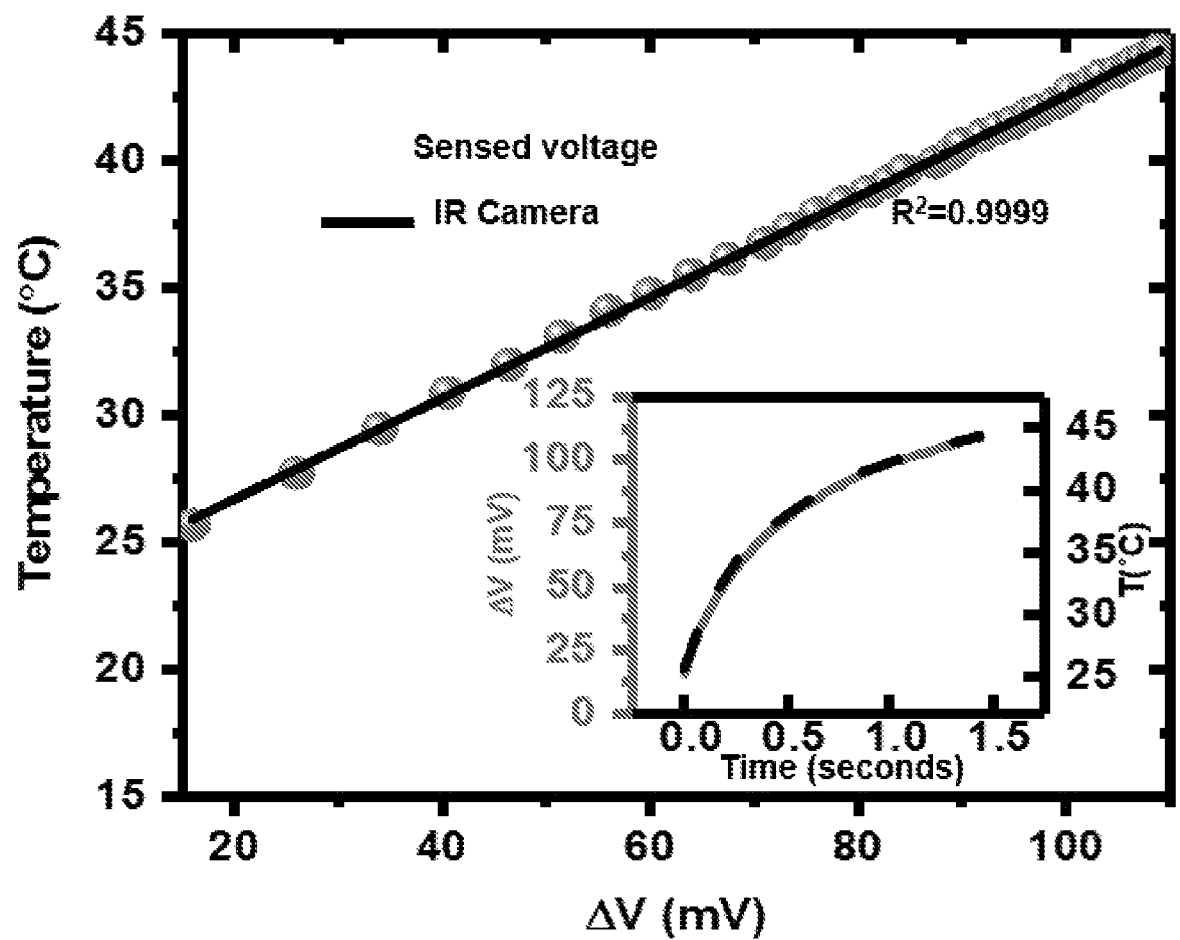

FIG. 41: Calibration of temperature sensor with IR camera.

Figure 42:
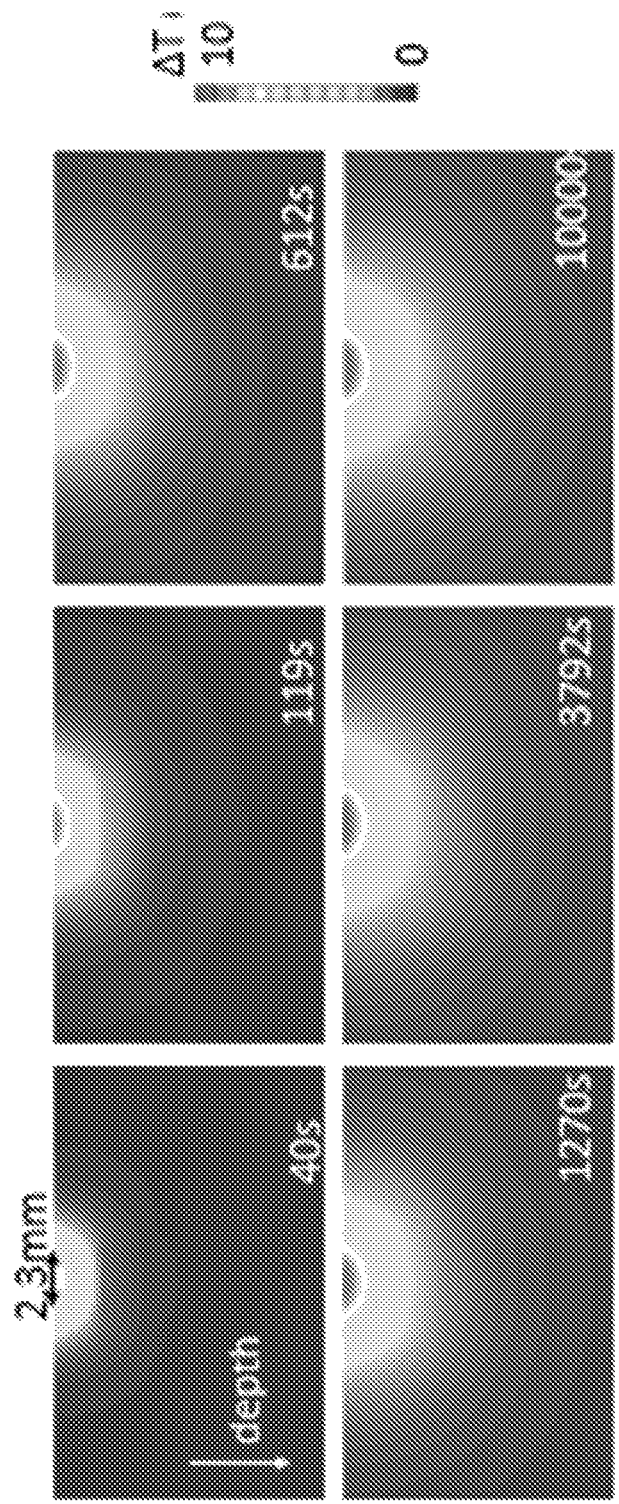

FIG. 42: Temperature distribution around NFC Chip during device operation.

Figure 43:
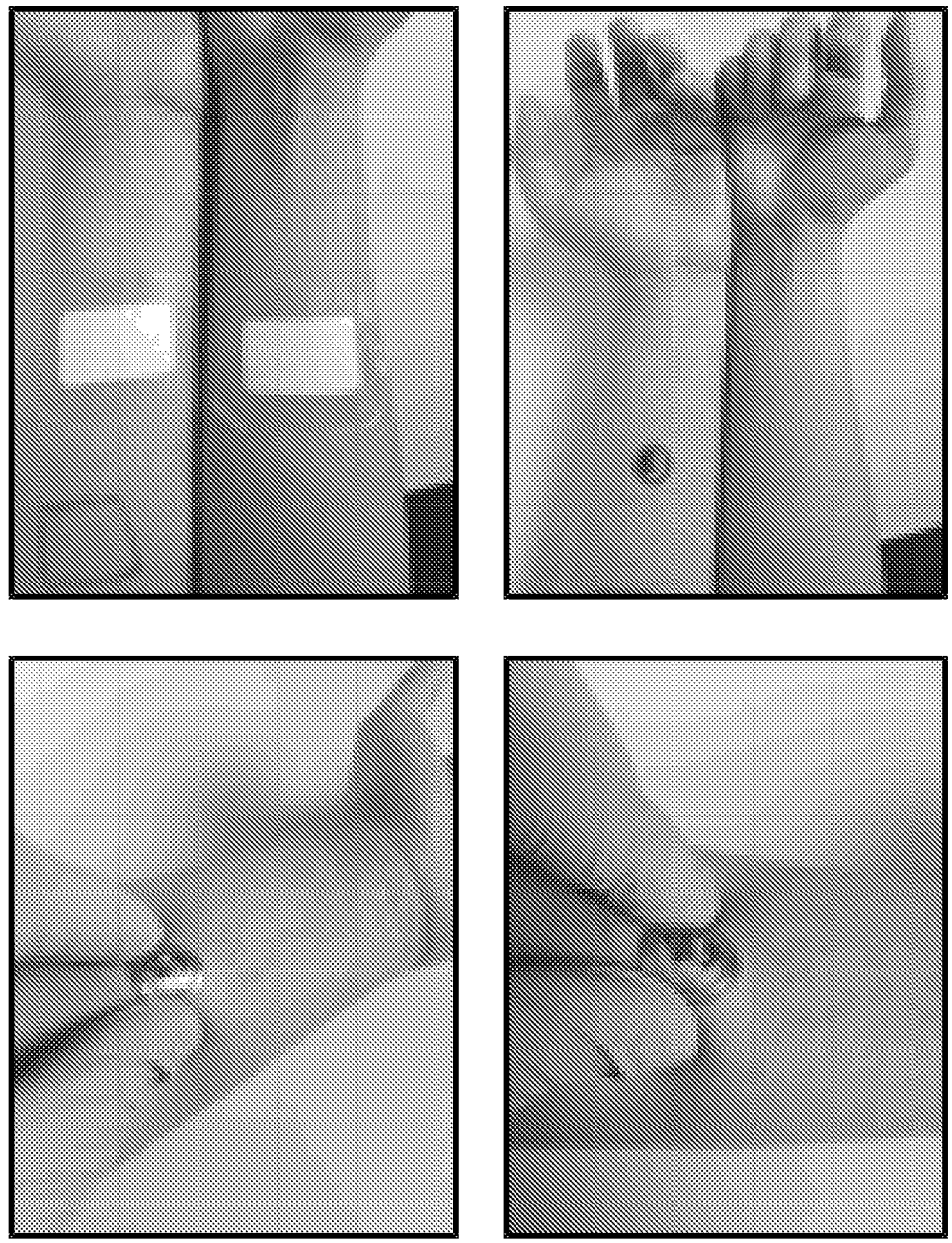

FIG. 43: Optical images of sensor during chronic wearability trials.

Figure 44:
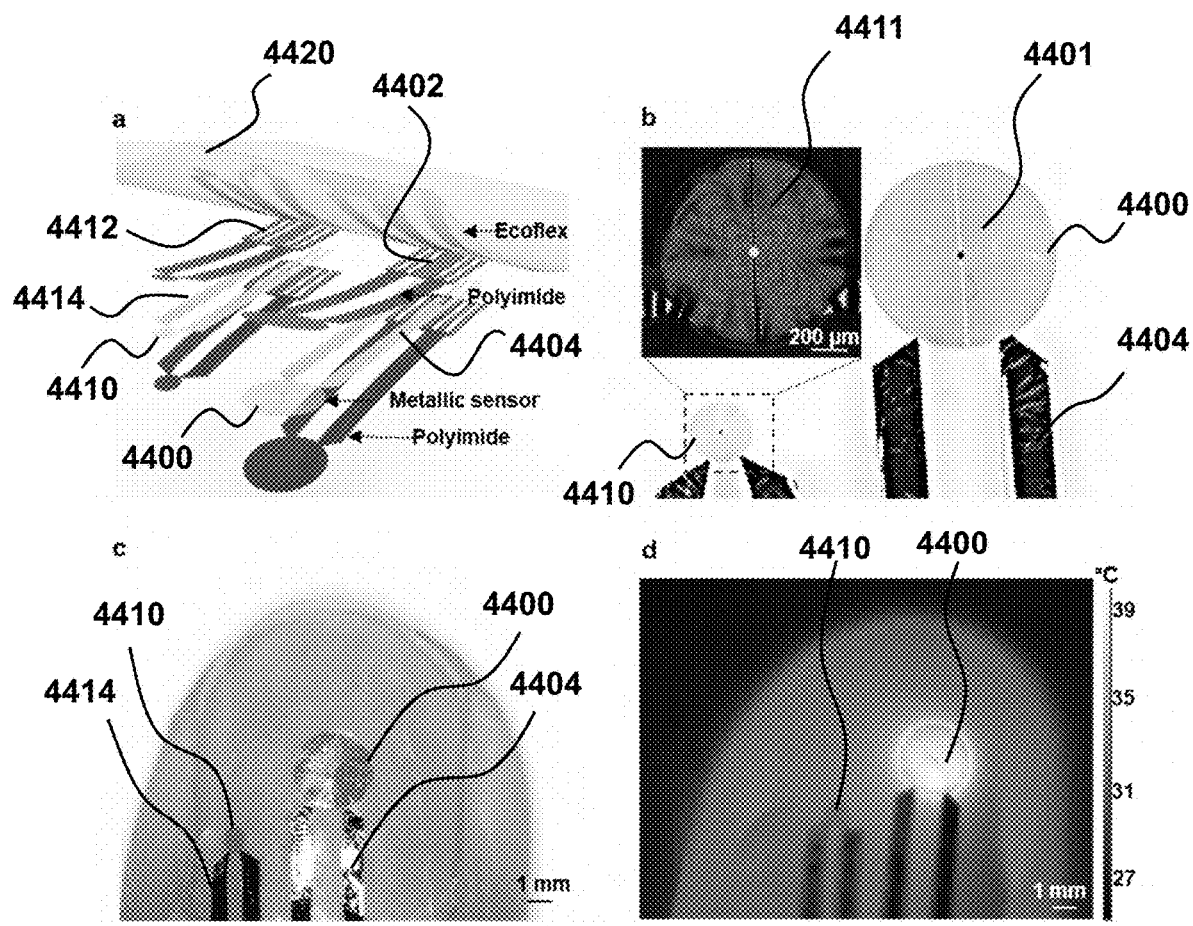

FIG. 44: Thin, flexible thermal sensors that laminate onto the surfaces of the fingernails enable measurements of the thermal transport properties of the nail bed tissues. a) Exploded view schematic illustration of a representative device that includes a small (radius 0.5 mm) and a large (radius ~1.5 mm) sensor. b) Optical image of a device. The inset provides a magnified view of the small sensor. c) Optical image of the sensor platform laminated on a fingernail and d) corresponding infrared image during operation.

Figure 45:
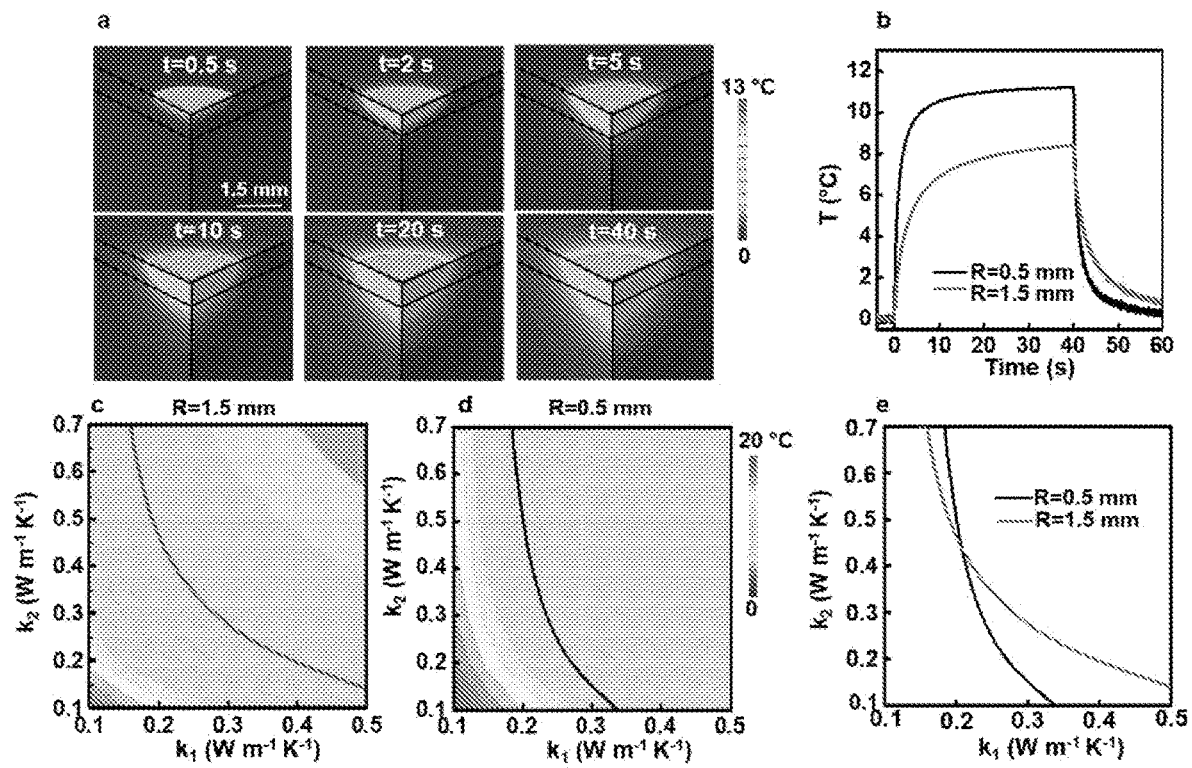

FIG. 45: Summary of procedures to determine the thermal conductivities of a bilayer sample. a) FEA results (quarter, cross sectional view) for the spatial distributions of increases in temperature induced by a thermal actuator placed on the surface of a bilayer sample at several times after actuation. The parameters in the FEA are R=1.5 mm (radius of the actuator), q=3 mW mm$^{-2}$ (thermal power from the actuator), h=0.5 mm (thickness of the top layer), $k_1$=0.21 W m$^{-1}$K$^{-1}$ (thermal conductivity of the top layer) and $k_2$=0.44 W m$^{-1}$K$^{-1}$ (thermal conductivity of the base layer). b) Measured increases in temperature as a function of time for operation of actuators with R=0.5 mm (q=10 mW mm$^{-2}$) and 1.5 mm (q=3 mW mm$^{-2}$). c, d) FEA results for the increases in temperature of the actuators at t=40 s, $T_{ss}$, plotted as a function of $k_1$ and $k_2$, c) R=1.5 mm and q=3 mW mm$^{-2}$ and d) R=0.5 mm and q=10 mW mm$^{-2}$. The curves in c) and d) correspond to combinations of $k_1$ and $k_2$ that yield a certain value of $T_{ss}$. The color in these graphs corresponds to the values of $T_{ss}$ that result for other values $k_1$ and $k_2$. e) The point of intersection of the two curves in (c) and (d) yields $k_1$ and $k_2$.

Figure 46:
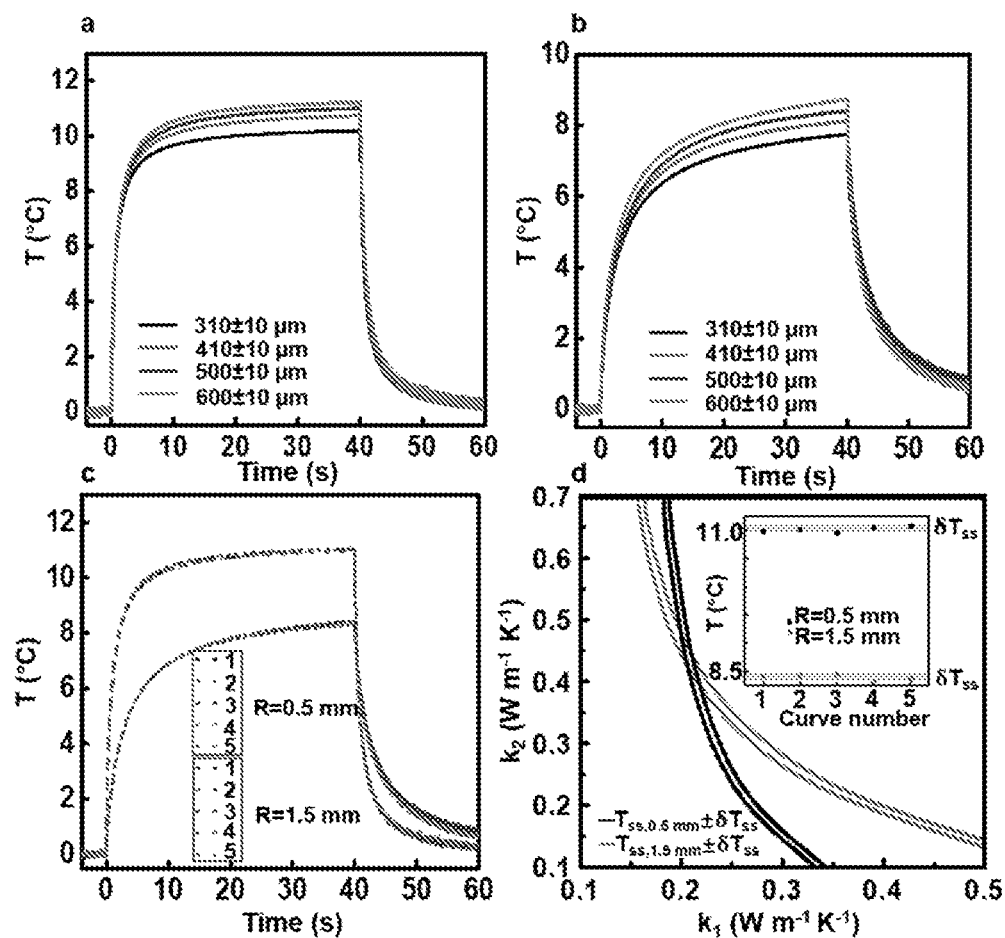

FIG. 46: Experimental and computational results for characterization of bilayer samples that consist of thin films (silicone, Ecoflex) with different thicknesses on a thick substrate (silicone, Sylgard 170), evaluated using sensors with radii, R, of 1.5 and 0.5 mm. (a) Increase in temperature as a function of time for sensors with R=0.5 mm and (b) R=1.5 mm, with bilayer samples that have different top layer thicknesses, with activation at 0 s and deactivation at 40 s. (c) Increase in temperature measured with the two sensors as a function of time for repeated measurements on a sample with top layer thickness of 0.5 mm. d) Analysis of error and uncertainty in the parameters extracted from the data, determined by FEA. Each curve represents the measured value of $T_{ss}$ shifted by $\pm\delta T_{ss}$. The inset shows a magnified view of $T_{ss}$ of each curve in (c). The experimental variations in $T_{ss}$ lead to values of $\delta T_{ss}$ that are generally less than 0.1° C. The points of intersection of these pairs of curves define the thermal conductivity values and their uncertainties, $k_{1,2} \pm \Delta k_{1,2}$.

Figure 47:
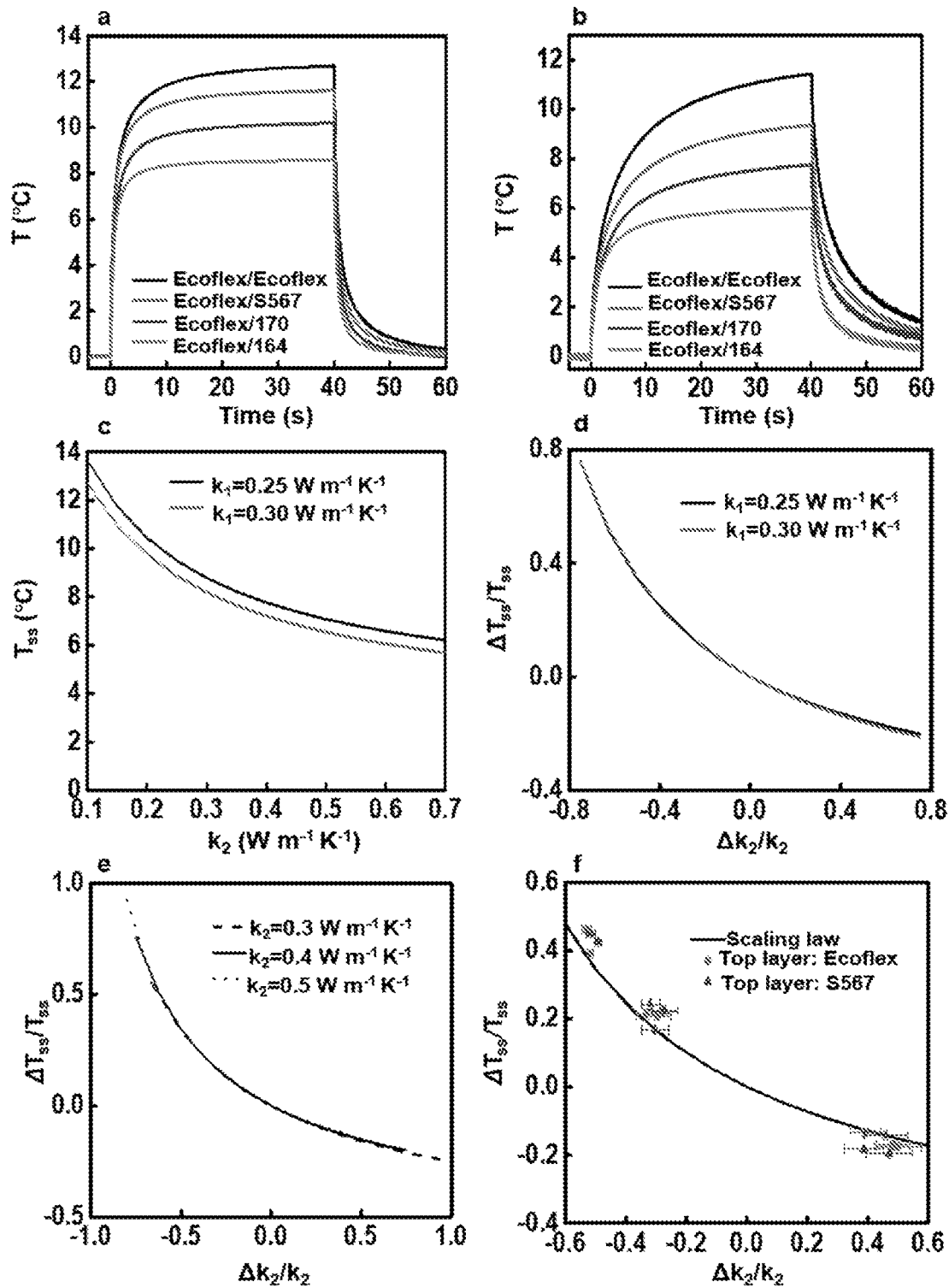

FIG. 47: Thermal characterization with a focus on the thermal conductivity of the bottom layer. (a) Increases in temperature as a function of time for actuators with R=0.5 mm and (b) 1.5 mm on bilayer samples of Ecoflex (top layer, thickness=0.3 mm) on bottom layers of different materials (Ecoflex, Sylgard567, Sylgard170, Sylgard164). (c) FEA results for $T_{ss}$ as a function of $k_2$ for different values $k_1$. (d) $\Delta T_{ss}/T_{ss}$ as a function of $\Delta k_2/k_2$ with different $k_1$. (e) $\Delta T_{ss}/T_{ss}$ as a function of $\Delta k_2/k_2$ with different $k_2$. (f) Comparison of $\Delta T_{ss}/T_{ss}$ as a function of $\Delta k_2/k_2$ from FEA and experimental results.

Figure 48:
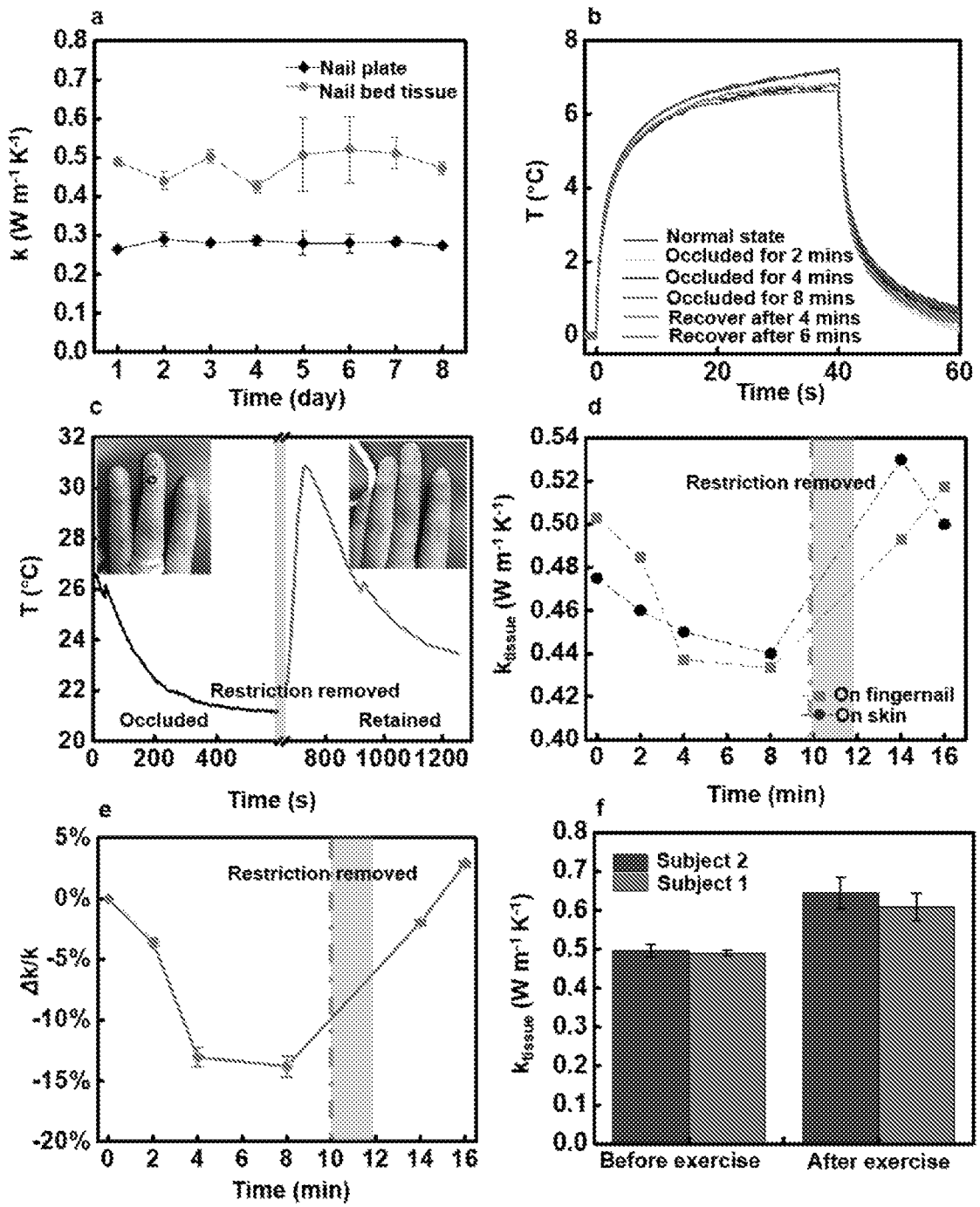

FIG. 48: Results of thermal characterization studies on volunteer subjects. (a) Thermal conductivity of the nail plate and nail bed tissue measured at room temperature each day for eight consecutive days. (b) Time dependent changes in temperature during before (<0 s), during (between 0 s and 40 s) and after (>40 s) activation of a sensor with R=1.5 mm on the left middle finger. (c) Temperature of the fingernail of a subject determined using an infrared camera during and after occlusion of blood flow. (d) Time dependent changes in the thermal conductivity of the nail bed tissue and adjacent skin during and after occlusion. Measurement locations on the fingernail and adjacent skin are indicated by red and black circle in the inset in (c). (e) Relative change in thermal conductivity $\Delta k_{nailbed}/k_{nailbed}$ of the nail bed tissue. (f) Thermal conductivity changes of subject 1 and 2 before and after exercise.

Figure 49:
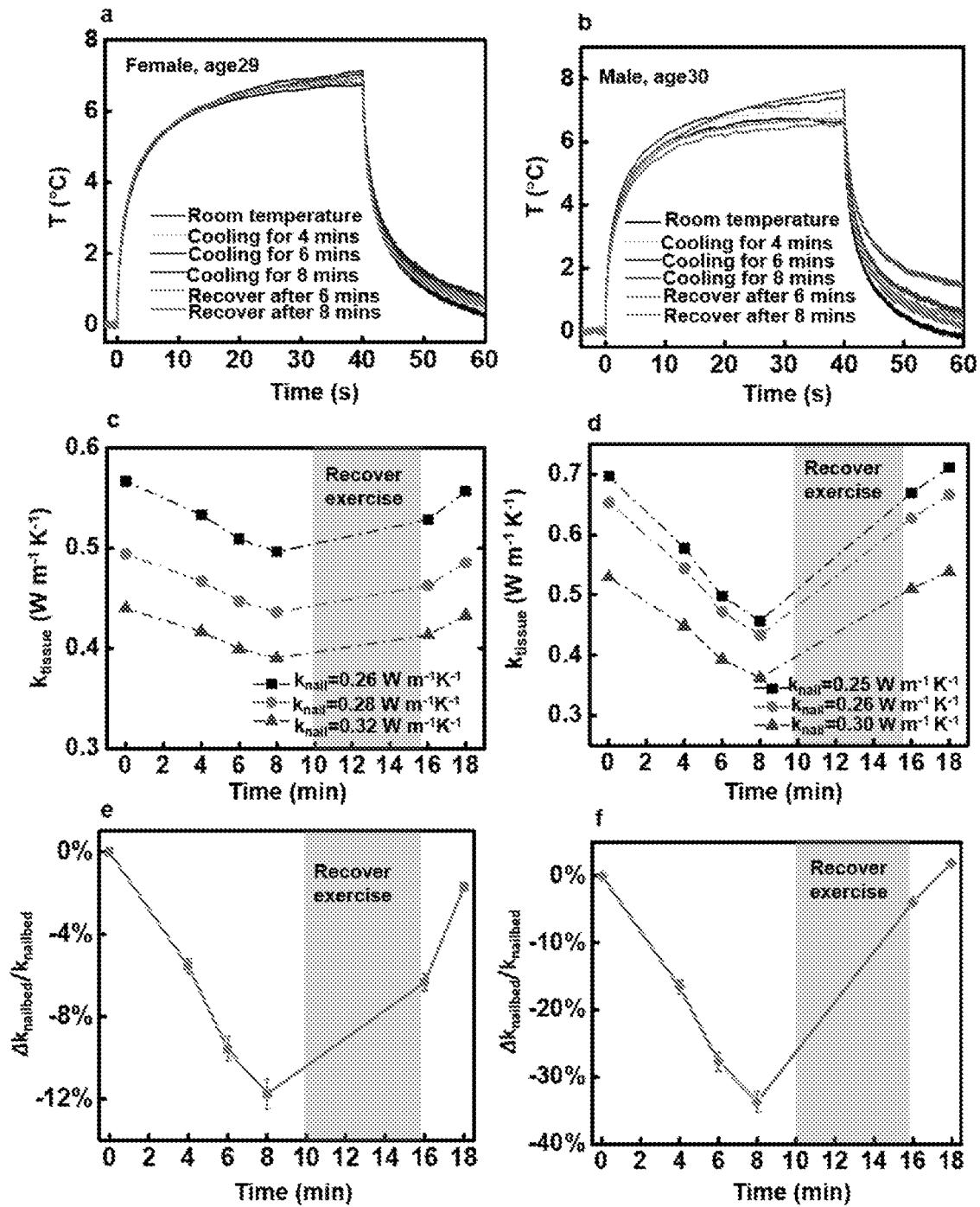

FIG. 49: Studies of changes in thermal transport characteristics of the nailbed tissue associated with cooling the finger. (a) and (b) temperature responses associated with operation of a sensor with R=1.5 mm measured on subject 1 (female, 29) and subject 2 (male, 30). (c) and (d) Fitted thermal conductivity of the nailbed with $k_{nail}$ fixed to the minimum, mean and maximum value of the thermal conductivity of the fingernail for each subject. (e) and (f) Relative change in thermal conductivity, $\Delta k_{nailbed}/k_{nailbed}$, during and after cooling for each subject. The error bar corresponds to the deviation of the $\Delta k_{nailbed}/k_{nailbed}$ calculated using values of $k_{nail}$ in (c) and (d).

Figure 50:
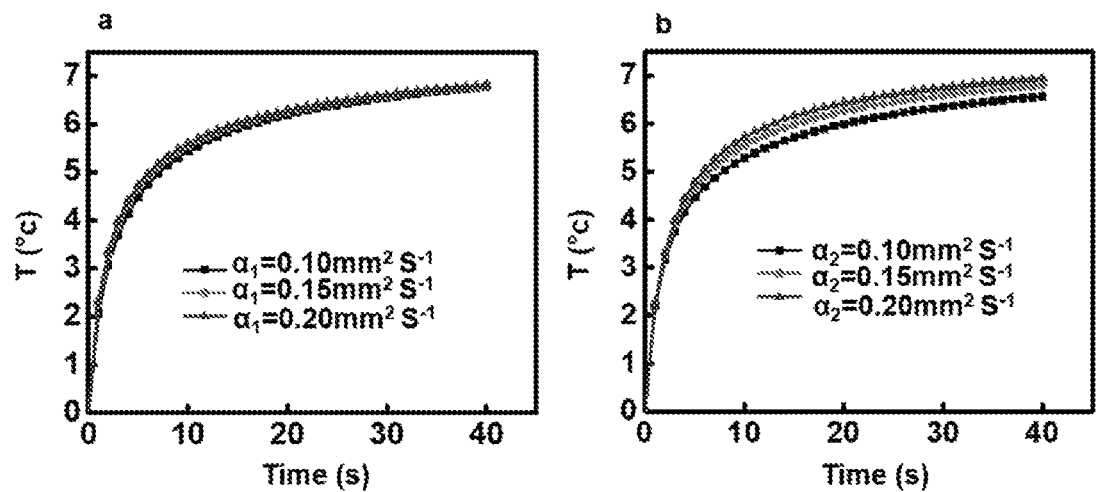

FIG. 50: Thermal diffusivity influence in the FEA simulation. FEA simulated temperature curves of R=1.5 mm sensor. Parameters adopted in the simulations are: (a) top layer thickness h=0.3 mm, power q=3 mw mm$^{-2}$, thermal conductivity of top layer $k_1$=0.24 W m$^{-1}$K$^{-1}$, thermal conductivity of bottom layer $k_2$=0.55 W m$^{-1}$K$^{-1}$. Thermal diffusivity of top layer $\alpha_1$=0.1 mm$^2$ s$^{-1}$ (black), 0.15 mm$^2$ s$^{-1}$ (red), 0.2 mm$^2$ s$^{-1}$ (blue), thermal diffusivity of bottom layer $\alpha_2$=0.15 mm$^2$ s$^1$. (b) $\alpha_1$=0.15 mm$^2$ s$^1$, $\alpha_2$=0.1 mm$^2$ s$^1$ (black), 0.15 mm$^2$ s$^1$ (red), 0.2 mm$^2$ s$^1$ (blue).

Figure 51:
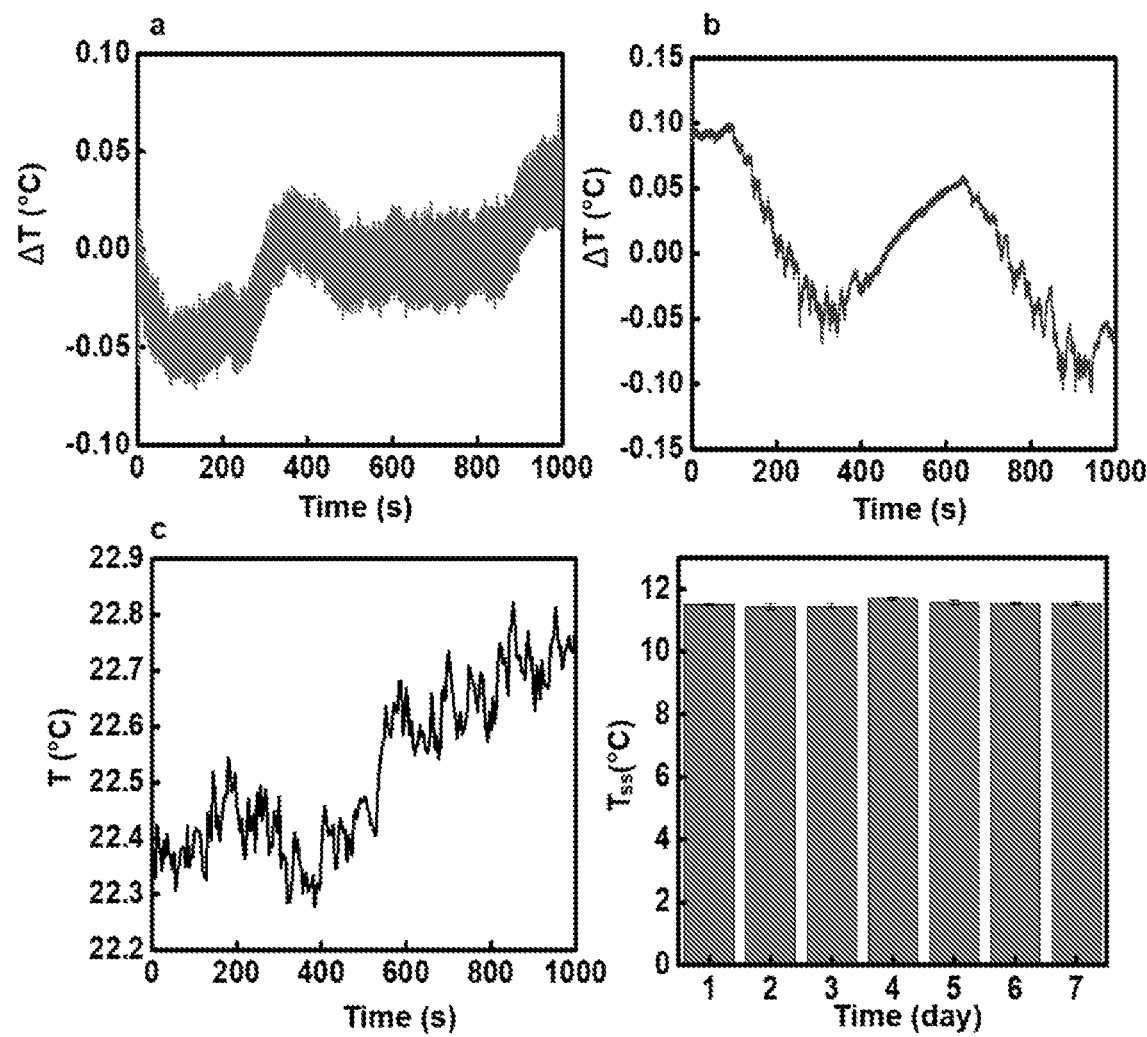

FIG. 51: Fluctuations in ambient temperature. (a) Temperature measured using a sensor with R=1.5 mm on Sylgard170 with a petri dish enclosure. (b) Temperature measured using a sensor with R=1.5 mm on Sylgard170 with a plastic foam enclosure. (c) Temperature of Sylgard170 recorded by an infrared camera without the petri dish enclosure. (d) Steady state temperature of a sensor with R=1.5 mm on Ecoflex measured over a period of 7 days with a plastic foam enclosure.

Figure 52:
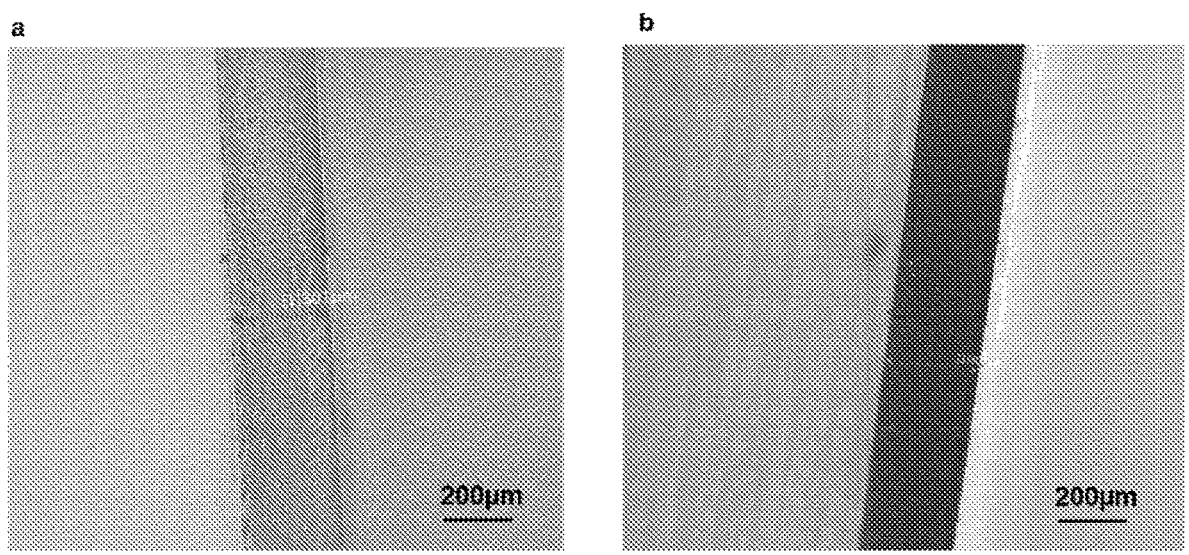

FIG. 52: Optical images of the cross-section of the top film in the bilayer model. (a) Ecoflex with thickness of 300 μm (b) Sylgard 567 with thickness of 300 μm.

Figure 53:
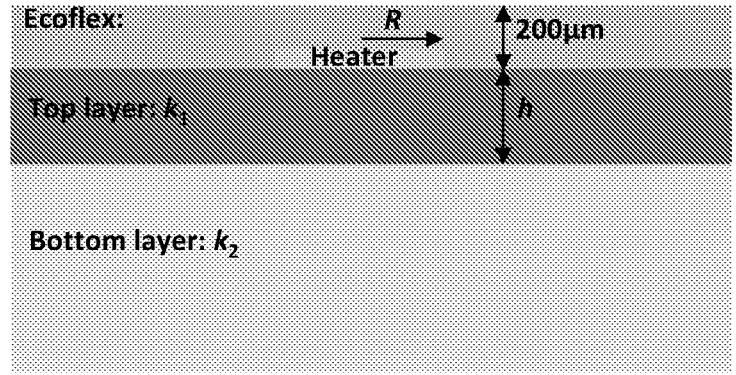

FIG. 53: Schematic diagram of the analytical model in the FEA simulation. A round heater (radius, R), covered by 200 um Ecoflex encapsulation layer, is placed on a bilayer sample with top layer thickness h and semi-infinite bottom layer. Bottom panel is a table summary of: Measured thermal conductivity of the double layered materials. Literature reported thermal conductivity $k_{Sylgard\ 567}$ in range of 0.29-0.3 W m$^{-1}$K$^{-1}$[3,4], $k_{sylgard170}$ in range of 0.40-0.48 W m$^{-1}$K$^{-1}$[5,6], $k_{sylgard}$ 164 is 0.64 W m$^{-1}$K$^{-1}$[7].

Figure 54:
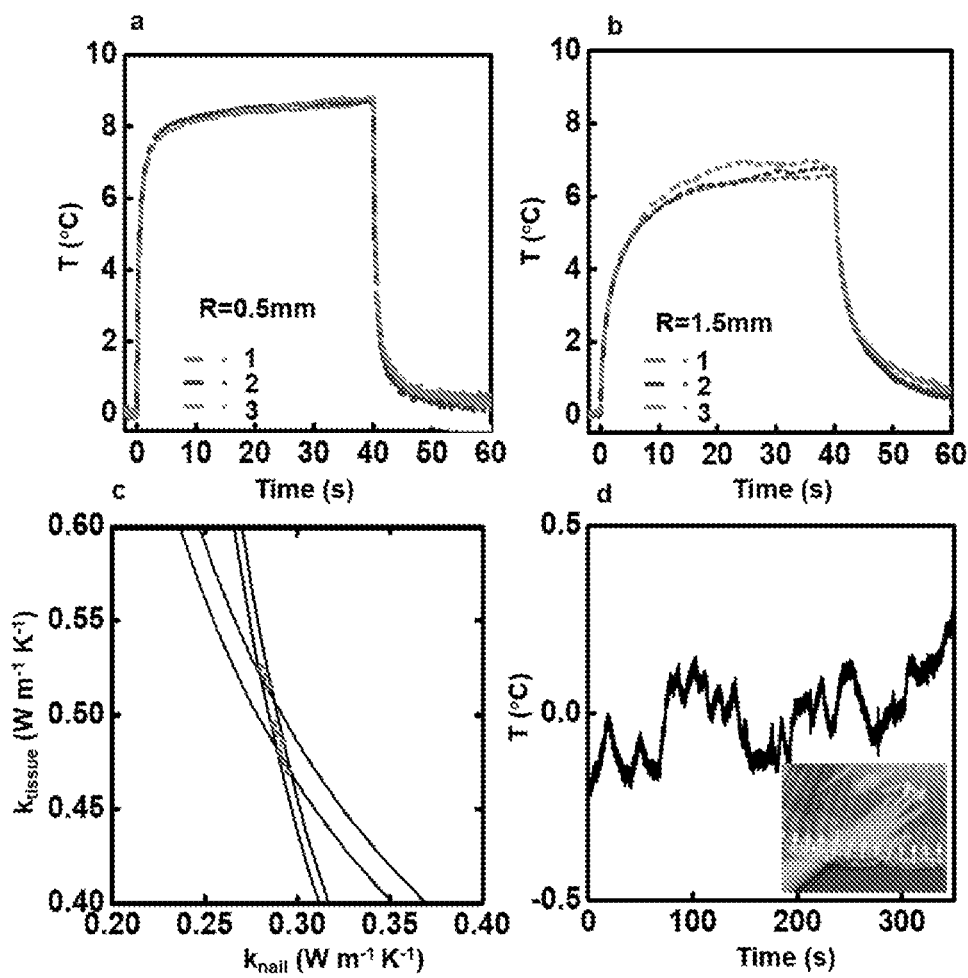

FIG. 54: Thermal characterization of the fingernail. (a) Temperature response of a sensor with R=0.5 mm and (b)

R=1.5 mm on a test subject (female, 29 years old). Red, blue, purple curves are measured at the same location. (c) FEA results from the measurements in (a) and (b), with fitted thermal conductivity, $k_{nail}$ and $k_{tissue}$ presented as red points in the area enclosed by minimum and maximum temperature contour lines. (d) Variation in surface temperature of the fingernail measured using a sensor with R=1.5 mm with plastic foam enclosure, as shown in the inset.

Figure 55:
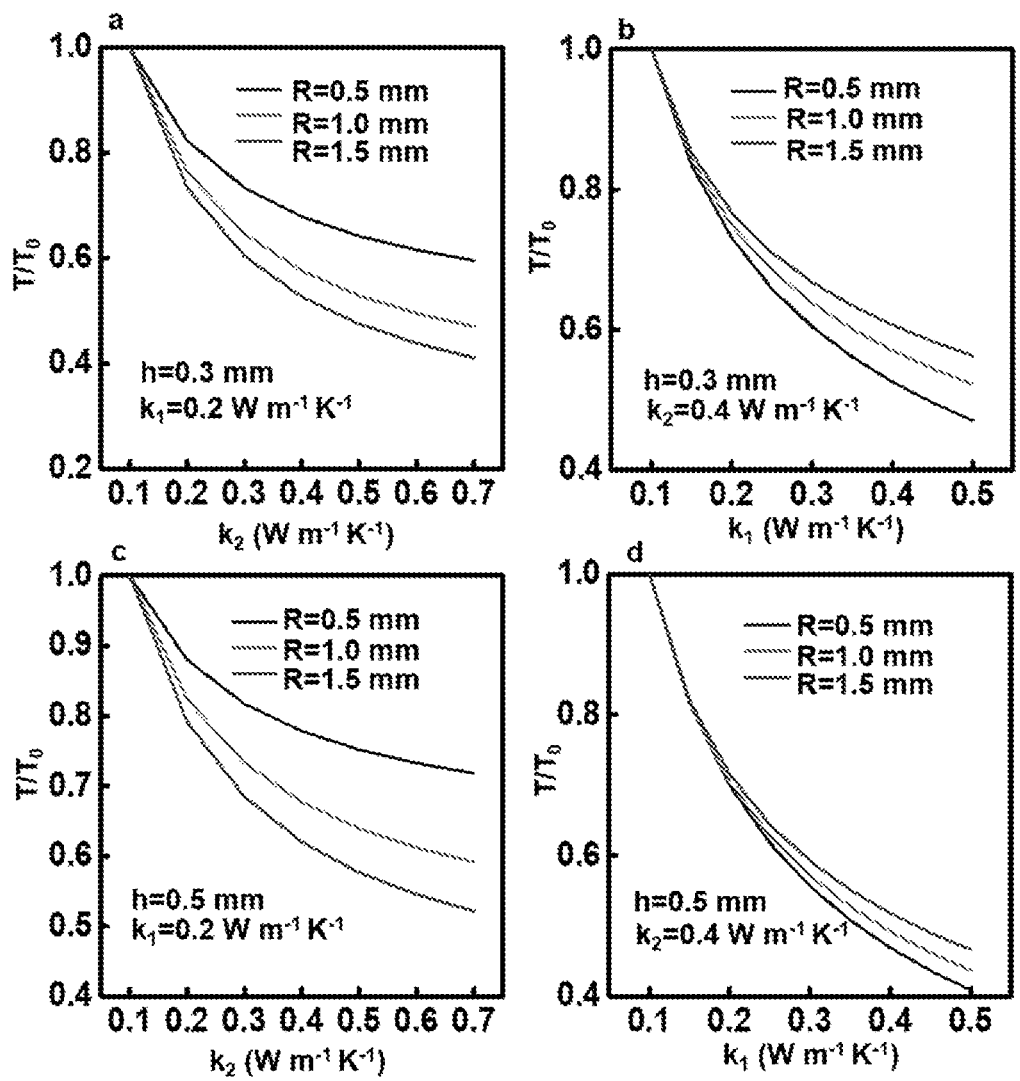

FIG. 55: Temperature responses for sensors with different sizes calculated by FEA for the case of a bilayer system. (a) Normalized temperature responses as function of the thermal conductivity of the bottom layer. The radii of the sensors are 0.5, 1.0 and 1.5 mm, and the thickness of the top plate is h=0.3 mm and (c) 0.5 mm, with $k_1$=0.2 W m$^{-1}$ K$^{-1}$. (b) Normalized temperature responses as function of the thermal conductivity of the top layer. The radii of the sensors are 0.5, 1.0, 1.5 mm, and the thickness of the top plate is h=0.3 mm and (d) 0.5 mm, with $k_2$=0.4 W m$^{-1}$ K$^{-1}$.

Figure 56:
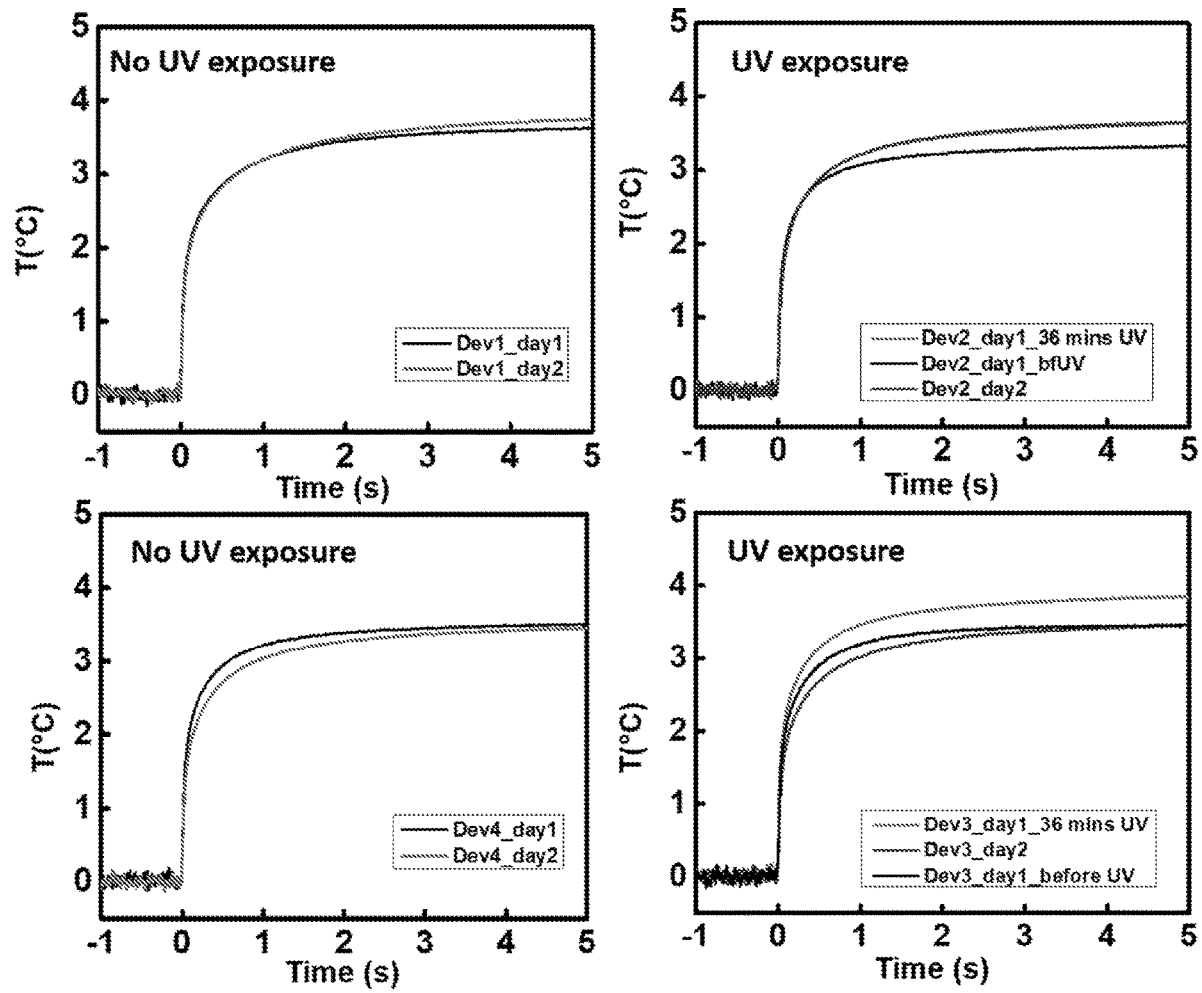

FIG. 56: Thermal study of UVB exposure of epidermis cell

Figure 57:
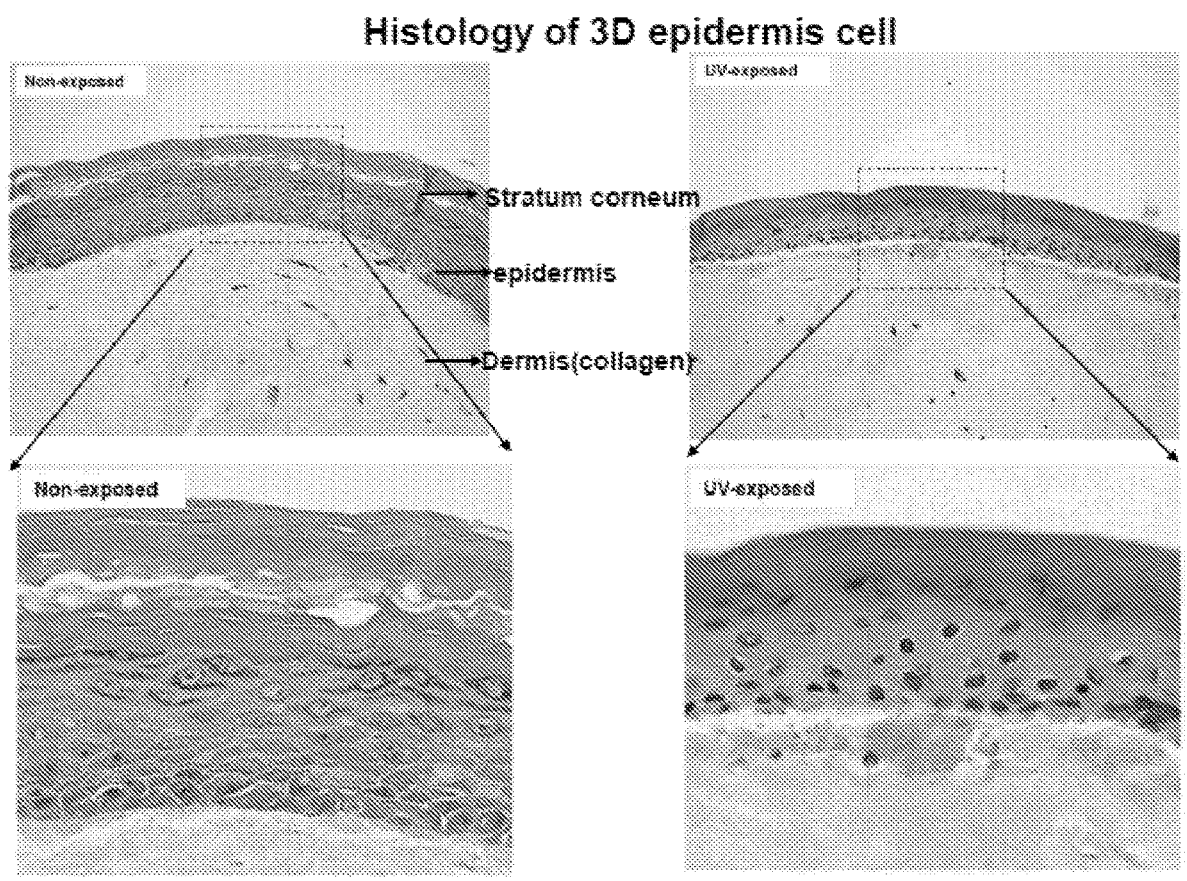

FIG. 57: Histological section of the cell layers.

FIG. 58: Response to sunburn of human skin.

DETAILED DESCRIPTION OF THE INVENTION

In general, the terms and phrases used herein have their art-recognized meaning, which can be found by reference to standard texts, journal references and contexts known to those skilled in the art. The following definitions are provided to clarify their specific use in the context of the invention.

"Interfacing" refers to the positioning of the device with tissue such that the device may affect the tissue, and vice versa. For example, a thermal actuator of the device may result in a thermal load provided to the tissue in the form of a "thermal input". The thermal input is preferable a heating action, although the device is also compatible with a cooling action. "Thermally interfacing", therefore, refers to the ability of the device to affect a thermal challenge on underlying tissue, and to detect a response thereto, such as a change in temperature over time, including for a time period after the thermal input ends. In this manner, one or more tissue parameters may be determined, such as tissue hydration, inflammation, blood flow, UV damage.

The terms "flexible" and "bendable" are used synonymously in the present description and refer to the ability of a material, structure, device or device component to be deformed into a curved or bent shape without undergoing a transformation that introduces significant strain, such as strain characterizing the failure point of a material, structure, device or device component. In an exemplary embodiment, a flexible material, structure, device or device component may be deformed into a curved shape without introducing strain larger than or equal to 5%, for some applications larger than or equal to 1%, and for yet other applications larger than or equal to 0.5% in strain-sensitive regions. As used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 100 microns, optionally less than 10 microns and optionally less than 1 micron) and device geometries such as thin film and mesh geometries.

Any of the devices provided herein may be described in terms of elasticity or elastic. "Elasticity" refers to a measure of a non-plastic deformation, such as a deformation that can undergo deformation and relaxation back to the original undeformed, state without substantial creep, including under repeated deformatory stresses and relaxation cycles. The creep may be defined as less than a 5%, less than 2%, or less than 1% permanent deformation or change in the original material property.

"Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. As used herein, many stretchable structures are also flexible. Some stretchable structures (e.g., device components) are engineered to be able to undergo compression, elongation and/or twisting so as to be able to deform without fracturing. Stretchable structures include thin film structures comprising stretchable materials, such as elastomers; bent structures capable of elongation, compression and/or twisting motion; and structures having an island—bridge geometry. Stretchable device components include structures having stretchable interconnects, such as stretchable electrical interconnects.

"Two-way communication" refers to the ability to wirelessly communicate with the device, such that power, commands or queries are sent to, and acted on, the device and the device itself can send information or diagnostics to an external controller that is wirelessly connected to the device. Accordingly, an "external controller" refers to an off-board component that can control and received information from the device. Examples include hand-held devices, computers, smartphones, and the like.

The devices and methods provided herein are suited for long-term use in that the device may be "worn" over long periods of time and remain functional. Accordingly, "continuous" refers to the time period any of the devices provided herein are deployed on or in biological tissue and is ready for use. While the device is continuously deployed, the measurement may be described as intermittent or periodic, such as for a continuous measurement time on the order of minutes, such as greater than or equal to 1 minute, 5 minutes, 10 minutes or 20 minutes. The periodic measurement, however, can be repeated over the time period the device is worn, such as in the morning, during the day, and in the evening, including on the order of 12 hours or more, 1 day or more, or 7 days or more.

"Thermal parameter" or "thermal transport property" may refer to a rate of change of a temperature-related tissue property, such as a heat-related tissue property, over time and/or distance (velocity). In some embodiments, the heat-related tissue property may be temperature, conductivity or humidity. The heat-related tissue property may be used to determine a thermal transport property of the tissue, where the "thermal transport property" relates to heat flow or distribution at or near the tissue surface. In some embodiments, thermal transport properties include temperature distribution across a tissue surface, thermal conductivity, thermal diffusivity and heat capacity. Thermal transport properties, as evaluated in the present methods and systems, may be correlated with a physical or physiological property of the tissue. In some embodiments, a thermal transport property may correlate with a temperature of tissue. In some embodiments, a thermal transport property may correlate with a vasculature property, such as blood flow and/or direction.

"Substrate" refers to a portion of the device that provides mechanical support for a component(s) disposed on or within the substrate. The substrate may have at least one skin-related function or purpose. For example, the substrate may have a mechanical functionality, for example, providing physical and mechanical properties for establishing conformal contact at the interface with a tissue, such as skin or a nail surface. The substrate may have a thermal loading or mass small enough so as to avoid interference with measurement and/or characterization of a tissue parameter. The substrate of any of the present devices and methods may be biocompatible and/or bioinert. A substrate may facilitate mechanical, thermal, chemical and/or electrical matching to the underlying tissue, such as skin or nail of a subject such that the mechanical, thermal, chemical and/or electrical properties of the substrate and the tissue are within 20%, or 15%, or 10%, or 5% of one another.

A flexible substrate that is mechanically matched to a tissue, such as skin, provides a conformable interface, for example, useful for establishing conformal contact with the surface of the tissue. Devices and methods described herein may incorporate mechanically functional substrates comprising soft materials, for example exhibiting flexibility and/or stretchability, such as polymeric and/or elastomeric materials. A mechanically matched substrate may have a Young's modulus less than or equal to 100 MPa, and optionally for some embodiments less than or equal to 10 MPa, and optionally for some embodiments, less than or equal to 1 MPa. In an embodiment, a mechanically matched substrate has a thickness less than or equal to 0.5 mm, and optionally for some embodiments, less than or equal to 1 cm, and optionally for some embodiments, less than or equal to 3 mm. In an embodiment, a mechanically matched substrate has a bending stiffness less than or equal to 1 nN m, optionally less than or equal to 0.5 nN m.

In some embodiments, a mechanically matched substrate is characterized by one or more mechanical properties and/or physical properties that are within a specified factor of the same parameter for an epidermal layer of the skin or nail, such as a factor of 10 or a factor of 2. For example, a substrate may have a Young's Modulus or thickness that is within a factor of 20, or optionally for some applications within a factor of 10, or optionally for some applications within a factor of 2, of a tissue, such as an epidermal layer of the skin or of the nail surface, at the interface with a device of the present invention. A mechanically matched substrate may have a mass or modulus that is equal to or lower than that of skin.

In some embodiments, a substrate that is thermally matched to skin has a thermal mass small enough that deployment of the device does not result in a thermal load on the tissue, such as skin, or small enough so as not to impact measurement and/or characterization of a physiological parameter. In some embodiments, for example, a substrate that is thermally matched to skin has a thermal mass low enough such that deployment on skin results in an increase in temperature of less than or equal to 2 degrees Celsius, and optionally for some applications less than or equal to 1 degree Celsius, and optionally for some applications less than or equal to 0.5 degree Celsius, and optionally for some applications less than or equal to 0.1 degree Celsius. In some embodiments, for example, a substrate that is thermally matched to skin has a thermal mass low enough that is does not significantly disrupt water loss from the skin, such as avoiding a change in water loss by a factor of 1.2 or greater. Therefore, the device does not substantially induce sweating or significantly disrupt transdermal water loss from the skin, while maintaining an effectiveness of determining hydration sate of the skin.

The substrate may be at least partially hydrophilic and/or at least partially hydrophobic.

The substrate may have a Young's modulus less than or equal to 100 MPa, or less than or equal to 50 MPa, or less than or equal to 10 MPa, or less than or equal to 100 kPa, or less than or equal to 80 kPa, or less than or equal to 50 kPa. Further, in some embodiments, the device may have a thickness less than or equal to 5 mm, or less than or equal to 2 mm, or less than or equal to 100 µm, or less than or equal to 50 µm, and a net bending stiffness less than or equal to 1 nN m, or less than or equal to 0.5 nN m, or less than or equal to 0.2 nN m. For example, the device may have a net bending stiffness selected from a range of 0.1 to 1 nN m, or 0.2 to 0.8 nN m, or 0.3 to 0.7 nN m, or 0.4 to 0.6 nN m.

A "component" is used broadly to refer to an individual part of a device.

In an embodiment, "coincident" refers to the relative position of two or more objects, planes, surfaces, regions or signals occurring together in space and time, including physically and/or temporally overlapping objects, planes, surfaces, regions or signals.

In an embodiment, "proximate" refers to the relative position of two objects, planes, surfaces, regions or signals that are closer in relationship than any one of those objects is to a third object of the same type as the second object. Proximate relationships include, but are not limited to, physical, electrical, thermal and/or optical contact. In an embodiment, epidermal tissue proximate to a thermal element is directly adjacent to the thermal element and closer to that thermal element than any other thermal element in an array of thermal elements. In an embodiment, two objects proximate to one another may be separated by a distance less than or equal to 50 mm, or less than or equal to 25 mm, or less than or equal to 10 mm, or two objects proximate to one another may be separated by a distance selected from the range of 0 mm to 50 mm, or 0.1 mm to 25 mm, or 0.5 mm to 10 mm, or 1 mm to 5 mm. The terms coincident and/or proximate may be used to refer to the position of a component relative to the neutral mechanical surface, including strain-sensitive components such as electronics, sensors and actuators, that may be vulnerable to fracture under strain or stress.

Accordingly, "coincident" may refers to the relative position of two or more objects, planes or surfaces, for example a surface such as a neutral mechanical surface (NMS) or neutral mechanical plane (NMP) that is positioned within or is adjacent to a layer, such as a functional layer, electronics layer, sensor or actuator layer, substrate layer, or other layer. In an embodiment, a NMS or NMP is positioned to correspond to the most strain-sensitive layer or material within the layer. "Proximate" refers to the relative position of two or more objects, planes or surfaces, for example a NMS or NMP that closely follows the position of a layer, such as a functional layer, substrate layer, or other layer while still providing desired flexibility or stretchability without an adverse impact on the strain-sensitive material physical properties. In general, a layer having a high strain sensitivity, and consequently being prone to being the first layer to fracture, is located in the functional layer, such as a functional layer containing a relatively brittle semiconductor or other strain-sensitive device element. A NMS or NMP that is proximate to a layer need not be constrained within that layer, but may be positioned proximate or sufficiently near to provide a functional benefit of reducing the strain on the strain-sensitive device element when the device is folded.

In this aspect, "strain-sensitive" refers to a material that fractures or is otherwise impaired in response to a relatively low level of strain. In an aspect, the NMS is coincident or proximate to a functional layer. In an aspect the NMS is coincident to a functional layer, referring to at least a portion of the NMS located within the functional layer that contains a strain-sensitive material for all lateral locations along the NMS. In an aspect, the NMS is proximate to a functional layer, wherein although the NMS may not be coincident with the functional layer, the position of the NMS provides a mechanical benefit to the functional layer, such as substantially lowering the strain that would otherwise be exerted on the functional layer but for the position of the NMS. For example, the position of a proximate NMS is optionally defined as the distance from the strain-sensitive material that provides an at least 10%, 20%, 50% or 75% reduction in strain in the strain-sensitive material for a given folded configuration, such as a device being folded so that the radius of curvature is on the order of the millimeter or centimeter scale. In another aspect, the position of a proximate NMS can be defined in absolute terms such as a distance from the strain-sensitive material, such as less than several mm, less than 2 mm, less than 10 µm, less than 1 µm, or less than 100 nm. In another aspect, the position of a proximate layer is defined relative to the layer that is adjacent to the strain-sensitive material, such as within 50%, 25% or 10% of the layer closest to the strain-sensitive-containing layer. In an aspect, the proximate NMS is contained within a layer that is adjacent to the functional layer.

"Sensing" refers to detecting the presence, absence, amount, magnitude or intensity of a physical and/or chemical property. Useful device components for sensing include, but are not limited to electrode elements, chemical or biological sensor elements, pH sensors, temperature sensors, strain sensors, mechanical sensors, position sensors, optical sensors and capacitive sensors.

"Actuating" refers to stimulating, controlling, or otherwise affecting a structure, material or device component. Useful device components for actuating include, but are not limited to, electrode elements, electromagnetic radiation emitting elements, light emitting diodes, lasers, magnetic elements, acoustic elements, piezoelectric elements, chemical elements, biological elements, and heating elements.

The terms "directly and indirectly" describe the actions or physical positions of one component relative to another component. For example, a component that "directly" acts upon or touches another component does so without intervention from an intermediary. Contrarily, a component that "indirectly" acts upon or touches another component does so through an intermediary (e.g., a third component).

In an embodiment, "epidermal tissue" refers to the outermost layers of the skin or the epidermis. The epidermis is stratified into the following non-limiting layers (beginning with the outermost layer): stratum corneum, stratum lucidum (on the palms and soles, i.e., the palmar regions), stratum *granulosum*, stratum *spinosum*, stratum germinativum (also called the statum basale). In an embodiment, epidermal tissue is human epidermal tissue.

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50%, or optionally 90% of the external surface of the structure is surrounded by one or more structures. "Completely encapsulated" refers to the orientation of one structure such that it is completely surrounded by one or more other structures. The encapsulation may be described in functional terms, such as being a fluid or electrical barrier, particularly in those locations where a fluid or electrical field would lead to an adverse impact on the device.

"Dielectric" refers to a non-conducting or insulating material.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components disclosed include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. Exemplary elastomers include, but are not limited to silicon containing polymers such as polysiloxanes including poly(dimethyl siloxane) (i.e. PDMS and h-PDMS), poly(methyl siloxane), partially alkylated poly (methyl siloxane), poly(alkyl methyl siloxane) and poly (phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrenebutadiene-styrene), polyurethanes, polychloroprene and silicones. A polymer may be an elastomer.

"Conformable" refers to a device, material or substrate which has a bending stiffness that is sufficiently low to allow the device, material or substrate to adopt any desired contour profile, for example a contour profile allowing for conformal contact with a curvilinear surface, including a surface whose shape may change over time, such as with physical exertion or normal every day movement, such as skin.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. Devices of certain aspects are capable of establishing conformal contact with internal and external tissue. Devices of certain aspects are capable of establishing conformal contact with tissue surfaces characterized by a range of surface morphologies including planar, curved, contoured, macro-featured and micro-featured surfaces and any combination of these. Devices of certain aspects are capable of establishing conformal contact with tissue surfaces corresponding to tissue undergoing movement, including an internal organ or skin.

"Young's modulus" is a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \quad (II)$$

where and p are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components having a low Young's modulus. In an embodiment, a device of the invention has an overall low Young's modulus.

"Low modulus" refers to materials having a Young's modulus less than or equal to 10 MPa, less than or equal to 5 MPa or less than or equal to 1 MPa.

Use of the term "effective" with any physical parameter reflects an average or bulk parameter. This reflects, for example, that the devices are not formed of a single unitary material, but can have materials ranging from elastomers, adhesives, thin films, metals, semiconductors, integrated circuits and other materials that span orders of magnitudes. An effective device modulus, accordingly, can reflect physical properties of the entire device, with a special geometry and configuration of components to ensure the bulk behavior of the device is tailored to the application of interest. For skin, the entire device can be configured to be highly flexible and stretchable, with certain portions that are by necessity less flexible and stretchable due to material requirements. For a nail, the entire device need not be so stretchable, but should still conform to the nail curvilinear surface contour.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

"Tissue parameter" refers to a property of a tissue including a physical property, physiological property, electronic property, optical property and/or chemical composition. Tissue parameter may refer to a surface property, a subsurface property or a property of a material derived from the tissue, such as a biological fluid. Tissue parameter may refer to a parameter corresponding to an in vivo tissue such as temperature; hydration state; chemical composition of the tissue; chemical composition of a fluid from the tissue; pH of a fluid from the tissue; the presence of absence of a biomarker; intensity of electromagnetic radiation exposed to the tissue; wavelength of electromagnetic radiation exposed to the tissue; and amount of an environmental contaminant exposed to the tissue. Devices of some embodiments are capable of generating a response that corresponds to one or more tissue parameters, such as for a low hydration state application of a hydrating material (e.g., a moisturizer), or for a UV damage state application of a UV block (e.g., sunscreen) or a warning to the individual wearing the device, such as a haptic feedback actuator that provides a vibratory signal, optical signal, or electrical signal, warning the user to take appropriate action. A tissue parameter may provide useful information about the health of a tissue. For example, a tissue parameter that is a "sunburn parameter" may be used to assess effectiveness of a compound as a sunscreen, to warn a user, or to automatically apply a treatment, including application of a sunscreen. The sunburn parameter may be an optical property, such as color, or may be a hydration property that, in turn, is related to thermal conductivity of the underlying tissue.

Any of the devices and methods provided herein may be personalized to a user. In this context, "personalized" refers to the device or method that is tailored to that of an individual user, recognizing there may be relatively significant person-to-person variability with respect to one or more baseline tissue parameters, and tissue behavior to a stimulus. For example, some people may have higher inherent thermal conductivity, or high resting hydration level. The devices or methods may accurately determine the baseline tissue parameter, with monitoring and corresponding treatment tailored to that individual's baseline tissue parameter.

"Haptic feedback element" refers to a device component that generates a physically-detectable stimulus by a user, such as be a haptic feedback element that is selected from the group consisting of a vibrator, an optical light source, or an electrode.

"Environmental parameter" refers to a property of an environment of a device, such as a device in conformal contact with a tissue. Environment parameter may refer to a physical property, electronic property, optical property and/or chemical composition, such as an intensity of electromagnetic radiation exposed to the device; wavelengths of electromagnetic radiation exposed to the device; a chemical composition of an environmental component exposed to the device; chemical composition of an environmental component exposed to the device; amount of an environmental contaminant exposed to the device; and/or chemical composition of an environmental contaminant exposed to the device. Devices of some embodiments are capable of generating a response that corresponds to one or more environmental parameters. For example, in low humidity conditions, application of a hydrating material; high UV conditions, application of a UV block material.

The following examples further illustrate the invention but, of course, should not be construed as in any way limiting its scope.

Referring to the figures, a wireless electronic device 10 comprises a flexible and/or elastic substrates 20 configured to reliably contact underlying tissue, including skin, and thereby establish a thermal interface. A thermal actuator 30 is supported by the flexible substrate and, upon actuation, provides a thermal input to the biological tissue 15 underlying the device. A temperature sensor 40 measures temperature to determine thermal conductivity of the underlying biological tissue 15. A wireless electronic system 50 provides two-communication with an external controller 65, including a handheld device as shown in FIG. 32. A haptic feedback element 170 may be incorporated into the system to provide the user a convenient and readily understood signal (e.g., vibration, shock, light, and the like). As desired, an additional sensor 430 may be incorporated into the system.

The devices are compatible with a moisturizer product 130 either on the skin surface between the skin and the device, or in a stand-alone configuration where the device is used to test a moisturizer product, including hydration characterization under various conditions.

The device may have a first active region 4400 and a second active region 4410, a first contact pad 4402 and a second contact pad 4412, a first electrically conductivity ribbon 4404 and a second electrically conductivity ribbon 4414, and an encapsulation layer 4420. A serpentine electrical interconnect 320 may electrically connect various components to contact pad 330. FIG. 44 shows thin, flexible thermal sensors that laminate onto the surfaces of the fingernails enable measurements of the thermal transport properties of the nail bed tissues. a) is an exploded view schematic illustration of a representative device that includes a small (radius ~0.5 mm) sensor (second active region) 4410 and a large (radius ~1.5 mm) sensor (first active region) 4400. b) is an optical image of the device. The inset provides a magnified view of the small sensor. c) is an optical image of the device laminated on a fingernail, and d) is a corresponding infrared image of the device during operation. Peripheral edges of said first active region 4400 and said second active region 4410 are spatially separated from each other by a distance such that said first active region 4400 and said second active region 4410 are not concentrically positioned relative to each other. That is, a geometric center of said first active region 4400 is laterally separated from that of said second active region 4410 by the distance. As disclosed in Example 3, the device in one embodiment is a dual e-TDS (epidermal thermal depth sensor) system shown in FIG. 31: experiments on human skin. (a) Optical image of a dual e-TDS (epidermal thermal depth sensor) system with device radii $R_1=0.75$ mm, and $R_2=3.5$ mm. Image of such a system mounted on (b) relaxed and (c) stretched human skin demonstrating flexibility and conformity. The dual e-TDS design chosen here is applicable to many locations of the body where the thickness of the E+D is ~1 mm. The e-TDS are conformal and stretchable shown in FIG. 31 (panels b and c) to ensure effective thermal coupling to the skin (provided is a description of mechanical stability). Operating the e-TDS consecutively eliminates active interference. Passive interference can be minimized by separating the peripheral edges of the two e-TDS by an amount greater than $h_{max}$ of e-TDS 1 (error less than 1% in $\Delta T$).

Example 1—Wireless Skin Hydration Sensor

The continuous measurement of the physical parameters of skin holds profound relevance in both cosmetics and medicine. In this example, we present a wireless, wearable, and miniaturized sensor capable of measuring thermal conductivity of skin—a parameter directly correlative to skin hydration and skin inflammation that simple surface temperature cannot. Current tools to assess skin hydration are large, bulky, and expensive (e.g. corneometers and transepidermal water loss meters). Furthermore, these tools preclude continuous measurements. Skin hydration, in the context of clinical dermatology, directly reflect that status of skin barrier function. Skin with excess water loss or low hydration prognosticate the development of skin conditions such as atopic dermatitis (eczema). The application of moisturizers and topical steroids directly lead to improved skin water content. In the context of cosmetics, well-hydrated skin appears youthful and plump. First, this technology can be used to assess the status of the skin prior to clinical evidence of dryness and potentiate the application of moisturizers or other topical medicines. Second, this tool can be used as an outcome tool for systemic medications used for the treatment of skin conditions. Third, the sensor can be used to determine the efficacy and performance of moisturizer products applied to the skin. Fourth, the sensor can be used directly on cosmetic products to quantify water content and provide an objective measure of moisturizer performance and feel. Fifth, thermal conductivity can also be used as a surrogate marker for skin inflammation and edema-thus, this technology can be utilized to assess skin injuries (e.g. extent of a sunburn) or to diagnose skin or deeper tissue infections (e.g. cellulitis). Finally, implantable (e.g. subdermal) version of this technology have the opportunity to service as a sentinel system of inflammation in deeper organs and tissues. For instance, this technology could be placed overlying a transplanted organ and act as a surveillance system for kidney rejection.

The devices and methods provided herein are useful in range of applications, including clinical dermatology and cosmetics dermatology and beauty.

Clinical Dermatology:

Atopic dermatitis (AD) or eczema affects 20% of children worldwide and represents the most common inflammatory skin condition. The hallmark of atopic dermatitis is an impaired skin barrier leading to excess skin water loss and low skin hydration. Currently, therapeutics for atopic dermatitis are reactionary—they require clinical evidence of skin irritation, dryness, and itching before a medicine is applied. A wearable skin hydration sensor would enable pre-emptive action prior to the onset of symptoms.

Currently, there are numerous drugs in development for the systemic treatment of atopic dermatitis. It represents one of the most active areas of pharmaceutical research. AD clinical trials depend on physician assessments on visual scales—these metrics are not sensitive to small, but clinically meaningful changes. There is a need for surrogate markers, such as skin hydration, that better capture the therapeutic benefit of these medications.

The skin hydration sensor can be used as a diagnostic tool for skin inflammation and skin injury that has implications across numerous disease states. Changes in thermal conductivity and surface temperature has diagnostic value for conditions such as cellulitis or serve as a surrogate marker for wound formation that may not be apparent clinically. In addition, this sensor can be used to predict for future skin healing potential. Sunburn is a common skin condition—this sensor can be used to assess early sunburn that may not be visually obvious or to grade the severity of a sunburn.

The nail bed represents a unique anatomical location without a stratum corneum covered via a water tight covering (nail plate). Interrogating the nail bed enables assessment of skin hydration related to deeper soft tissue structures-which provides additional insights in blood flow, and core hydration.

Cosmetics Dermatology and Beauty:

Skin hydration is critical to the appearance of healthy, plump skin. Moisturizers represent a multi-billion dollar yearly market. However, there is minimal real-world patient specific feedback on skin hydration status as it relates to the use of these products. Analogous to how a wearable a UV-sensor increases the use of sunscreens, a wearable skin hydration sensor will drive increases in moisturizer use. The implications for moisturizer manufacturers is self-evident.

Personalized hydration metrics: the sensor can create baseline values of skin hydration and detect % deviations from this baseline that may indicate worsening dry skin.

Quantification of moisturizer performance: the sensor itself can be applied to moisturizer products to assess water content. The percentage of water content in a moisturizer is correlative to its 'cosmetic feel' and also its 'hydration potential'. Thus, the sensor can be used to create a novel metric, "skin hydration factor", that describes the moisturizing potential of a product.

The sensor can be applied on skin to measure skin hydration in various anatomical locations. For instance, the lower legs are frequently dry in winter, cold conditions. The face is an area that frequently is treated with moisturizers to create a plumper appearance. The nail is also an anatomical location of interest and value. Brittle nails represent a significant cosmetic problem—supporting a multi-billion dollar industry for cosmetics directed towards nail health. A skin hydration sensor deployed on the nail would create objective metrics for nail health.

Any of the devices and methods provided herein may be used as an implantable device. Implantable versions of this technology may serve as early warning indicators of inflammation in a localized area of the body (e.g. transplanted organ). This information may then enable future prediction of organ transplant rejection prior to laboratory or imaging evidence—this would then trigger changes to immunosuppressant drug dosing. Other embodiments can include interrogation of infection in implantable orthopedic or soft tissue implants.

The systems methods and devices described herein may have a fully wireless form factor, optimized antennae configuration to enable reading with standard smartphones or custom NFC readers, soft, thin flexible and waterproof form factor enabling comfortable continuous wear, mm-scale (<1 cm) allow deployment on specific anatomical sites (e.g. human nail) and a sensor that enables derivation of novel and personalized patient metrics, for example, skin hydration factor, which can describe the objective performance of various moisturizers.

The thermal sensor measurement described herein is based on the well-established transient plane source (TPS)[1] method. Briefly, the active element in the TPS approach delivers thermal power to the sample via Joule heating that results from application of DC current. The same device simultaneously enables time-dependent measurements of resulting changes in temperature through the temperature coefficient of resistance (TCR) of the metal. Data recorded in this manner can be combined with computational techniques to determine the intrinsic thermal transport properties, i.e., the thermal conductivity and thermal diffusivity, of the material under test. The characteristic probing depth $\lambda$ associated with the TPS method increases with the thermal diffusivity ($\alpha$) and the time for thermal actuation (t)[1-3], i.e. For a bi-layer sample, characterization of the thermal properties of the bottom layer requires actuation times sufficient for heat to diffuse through the top layer. At long times, the temperature approximately saturates to a value that depends mainly on the thermal conductivity and only weakly on the thermal diffusivity.

REFERENCES FOR EXAMPLE 1

1. US 20080275319A1; 2. WO2016025438A1; 3. US20170347891A1; 4. A Wearable Hydration Sensor with Conformal Nanowire Electrodes. Adv. Healthcare Mater. 2017, 1601159; 5. Xian Huang, Woon-Hong Yeo, Yuhao Liu, John A. Rogers. Epidermal Differential Impedance Sensor for Conformal Skin Hydration Monitoring. Biointerphases (2012) 7:52; 6. Flexible and Stretchable 3ω Sensors for Thermal Characterization of Human Skin. Advanced Functional Materials (2017), 27(26): 1701282; 7. S Krishnan, Y Shi, R C Webb, Y Ma, P Bastien, K E Crawford, A Wang, . . . J A Rogers. Multimodal epidermal devices for hydration monitoring. Microsystems and Nanoengineering 3 (17014); 8. R C Webb, S Krishnan, JA Rogers. Ultrathin, Skin-Like Devices for Precise, Continuous Thermal Property Mapping of Human Skin and Soft Tissues. Stretchable Bioelectronics for Medical Devices and Systems, 117-132. 2016.

Example 2: Advanced Approaches for Quantitative Characterization of Thermal Transport Properties in Soft Materials Using This, Conformal Resistive Sensors Noninvasive methods for precise characterization of the thermal properties of soft biological tissues such as the skin can yield vital details about physiological health status including at critical intervals during recovery following skin injury. Here, we introduce quantitative measurement and characterization methods that allow rapid, accurate determination of the thermal conductivity of soft materials using thin, skin-like resistive sensor platforms. Systematic evaluations of skin at eight different locations and of six different synthetic skin-mimicking materials across sensor sizes, measurement times, and surface geometries (planar, highly curvilinear) validate simple scaling laws for data interpretation and parameter extraction. As an example of the possibilities, changes in the thermal properties of skin (volar forearm) can be monitored during recovery from exposure to ultraviolet radiation (sunburn) and to stressors associated with localized heating and cooling. More generally, the results described here facilitate rapid, non-invasive thermal measurements on broad classes of biological and non-biological soft materials.

Skin is a critical, multi-purpose organ within the integumentary system [1]. Accounting for 12 to 15 percent of the total body weight, the skin serves many purposes such as a: 1) protective barrier against pathogens and microbes, 2) sensory interface to the surrounding environment (i.e. touch, heat, cold, pain), and 3) physiology regulator (hydration, sweat, hair, Vitamin D synthesis, and temperature etc.) [2]. Devices, particularly wearable systems, for measuring the thermal properties of the skin can provide vital information about physiological health status. Designs that 1) minimize the mechanical mismatch at the skin-device interface, 2) maximize conformal contact between skin and device, 3) eliminate any constrains in natural motions of the skin, 4) avoid any thermal load on the skin and 5) operate in a physically imperceptible, non-irritating manner are particularly attractive [3-12]. Recent reports describe approaches to such skin-like, or 'epidermal', devices and outline their capabilities for precision, continuous measurements of hydration, cutaneous wound healing, blood flow, temperature, thermal conductivity and thermal diffusivity [13-24].

The following describes the development, validation and application of advanced methods for using such devices in a transient plane source (TPS) mode [25] to yield the thermal conductivity in a computationally efficient, accurate manner that avoids experimental uncertainties associated with previous approaches. An application example focuses on characterization of erythema as a sign of skin injury. Erythema is a physiological phenomenon characterized by a reddening of the skin caused by vasodilation of near-surface capillaries that appears following exposure to heat/cold stresses, pressure, infection, inflammation, allergic reaction, and prolonged exposure to solar radiation (sunburn) [25]. Results show that the near-surface thermal conductivity changes in a manner that can be used for non-invasive monitoring of erythema recovery, of utility for diagnostic and prognostic purposes.

Materials and Methods: Fabrication of the sensor and its operating principles. The device architecture consists of a resistive sensor formed with photolithographically defined serpentine metal wires (15-20 μm wide; Cr/Au 8/100 nm thick). An expanded view illustration and a microscope image are in FIG. 18A. The resistive sensors have circular layouts with radii selected between 0.5 mm-2.0 mm. The wire connecting the resistive sensor to the power source has a serpentine geometry consistent with design rules in epidermal electronics (100 μm wide; Ti/Cu/Ti/Au 8/550/8/25 nm thick) [3-12]. Encapsulating layers of polyimide (4 μm thick; Dow Chemical Co.) above and below place the sensing element in the neutral mechanical plane of the assembly, thereby shielding it from strain-induced resistance changes [3-12]. An ultra-soft (shore-A 00 with ~60 kPa Young's modulus), thin film of silicone (50±10 μm thickness; Ecoflex, Smooth-On) chemically adheres to both sides of the device to produce a reusable and mechanically conformal system compatible with deployment on flat or curvilinear surfaces. As a visual example of the high degree of conformality to surfaces, separate digital images display a representative device wrapped around the $4^{th}$ digit of a left hand, and woven through three parallel, transparent glass rods (rod radii: 1.3 mm) in an over-under-over surface lamination, FIGS. 18B and 18C, respectively.

During operation, the sensor acts as a thermal actuator upon application of direct electrical current (Keithley 6220, A Tektronix Co.). The device connects to the current source by bonding to a conductive ribbon (250 μm spacing, 3M) and small PC board (~2.5 cm×5 cm). With thermal actuation, the resistive sensor undergoes self-heating where the resistance of the sensor linearly increases with temperature per the coefficient of resistance of the metal (Au), FIG. 19. Direct conversion between resistance and temperature is achieved by device calibration. Each device is calibrated by measuring its resistance at five different temperatures, then plotting temperature vs. resistance to determine the slope. An infrared camera (FLIR One) is used to determine temperature.

Models for finite element analysis of thermal transport. Finite element analysis (FEA) modeling exploits commercial software ABAQUS [26] to capture the thermal response of the device on flat and curved-cylindrical samples. Inputs for FEA include approximations in conjunction with known and experimentally determined parameters. The known and experimental parameters include: (1) the thickness, and thermal conductivity (k) and diffusivity ($\alpha$) of the two encapsulation layers, polyimide (4 μm thick, k=0.52 W/mK, $\alpha$=0.32 $mm^2$/s [17,27]) and Ecoflex (50 μm thick, k=0.21 W/mK, $\alpha$=0.11 $mm^2$/s [17]), and (2) the temperature change ($\Delta T$) due to thermal actuation across select time points (i.e. $\Delta T$ at 2 s, 20 s, and 40 s etc.). FEA inputs also include: (A1) approximate resistive sensor area, and (A2) room air convection coefficients and (A3) the thermal diffusivity ($\alpha$) of the sample materials, which are assumed from literature or commercial standards. In the case of A1, the resistive sensor is treated as a circular surface with homogeneous outer contour and power. The FEA with and without the round resistive sensor approximation differs by only 1%, FIGS. 20A-20B. This approximation is valuable because it reduces the computation time. In the case of A2, a simple bench-experiment involving two different devices aids in the determination of the appropriate convective heat transfer coefficients that correspond to airflow over the device. Briefly, the first device, encapsulated with the normal Ecoflex thickness (50 μm), is laminated directly on a large, thick (10 mm), flat sample of Ecoflex (e.g. sample is considered a semi-infinite plane). Two different airflow environments (controlled and uncontrolled) are used when collecting experimental measurements: (1) controlled (i.e. a glass enclosure is placed over the device, protecting it from the low forced-flow of room air conditioning), and (2) uncontrolled (i.e. the forced convection airflow from standard room air conditioning is allowed to flow over the device). The second device, encapsulated on both the top and bottom sides with excess Ecoflex such that a semi-infinite plane can be considered for both sides of the device, allows for an effective air convection coefficient of 0 W/$m^2$K during heating. All other experimental conditions are the same for both devices. FEA is used to evaluate the point of minimum error (%) for both airflow environments considered with device 1 to determine the appropriate air convection coefficients. Based on minimum error FEA simulation, 6 W/m²K is the thermal coefficient for the "controlled" airflow case (this value is used in all FEA simulations unless otherwise noted) and 15 W/m²/K is the thermal coefficient for the "uncontrolled" airflow case, FIGS. 20C-20D.

The error between FEA and experimental data is minimized with respect to k for a given a. Here the error is defined as $$\text{Error} = \sqrt{\frac{1}{t_{total}} \int_0^{t_{total}} \left(\frac{\Delta T_{Exp} - \Delta T_{FEA}}{\Delta T_{FEA}}\right)^2 dt}, \quad (1)$$

where $\Delta T_{Exp}$ and $\Delta T_{FEA}$ are temperature increases in the experiment and FEA, respectively, and $t_{total}$ is the total measuring time. 2-dimensional (2D) error surfaces, with a (mm²/s) on the y-axis and k (W/mK) on the x-axis, show the points of minimum error, FIGS. 21 and 22.

Description of scaling law and related approximations. FEA techniques require considerable computing time when used as the basis for parameter extraction. The value of these methods for routine data analysis or for gaining insights into the thermal physics is limited. An alternative uses an analytical scaling law established based on the model illustrated in FIG. 23. The model approximates the device geometry as a uniform circular disk with equal power distribution, and it neglects the effects of air convection and the encapsulation layers (polyimide and Ecoflex). For a constant power density q (power per unit area), the temperature change ($\Delta T_p$) at any point in the cross-section (Point P in FIG. 24B) is obtained as $$\Delta T_p = \frac{Rq}{2k} \int_0^\infty J_0\left(\frac{r_p x}{R}\right) J_1(x) \quad (2)$$

$$\left[e^{-\frac{xz}{R}} \text{erfc}\left(\frac{z}{2\sqrt{\alpha t}} - x\sqrt{\frac{\alpha t}{R^2}}\right) - e^{\frac{xz}{R}} \text{erfc}\left(\frac{z}{2\sqrt{\alpha t}} + x\sqrt{\frac{\alpha t}{R^2}}\right)\right] \frac{dx}{x},$$

where R is the radius of the resistive sensor, $r_p$ and z are the coordinates of P (FIG. 23B), $J_0$ and $J_1$ are the Bessel functions of the first kind with zero- and first-orders, respectively, and erfc is the complementary error function [28]. The average temperature change of the resistive sensor (z=0, $r_p$<R) is $$\Delta T = \frac{1}{\pi R^2} \int_0^R 2\pi r_p \Delta T_p dr = \frac{2qR}{k} \int_0^\infty \left\{[J_1(x)]^2 \text{erf}\left(x\sqrt{\frac{\alpha t}{R^2}}\right)\right\} \frac{dx}{x^2}, \quad (3)$$

where erf is the error function. Therefore, the normalized temperature change, $\Delta Tk/(qR)$, and the normalized time, $\alpha t/R^2$ satisfy the following scaling law $$\frac{\Delta Tk}{qR} = f\left(\frac{\alpha t}{R^2}\right). \quad (4)$$

Experimental procedures for measuring the thermal conductivity. Described herein are three different device sizes (R=0.5 mm, 1.5 mm and 2.0 mm) are used across three different durations of heating (i.e. thermal actuation for t=2 s, 20 s and 40 s), at a power density of 3 mW/mm² unless noted otherwise. To reduce the influence of air convection, a glass dish (~200 mm diameter×~100 mm deep) is placed over both the device and the sample area during data collection. The recorded data consist of temperature changes ($\Delta T$, °C.) inferred from measured changes in resistance as a function of time before and after thermal actuation. In all cases, the temperature remains constant prior to actuation, it increases during actuation and then decreases after actuation ceases, as in FIG. 21 and FIG. 22. Sample surface types include six different polymeric skin-mimicking substrates (either flat or curved) as well as directly on skin (measurements taken on volunteers). All measurements are collected in triplicate and error is reported as the standard deviation of the corresponding experimental variation for each dataset (c.f FIG. 24).

Preparation of samples with flat surfaces. Thermoplastic molds are used to create sample disks (radius 30 mm, thickness 10 mm), large enough to be considered as semi-infinite planes when used for data collection, composed of skin-mimicking polymeric materials. The thermal conductivities are well established for the selected materials, also their k values are similar to those seen for different layers of biological skins [17, 29, 30]. The six materials include: polyisobutylene (PIB; BASF), Sylgard 184, and Sylgard 170 (S184, S170; Dow Chemical Co.), Ecoflex (EF; Smooth-On), low density polyethylene (LDPE; Sigma Aldrich), and polyacrylic (PA; Plastics Inc.).

Preparation of samples with curved surfaces. Casting and curing (70° C. for 24 h) liquid silicone (S184) prepolymers in cylindrical thermoplastic molds yield curved samples with curvature ratios, r/R, of 2.6, 4.8 and 7.2, where r is the radius of the cylindrical mold and R is the radius of the resistive sensor, FIG. 25A.

Measurements of the thermal conductivity of skin. Measurements involve application of devices (R=1.5 mm) onto the anterior bicep, volar forearm, mid cheek, lateral aspect of neck, nose, palm, edge-most shoulder region, and ankle of two healthy volunteers (Subject 1: 33 yo female; Subject 2: 33 yo male) for a thermal actuation period of 2 s at a power density of 3 mW/mm². Gently cleaning the skin with medical grade isopropyl alcohol pad prepares the skin for measurement. Values of k derived from application of FEA and the scaling law appear in Table 1.

Measurements following the development of erythema. The erythema recovery studies involve measurements of changes in the thermal properties (surface temperature in ° C., k and $\Delta T$) of Fitzpatrick Type 1 skin as a function of recovery time following erythema induced by solar radiation (sunburn), heat-stress (induced via medical grade heating pad; Sunbeam Health at Home Heating Pad, ~50° C.), and cold-stress (induced via ice pack; homemade ice pouch enclosed in plastic bag), FIG. 27. Gently cleaning the skin with medical grade isopropyl alcohol pad prepares the skin for measurement. A device with R=2.0 mm, operated with a thermal actuation period of up to 60 s and a power density of 2 mW/mm², serves as the basis for the assessments. Note that the 60 s measurement time for skin characterization is longer than the 40 s thermal actuation interval for synthetic samples. The calculation of k remains the same regardless of the 40 s vs 60 s time interval. Here, the additional measurement time simply provides a clearer visualization of the differences in $\Delta T$ across sample times.

Results and Discussion

Measurement time, procedures for parameter extraction and device dimensions. Systematic studies of the influence of procedures for modeling and parameter extraction, measurement time (i.e. duration of thermal actuation), and device size reveal key considerations in accurate determination of k. Evaluation and discussion of these contributions appear in the following.

Measurement time. As previously stated, thermal actuation of the resistive sensor causes an increase in its temperature. The temperature increases rapidly for short durations (i.e. 2 s) of thermal actuation (measurement time) and increases incrementally at longer durations (i.e. >40 s) of thermal actuation with the latter resembling a pseudo steady-state system of $\Delta T$ as a function of time (i.e. $\Delta T$ appears to reach a stable non-changing value after long periods of time; however, it is known that the transient plane source system does not reach a true stead-state, hence use of the phrase: pseudo steady-state). For example, consider the temperature profile for experimental data collected using a resistive sensor (R=1.5 mm) on a flat Ecoflex surface at q=3 mW/mm$^2$, over the course of three separate time points: 2 s, 20 s, and 40 s. At 2 s, the temperature increases ($\Delta T$) by 5.65±0.01° C. At 20 s, $\Delta T$=10.62±0.02° C., and at 40 s, $\Delta T$=11.68±0.02° C., FIG. 21B. The k's determined by FEA at each time point are 0.22±0.02 W/mK, 0.22±0.01 W/mK, and 0.22±0.00 W/mK at 2 s, 20 s, and 40 s, respectively. The general shape of the temperature profiles across all sample data sets are similar (i.e. sharp increase in $\Delta T$ at shorter measurement times followed by incremental differences in $\Delta T$ at longer measurement times) and the influence of $\Delta T$ at a given time point on k extracted from FEA is small. However, while the value of k does not change significantly as a function of measurement times between 2 s and 40 s, the shape of the 2D error surface shifts from a more horizontal to a more vertical position, see for example FIGS. 21E, 21H and 21K. This shift occurs because, in general, a can be considered as the ratio of the time derivative of temperature to its curvature; thus, a is a measure of 'thermal inertia' such that the effect of a diminishes as a function of longer heating times [31]. This phenomenon leads to calculations that depend mainly on k and less on a at long measurement times when the sample surface is a semi-infinite plane. Table 2 provides a compilation of k determined by FEA at 2 s, 20 s, and 40 s, for the six-different skin-mimicking materials, which closely resemble values reported in literature [37-41].

Sensor size. The size of the resistive sensor is also important to consider in determining k, as illustrated in a series of measurements using devices with R of 0.5 mm, 1.5 mm and 2.0 mm and thermal actuation times of 2 s, 20 s, and 40 s. In general, the 2D error surface plots suggest that the error in FEA simulated k is largest for the smallest device (R=0.5 mm), FIGS. 21D-21L, compared to the minimum error for k values determined using the two larger devices (R=1.5 mm and 2.0 mm), which have similar minimum error results. To explain the improved minimum error for the larger sensor size observed in the 2D error surface plots, two additional components are considered. First, the FEA input includes consideration of a 50 μm thick bilayer encapsulation of Ecoflex, but the impact of the encapsulation layer is not weighted based on the sensor size. Thus, increasing error with decreasing heater size may be attributed to the encapsulation layer. For example, at R=0.5 mm, the ratio of the encapsulation thickness to the device radius is significant (i.e. 50 μm/500 μm~10% vs. 50 μm/1500 μm~3.3%, and 50 μm/2000 μm~2%), thereby resulting in uncertainties associated with uncertainties in the thickness and wear of the Ecoflex encapsulation layer. Second, because conduction scales linearly with (device) surface area, when a larger resistive sensor size is considered in FEA, the temperature is averaged over a larger area. As a result, the effect of in-plane (x-y-direction) heat dissipation diminishes relative to heat conduction into the material (z-direction) as the sensor size decreases. As a visual demonstration, thermal actuation (t=~5 s, R=2.0 mm, q=2 mW/mm$^2$) is used to compare thermal images of two device sizes, FIG. 27. Similar results are observed across the skin-mimicking sample types, which are tabulated in Table 2. All results for k are in excellent agreement with previous literature reports and commercial values [37-41].

Scaling law. The scaling law, introduced in equation 4, is of interest as a straight forward method to yield k without the need for laborious FEA simulations (or the need to analytically solve the heat equation). Plots of $\Delta Tk$ qR vs. at $R^2$ with corresponding FEA overlay allow for initial evaluation of the scaling law, FIG. 23. The plotted scaling law and FEA profiles are in excellent agreement with each other, thereby validating that the scaling law could be a suitable alternative for determination of k. To further evaluate scaling law reliability, the 6 skin-mimicking materials are used for data collection at three different actuation times (2 s, 20 s, and 40 s) and three resistive sensor sizes (R=0.5 mm, 1.0 mm, and 1.5 mm), enabling the direct comparison of the k values calculated by both the scaling law and FEA, Table 2 and Table 3, respectively. Here, k is reported as a narrow range instead of a single value to exemplify the effect of differences in a. Specifically, while a values for the current skin-mimicking materials have been reported, we acknowledge that there could be variation in the exact value of a across sample batches. To account for these differences, we allow a to vary by 10% from the literature value. As a result, the reported k values represent the lower and upper bounds of a. The a values relevant to this work are: S170: 0.11-0.17 mm$^2$s, LDPE: 0.14-0.20 mm$^2$/s, EF: 0.09-0.13 mm$^2$/s, PIB: 0.08-0.12 mm$^2$/s, and PA: 0.09-0.13 mm$^2$/s [17, 30a-e]. In some cases, the k values observed between the scaling law (SL) and FEA are similar such as for S170 at 2 s (FEA: 0.42±0.03 W/mK vs SL: 0.41±0.03 W/mK), 20 s (FEA: 0.52±0.02 W/mK vs SL: 0.51±0.02), and 40 s (FEA: 0.55±0.01 W/mK vs. SL: 0.54±0.01 W/mK). In other cases, the average k values deviate slightly but remain within the values reported by literature such as for S184 at 2 s (FEA: 0.21±0.02 W/mK vs SL: 0.24±0.02 W/mK), 20 s (FEA: 0.21±0.01 W/mK vs SL: 0.24±0.01 W/mK), and 40 s (FEA: 0.22±0.01 W/mK vs SL: 0.25±0.01 W/mK). Deviations in the latter case are anticipated and may be explained by the difference in initial approximations incorporated with FEA compared to the scaling law. Recall that the scaling law does not account for the encapsulation bilayers of PI and Ecoflex or the effects of the small, albeit measurable, airflow generated by room air conditioning. As a result of the overall excellent agreement between the scaling law and FEA, the scaling law is used hence force for determining k on curves surfaces, healthy skin and during erythema recovery.

Measurements on samples with curved surfaces. Most biological samples have curved, non-planar surfaces. A relevant parameter in this context is the radius ratio, r/R, where r is the radius of curvature of the sample at the measurement location and R is the radius of the device (FIG. 25A). For example, the radius of a forearm of a healthy, medium-sized adult is ~80 mm, such that a device with R=1.5 mm has a radius ratio of ~53. For the neck of a typical adult (r=60 mm), the radius ratio is 40. Values for an index finger (6.5), a toddler's forearm (~25) [32], or the index finger of a toddler (5) [33] lie in the lower range. Experimental studies to determine k across this range establish the effects of curvature on the measurement. Specifically, a device with R=0.5 mm applied to cylinders of S184 with r=1.3 mm, 2.4 mm and 3.6 mm results in radius ratios of 2.6, 4.8 and 7.2, FIG. 25B. Parameter extraction using the scaling law yield k=0.18±0.01 W/mK, which is within 0.02 W/mK compared to the k measured from S184 with a flat surface (r/R=∞; 0.16±0.00 W/mK). Data collection involve recording the ΔT (° C.) immediately following thermal actuation for 2 s. Analysis by FEA and application of the scaling law on data collected from curved S184 samples yields k, FIG. 25B. An example of temperature plotted as a function of time (t=2 s) for a representative sample (r/R=2.6) is provided in conjunction with an FEA overlay in FIG. 25C. In the limit of small r/R, the sample itself is sufficiently small/thin such that the effect of the bottom side of the sample surface is not negligible. Simulations reveal the errors in extracted parameter values as a function of r/R (FIG. 25D). For a radius ratio 2.6, the simulated error is 10%. Based on the simulation in FIG. 25D, we estimate that the smallest radius ratio that can be approximated as a semi-infinite sample is 5 because the error at an r/R of 5 is 5%, which is similar to the accuracy limit seen with commercial measurement of k using the transient plane source method [34].

Measurements of the thermal conductivity of healthy skin. Applying devices to eight locations (ankle, anterior bicep, mid cheek, volar forearm, lateral aspect of neck, nose, palm, edge-most shoulder region) across two healthy adult volunteers (Subject 1 (Sub1): 33 yo female; Subject 2 (Sub2): 33 yo male) and analyzing the data using the scaling law and FEA yields corresponding values of k. Thermal diffusivity is selected as 0.15 mm$^2$/s because it is a value typical for healthy skin [20], however, α is known to deviate from this value across skin locations and types. To account for this deviation, all k values within 10% of α=0.15 mm$^2$/s are considered and are reported here as a 'k-range'. The k-range (based on α±10%) and radius of curvature ($R_c$) for the eight skin locations appear in Table 1 for both volunteers. In all cases, the deviation in k across a 10% is small. For Sub2 the lowest values of k appear at the nose (k=0.34 W/mK) and the palm (k=0.35 W/mK), while the ankle and shoulder exhibit relatively large values (k=0.46 W/mK). The remaining six locations for Sub2 have k values that fall between 0.34 W/mK and 0.46 W/mK with an average of 0.40±0.04 W/mK. The lowest k for Sub1 is at the palm (k=0.35 W/mK) and ankle (k=0.36 W/mK), while the highest occurs at the forearm and neck (k=0.47 W/mK). The remaining six locations for Sub1 have k values that fall between 0.35 W/mK and 0.47 W/mK with an average of 0.42±0.04 W/mK. In all cases, the k values extracted using the scaling law agree well with those determined by FEA, and with representative literature reports for skin Table 1 [15-23,35].

Assessing erythema recovery time. Currently, visual inspection of skin redness (intensity and surface coverage) is the most common method to determine erythema severity and recovery. This method, while visually informative, is qualitative. Thus, new characterization methods are needed to better quantify erythema recovery. Here, ΔT and k (calculated from the scaling law) are compared side-by-side to visual inspection of erythema to evaluate the potential of our resistive sensor to enable numerical quantification during recovery. Measurements of recovery involve skin exposed to: (1) one hour of sun (i.e. sunburn) on right forearm, (2) a heating pad over the left forearm for 20 min., and (3) an ice-pouch over the left forearm for 20 min (volunteer is a healthy, 33 yo female with Type I skin according to the Fitzpatrick scale (always burns, never tans)) [36]. In each case, measurements performed prior to the skin stressor (UV radiation, heat and cold) establish baseline values for the temperature ($T_{skin}$) and k of the skin, and the increase in temperature ($\Delta T_{skin}$) induced by 60 s of thermal actuation using a device with R=2.0 mm radius at a power density of 2 mW/mm$^2$.

For case 1 (solar radiation), exposure involves placing the right forearm of the volunteer under direct sunlight for 1 hour (UV-index 9, Urbana, IL, Jun. 3, 2017, 12-1:00 PM). Immediately afterward (t=0 h), the $T_{skin}$, $\Delta T_{skin}$, and k are 36.50±0.02° C., 5.83±0.04° C., and 0.46±0.01 W/mK, respectively, are comparable to the baseline values of 36.60±0.02° C., 5.75±0.08° C., and 0.46±0.00 W/mK. A non-blistered, evenly distributed, red color, corresponding to a common sunburn, appears 3-5 hours after exposure (FIG. 27C, image 2). By visual inspection (see digital images of forearm in FIG. 26C), the degree of erythema is high at t=5 h, then decreases slowly over the course of 15 days to return to the normal pale color of Fitzpatrick Type I skin. The lowest $\Delta T_{skin}$, and k occur at t=5 h (4.76±0.14° C. and 0.57±0.02 W/mK, respectively) when erythema, by visual indication, is the greatest. These values show monotonic trends until t=93 hrs (~4 days) when the erythema is faint in appearance, and the $\Delta T_{skin}$, and k (6.08±0.10° C., and 0.44±0.01 W/mK, respectively) resemble the baseline values. The $\Delta T_{skin}$, and k from 93 hrs-360 hrs remain nearly constant. The value of $T_{skin}$ changes very little throughout the erythema recovery, maintaining an average of 36.57±1.01° C. The result suggests that surface skin temperature may not strongly correlate with erythema recovery, and that $\Delta T_{skin}$, and k provide more meaningful measurements in this context, (FIGS. 27A and 27B).

For case 2 (heat-stress), placing the left forearm of the volunteer under a heating pad (~50° C.) for 20 min creates a thermal stress. The left forearm is measured directly following the heat-stress (Time, T=0 min.) at which time the skin is homogeneously light red in color suggesting moderate erythema (FIG. 27D, image 2). The average $\Delta T_{skin}$ and k at T=0 min. (4.57±0.03° C., and 0.58±0.00 W/mK, respectively) measured immediately afterward are lower than the respective baseline values (baseline at t=−20 min.: 5.87±0.21° C., and 0.45±0.02 W/mK). The skin temperature, however, is higher than baseline, consistent with expectation (at t=0 hr, $T_{skin}$=34.59±0.20° C. compared to t=−20 min and −60 min with $T_{skin}$=32.99±0.20° C.). Visual inspection indicates that the erythema decreases significantly within 15 min. following removal of the heat source (FIG. 27D, image 3). This result corresponds well with the change in thermal properties; for example, the $\Delta T_{skin}$ and k at T=15 min are 5.39±0.13° C. and 0.49±0.01 W/mK, respectively, and the skin temperature decreases to 33.51±0.20° C. Visually, full erythema recovery occurs within 45 min. (FIG. 27D, image 4). By contrast, the thermal properties recover to baseline values only after 2 h (FIGS. 27E-27F). Similar to case 1, the results suggest that skin temperature is a poor indicator erythema recovery, and that $\Delta T_{skin}$ and k are more informative.

For case 3 (cold-stress) and ice-pouch rests over the left forearm of the volunteer for 20 min. The average $\Delta T_{skin}$ and k at t=0 min (5.63±0.09° C., and 0.47±0.01 W/mK, respectively), when the skin is bright red, are approximately the same as baseline values (baseline at T=−5 min: 5.67±0.15° C., and 0.47±0.01 W/mK, respectively; baseline at T=−20 min.: 5.87±0.02° C., and 0.45±0.00 W/mK), (FIG. 27G, image 2). Immediately after removing the ice-pack (T=0 min) the skin temperature is lower than baseline (at T=0 hr, $T_{skin}$=24.59±0.20° C. compared to T=−5 min with $T_{skin}$=32.39±0.20° C. and −20 min with $T_{skin}$=31.88±0.23° C.). At t=6 min the erythema visually appears to be resolved (FIG. 27G, image 3). At this point, $\Delta T_{skin}$ is 5.67±0.10° C.; $T_{skin}$ is 28.35±0.25° C. at t=10 min and k=0.47±0.01 W/mK. The skin temperature returns to baseline within −30 min. ($T_{skin}$=30.21±0.23° C. at t=20 min, $T_{skin}$=33.57±0.23° C. at t=40 min., and $T_{skin}$=33.81±0.23° C. at t=60 min. The values of $\Delta T_{skin}$ and k show no significant changes throughout the recovery (FIGS. 27H-27I). Visually, the erythema is nearly completely resolved in less than 5 min. These results suggest that $\Delta T_{skin}$ and k may have limited value in monitoring erythema recovery following exposure to cold-stress compared to heat- and solar-stress. The visual imagery and numerical $\Delta T$ and k values compared above provide the initial groundwork that now enables this mode of thermal sensing to be further investigated as a non-invasive, highly conformal evaluation tool during additional studies of erythema recovery across various skin types and skin-stress intensities.

Conclusions. The thin, skin-like resistive sensors presented here build on existing concepts in epidermal electronics, and are used, in conjunction with FEA, to validate scaling laws for data interpretation and extraction of thermal conductivities of skin and non-biological soft materials. The quantitative measurement and characterization methods described in this report for determination of thermal conductivity are successfully employed to evaluate the thermal properties of skin during recovery from exposure to ultraviolet radiation (sunburn) and to stressors associated with localized heating and cooling. These results provide a foundation to extend the use of the resistive sensors and scaling laws to facilitate rapid, noninvasive thermal measurements on broad classes of biological and non-biological soft materials, as well as the opportunity to further study skin injury in clinically relevant settings.

REFERENCES FOR EXAMPLE 2

[1] Marieb, Elaine; Katja Hoehn (2007). Human Anatomy & Physiology (7th ed.). Pearson Benjamin Cummings. p. 142.
[2] Martini & Nath: "Fundamentals of Anatomy & Physiology" 8th Edition, pp. 158, Pearson Education, 2009.
[3] Kim, D. H.; Lu, N. S.; Ma, R.; Kim, Y.-S.; Kim, R.-H.; Wang, S.; Wu, J.; Won, S. M.; Tao, H.; Islam, A.; Yu, K.-J.; Kim, T.-I; Chowdhury, R.; Ying, M.; Xu, L.; Li, M.; Chung, H.-J.; Keum, H.; McCormick, M.; Liu, P.; Zhang, Y.-W.; Omenetto, F. G.; Huang, Y.; Coleman, T.; Rogers, J. A. Epidermal Electronics. Science 2011, 333, 838-843.
[4] Wang, S. D.; Li, M.; Wu, J.; Kim, D.-H.; Lu, N.; Su, Y.; Kang, Z.; Huang, Y.; Rogers, J. A. Mechanics of Epidermal Electronics. J. Appl. Mech. 2012, 3, 031022.
[5] Rogers, J. A.; Someya, T.; Huang, Y. Materials and Mechanics for Stretchable Electronics. Science 2010, 327, 1603-1607.
[6] Zhang, Y.; Huang, Y.; Rogers, J. A. Mechanics of Stretchable Batteries and Supercapacitors. Curr. Opin. Solid. St. M. 2015, 19, 190-199.
[7] Zhang, Y.; Fu, H.; Su, Y.; Xu, S.; Cheng, H.; Fan, J. A.; Hwang, K.-C.; Rogers, J. A.; Huang, Y. Mechanics of Ultra-Stretchable Self-Similar Serpentine Interconnects. Acta Mater. 2013, 61, 7816-7827.
[8] Zhang, Y.; Wang, S.; Li, X.; Fan, J. A.; Xu, S.; Song, Y. M.; Choi, K.-J.; Yeo, W.-H.; Lee, W.; Nazaar, S. N.; Lu, B.; Yin, L.; Hwang, K.-C.; Rogers, J. A.; Huang, Y. Experimental and Theoretical Studies of Serpentine Microstructures Bonded to Prestrained Elastomers for Stretchable Electronics. Adv. Func. Mater. 2014, 24, 2028-2037.
[9] Guo, C. F.; Liu, Q.; Wang, G.; Wang, Y.; Shi, Z.; Sou, Z.; Chu, C. W.; Ren, Z. Fatigue-Free, Superstretchable, Transparent, and Biocompatible Metal Electrodes. P. Natl. Acad. Sci. USA. 2015, 112, 12332-12337.
[10] Kim, D. H.; Ahn, J. H.; Won, M. C.; Kim, H.-S.; Kim, T.-H.; Song, J.; Huang, Y. Y.; Liu, Z.; Lu, C.; Rogers, J. A. Stretchable and Foldable Silicon Integrated Circuits. Science 2008, 320, 507-511.
[11] a. White, M. S.; Kaltenbrunner, M.; Gtowacki, E. D.; Gutnichenko, K.; Kettlegruber, G.; Graz, I.; Aazou, S.; Ulbricht, C.; Egbe, D. A.; Miron, M. C.; Major, Z.; Scharber, M. C.; Sekitani, T.; Someya, T.; Seigfried, B.; Sariciftci, N. S. "Ultrathin, highly flexible and stretchable PLEDs" Nat. Photonics, 2013, 7, 811-816. b. Melzer, M.; Kaltenbrunner, M.; Makarov, D.; Karnaushenko, D.; Karnaushenko, D.; Sekitani, T.; Someya, T.; Schmidt, O. G. Imperceptible Magnetoelectronics. Nat. Commun. 2015, 6, 6050. c. Bauer, S.; Bauer-Gogonea, S.; Graz, I.; Kaltenbrunner, M.; Keplinger, C.; Schwodiauer, R. $25^{th}$ Anniversary Article: A Soft Future: From Robots and Sensor Skin to Energy Harvesters. 2014, 1, 149-161.
[12] a. Benight, S. J.; Wang, C.; Tok, J. B. H.; Bao, Z. Stretchable and Self-Healing Polymers and Devices for Electronic Skin. Prog. Polym. Sci. 2013, 12, 1961-1977. b. Hammock, M. L.; Chortos, A.; Tee, B. C.-K.; Tok, J. B.-H.; Bao, Z. $25^{th}$ Anniversary Article: The Evolution of Electronic Skin (E-Skin): A Brief History, Design Considerations, and Recent Progress. Adv. Mater. 2013, 42, 5997-6038.
[13] Klinker, L; Lee, S.; Work, J.; Wright, J.; Ma, Y.; Ptaszek, L.; Webb, R. C.; Liu, C.; Sheth, N.; Mansour, M.; Rogers, J. A.; Huang, Y.; Chen, H.; Ghaffari, R. Balloon Catheters with Integrated Stretchable Electronics for Electrical Stimulation, Ablation and Blood Flow Monitoring. Extreme Mechanics Lett. 2015, 3, 45-54.
[14] Hattori, Y.; Falgout, L.; Lee, W.; Jung, S. Y.; Poon, E.; Lee, J. W.; Na, I.; Geisler, A.; Sadhwani, D.; Zhang, Y.; Su, Y.; Wang, X.; Liu, Z.; Xia, J.; Cheng, H.; Webb, R. C.; Bonifas, A. P.; Won, P.; Jeong, J. W.; Jang, K. I.; Song, Y. M.; Nardone, B.; Nodzenski, M.; Fan, J. A.; Huang, Y.; West, D. P.; Paller, A. S.; Alam, M.; Yeo, W. H.; Rogers, J. A. Multifunctional Skin-Like Electronics for Quantitative, Clinical Monitoring of Cutaneous Wound Healing. Adv. Health. Mater. 3, 2014, 1597-1607.
[15] Zhang, Y.; Webb, R. C.; Luo, H.; Xue, Y.; Kurniawan, J.; Cho, N. H.; Krishnan, S.; Li, Y.; Huang, Y.; Rogers, J. A. Theoretical and Experimental Studies of Epidermal Heat Flux Sensors for Measurements of Core Body Temperature. Adv. Health. Mater. 2016, 5, 119-127.
[16] a. Krishnan, S.; Shi, Y.; Webb, R. C.; Ma, Y.; Bastien, P.; Crawford, K. E.; Wang, A.; Feng, X.; Manco, M.; Kurniawan, J.; Tir, E.; Huang, Y.; Balooch, G.; Pielak, R. M.; Rogers, J. A. "Multimodal Epidermal Devices for Hydration Monitoring," Microsystems & Nanoengineering 2017, 3, 17014. b. Huang, X.; Yeo, W.-H.; Liu, Y.; Rogers, J. A. Epidermal Differential Impedance Sensor for Conformal Skin Hydration Monitoring. Biointerphaces 2012, 7, 52.
[17] Tian, L.; Li, Y.; Webb, R. C.; Krishnan, S.; Bian, Z.; Song, J.; Ning, X.; Crawford, K.; Kurniawan, J.; Bonifas, A.; Ma, J.; Liu, Y.; Xie, X.; Chen, J.; Liu, Y.; Shi, Z.; Wu, T.; Ning, R.; Li, D.; Sinha, S.; Cahill, D. G.; Huang, Y.;

Rogers, J. A. Flexible and Stretchable 3-Omega Sensors for Thermal Characterization of Human Skin. *Adv. Func. Mater.* 2017, 27, 1701282.

[18] Koh, A.; Gutcrog, S. R.; Meyers, J. D.; Lu, C.; Webb, R. C.; Shin, G.; Li, Y.; Kang, S. K.; Huang, Y.; Efimov, I. R.; Rogers, J. A. Ultrathin Injectable Sensors of Temperature, Thermal Conductivity, Heath Capacity for Cardiac Ablation Monitoring. *Adv. Health. Mater.* 2016, 5, 373-381.

[19] Gao, L.; Zhang, Y.; Malyarchuk, V.; Jia, L.; Jang, K. I.; Webb, R. C.; Fu, H.; Shi, Y.; Zhou, G.; Shi, L.; Shah, D.; Huang, X.; Xu, B.; Yu, C.; Huang, Y.; Rogers, J. A. Epidermal Photonic Devices for Quantitative Imaging of Temperature and Thermal Transport Characteristics of the Skin. *Nature Commun.* 2014, 5, 4938.

[20] Webb, R. C.; Pielak, R. M.; Bastien, P.; Ayers, J.; Niittynen, J.; Kurniawan, J.; Manco, M.; Lin, A.; Cho, N. H.; Malyrchuk, V.; Balooch, G.; Rogers, J. A. Thermal Transport Characteristics of Human Skin Measured in Vivo using Ultrathin Conformal Arrays of Thermal Sensors and Actuators. *PLoS ONE* 2015, 10, e0118131.

[21] Webb, R. C.; Ma, Y.; Krishnan, S.; Li, Y.; Yoon, S.; Guo, X.; Feng, X.; Shi, Y.; Seidel, M.; Cho, N. H.; Kirniawan, J.; Ahad, J.; Sheth, N.; Kim, J.; Taylor, J. G.; Darlington, T.; Chang, K.; Huang, W.; Ayers, J.; Gruebele, A.; Pielak, R. M.; Slepian, M. J.; Huang, Y.; Gorbach, A. M.; Rogers, J. A. Epidermal Devices for Noninvasive, Precise, and Continuous Mapping of Macrovascular and Microvascular Blood Fow. *Science Adv.* 2015, 1, e1500701.

[22] Bian, Z.; Song, J.; Webb, R. C.; Bonifas, A. P.; Rogers, J. A.; Huang, Y. Thermal Analysis of Ultrathin, Compliant Sensors for Characterization of the Human Skin. *RSC Adv.* 2014, 4, 5694-5697.

[23] Webb, R. C.; Bonifas, A. P.; Behnaz, A.; et al. Ultrathin Conformal Devices for Precise and Continuous Thermal Characterization of Human Skin. *Nature Mater.* 2013, 12, 938-944.

[24] Wilkin, J. K. Oral Thermal-Induced Flushing in Erythematotelangiectatic Rosacea. *J. Investigative Dermatology,* 1981, 76, 15-18.

[25] *Mosby's MedicalDictionary* (9$^{th}$ Ed.). St. Louis, Missouri: Elsevier. 2013, ISBN 978-0-323-08541-0.

[26] ABAQUS Analysis User's Manual 2014, V6.14.

[27] Mit.edu/~6.777/matprops/polyimide.htm (accessed 12/4/17).

[28] Carslaw, H. S.; Jaeger, J. C. (1959) *Conduction of Heat in Solids*. Oxford: Clarendon Press. 510 pp.

[29] Cohen, M. L. Measurement of the Thermal Properties of Human Skin. A Review. *J. Invest. Dermatol.* 1977, 69, 333-338.

[30] a. I. Benedek and M. M. Feldstein (Eds), Handbook of Pressure Sensitive Adhesives and Products, Taylor and Francis Group, Boca Raton 2009. b. Tucker, G., Development and application of time-temperature integrators to thermal food processing, Ph.D. thesis, University of Birmingham 2008. c. http://www.aetnaplastics.com/site_media/media/documents/acrylite_ff_material_data_sheet.pdf. accessed 022518. d. http://www.abgrp.co.uk/downloads/abg-datasheets/ldpe.pdf. accessed 022518. e. http://www.professionalplastics.com/professional plastics/thermalpropertiesofplasticmaterials. pdf. accessed 022518.

[31] Fundamentals of Heat and Mass Transfer (1$^{st}$ ed.). PHI Learning Pvt. Ltd., 2010. ISBN 8120340310.

[32] WHO child growth standards: length/height-for-age, weight-for-age, weight-for-length, weight-for-height and body mass index-for-age: methods and development. ISBN92-4-154693-X.

[33] Hohendorff B, Weidermann C, Burkhart J K, Rommens P M, Prommersberger K J, Konerding M A. Lengths, Girths, and Diameters of Children's Fingers from 3 to 10 years of age. Ann Anat. 3, 2010, 156-161.

[34] http://ctherm.com/files/C-Therm_TCi_Thermal_Conductivity_-_2016.pdf. Accessed 0215018.

[35] van de Staak, W. J. B.; Brakker, A. J. M.; de Rijke-Herweijer, H. E.; Measurements of the Thermal Conductivity of the Skin as an Indication of Skin Blood Flow. *J. Invest. Dermatol.* 1968, 5, 149-154.

[36] Fitzpatrick, T. B. The Validity and Practicality of Sun-Reactive Skin Types I through IV. *Arch. Dermatol.* 1988, 124, 869-871.

[37] a. https://www.professionalplastics.com/professional-plastics/ThermalPropertiesofPlastic Materials.pdf. accessed 022518. b. https://www.makeitfrom.com/material-properties/Low-Density-Polyethylene-LDPE. c. www.spring.com/978-3540-44376-6. Accessed 022518.

[38] a. http://research.engineering.ucdavis.edu/ncnc/wp-content/uploads/sites/11/2013/05/Sylgard_184_data_sheet.pdf. accessed 022518. b. https://krayden.com/sylgard-184/. accessed 022518. c. Erickson, D.; Sinton, D.; Li, D. Joule Heating and Heat Transfer in Poly(dimethylsiloxane) Microfluidic Systems. *Lab Chip* 2003, 3, 141-149.

[39] a. https://worldaccount.basf.com/wa/NAFTA/Catalog/ChemicalsNAFTA/doc4/BASF/PRD/30041534/Product%20information.pdf?title=&asset_type=pi/pdf&language=EN&urn=urn:do cumentum: eCommerce_sol_EU:09007bb28001eca2.pdf. accessed 022518. b. Andersson, S. P. Pressure and Volume Dependence of Thermal Conductivity and Isothermal Bulk Modulus up to 1 GPa for Poly(isobutylene). *J. Polym. Sci. B Polym. Phys.* 1998, 36, 1781-1792.

[40] a. Springer Handbook of Condensed Matter and Materials Data. Martienssen, W.; Warlimont, H. Springer-Verlag Berlin Heidelberg. 2005, 488 pp. ISBN: 978-3-540-30437-1. b. https://www.makeitfrom.com/material-properties/Polymethylmethacrylate-PMMAAcrylic. Accessed 022518.

[41] a. Dow Corning Sylgard 170 Silicone Elastomer Product Information. Accessed 022518.

Example 3: Epidermal Electronic Systems for Measuring the Thermal Properties of Human Skin at Depths of Up to Several Millimeters (and appended supplemental 23 page section, with FIGS. S1-S11, Tables S1-S4 and explanatory text, available at onlinelibrary.wiley.com/doi/pdf/10.1002/adfm.201802083 for corresponding paper described as published 25 Jun. 2018 by the journal Advanced Functional Materials, and specifically incorporated by reference herein).

Monitoring the composition, blood flow properties, and hydration status of human skin is essential for diagnosing disease and tracking overall health. Current methods are largely limited to clinical environments, and primarily measure properties of superficial layers of the skin, such as the stratum corneum (10-40 μm). This example introduces soft, skin-like epidermal thermal depth sensors (e-TDS) in designs that seamlessly couple with human skin capable of reliably measuring thermal subdermally, such as up to 6 millimeters in depth from a surface. Guidelines for tailoring devices to enable measurements through different effective depths follow from a systematic set of experiments, supported by theoretical modeling. On-body testing validates the physiological relevance of measurements using the e-TDS platform, with potential to aid diagnosis of deep cutaneous and systemic diseases. Specific demonstrations include measurements that capture responses ranging from superficial changes in skin properties that result from application of a moisturizer, to changes in microvascular flow at intermediate depths induced by heating/cooling, to detection of inflammation in the deep dermis and subcutaneous fat in an incidence of a local bacterial infection, cellulitis.

Biophysical/chemical measurements performed through human skin represent an attractive modality for the noninvasive assessment of a wide range of bodily structures and functions.[1] Deriving insights on physiological processes that extend beyond the uppermost layers of skin like the epidermis (~100 μm thickness) by capturing parameters related to deep tissue inflammation, core body temperature, or core body hydration remain as key challenges.[2] Quantitative techniques such as corneometry and laser doppler flowmetry immobilize patients and require specialized, expensive equipment. Imaging methods such as ultrasound, computer aided tomography (CT), and magnetic resonance imaging (MRI) require long measurement times, clinical expertise for interpretation, high cost, and the risk of irradiation.[3] Clinical visual inspection often leads to high misdiagnosis rates for pathologies that appear similar at the surface of the skin.[4] Thus, there is a continued need for inexpensive and robust point-of-care sensors capable of capturing broader insights into human physiology and disease.

Measurements of the thermal properties of human skin are attractive because they can be accomplished in a noninvasive manner, without significant motion artifacts or direct input of electrical current into the skin.[5] Thermal conductivity (k) and thermal diffusivity ($\alpha$) are useful parameters as they lend insight into a wide range of physiological characteristics including tissue composition, local blood flow, and tissue hydration.[6] The transient plane source (TPS) technique can capture these properties in a real time fashion, with capabilities in depth-profiling that follow from the governing physics of thermal diffusion and conduction.[7] Advanced device embodiments in thin, elastomeric forms facilitate such measurements on human skin, yet prior studies focus only on measurements of superficial layers (~5 μm-1 mm), thereby limiting applications to the skin surface.[5b,6,8]

In this example, we present soft, skin-like sensors that evaluate k at different depths of skin and tissue, including up to 6 mm. The epidermal sensors are conformal to the skin, soft, stretchable, reusable, and non-invasive. The good adhesion and conformity of the device assists in efficient heat transfer between the sensor and the skin. Studies of heat transport reveal optimized measurement conditions and sensor designs for controlled levels of depth sensitivity. Specifically, experimental and theoretical investigations on well-defined materials structures that mimic the skin establish key parameters that provide the framework for a tunable depth-sensing system. Use of these sensors in various investigations with human subjects yield insights into physiological changes in the skin via thermal property measurements. The results represent the first demonstrations of a non-invasive, skin-interfaced sensor with capabilities for large measurement depths, and provide a platform to uncover important physiological and clinical parameters in ways that bypass limitations of other approaches.

Device structure and operation using a single-layer model: Each epidermal thermal depth sensor (e-TDS) comprises a thin metal trace (Au, 5-10 μm width) in a circular, coil geometry (radius R), with a pair of serpentine interconnects (Au, less than or equal to 200 μm, such as 100 μm width and length less than or equal to 2.5R, such as about 2R, with resistance <100Ω) and corresponding bond pads for external wiring (FIG. 28). Layers of polyimide (PI) on top and bottom electrically insulate these traces. A thin layer of a flexible material, such as silicone elastomer, serves as a substrate that allows repeated cycles of conformal contact and release from surfaces of samples under test.

To understand the physics of heat transport associated with these devices, consider measurements on a homogeneous, semi-infinite substrate (silicone, whose thermal properties are in the range of those of human skin) doped with a thermochromic dye that changes in color from black to pink at T~25° C. Injecting direct current (DC) electrical power into the sensing coil, with power per unit area of q, at some initial time creates an increase in temperature throughout a localized area of material. The corresponding changes in color occur with spatio-temporal characteristics, reflecting the thermal physics (FIG. 28, middle panels). Specifically, the heat spreads with time, downward into the substrate and radially in the plane by similar distances due to the isotropic nature of heat conduction in this material system. Wiring and data acquisition are described herein. Finite element analysis (FEA) (FIG. 28, bottom panels) quantitatively captures the observed behaviors and their dependence on the thermal conductivity and diffusivity (k and $\alpha$) of the material and the value of q. The temperature of the sensing coil (T) increases from its initial value by an amount $\Delta T$ that depends on time (t) after initiation of thermal actuation. $\Delta T$ depends linearly on q for all materials and heating conditions investigated in this work. As a result, linear thermal analysis by FEA can used to extract k from the measured $\Delta T$, given known values of a, R, t and q (details on TPS measurements and FEA fitting are in the methods section). All FEA simulations consider the thermal properties of each layer of the e-TDS, including the PI encapsulation and elastomer substrate.

Unlike silicone and other standard materials, human skin can display large variations in thermal properties, and thus the values a and k are generally unknown.[6a,9] This example considers k as the most relevant thermal parameter to characterize human skin because it is linearly related to physiological properties such as skin water content and, by comparison to a, it can be extracted with higher accuracy using fits to FEA.[6c] During the initial rise in temperature after initiating thermal actuation, both a and k affect the thermal response; at longer times, when $\Delta T$ reaches a quasi-steady state value, only k is important. For practical applications outlined here, the e-TDS operates in this regime (when $t > t_{min}$, typically a few tens of seconds for skin). In addition to FEA, an analytical scaling law that relates a to $\Delta T$ reveals that knowledge of a is not necessary for accurate extraction of k from $\Delta T$ measured for $t > t_{min}$. Specifically, calculations show that in this quasi-steady state regime, $\Delta T$ varies by <5% for values of a across the full physiological range. The following studies focus on measurements in this regime.

Depth sensitivity of e-TDS using a multilayer model for human skin: Human skin is inhomogeneous and comprises three layers. The outermost layer is the epidermis and acts as a waterproof barrier. Beneath it, the dermis consists of collagen and imparts the mechanical strength of skin. Finally, deeper subcutaneous tissue contains fat and additional connective tissue. Each layer exhibits different a and k due to variations in composition, blood flow, and water content.[5b,6a,6d] All of these layers affect, to different degrees, the ΔT measured by an e-TDS. Studies reported here approximate the skin as a bilayer system to simplify analysis and allow assessment of the choice of e-TDS designs and measurement conditions on ΔT, all in the context of extracting accurate values of k. In this treatment, the epidermis and dermis (E+D) form the top layer (the epidermis is 0.1× as thick as the dermis)[10] and the subcutaneous fat constitutes the bottom layer. A test bilayer sample of tailored formulations of poly(dimethylsiloxane) (PDMS) can approximate the thermal properties of human skin and fat (FIG. 29). In particular, silicone A (Sylgard 170 (S170), Dow-Corning, $k_A$=0.47 W m$^{-1}$K$^{-1}$ and $\alpha_A$=0.14 mm$^2$[11]) has thermal properties similar to those of human skin (E+D, k=0.25-0.45 W m$^{-1}$K$^{-1}$[6d,9,12]) and silicone B (Sylgard 184 (S184), Dow-Corning, $k_B$=0.21 W m$^{-1}$K$^{-1}$ and $\alpha_B$=0.11 mm$^2$ s$^{1}$[6b]) has thermal properties comparable to subcutaneous fat (k=0.18-0.23 W m$^{-1}$K$^{-1}$[9,12]).

Figure 2:
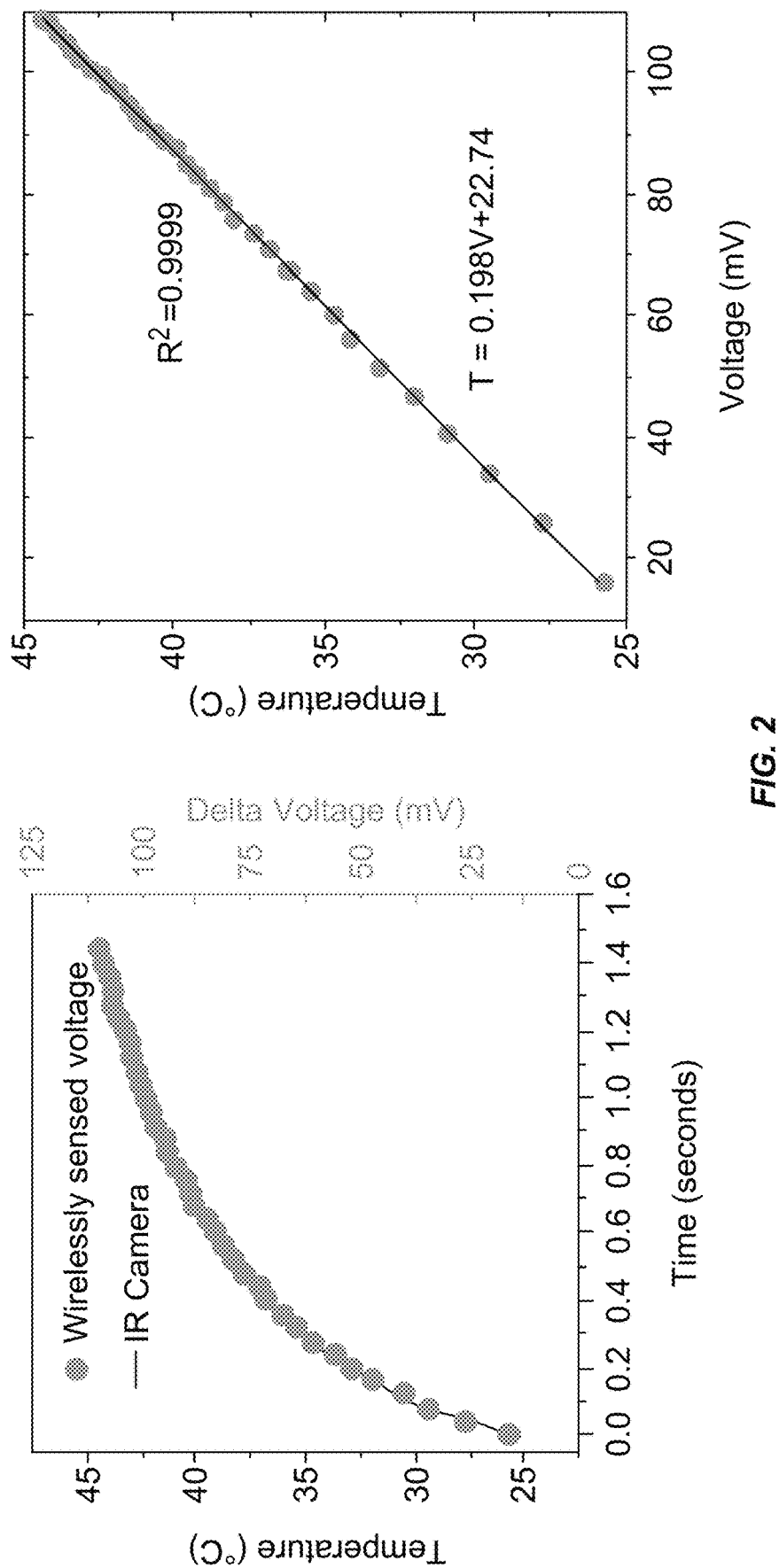
Figure 3:
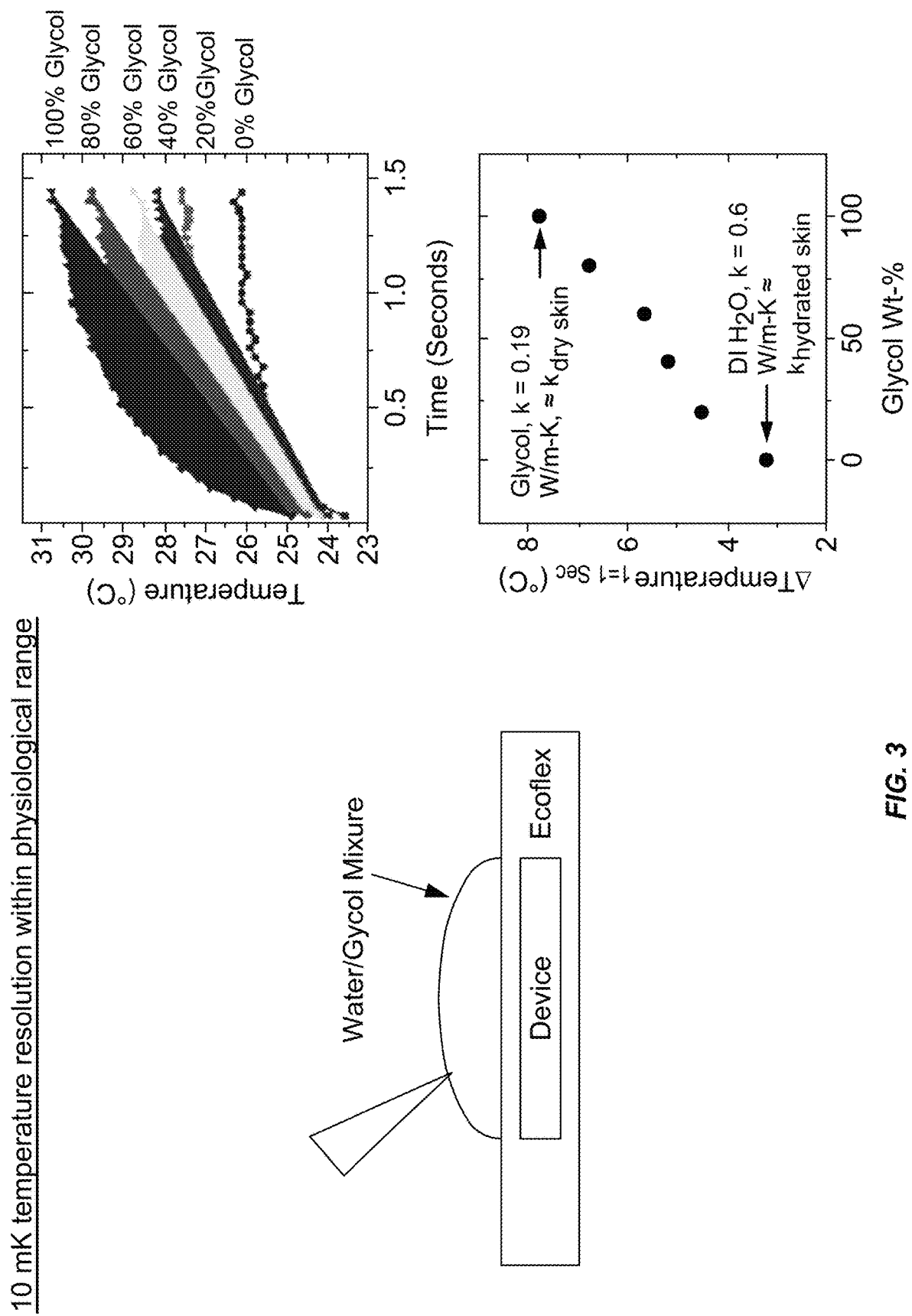

The maximum depth below the surface ($h_{max}$) up to which the e-TDS can sense thermal properties depends on the sensor design (R) and measurement conditions (t) for a fixed bilayer system ($k_A$, $k_B$, $\alpha_A$, $\alpha_B$) (As discussed in the methods section on FEA modeling, $h_{max}$ also depends on the nature of heat transport into the air.) Measurements with a given e-TDS (R=1.5 mm and q=3 mW mm$^{-2}$) on silicone bilayer samples with various thicknesses of silicone A (h) reveals the functional dependence of the response on $h_{max}$ (FIG. 2b). The ΔT versus t curves captured from such samples overlap with measurements on a semi-infinite substrate of silicone A (ΔT$_A$) when h>$h_{max}$. We consider ΔT at t=60 s>$t_{min}$ (and hence the quasi-steady state regime) for all values of h, extracted from the sensors' ΔT vs. h output (FIG. 2c), for the purpose of analyzing k. The largest value of h for which ΔT is larger than ΔT$_A$ by 5% (Equation 1) defines $h_{max}$. In particular, $$\frac{\Delta T(h = h_{max}) - \Delta T_A}{\Delta T_A} = 5\% \quad (1)$$

The 5% threshold corresponds to the maximum relative standard error (RSE) in ΔT$_A$. Three-fold measurements of ΔT$_A$ for every e-TDS of radius R yields the RSE, as given by, $$RSE = \frac{(1/\sqrt{3})\sigma_{\Delta T_A}}{\overline{\Delta T_A}}, \quad (2)$$

where $\sigma_{\Delta T_A}$ is the standard deviation of ΔT$_A$, $(1/\sqrt{3})\sigma_{\Delta T_A}$ is the standard error for the three data points and $\overline{\Delta T_A}$ is the mean of the data. The RSE varies from 0.1-4.6% for R=0.5 to 4.5 mm at t=60 s. In addition, RSE remains nearly constant for a fixed R in the range of powers studied (e.g., for R=0.75 mm, q=2-7 mW mm$^{-2}$ RSE=0.22-0.23%). These findings are consistent with mean and standard deviation values that are linearly dependent on q.

Using approaches similar to those described above, $h_{max}$ can be determined for R between 0.5 to 4.5 mm. The results show that $h_{max}$ approaches a limiting value as R→∞, which corresponds to the case where lateral heat flow is negligible and the system is approximately one-dimensional (1D), with heat flow predominantly into the depth of the material. Temperature contour maps derived from FEA modeling confirm this behavior (FIG. 2e). Large values of R facilitate measurements of properties of deep layers of skin. The available anatomical measurement area can, however, limit the practical size of R. In such cases, other parameters to adjust $h_{max}$ can be useful, as described in the following.

Additional studies reveal the dependence of $h_{max}$ on t, using the same bilayer silicone structure and an e-TDS with R=1.5 mm and q=3 mW mm$^{-2}$. FIG. 30 (panel a) shows the results of measurements of ΔT as a function of t with samples that have different values of h. FEA results are in good agreement with measurements, as in FIG. 30 (panel b). In particular, $h_{max}$ increases with increasing t (FIG. 30 (panel c) and eventually reaches a limiting value as t→∞ when the system achieves steady state (FIG. 30 (panels d-e). Values of t should be chosen above $t_{min}$ to avoid uncertainties introduced by a. The upper bound for t based on practical considerations is in the range of a few minutes.

Figure 4:
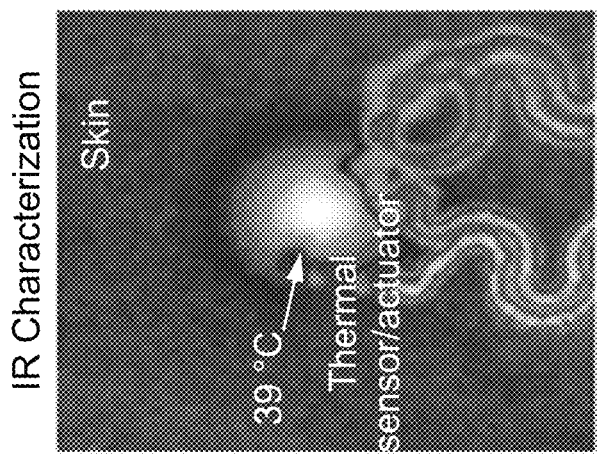
Figure 4:
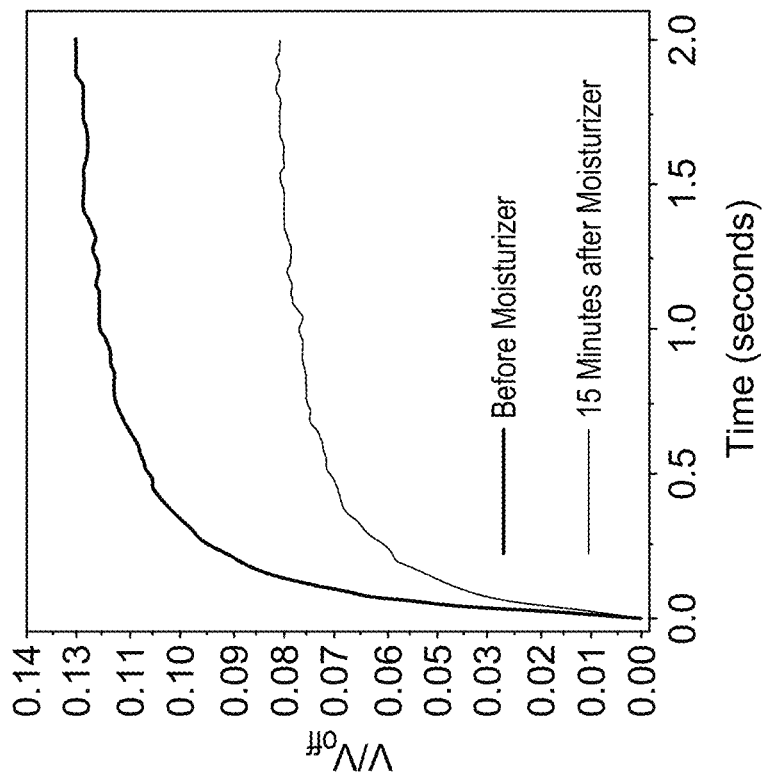
Figure 10:
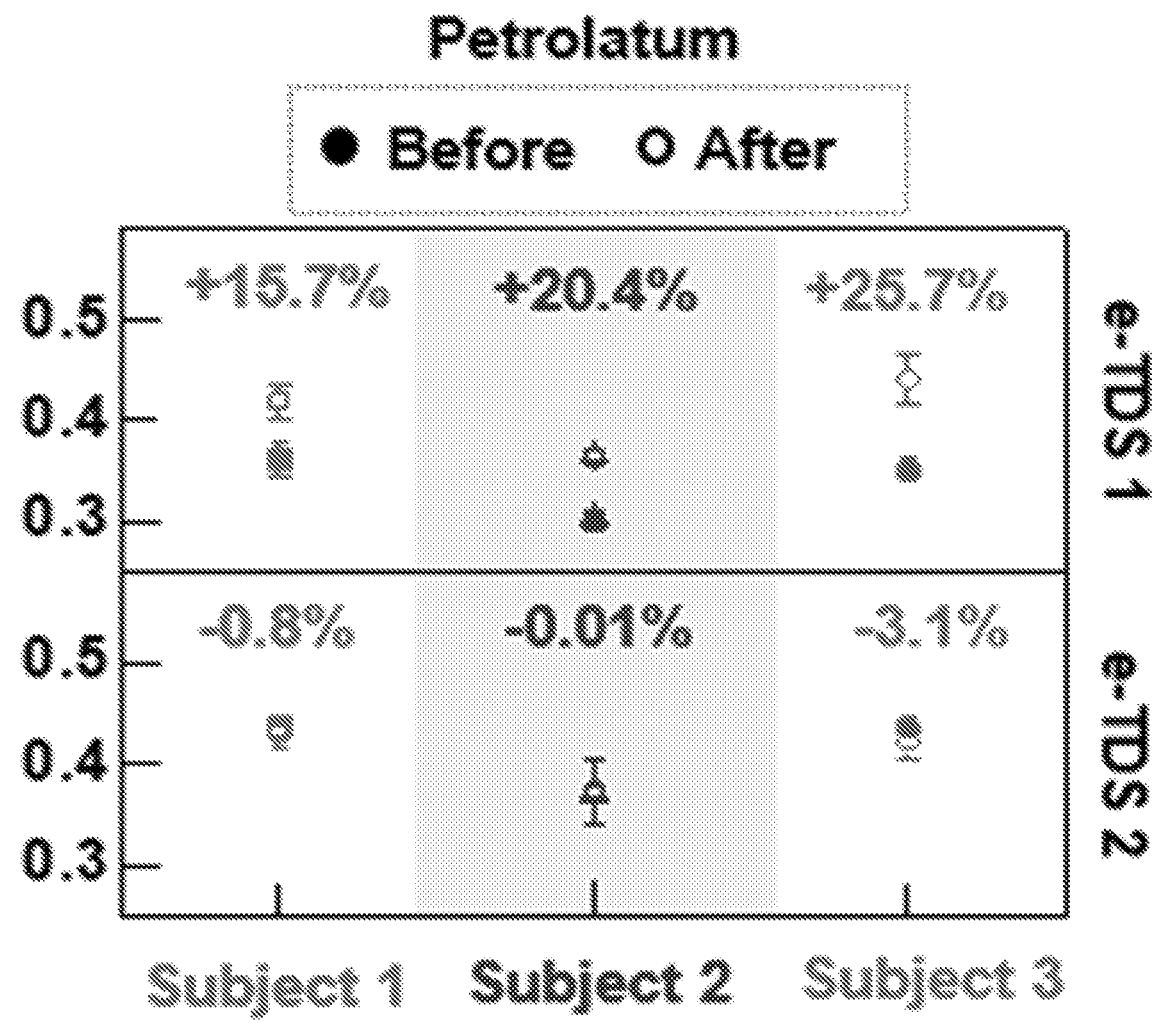
Figure 11:
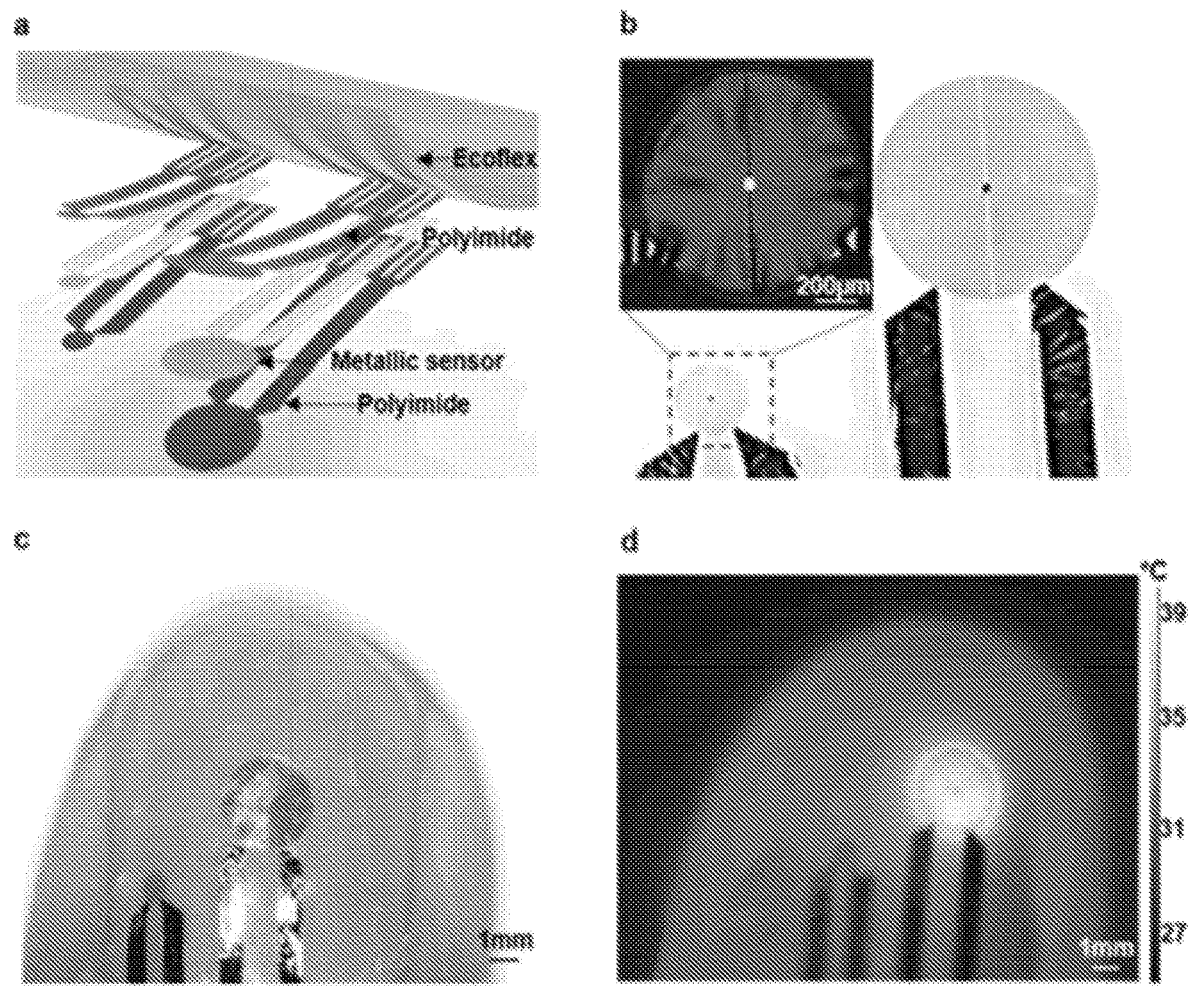
FIG. 11 illustrates deployment of the sensor on the nail-based on the sensor's size configurations the assessment of the nail.
Figure 12F:
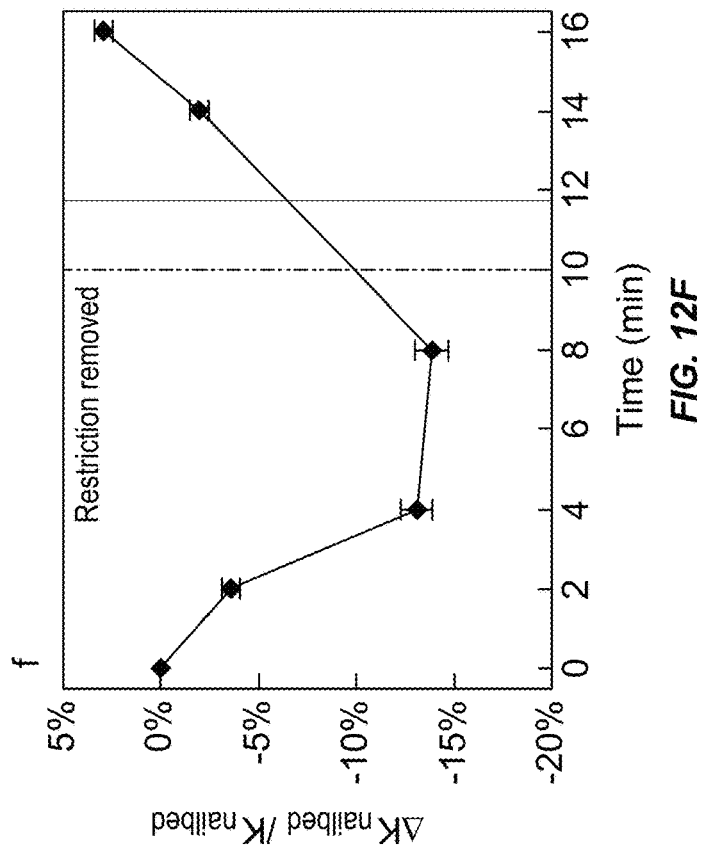
FIG. 12 illustrates of the use of the nail bed thermal sensor to detect changes in local blood flow. This illustrates the ability for the sensor to detect occlusion with implications for a diagnostic system for Raynaud's, thromboembolic diseases, or peripheral artery diseases.
Figure 12E:
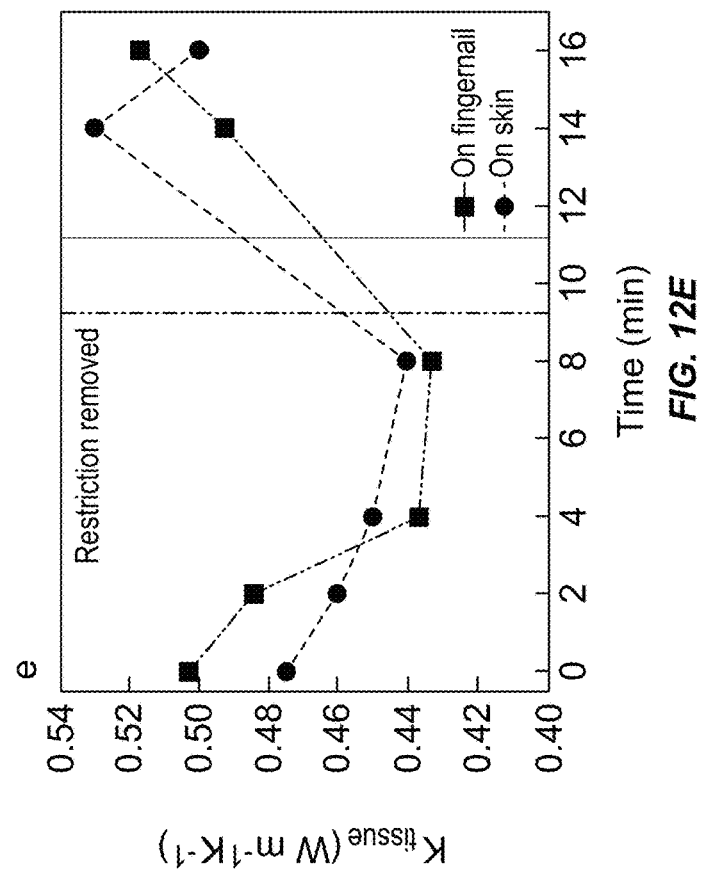

The dependence of $h_{max}$ on R and t is shown in FIG. 10. FEA calculations of $h_{max}$ in FIG. 4b indicate that the e-TDS can sense thermal properties at depths up to 6 mm. To aid in optimization of e-TDS design, an FEA-derived scaling law can be formulated that relates $h_{max}$ to t and R (FIG. 10). In the derivation of the scaling law the encapsulation layers and the substrate for the sensor are not considered explicitly, nor is the effect of air convection. For a circular sensor placed on a bilayer system as shown in FIG. 4a, the relationship between $h_{max}$, R and t is provided in Equation 3 and FIG. 10 (panel c):

$$\frac{h_{max}}{R} = g\left(\frac{\alpha_A t}{R^2}\right) \quad (3)$$

Thus, to measure the thermal properties of the top layer in a bilayer sample, the e-TDS is preferably designed such that $h_{max}$<h. Similarly, for measuring the thermal properties of the bottom layer, $h_{max}$>h.

Extraction of an Effective Thermal Conductivity, $k_{effective}$

The aforementioned analysis mainly concerns the depth sensitivity of the measurement. In this section, the focus pertains to extraction of thermal properties for the bilayer silicone system at different depths using the measured ΔT values. Extracting $k_A$ and $k_B$ is difficult, due to large fitting uncertainties associated with multiple free parameters. Instead, consider a single effective parameter, $k_{effective}$, for the bilayer system, as $$k_{effective} = C_1 k_A + (1 - C_1) k_B \quad (4)$$

$C_1$ is a constant that follows the scaling law given by Equation 5 and FIG. 4d.

$$C_1 = f\left(\frac{k_A}{k_B}, \frac{\alpha_A}{\alpha_B}, \frac{\alpha_A t}{R^2}, \frac{h}{R}\right) \quad (5)$$

For known values of $k_A$, $k_B$, $\alpha_A$, $\alpha_B$ (for R=1.5 mm and t=60 s), $C_1$ depends only on h/R (FIG. 4d). From FIG. 10 (panel d), for R=1.5 mm, a large value of h leads to $C_1$→1, and thus $k_{effective}$→$k_A$. At large h, the spread of heat from the e-TDS is localized to the top layer, and $k_A$ dominates the value of $k_{effective}$. For small values of h, $C_1$→0 and $k_{effective}$→$k_B$, consistent with a measurement depth that significantly exceeds h. Thus, for a known value of h, a sensor with small R and t such that $h_{max}$<h enables measurement of $k_A$, whereas a sensor with sufficiently large R and t such that $h_{max}$>>h enables measurements of $k_B$. These observations suggest a device platform that includes a pair of e-TDS's, with one configured for sensitivity to the top layer, and the other to the bottom.

Experiments on Human Skin

Using the FEA predictions in FIG. 10, an ideal system of this type for studying human skin consists of e-TDS 1 with $R_1=0.75$ mm ($h_{max}$ (t=60 s)=1.42 mm) and e-TDS 2 with $R_2=3.5$ mm ($h_{max}$(t=60 s)=2.66 mm), for sensitivity to E+D and to subcutaneous fat, respectively (FIG. 31). Based on the application, or part of body under examination, values of R and t may be selected to achieve a relevant value of $h_{max}$. The dual e-TDS design chosen here is applicable to many locations of the body where the thickness of the E+D is 1 mm. The e-TDS are conformal and stretchable[13] as shown in FIG. 31 (panels b and c) to ensure effective thermal coupling to the skin (provided is a description of mechanical stability). Operating the e-TDS consecutively eliminates active interference. Passive interference can be minimized by separating the peripheral edges of the two e-TDS by an amount greater than $h_{max}$ of e-TDS 1 (error less than 1% in ΔT). Further sources of measurement error, such as sample curvature, roughness, and local air convection are discussed.

A selection of on-body tests demonstrates the clinical relevance of $k_{effective}$ of human skin. For all experiments, the maximum ΔT is less than 10° C. The values of k for healthy biological tissues are invariant to surrounding temperature, over a relevant range.[14] The good agreement between our simple models, which assume time-invariant constitutive properties, and the measured data suggest that active body processes do not play a significant role for the skin system being investigated. The following experiments use healthy, normal skin of the same subject as a reference for quantifying changes in thermal properties. This reference point, for introduced changes, corresponds to the same location just before the relevant changes are introduced, and for other cases, the contralateral location on the body. Thus, changes in thermal properties are measured on an individual basis, eliminating the need for absolute comparisons to a single reference point. Measurements taken three times each yield error bars to account for effects of air convection and human motion. In some cases, the error bars are too small to be visualized beyond the symbols (i.e., <1%). This can be attributed to excellent adhesion between the device and skin. The first studies examine the effect of petrolatum (Vaseline, Unilever), an occlusive moisturizer.[15] Measurements involve three subjects evaluated before, and 15 minutes after application of ~5 mg/cm² of petrolatum to the forearm. In all cases, $k_{effective}$ extracted from e-TDS 1 increases by 15-25%, while the value extracted from e-TDS 2 remains nearly unchanged. These results suggest modulation of the properties only of superficial tissue, the stratum corneum (100 μm). The finding that $k_{petroiatum}=0.19$ W m⁻¹K⁻¹ (determined using e-TDS 1) indicates that the e-TDS does not measure a change due to the thermal properties of petrolatum, but rather an increase in $k_{effective}$ by prevention of transepidermal water loss (TEWL), consistent with previous studies using conventional devices for measuring TEWL.[15c]

Measurements that involve localized skin heating and cooling (FIG. 31 panels e-f) illustrate the ability to determine $k_{effective}$ at intermediate depths (~500 μm-1 mm). The former involves application of a hot pack (average temperature=46 to 48° C., HotHands® Super Warmers) to the front of the arm for ten minutes. Recording $k_{effective}$ before, immediately after, and at two consecutive ten-minute intervals after the heating period captures the responses of the skin to the applied heat. The $k_{effective}$ determined from e-TDS 1 increases dramatically after heating, consistent with increased blood flow. e-TDS 2 also measures a significant rise in $k_{effective}$, but to a lesser extent than e-TDS 1, thereby suggesting the depth of tissue affected by the hot pack is larger than that affected by petrolatum. Over time, $k_{effective}$ approaches its initial value. Localized cooling induces dermal changes due to constriction of blood flow. After 10 minutes of cooling the front of the arm with a cold pack (average temperature=9 to 11° C., Instant Cold Pack, Primacare), measurements of $k_{effective}$ from e-TDS 2 indicate changes smaller than those from e-TDS 1 for all three patients. The results suggest that the effects of localized cooling occur mainly in the dermis, similar to the case for heating.

One clinical application for this technology is as a diagnostic aid for cellulitis. Cellulitis is a potentially fatal infection of the deep dermis and subcutaneous tissue, with 14 million cases annually resulting in more than 600,000 yearly hospital admissions.[4a] However, 30-40% of cellulitis cases are misdiagnosed given similar clinical presentations of common mimicking conditions that do not require antibiotics (e.g., venous stasis dermatitis).[4a] Currently, there is no existing laboratory or imaging tool approved for the diagnosis of this common condition. Studies reported illustrate use of the e-TDS system to detect changes in the deep dermis and subcutaneous fat (FIG. 31) in one case of cellulitis. Measurements with e-TDS 1 and 2 applied to the center of a cellulitis lesion, its perilesional area, and the corresponding location on the healthy, contralateral leg (as an internal control) allow study of cellulitis on a single patient. Values of $k_{effective}$ determined with e-TDS 1 show no apparent temporal changes in the thermal conductivity at the lesion or perilesional area ($k_{lesion}$ and $k_{perilesional}$). By contrast, e-TDS 2 shows evidence of inflammation, since $k_{contralateral}<k_{perilesional}<k_{lesion}$. $k_{contralateral}$ on Day 1 and Day 4 remains constant for e-TDS 2, but not for e-TDS 1. The thermal properties of the superficial E+D vary greatly on a scale of days due to ambient conditions and hydration state, so this disagreement between $k_{contralateral}$ for Day 1 and Day 4 for e-TDS 1 is not unexpected. The deep dermis and fat, however, do not display variations in thermal properties to this extent because they are insulated from ambient changes by the epidermis. On Day 4 of measurement, $k_{lesion}$ and $k_{perilesional}$ approach $k_{contralateral}$, suggesting healing, which is also apparent from the optical image on Day 4. These results indicate a clear decrease in erythema and lesion size in contrast to the image taken on Day 1 (the lesion diameter decreases from ~2.5 cm to ~1 cm). This analysis reveals that both e-TDS 1 and 2 may hold clinical relevance as a diagnostic tool. The ability to measure thermal properties of tissue at different depths may improve diagnostic discrimination of conditions such as cellulitis (minimal superficial or epidermal change but significant deep dermal subcutaneous fat change) with mimickers such as venous stasis dermatitis (greater epidermal inflammation). Depth profiling human skin is thus essential to the clinical applications of e-TDS, as different skin conditions have different thermal characteristics.

The findings reported here suggest that e-TDS technology enables monitoring of thermal properties of human tissue at depths of up to ~6 mm. Detailed studies of the thermal physics associated with the measurement quantify the key design parameters that define the depth sensitivity, thereby allowing controlled, and targeted measurements for various skin conditions. Capabilities of the e-TDS system include detection of subtle changes in skin hydration, microvascular blood flow, and composition as a function of tissue depth. Depth sensitivity to subcutaneous fat may create new opportunities for diagnostics across a wide range of cutaneous and systemic diseases, and the noninvasive, reusable nature of the devices promotes at-home use for long-term monitoring.[2c,4a] The e-TDS platform may offer a valuable alternative to invasive diagnostic approaches and costly imaging techniques. Use with a wireless system for control and data extraction and expanded clinical studies on patients with various diseases can further define the diagnostic relevance of thermal depth sensors. In certain unique anatomical locations, the epidermis, dermis, and subcutaneous fat have total thickness <6 mm, thereby enabling interrogation of tissues beneath the skin. Such locations include the eyelid (<2 mm in thickness) or areas overlying bony prominences (e.g. trochanter, sacrum, or ischium, <4 mm in thickness.[16] Thus, these sensors can be useful in assessing the joint space or bone for signs of infection (osteomyelitis) or bleeding (hemoarthrosis). Thus, with specific anatomical placement, these sensors enable insights into other tissue types such as joint spaces, or bone.

Experimental Section: FEA to determine critical depth: The commercial software ABAQUS was used to study the thermal response of the e-TDS device on the surface of single-layer or bilayer samples. Here, the e-TDS is a resistive sensor encapsulated by a layer of PI (1.6 μm thickness; $k_{PI}$=0.52 W m$^{-1}$K$^{-1}$ and $\alpha_{PI}$=0.32 mm$^2$ s$^{1[6b,11]}$) on both sides and printed on a layer of Ecoflex (100 μm thickness; $k_{ecoflex}$=0.21 W m$^{-1}$K$^{-1}$ and $\alpha_{ecoflex}$=0.11 mm$^2$ s$^{-1[6b]}$) that contacts the sample, as illustrated in FIG. 28. FIG. 10 show FEA models of the e-TDS (the resistive sensor is approximated as a circle with the same outer contour and total power) placed on single-layer and bilayer samples, respectively. The air convection coefficient is 6 W m$^{-2}$K$^{-1}$. The following two FEA models were compared to study the depth sensitivity: (1) the bilayer sample (top layer: silicone A, thickness h, $k_A$=0.47 W m$^{-1}$K$^{-1}$ determined by measurement of the pure, single-layer sample, and $\alpha_A$=0.14 mm$^2$ s$^{-1}$ found from literature[17]; bottom layer: silicone B, $k_B$=0.21 W m$^{-1}$K$^{-1}$ determined by measurement of the pure, single-layer sample, $\alpha_B$=0.11 mm$^2$ s$^1$ found from literature[6b]) as in FIG. 4a; (2) the single-layer sample (pure silicone A). The definition of the sensitivity and critical thickness ($h_{max}$) for FEA are the same as those for the scaling law. We illustrate the sensitivity as a function of h for different R and t. FIG. 10 shows that $h_{max}$ and thus sensitivity increase with R and t.

Fabrication of Thermal Depth Sensors: Spin-coating (3000 rpm) a thin (~200 nm) layer of poly(methyl methacrylate) (PMMA A4, MicroChem) onto a carrier substrate (silicon wafer, glass slide, or glass wafer) followed by baking at 180° C. for three minutes formed a sacrificial release layer. Next, spin-coating a film of poly(amic) acid (PI-2545, HD MicroSystems) onto the same substrate at 5000 rpm, followed by soft-baking on a hot plate at 90° C. for 30 seconds, then at 150° C. for 5 minutes and finally at 250° C. for one hour in a vacuum oven yielded a ~1.6 μm thick layer of polyimide (PI) as electrical insulation. Electron beam evaporation formed a bilayer of Ti (20 nm) and Au (100 nm). Photolithography and wet etching defined metal traces for the devices.

Spin-coating and curing poly(amic) acid using the conditions mentioned above formed an upper insulation layer. These two layers of PI placed the metal in the neutral-mechanical plane, thereby minimizing strains due to bending/stretching. Photolithography and reactive ion etching ($O_2$ plasma, March RIE) patterned the PI in geometries that match those of the metal traces. Immersion in acetone dissolved the PMMA sacrificial layer, to allow removal of the structures from the carrier substrate onto the surface of a piece of water-soluble tape (Water-Soluble Wave Solder Tape, 3M). Sputter deposition of ~70 nm of $SiO_2$ onto the backside of the structure created a reactive surface for chemical bonding. Separately, spin-coating (1000 rpm, 100 μm) a low modulus formulation of silicone (Ecoflex, Smooth-On) onto a glass slide coated with a thin layer of PMMA produced a thin, soft elastomer support. Exposure to UV light functionalizes the surface of the silicone with —OH groups for bonding to the $SiO_2$ coated surface of the sensor structure. Immersion in boiling water dissolved the water-soluble tape. Drying the sensors by baking in an oven at 70° C. and pressure bonding using a hot iron set to 193° C. and thin cables (ACF, Elform) as connections to a current source completed the fabrication process.

Transient Plane Source Measurements: The TPS measurements used a commercial current source (Keithley 6220) to set the thermal power per unit area, q. The resultant heating led to changes in resistance, Δr, determined by corresponding changes in voltage, ΔV, recorded with a digital multimeter (National Instruments). The measured Δr allowed determination of ΔT through the temperature coefficient of resistance (TCR) of Au. Each sensor was carefully calibrated against measurements using an infrared (IR) camera to determine the TCR. After applying heating current for the measurement time, application of low current for the same time cools the sensor down such that ΔT=0° C. Typical applied currents for the q used in this study are <1.5 mA. However, because of the PI electrical insulation layer, and Ecoflex substrate, no current enters the skin.

Heat Transport Studied with Thermochromic Pigment/Ecoflex: A single sensor (R=1.5 mm) laminated onto a substrate of Ecoflex mixed with thermochromic pigment (Temperature Activated Thermochromic Bi-Color Powder Pigment, Atlanta Chemical Engineering) defined the experimental layout in FIG. 28 and the parameters for the FEA temperature maps assume the thermal conductivity $k_{silicone}$=0.21 W m$^{-1}$K$^{-1}$ and $\alpha_{silicone}$=0.11 mm$^2$s$^{-1[6b]}$, respectively. This thermochromic pigment changes color from black to pink at or above 25° C. The experiments involved observations in an ambient laboratory environment (T=22° C.) and q=10 mW mm$^{-2}$.

Fabrication of Bilayer PDMS Structures: Mixing the base and curing agent at a ratio suggested by the vendor (10:1; Sylgard 184, Dow Corning) followed by curing at room temperature for 24 hours yielded the Silicone B elastomer. All experiments used the same 15 mm thick cylindrical sample of Silicone B with diameter d=100 mm to maintain a constant sample temperature approximation. The conditions for constant sample temperature are thickness >2√αt and d>2(2√αt+R), which are maintained. Synthesis of Silicone A (Sylgard 170, Dow Corning) involved a separate mixing step for the individual base and curing agent for 3-5 minutes, followed by combining the two components together at a ratio of 1:1 for an additional 3 minutes. The specific gravity of Silicone A provided by the vendor multiplied by the volume of a cylindrical sample (d=100 mm) of height h determines the masses of mixture required to create different h of Silicone A, producing the measurement samples. The thicknesses of these samples ranged from 0.5 mm-10 mm in steps of 1.0-1.5 mm. Curing occurred at room temperature for ~24 hours. Measurements with digital calipers with 0.01 mm resolution yielded the thicknesses of these Silicone A samples. Physically laminating a film of this type onto the Silicone B substrate formed the bilayer Silicone A/Silicone B structures for testing. The reversible van der Waals adhesion allowed repetitive lamination and removal of such films to yield a collection of samples with only a single Silicone B substrate. A shallow plastic dish covered the devices during measurements to minimize effects of air convection.

On-body experiments: Nine different subjects participated across the four unique on-body tests. For all tests, chosen values of q (and thus applied current,) ensured that ΔT=60 s<10° C. The first test served to demonstrate detection of superficial (epidermal, 100 μm) changes using the e-TDS system. Four healthy/normal subjects (Female, Age 23; Male, Age 22; Female, Age 27; Male, Age 23) participated in this experiment. Subjects sat still in a laboratory setting during the test. A commercial occlusive moisturizer, petrolatum (Vaseline, Unilever) served to induce changes in hydration level in the stratum corneum and epidermis. Placing the dual e-TDS system first on each subject's bare forearm allowed measurement of thermal properties. First, e-TDS 1 measured ΔT as a function of t for a duration of 60 s, followed by a 60 s cooling period when the sensor was OFF, allowing the sensor to return to its initial temperature. Then, e-TDS 2 measured ΔT as a function of t for the same duration (60 s), followed by a cooling period of the same time (60 s). Repeating measurements by e-TDS 1 and e-TDS 2 three times each produced the data, with symbols as the mean of the data and error bars representing the standard deviations. The e-TDS system was peeled off the forearm (pen marks on the forearm denoted the location of the dual e-TDS system). Applying 5 mg/cm$^2$ of petrolatum to each subjects' volar forearm and waiting for 15 minutes allowed for a sufficient increase in hydration. Laminating the dual e-TDS system on the subjects' volar forearm according to the corresponding marked locations and repeating the measurements for both e-TDS 1 and e-TDS 2, three times each, completed the experiment. In FIG. 31 (panel d), the symbols represent the mean of the data for each individual subject, and the error bars represent the corresponding standard deviations.

The next test involved changes in blood flow due to application of commercial heating and cooling packs to induce changes in blood flow at intermediate depths (dermis, 100 μm-1 mm). Four healthy/normal subjects (Female, Age 26; Male, Age 22; Female, Age 23; Male, Age 18) participated in the heating pack study for blood vessel dilation and four other healthy/normal subjects (Male, Age 30; Female, Age 23; Female, Age 21, Male, Age 18) participated in the cooling pack study for blood vessel constriction. Subjects sat relatively still in a laboratory environment during the tests. The procedure for heating/cooling pack studies were identical, as described here. The dual e-TDS was applied to the front of each subjects' arm. Pen marks identified the location of the device on the skin. In the same way for the first on-body experiment, e-TDS 1 measured ΔT as a function of t for a duration of 60 s, followed by a 60 s cooling period when the sensor was OFF, allowing the sensor to return to its initial temperature. Then, e-TDS 2 measured ΔT as a function of t for the same duration (60 s), followed by a cooling period of the same time (60 s). The sensors were removed from the arm. The commercial heating or cooling pack was placed on the location marked by pen for 10 minutes. Removing the heating or cooling pack and laminating the sensors back onto the skin according to the marked location prepared the subject for subsequent measurements. Measurements taken immediately after, 10 minutes after, and 20 minutes after removal of the hot/cold pack from the skin completed the study. In this case, measurements were only taken one time for each time interval (for both e-TDS 1 and 2) because the effects of the hot/cold pack were transient, as the data in FIG. 31 (panels e-f) show evidence that the skin returns to normal overtime, as expected. However, because four randomly chosen subjects show similar trends for both tests, the results are consistent.

Figure 5:
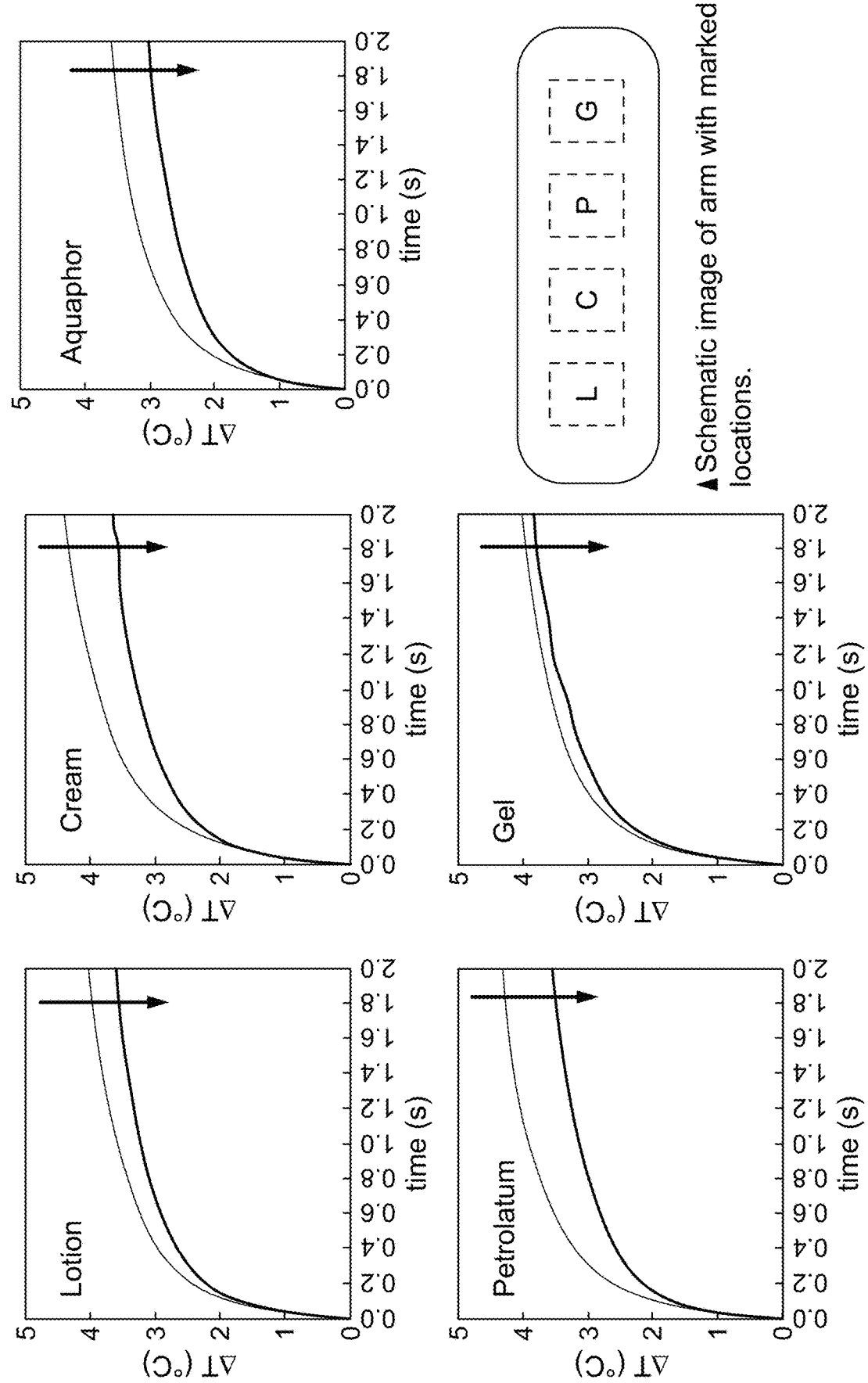
Figure 6:
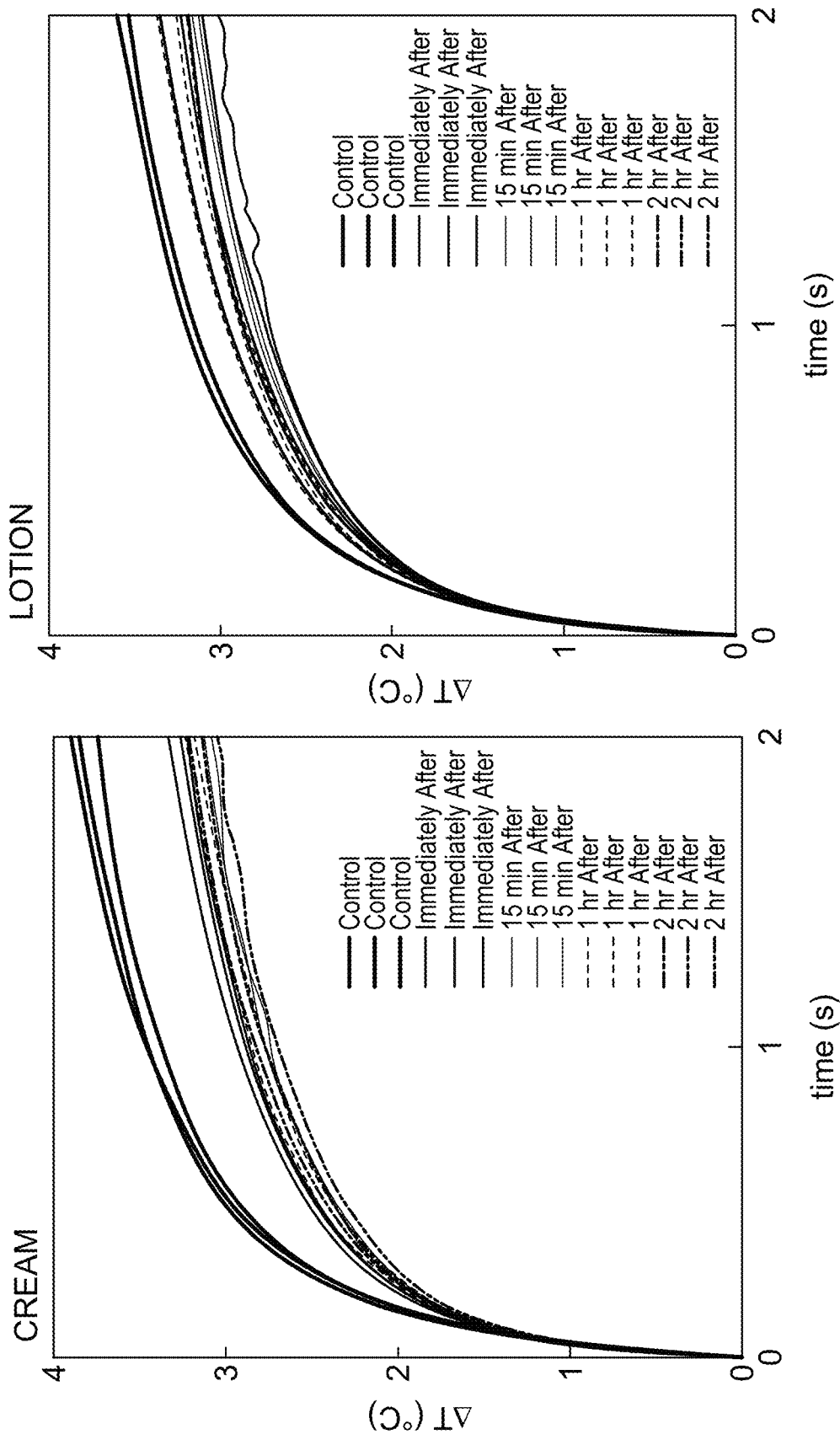
Figure 7:
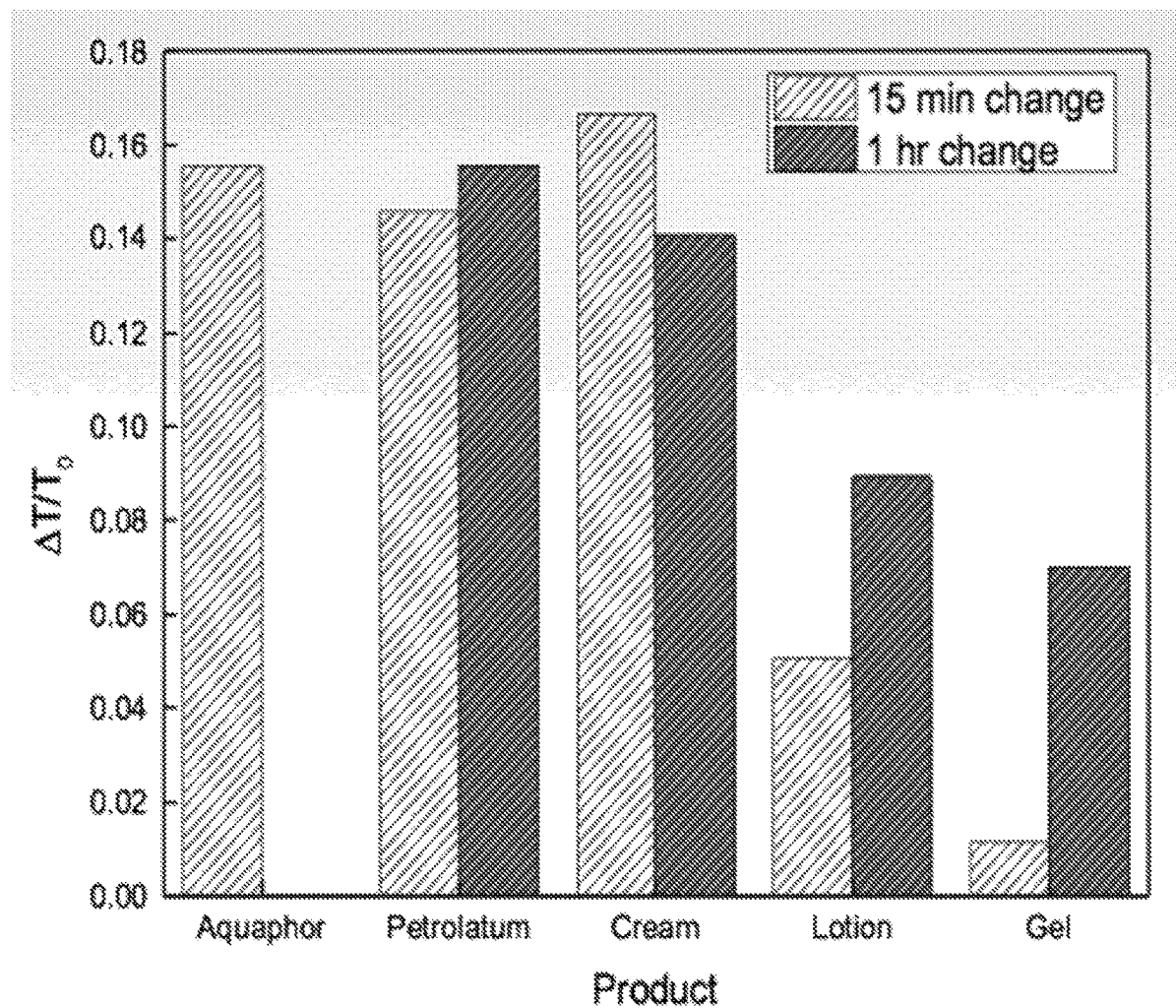
Figure 8:
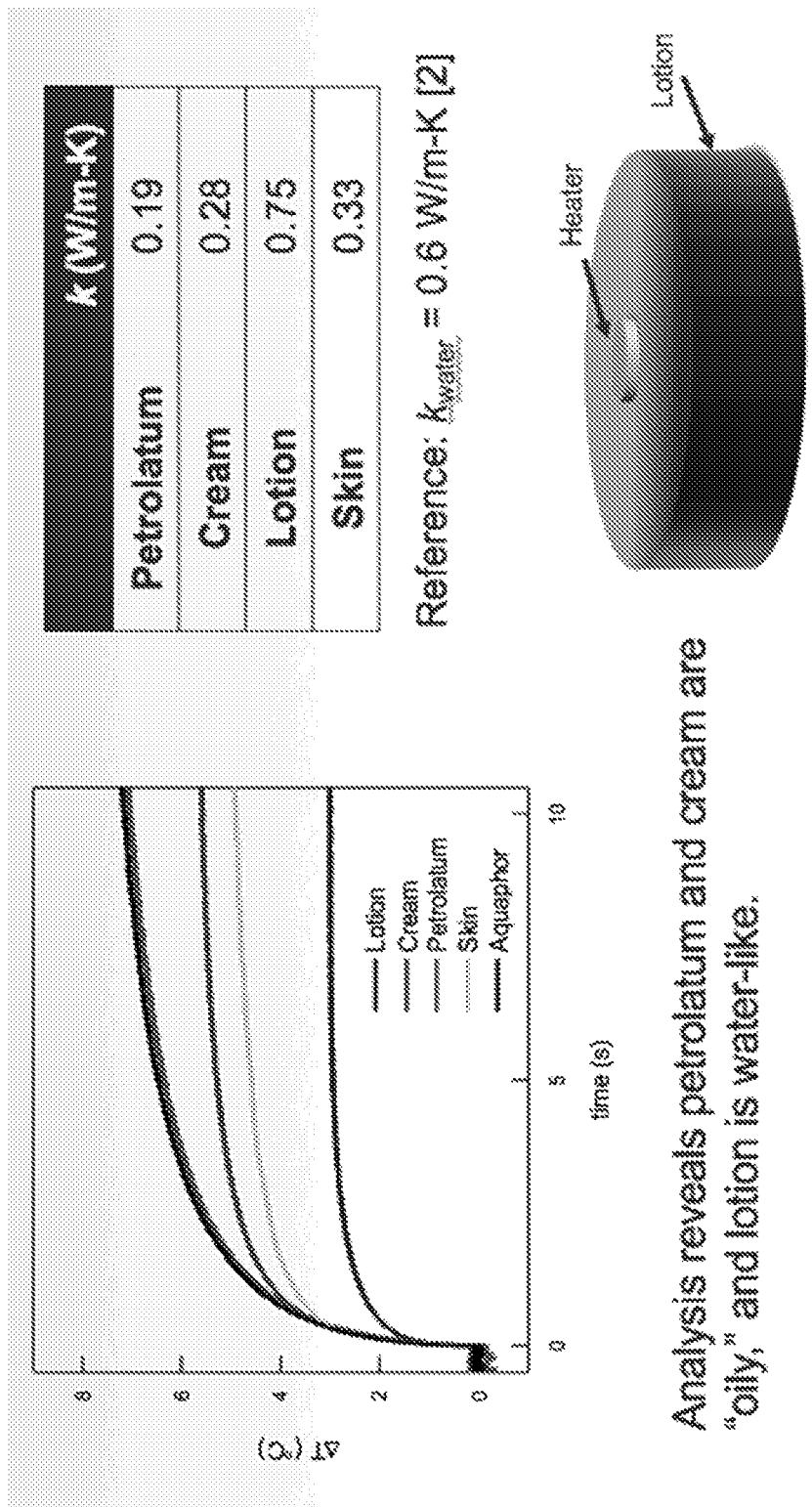

The final test involved measurements on a cellulitis lesion. Only one subject participated in the study since cellulitis is not an induced change, in contrast to the studies mentioned above. The subject (Male, Age 30) had cellulitis on his left leg (thigh). The subject removed hair from the area of the cellulitis lesion using a tweezer to ensure conformal contact between the device and skin. Measurements taken on one day, and four days following comprised the study. Measuring ΔT as a function of t on the two separate days with e-TDS 1 and e-TDS 2 sequentially, three times each, on the center of the cellulitis lesion, perilesional area, and contralateral leg produced the data in FIG. 5g. Images of the contralateral leg, and the cellulitis lesion taken on the two separate days also appear in FIG. 5 panel g.

REFERENCES FOR EXAMPLE 3

[1] J. Kottner, A. Lichterfeld, U. Blume-Peytavi, *British Journal of Dermatology* 2013, 169, 528.

[2] a) M. N. Sawka, S. J. Montain, W. A. Latzka, *Comp Biochem Physiol A Mol Integr Physiol* 2001, 128, 679; b) L. S. Jutte, M. A. Merrick, C. D. Ingersoll, J. E. Edwards, *Arch Phys Med Rehabil* 2001, 82, 845; c) P. V. Pople, K. K. Singh, *Int J Pharm* 2012, 434, 70.

[3] a) P. Clarys, R. Clijsen, J. Taeymans, A. O. Barel, *Skin Res Technol* 2012, 18, 316; b) E. Alanen, J. Nuutinen, K. Nicklen, T. Lahtinen, J. Monkkonen, *Skin Res Technol* 2004, 10, 32; c) J. E. Tooke, J. Ostergren, B. Fagrell, *Int J Microcirc Clin Exp* 1983, 2, 277; d) M. Vogt, H. Ermert, *IEEE Trans Ultrason Ferroelectr Freq Control* 2005, 52, 375; e) F. Mirrashed, J. C. Sharp, Skin Res Technol 2004, 10, 149; f) J. Welzel, C. Reinhardt, E. Lankenau, C. Winter, H. H. Wolff, *British Journal of Dermatology* 2004, 150, 220.

[4] a) A. B. Raff, D. Kroshinsky, *JAMA* 2016, 316, 325; b) Q. Weng, A. B. Raff, J. M. Cohen, et al., *JAMA Dermatology* 2017, 153, 141.

[5] a) T. Someya, Y. Kato, T. Sekitani, S. Iba, Y. Noguchi, Y. Murase, H. Kawaguchi, T. Sakurai, *Proc Natl Acad Sci USA* 2005, 102, 12321; b) R. C. Webb, A. P. Bonifas, A. Behnaz, Y. Zhang, K. J. Yu, H. Cheng, M. Shi, Z. Bian, Z. Liu, Y. S. Kim, W. H. Yeo, J. S. Park, J. Song, Y. Li, Y. Huang, A. M. Gorbach, J. A. Rogers, NatMater 2013, 12, 938.

[6] a) R. C. Webb, Y. Ma, S. Krishnan, Y. Li, S. Yoon, X. Guo, X. Feng, Y. Shi, M. Seidel, N. H. Cho, J. Kurniawan, J. Ahad, N. Sheth, J. Kim, J. G. t. Taylor, T. Darlington, K. Chang, W. Huang, J. Ayers, A. Gruebele, R. M. Pielak, M. J. Slepian, Y. Huang, A. M. Gorbach, J. A. Rogers, *Sci Adv* 2015, 1, e1500701; b) L. Tian, Y. Li, R. C. Webb, S. Krishnan, Z. Bian, J. Song, X. Ning, K. Crawford, J. Kurniawan, A. Bonifas, J. Ma, Y. Liu, X. Xie, J. Chen, Y. Liu, Z. Shi, T. Wu, R. Ning, D. Li, S. Sinha, D. G. Cahill, Y. Huang, J. A. Rogers, *Advanced Functional Materials* 2017, 27, 1701282; c) S. Krishnan, Y. Shi, R. C. Webb, Y. Ma, P. Bastien, K. E. Crawford, A. Wang, X. Feng, M. Manco, J. Kurniawan, E. Tir, Y. Huang, G. Balooch, R. M. Pielak, J. A. Rogers, *Microsystems &Amp; Nanoengineering* 2017, 3, 17014; d) R. C. Webb, R. M. Pielak, P. Bastien, J. Ayers, J. Niittynen, J. Kurniawan, M. Manco, A. Lin, N. H. Cho, V. Malyrchuk, G. Balooch, J. A. Rogers, *PLoS One* 2015, 10, e0118131.

[7] S. E. Gustafsson, *Review of Scientific Instruments* 1991, 62, 797.

[8] a) A. Koh, S. R. Gutbrod, J. D. Meyers, C. Lu, R. C. Webb, G. Shin, Y. Li, S. K. Kang, Y. Huang, I. R. Efimov, J. A. Rogers, *Adv Healthc Mater* 2016, 5, 373; b) Y. Hattori, L. Falgout, W. Lee, S. Y. Jung, E. Poon, J. W. Lee, I. Na, A. Geisler, D. Sadhwani, Y. Zhang, Y. Su, X. Wang, Z. Liu, J. Xia, H. Cheng, R. C. Webb, A. P. Bonifas, P. Won, J. W. Jeong, K. I Jang, Y. M. Song, B. Nardone, M. Nodzenski, J. A. Fan, Y. Huang, D. P. West, A. S. Paller, M. Alam, W. H. Yeo, J. A. Rogers, *Adv Healthc Mater* 2014, 3, 1597; c) L. Gao, Y. Zhang, V. Malyarchuk, L. Jia, K. I. Jang, R. C. Webb, H. Fu, Y. Shi, G. Zhou, L. Shi, D. Shah, X. Huang, B. Xu, C. Yu, Y. Huang, J. A. Rogers, *Nat Commun* 2014, 5, 4938.

[9] K. R. Holmes, Thermal Properties, http://users.ece.utexas.edu/~valvano/research/Thermal.pdf, accessed: 10 May 2017.

[10] a) Y. Lee, K. Hwang, *Surgical and Radiologic Anatomy* 2002, 24, 183; b) O. Akkus, M. Kizilgul, *Evaluation of Skin and Subcutaneous Adipose Tissue Thickness for Optimal Insulin Injection*, 2012.

[11] Dupont, Dupont Kapton Summary of Properties, http://www.dupont.com/kapton/general/H-38479-4.pdf, accessed: 5 Feb. 2017.

[12] M. L. Cohen, J Invest Dermatol 1977, 69, 333.

[13] S. Wang, M. Li, J. Wu, D.-H. Kim, N. Lu, Y. Su, Z. Kang, Y. Huang, J. A. Rogers, *Journal of Applied Mechanics* 2012, 79, 031022.

[14] J. W. Valvano, J. R. Cochran, K. R. Diller, *Int J Thermophys* 1985, 6, 301.

[15] a) R. Ghadially, L. Halkier-Sorensen, P. M. Elias, *J Am Acad Dermatol* 1992, 26, 387; b) A. V. Rawlings, D. A. Canestrari, B. Dobkowski, *Dermatol Ther* 2004, 17 Suppl 1, 49; c) R. L. Rietschel, *J Invest Dermatol* 1978, 70, 152.

[16] a) K. Hwang, D. J. Kim, S. H. Hwang, *Journal of Craniofacial Surgery* 2006, 17, 54; b) E. Yalcin, M. Akyuz, B. Onder, H. Unalan, I. Degirmenci, *Journal of Spinal Cord Medicine* 2013, 36, 225.

[17] Professional Plastics, Thermal Properties of Plastic Materials, https://www.professionalplastics.com/professionalplastics/ThermalPropertiesofPlastic Materials.pdf, accessed: 5 Feb. 2017.

Example 4: Wireless, Battery-Free Epidermal Electronics for Continuous, Quantitative, Thermal Characterization of Skin Skin is the largest organ of the body and plays a critical role in homeostasis, thermoregulation and as a barrier to airborne toxins, preventing the diffusion of pathogens, pollutants and particulates, in addition to playing an important role in regulating external appearance. Conventional means of skin-monitoring require complex, wired schemes, or visual inspection from trained medical professionals, and suffer some combination of disadvantages in cost or convenience. Recent advances in materials science and mechanical engineering have allowed for a class of electronic devices that are soft, thin, stretchable and skin-like in their construction. These devices sometimes collectively referred to as 'epidermal electronics' have already demonstrated the ability to produce clinical-quality data streams in a range of settings and have created a number of opportunities for novel sensing modalities. One such opportunity revolves around the precise, and continuous thermal characterization of human skin, with recent embodiments demonstrating the ability to measure temperature, blood flow, skin hydration, wound healing and skin-based pathologies such as cellulitis and sunburn up to depths of several millimeters, over several locations including skin and the fingernail. However, while this class of thermal characterization devices represents an extremely promising set of multimodal diagnostic and monitoring tools, all demonstrated embodiments thus far have relied on wired cable connections for power supply and data transmission, thereby limiting their usability.

Presented herein are a set of concepts in materials, mechanics, electronics design and wireless power transfer that, when taken together, allow for the construction of a continuously wearable, wireless, battery-free epidermal thermal sensor. Any of the devices and methods described herein are compatible with the wireless data and power transmission described in this section. Data-transmission and power transmission occur via inductive coupling, through near-field communication (NFC) protocols. Systematic experimental and theoretical studies establish key modes of device operation, that include the ability to measure skin temperature, hydration and trauma. Its rugged, lightweight design allows for continuous use over long time-periods, including up to a 7-day period, with capabilities in power transfer and data transmission directly through a commercially available NFC-enabled smartphone, tablet computer or other portable device.

Extensive work establishes the feasibility of using soft, conformal thermal elements that can simultaneously function as a high-precision (30 mK) thermometers and controlled, low-power DC thermal actuators to measure the thermal properties of soft tissue. Briefly, low-power thermal actuation (~8 mW/mm$^2$) results in local thermal transport from the actuator into intimately physically coupled underlying skin layers. The rate of thermal transport through these skin layers is determined by their thermal conductivities ($k_{skin}$) and thermal diffusivities ($\alpha_{skin}$). Precise, continuous, local thermometry at the point of actuation generates a transient temperature rise curve ($\Delta T(t)$) that can be analyzed using well-established algorithms to measure subtle changes in the skin's thermal transport associated with compositional and structural changes. This type of epidermal, wireless, thermal sensor (eWTS). can be used to measure a range of skin changes pertaining to hydration levels, hyperemia, injury and healing.

A schematic illustration of the eWTS appears in FIG. 32, highlighting its key features. The eWTS can be broadly divided into two, mechanically dissimilar components, each with an associated set of advantages in mechanics and thermal transport. Inductive coils for wireless power harvesting, commercially available components for efficient NFC-based power coupling, data transmission and analog signal conditioning, assembled on a flexible printed circuit board, comprise the first component (together referred herein generally as a "wireless electronic system"). A thin-film metallic bi-layer of Cr/Au (10/100 nm) encapsulated in 3 um of PI, mounted onto an elastomeric substrate (80 um) forms the second, 'soft', stretchable, low-modulus component (e.g., the substrate, actuator and sensor portion), as shown in FIG. 32 (panel B). The softness and high degree of deformability of the soft component are apparent in FIG. 32. This type of heterogeneous integration provides options in sensor design that combine recent advances in epidermal electronics with commercially mature flexible-PCB manufacturing.

The double-sided flex-PCB component constructed via laser structuring from a Cu/PI/Cu laminate (18 um/90 um/18 um, Pyralux, DuPont), allows for robust mounting of rigid, packaged, components, while maintaining system-level flexibility, consistent with recently developed design rules and advances in NFC-based epidermal and implantable electronics. Recent work in wearable skin-mounted thermal characterization informs key features of the soft system, including its low thermal mass (~10 mJ/cm$^2$K), highly linear temperature coefficient of resistance (TCR), and ability to function simultaneously as a temperature sensor and thermal actuator.

Figure 1:
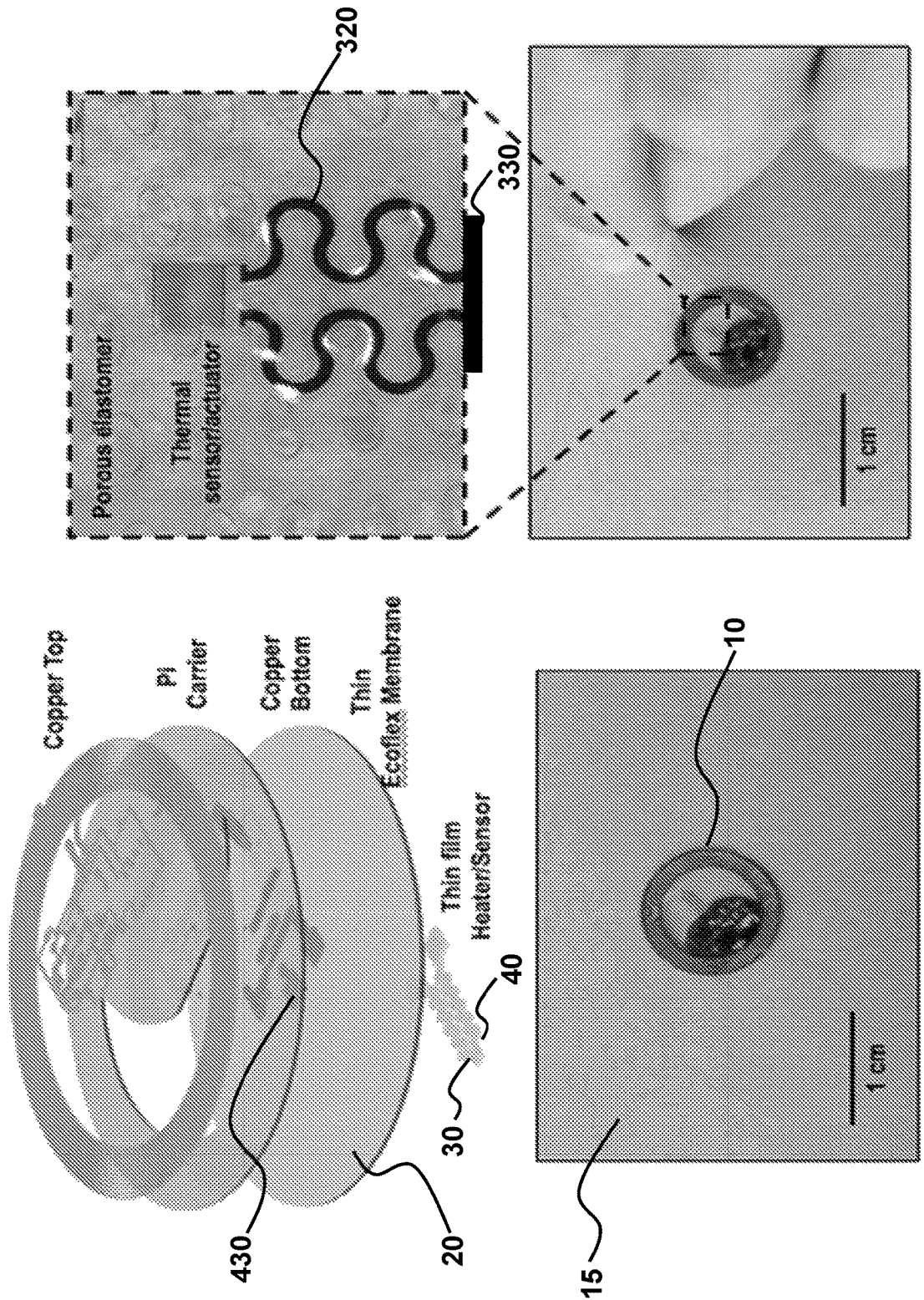

A window-like opening in the flex-PCB allows for mounting of the soft component, and mechanical integration between the two components, such as by an adhesive, while reflow soldering using low-temperature Indium-based solder establishes electrical contact between the reverse side of the flex-PCB and the thin-film sensing/actuating element. An ultrathin (80 μm) medical grade, acrylate-based fiber adhesive establishes strong, reversible adhesion between the skin and the flex-PCB, while the soft component relies on Van der Waals forces alone to adhere to skin, owing to its exceptionally low mass density [NUMBER] and strong adhesion of the surrounding flex-PCB to skin. Taken together, the, miniaturization (D=2.5 cm), low mass (200 mg), system-level flexibility of the eWTS allow for facile, reversible application on a range of body locations. An optical image of a fully assembled eWTS on a subject's neck appears in FIG. 1D, with enlarged views highlighting the key features outlined above.

The overall construction enables easy mounting, and advanced electronics designs allow for wireless measurement and readout from an external controller, such as a commercial, NFC-enabled smartphone or tablet computer as shown in FIG. 32 (panels E-F). A schematic of the overall circuit appears in FIG. 33 (panel A). The soft, sensing/actuating resistor (S1) forms the sensing arm of a finely balanced Wheatstone bridge (R2, R3, R4). Changes in temperature cause changes in resistance (~5Ω), that result in differential voltage changes (~500 V) across the arms of the bridge. This differential voltage is amplified by an operational amplifier whose closed-loop gain is set by the choice of feedback resistor (R5). To induce thermal actuation, R2 can be tuned, allowing for precise control of the power dissipated by the sensing arm. The amplified signal is then fed into the analog-digital converter (ADC) of a commercially available, bare-die near-field communication (NFC) chip, with a full-swing range of 400 mV (700 mV-300 mV). An on-board microcontroller allows for controlled power delivery at a programmable frequency and duty cycle through S1, causing local heating, with a buffering amplifier ensuring stable output. The resulting temperature increase results in measured, changing voltage, as shown in FIG. 33 (panel B).

Mechanical strains can affect device performance by inducing mechanical delamination of the sensor, altering the Q-factor and frequency peak of the inductive coil and inducing strain effects on the resistive temperature sensor. Consequently, mechanical considerations are essential to robust, stable device operation. Local delamination from skin results in measurements that are strongly influenced by the thermal properties of localized air pockets, with thermal conductivities that are an order of magnitude lower than that of skin and other soft tissue. A full, 3D finite element analysis (3D-FEA) reveals the minimum work of adhesion required to maintain conformal contact between the skin and the eWTS, across a range of uniaxial strains, with the yield strain of skin (15%) representing a practical outer limit. The work of adhesion at this strain, 10 N/m is easily supplied by even a mild, reversible, skin-safe silicone or acrylate-based adhesive ($Q_{adhesion}$>50 N/m). as shown in FIG. 33 (panel C).

The adhesive, taken together with the relatively low deformability of the flex-PCB compared to skin, serve to limit strain effects on the device, resulting in minimal delamination and air pockets. This is seen in 3D-FEA simulations of strain distributions shown in FIG. 33 (panel D), where twisting and bending result in peak strains of <0.1% in the inductive copper coil. Additionally, the placement of the ultrathin, resistive element in the middle plane between a PI substrate and superstrate renders it in the neutral mechanical plane of the soft assembly, resulting in close to 0% strain during bending and twisting, as shown in the inset images in FIG. 33 (panel D). Accordingly, any of the devices and methods provided herein place the temperature sensor and actuator at or near the neutral mechanical plane. Optical images of the device on skin under deformations due to pinching appear in FIGS. 31 and 43.

Wireless, In vitro thermal characterization of soft materials and fluids: Extensive in-vitro measurements with the eWTS on a variety of soft materials and fluids validates its ability to precisely, thermally characterize thermal transport properties in a range of conditions. Here, IR imaging serves as useful validation of sensor operation, and as a useful point of comparison, as IR thermography has gained widespread acceptance as a clinical diagnostic tool. FIG. 34 shows IR thermographs of the sensor operating in air (left) and on human skin (right), revealing key aspects of thermal operation. During an 'On' period, 8 mW of power is transferred from the NFC to the sensing/actuating element, resulting in controlled, localized actuation. The low thermal conductivity of air (~0.02 W/m-K CITE) relative to skin (~0.35 W/m-K CITE) results in a much higher local temperature rise in air (~15 K). 3D-FEA simulations of heat flow through skin reveal the depth of penetration of heat from the sensor to be 1 mm after 6s, resulting in a localized temperature rise of <8 K, entirely contained in the epidermal layers, with recent work from our group establishing design considerations to tune this depth. During device operation, the bare-die NFC chip is itself a major source of localized heating, as seen in FIG. 34. However, further 3D FEA establishes the steady-state depth of penetration of heat from the NFC to be <5 mm, less than the distance to the thermal field of the sensor itself.

During actuation, conversion of the raw, sensed voltage from the eWTS proceeds via calibration to IR thermographs focused on the sensor, as in FIG. 34. Operation of the eWTS at 0.05 Hz and 33% duty cycle at stable and drifting baseline temperatures, respectively, results in the data shown in FIG. 34 (panel C). Overlaying the raw measured voltage (red curve) with temperature data from IR thermographs (black curve) results in a nearly perfect overlay, allowing for easy, linear conversion to temperature. In this way, both the temperature rise ($\Delta T(t)$) and the starting temperature ($T(t=0)$) before each actuation cycle can be used, to simultaneously make measurements of thermal transport and baseline temperature, respectively. Further calibrations at a higher sampling rate are obtained.

The effects of different rates of thermal transport in soft materials are illustrated in FIG. 34 (panel D). Two different, commercially available silicone-based elastomers, Sylgard 184 (k=0.19 W/m-K) and Sylgard 170 (k=0.45 W/m-K), chosen due to the similarities in their thermal properties to those of skin, are prepared, with Sylgard 170 exhibiting a well-established increased thermal conductivity due to the presence of carbon black as a dopant. The samples are otherwise identical in size and geometry. The measured $\Delta T(t)$ exhibits dramatic differences, with the measured curve Syl 170 exhibiting a lower slope (dT(t)/dt) at short time scales (t<1s) and a lower saturation temperature (~4 K) at longer time scales T(t=6s) than Sylgard 184 (>8 K), by nearly a factor of 2.

The presence of near-surface fluid flow, in the form of blood vessels, implanted catheters or other conduits, is another source of altered rates of thermal transport. The ability to measure subtle changes in thermal transport can therefore be utilized to characterize flow rates in these conduits. As an illustration of this effect, the eWTS is mounted on the surface of a silicone skin-phantom with a near-surface, embedded catheter at a depth of 1 mm, corresponding to the depth associated with numerous veins in the body, in addition to, for example, superficial locations for ventricular shunt catheters. This assembly is illustrated in FIG. 34 (panel E top). Introducing controlled fluid flow through this catheter and operating the eWTS at 0.05 Hz and 33% duty cycle results in continuously measured $\Delta T(t)$ data at two different flow rates that fall within the range of flows expected in both of the above systems ($Q_{flow}$=0.5 ml/min, 1.0 ml/min) revealing the strong, convective effects of the flow, as shown in FIG. 34. The different levels of cooling associated with different flow rates can be converted into quantitative flow rates either using numerical models or via calibration.

In skin regions free of near-surface macro vessels, the ability to measure thermal transport changes associated with differing levels of hydration form a key application of the eWTS. Desiccated skin exhibits a thermal conductivity close to the value of dry, amorphous matrix of collagen (~0.19 W/m-K), while hydrated skin exhibits a thermal conductivity close to that of pure water (0.5 W/m-K), with physics of the system well-captured by a simple rule of mixtures. The two extreme cases for dry and hydrated skin are easily modeled by glycol (k=0.19 W/m-K) and water (k=0.6 W/m-K). Mixtures of these compounds with precisely controlled ratios (0%, 20%, 40%, 60%, 80%, 100% glycol by wt) serve as valuable phantoms to validate the ability of the sensor to capture subtle changes associated with water content, as shown schematically in FIG. 34 (panel F), and with an IR image in FIG. 34 (panel G). Measurements of $\Delta T(t)$ for each of these ratios appear in FIG. 34 (panel G), with $\Delta T(t=2s)$ appearing in FIG. 34 (panel H), and exhibiting a strongly linear correlation ($R^2$=0.994) with glycol content.

In vivo skin hydration measurements: Skin hydration is influenced by several factors, including genetics, ambient conditions, diet and activity levels. Hydration levels in the outermost layers of skin, such as the stratum corneum, critically affect its ability to act as a diffusion barrier against airborne particulates, pathogens and other pollutants. Added to the medical benefits of healthy skin hydration, its large role in regulating appearance drive significant economic activity in topical moisturizing compounds. Systematic in vivo trials on healthy volunteers revealed the effects of several different compounds on multiple body locations. The existing commercial gold standard, an impedance-based measurement probe (moisturemeter, Delfin Systems gmbh), serves as validation. The application procedure involves applying 5 mg/cm² on clearly marked regions of the skin and waiting for 15 minutes for complete absorption. Any remaining moisturizer was removed by first wiping thoroughly with a clean, dry wipe, followed by tape exfoliation with commercially available Scotch Tape (3M, Inc.), after which the eWTS was applied. This procedure is illustrated in the series of images in FIG. 35. Every trial involving a measurement made after a topically applied moisturizing compound ('after') utilized the above protocol.

As a simple control trial, three adjacent locations on right volar arm of a healthy subject (Female, age 23) are marked and two are treated with an alcohol wipe and a commercially available moisturizer (Nivea, Inc.) respectively, while a third is cleaned with a dry wipe but left untreated. As an example of a trial that is extremely difficult without a miniaturized, wireless design, the same control and readout electronics are used to successively and rapidly interrogate each adjacent sensor, with an optical image of this experiment appearing in FIG. 35 (panel B). Measurements before and after the three types of treatment reveal very little difference between the untreated location and the location treated with an alcohol wipe, but dramatically improved thermal transport associated at the moisturized location, associated with improved thermal transport due to increased water content, as shown in FIG. 35 (panel C).

Measurements on three different healthy subjects appear in FIG. 35 (panel D) reveal high levels of inter-person variability in the efficacy of topical moisturizers. Subject 1 (Male, Age 26) exhibited visibly dry, flaking skin on the volar forearm, and the application of a topical moisturizer resulted in a dramatic change, as captured by both the moisturemeter and the eWTS. Here, the eWTS measurement is recorded by $\Delta T(t=6s)$. Subjects 2 (Male, age 23) and 3 (Female, age 24) exhibited outwardly healthy skin, but the effect of the topical compound induced a moderate increase in hydration in subject 2, as measured by both the moisturemeter and the eWTS, and almost no change in subject 3 (moisturemeter: 24 before to 35 after). In all three cases, the effect of the moisturizer degraded mildly over the 60 mins, as measured by both the eWTS and the moisturemeter.

The miniaturized design allows for facile application onto a large range of body surfaces. Three practical use cases, the arm, neck and leg are illustrated in the optical images in FIG. 35 (panel E—left). Measurements made before and after the application of a commercially available moisturizer on a healthy subject (Female, age 24) reveal the strongest effects on the arm, followed by the neck, and then the leg, though clear changes are visible for each location, as shown in FIG. 35 (panel E—right).

Finally, the effects of moisturizer type are evaluated with 4 different types of compounds: petrolatum, aloe gel, lotion and cream, each representing different chemistries and actions. Optical images immediately after, and 15 minutes after application (in addition to wiping and exfoliating), respectively, appear in FIG. 35 (panel F). In general, moisturizers rely either on the occlusive action of humectants (e.g, Vaseline, a type of petrolatum) to trap escaping transepidermal water loss, the absorptive effects of emollients (e.g, gel) to trap ambient moisture or some combination of these. Our measurements, as shown in FIG. 35 (panel F), reveal the strongest action to be that of pure petrolatum (Vaseline), consistent with previous studies. Due the large inter-person variability in these measurements, it is difficult to extrapolate meaningful trends. More generally, however, eWTS provides a straightforward path to larger cohort studies due to its size and relative mechanical invisibility. Furthermore, the devices are suited to personalized use and treatments, including in any of a medical or beauty context.

In vivo measurements of skin thermal transport changes due to trauma: Skin trauma is associated with changes in perfusion through near-surface microvessels such as capillaries and arterioles. We examined two representative cases of skin trauma, burns and skin inflammation associated with blunt impact. Optical images of burn marks on the arms of an otherwise healthy subject appear in FIG. 36 (panel A), showing exhibiting suffering maximum burn trauma, surrounding perilesional regions and adjacent healthy locations. Burnt skin suffers loss in vasculature at a depth of up to several millimeters, and as a result displays reduced thermal transport. Perilesional skin and healthy skin exhibit near-baseline and normal, baseline levels of perfusion respectively. These changes are seen in FIG. 36 (panel B), where eWTS measurements of thermal transport display expected trends, with burnt skin exhibiting the lowest rates of thermal transport, as measured by $\Delta T(t=6s)$.

Skin trauma due to slap-induced dermatographic urticaria results in inflammation, hyperemia and easily apparent redness as seen on the volar forearm of an otherwise healthy subject (Male, Age 26) in FIG. 36 (panel C). Hyperemia results in increased rates of thermal transport due to the increased volume of blood perfusing the same control volume of tissue. Typical symptoms of inflammation due to urticaria last ~10 minutes, and the effect of this trauma and a subsequent recovery period are clearly seen in FIG. 36 (panel D), with perfusion levels that significantly increase immediately after urticaria and then gradually return to their baseline values.

Continuous, stable operation in a range of conditions: The miniaturized, rugged construction and battery-free operation of the eWTS allow for continuous wear over many days. As a demonstration of its capabilities, a subject (Female, age 24) wore the eWTS for 7 successive days, while continuing to perform routine daily activities such as exercise, showering and sleeping with only a single, thin breathable layer of medical tape (Tegaderm, 3M Inc) used to cover the device. While water directly above the soft sensing/actuating element affects the thermal measurement, key aspects of the design render the entire eWTS assembly waterproof. Specifically, the negligible dispersion of EM waves at 13.56 MHz in water, and the presence of a thin, UV-Curable layer of adhesive (Norland, EFD) over the bare-die NFC chip allow for stable operation even after interaction with water, as illustrated in FIG. 37 (panel A).

Raw data from measurements made twice a day at fixed times (10:00 am, 5:00 μm) during each day of the testing period showcase stability of the sensor's measurement and are shown in FIG. 37 (panel B). Corneometer measurements made at a fixed, adjacent skin location show an expected inverse correlation with eWTS measurements ($\Delta T(t=s)$) and are in FIG. 37 (panel C) for each of the 14 measurements.

As an example of a comparison that would be difficult or impossible with conventional measurement tools, ambient weather data (temperature and humidity) for the 7-day testing period in Evanston, IL, where the tests were performed, were gathered and correlated to moisturemeter readings and two key eWTS measurements: $\Delta T(t=6)$, $T(t=0)$. The former is a measure of thermal transport ($\Delta T_{sensor}$), and the latter is a measure of baseline skin temperature ($T_{sensor}$). These correlations appear in the scatterplot matrices in FIG. 37 (panel D), along with best-fit lines and 95% confident intervals. Interestingly, while both the moisturemeter and the eWTS showed little correlation to ambient weather conditions ($R^2<0.1$), a relatively strong correlation appears to exist between $T_{sensor}$ and humidity ($R^2=0.6$), and $T_{sensor}$ and the ambient temperature, $T_{ambient}$ ($R^2=0.5$), possibly an indicator of sweat-induced evaporative cooling. While correlations on a single person are difficult to interpret, the robustness of the eWTS imply straightforward pathways to larger-scale volunteer studies from which meaningful correlations over long periods of time can be recorded.

Fabrication of device: Soft Sensor: A 1.2 μm thick sacrificial layer (Poly)Methyl Methacrylate (PMMA 495, A5, Microchem) is spin cast onto a clean, 4", undoped Si-wafer. A layer of polyimide (PI 2545 HD Microsystems, 3 m) is then spun on and cured. A metallic bilayer thin film of Cr/Au (10/100 nm) is then deposited via e-beam evaporation, and photolithographically defined into the sensing/actuating thermal element. A second layer of PI (3 m) is spun on and cured, to completely encapsulate the metallic device elements. Photolithography followed by $O_2$ plasma reactive ion etching (RIE) define the final pattern and create via holes for external electrical connections. The devices are then released in warm acetone and picked up via a cellulose-based water-soluble tape (Aquasol Inc.). The back-side of the device is made reactive by sputtering a fresh layer of $SiO_2$. In parallel, 75 mm×50 mm glass slides are rendered hydrophobic by spin-casting a layer of PMMA, after which a layer of (poly)-dimethyl siloxane (PDMS) (Sylgard 184, Dow Corning) is spun cast to a thickness of 100 m. The PDMS is made reactive by treating in a UV-O cleaner for 5 minutes. Permanent adhesion between the back-side of the device with a thin layer of $SiO_2$ and the PDMS proceeds via condensation reactions of —OH groups at the surface. Warm water dissolves the water-soluble tape, leaving behind the device on the PDMS substrate.

Flex-PCB and integration: Fabrication began with laser structuring a commercially available high-density, electrodeposited trilayer film of Copper/PI/Copper (18 μm/75 μm/18 μm, Pyralux, DuPont Inc.), followed by successive cleaning in baths of flux, Isopropanol and De-ionized water. Key active and passive components (NFC Chip, Microcontroller, Operational-Amplifier, matching capacitors, bridge resistors, tuning resistors) were assembled via reflow soldering with low-temperature solder (the Indium Corporation). A commercially available acrylate-based, pressure sensitive adhesive (JMS, 1170) mechanically bonded the flex-PCB to the soft sensor, and low-temperature reflow soldering established electrical connections.

LTSpice Circuit Simulations: The device elements associated with the analog front end were simulated using a circuit model on a commercially available software package (LTSpice). Varying critical parameters allowed for facile tuning of the circuit, that allowed for efficient, high-throughput fabrication.

Thermal and mechanical FEA models: ZHAOQIAN

In vitro thermal characterization: The eWTS was mounted on specially designed materials with thicknesses that exceeded the penetration depth of the thermal field (>5 mm). Data from 5 successive actuation cycles were recorded. The highest and lowest values were discarded and the remaining three were averaged, with the error bars representing standard deviations. Simultaneously, IR videos were recorded using a commercially available IR camera (FLIR A6255sc, FUR Systems Inc.) and software, with a zoom lens facilitating high temporal resolution imaging.

In vivo hydration trials: Each location was first cleaned with a fresh, dry wipe. Measurements were made by mounting the eWTS on the relevant skin locations and recording 5 successive actuation cycles. The highest and lowest values were discarded and the remaining three were averaged, with the error bars representing standard deviations. After 15 minutes, the remaining compound was thoroughly removed with a dry wipe and via tape exfoliation, after which the eWTS was mounted at the same procedure highlighted above was followed. An acrylate fiber based ultrathin (80 m) medical grade adhesive, laser cut into the shape of the device facilitated mounting on skin. Three successive moisturemeter measurements were recorded and averaged over these locations for each time point, with error bars representing standard deviations.

In Vivo Trauma Trials:

Skin Burns: Skin regions suffering severe burns were identified on the right volar forearm of a volunteer (Female, age 24), and were then further demarcated into burnt and perilesional locations. Adjacent healthy skin was facilely identified. On each type of location, the eWTS was mounted using the procedures highlighted above, and data from 5 successive actuation cycles were recorded. The highest and lowest values were discarded and the remaining three were averaged, with the error bars representing standard deviations.

Slap-induced dermatographic urticaria: A location on the volar forearm of a volunteer (Male, age 26) devoid of prominent near-surface vessels was identified. The eWTS was mounted on this skin location following the procedures listed above. A single slap was then administered via three fingers onto the location, and almost immediately, with localized hyperemia apparent almost immediately after. The first eWTS measurement was made about 120s after this. Follow-up measurements were made 300s and 600s after the slap was induced. For each measurement, data from 5 successive actuation cycles were recorded. The highest and lowest values were discarded and the remaining three were averaged, with the error bars representing standard deviations.

In vivo long-term monitoring trials: A location on the right volar forearm of a volunteer (Female, age 24) was identified that was devoid of any prominent near-surface blood vessels. The location was cleaned and tried with an alcohol wipe, after which the eWTS was laminated following the procedure listed above. A single layer of conformal, breathable medical dressing (Tegaderm, 3M Inc) was used to cover the location. The volunteer was then given no special instructions, and performed normal routine activities such as sleeping, showering and exercising over 7 successive days. Two measurements were made each day at 10:00 am and 5:00 μm, respectively, over 5 successive actuation cycles were recorded. The highest and lowest values were discarded and the remaining three were averaged, with the error bars representing standard deviations. Three successive moisturemeter measurements were recorded and averaged over adjacent locations, with error bars representing standard deviations. Weather logs for Evanston, IL, USA, for the dates and times of the study (weather.com, Inc.) yielded ambient temperature and humidity data that were tabulated.

Example 5: Thin, Millimeter Scale Fingernail Sensors for Thermal Characterization of Nail Bed Tissue (Li, Yajing et al. (2018). Thin, Millimeter Scale Fingernail Sensors for Thermal Characterization of Nail Bed Tissue. *Advanced Functional Materials*. 1801380. 10.1002/adfm.201801380)

Thin, flexible, body-worn technologies that allow precise, quantitative monitoring of physiological status are of broad current interest due to their potential to improve the cost and effectiveness of healthcare. Although the surface of the skin represents one of the most widely explored points of integration, recently developed millimeter scale wireless sensor platforms allow deployment on alternative surfaces of the body, such as the finger/toenails and the teeth. The work described here introduces a collection of ideas in materials science, device engineering and computational techniques that enables precise characterization of the thermal transport characteristics of the nail bed tissue from measurements on the surface of the nail. Systematic in-vitro studies demonstrate the underlying measurement principles, the theoretical models for optimized sensor design and the associated experimental procedures for determining the thermal conductivity of the tissue. Measurements performed on human subjects highlight capabilities in tracking changes in perfusion of the nail bed tissues in response to various external stimuli.

In clinical medicine, the nail unit is a well-known, useful source of information on health status and an important component of the physical exam.[1-3] Any alterations in the nature of the nail plate, the nail matrix, the hyponychium, the proximal nail fold, the lateral nail folds or the nail bed, may reflect nutritional, endocrine, congenital, infectious, neoplastic, traumatic, inflammatory or vascular imbalances both locally and systemically. The optical transparency of the nail plate allows this structure to serve as a non-invasive window into microvascular integrity through direct visualization of nail fold capillaries. As such, non-invasive and point-of-care tools such as digital platforms for dermoscopy and proximal nail fold capillaroscopy serve as diagnostic instruments in evaluation of connective tissue diseases (e.g. Raynaud's phenomenon and systemic sclerosis[4]) and nail tumors[5]. Operation of these technologies and interpretation of data collected with them require, however, clinical expertise and they cannot be used for continuous monitoring outside of a hospital or laboratory setting.

Recent work shows that advanced imaging techniques such as ultrasound, CT (Computed Tomography), MRI (Magnetic Resonance Imaging), and PET (Positron Emission Tomography) can be used to examine the dynamics and structure of tissues of the fingers and nails for diagnostic purposes. Although modern imaging technologies allow for visualization of multi-parameter data at multi-dimensional resolution, these systems are expensive and have limited utility at the point-of-care. While cutaneous skin biopsies are largely non-invasive and straightforward, tissue sampling of the nail unit is a complex procedure that often requires nail avulsion, post-operative discomfort, along with risk of infection and long-term nail dystrophy.[6,7] Thus, technologies that can derive additional information from the nail unit non-invasively at the point-of-care and/or in a continuous monitoring mode without significant cost or complex imaging systems could offer significant clinical value for both diagnosis and treatment management. Beyond acting as a useful source of clinical information, the nail unit also represents an ideal, hard and mechanical interface for mounting and bonding advanced device technologies. Specifically, the nail plate is a semi-transparent material composed of cornified keratinocytes and keratin proteins, which imparts significant mechanical strength and resistance to environmental insult[8]. This construction enables stable coupling of sensors and devices with the human body without the risk of irritation, redness, or allergic reactions. Furthermore, the nail plate grows slowly at approximately 1 to 3 mm per month, thereby allowing long-term sensing.[9]

Advanced sensing techniques developed for skin-like, or 'epidermal', electronics use precision thermal sensors and actuators to determine thermal transport properties of living tissues in a real-time, non-invasive fashion.[10-13] These systems integrate metallic filaments with soft, thin supporting substrates to allow operation while in intimate contact with curvilinear skin, without irritation or sensory perception at the skin interface. Direct measurement of the body surface temperature and quantification of the thermal transport properties (i.e. thermal conductivity) associated with physiological conditions such as perfusion and hydration level are both possible, with clinical-grade accuracy. Past demonstrations focused on characterization of the upper layer of the skin[10-13], without consideration of its naturally layered structure or its properties significantly below the surface. The assessment of the thermal characteristics of deep tissues is challenging and of great interest. Here we present a non-invasive method of exploiting nail-mounted thermal sensors to measure the thermal conductivity of the nail bed, independent of the thermal properties of the nail. Combined with thermal analysis techniques, the responses of such sensors provide quantitative information of the perfusion of the nailbed tissue, and of other processes that alter the thermal transport characteristics. These thin, miniaturized devices yield data of direct relevance to physiological health and offer the potential for continuous monitoring as an unusual class of wearable technology with integration of wireless power source and data communication functionality.

FIG. 44 presents an exploded view illustration of a representative fingernail sensor for temperature and thermal transport. The device involves a multilayer construction, where the two active areas (one with radius 0.5 mm and the other 1.5 mm; each serves simultaneously as a temperature sensor and a thermal actuator) comprise lithographically defined, narrow (10 μm) traces of gold in spiral disk geometries. The traces for each disk emerge at the edges into wide (~0.8 mm) ribbons that lead to contact pads as interfaces to external electronics for control and data acquisition. Layers of polyimide (3 μm thickness) encapsulate these conductive traces from above and below as barriers to biofluids and water, thereby also positioning them at the neutral mechanical plane for enhanced bendability. A thin (200 μm) sheet of a silicone elastomer serves as a mechanical support for handling and manipulation. The low modulus of this material and its tacky surface ensure intimate, conformal contact, and therefore efficient thermal coupling, to the nail via reversible van der Waals interactions.

For simplicity, the devices connect to a power supply (6220, Keithley Instrument) and a digital multimeter (DMM, National Instruments) to allow delivery of controlled, direct current (DC) inputs to the sensors/actuators and simultaneous measurements of their resistance; as described herein, the power and communication may be wireless. In this way, the devices serve simultaneously as thermal actuators and temperature sensors. The resulting measurement physics relies on the well-established transient plane source (TPS) method[14]. Briefly, the active element in the TPS approach delivers thermal power to the sample via Joule heating that results from application of DC current. The same device simultaneously enables time-dependent measurements of resulting changes in temperature through the temperature coefficient of resistance (TCR) of the metal. Data recorded in this manner can be combined with computational techniques to determine the intrinsic thermal transport properties, i.e., the thermal conductivity and thermal diffusivity, of the material under test. FIG. 44 (bottom right panel) shows an infrared image of the devices operating in this manner on the surface of the fingernail. Accordingly, any of the devices and systems may have a temperature sensor and actuator that is formed from the same element.

The fingernail consists of a rigid plate (typically with thickness ~0.5 mm that varies by only ~50 μm from the proximal to distal end)[15-17] mechanically and thermally coupled to the underlying tissue. The nail plate is made of alpha-keratin, with thermal conductivity between ~0.2 and 0.4 W m$^{-1}$K$^{-1}$[18]. The nail bed is made of two types of tissues: the epidermis and the deeper dermis which includes rich capillaries and glands, with thermal conductivity between 0.2 and 0.5 W m$^{-1}$ K$^{-1}$[19-23] Experiments to establish the basic operating principles of the sensors and the methods to interpret data collected by them use test platforms that consist of a thin film of silicone on a thick base layer of a silicone, each with a formulation to yield thermal properties and thicknesses comparable to those of skin tissues and nail plate. The corresponding computational modeling assumes a semi-infinite substrate.

The characteristic probing depth associated with the TPS method increases with the thermal diffusivity ($\alpha$) and the time for thermal actuation (t).[14,24,25] For a bi-layer sample, characterization of the thermal properties of the bottom layer requires actuation times sufficient for heat to diffuse through the top layer. At long times, the temperature approximately saturates to a value that depends mainly on the thermal conductivity and only weakly on the thermal diffusivity.[14] FIG. 45 illustrates the spatial-temporal characteristics of heat transport obtained by finite element analysis (FEA) for an actuator with radius, R=1.5 mm and power density, q=3 mW mm$^{-2}$ on a bi-layer sample with a 0.5 mm-thick top layer (thermal conductivity, $k_1$=0.21 W m$^{-1}$K$^{-1}$; thermal diffusivity, $\alpha_1$=0.15 mm s$^{-2}$) and semi-infinite bottom layer ($k_2$=0.44 W m$^{-1}$K$^{-1}$ and $\alpha_2$=0.15 mm s$^{-2}$). At short times (0.5 s and 2 s), heat transport occurs mainly in the top layer, with little increase in temperature in the bottom layer. At long times (20 s and 40 s), the heat passes into both layers, and the temperature increase of the actuator saturates, as expected.

For a bi-layer sample with a top layer whose thickness is known, the temperature increases associated with two actuators that have different radii, both operated in this long time (~40 s) regime, can be used to determine $k_1$ and $k_2$. FIG. 45 (top right panel) presents the measured temperature increase (T) of the actuator on a bi-layer sample with a thin top layer (0.5 mm; Ecoflex) and thick bottom layer (13 mm; Sylgard 170) as a function of thermal actuation time for each of the two actuators operated with DC current (~100 μA) for activation at 0 s and deactivation at 40 s. Measurements involve an enclosure around the sample to reduce fluctuations in temperature induced by convective heat transfer to the room. The quasi-steady state increase in temperature, i.e. T at t=40 s, or $T_{ss}$, is 11.0° C. for the small actuator (R=0.5 mm and q=10 mW mm$^{-2}$) and 8.4° C. for the large actuator (R=1.5 mm and q=3 mW mm$^{-2}$). Both values fall below the threshold for damaging tissue.[26,27] FIGS. 2c and d show the corresponding temperature increases of the two actuators (radii and powers specified in FIG. 2b) obtained by FEA for different $k_1$ and $k_2$. FEA results yield curves that define pairs of $k_1$ and $k_2$ that are consistent with the experimentally measured $T_{ss}$ for both the small and the large actuator. The point of intersection of these two curves gives $k_1$ and $k_2$ for the bi-layer sample, i.e. $k_1$=0.21 W m$^{-1}$K$^{-1}$ for Ecoflex and $k_2$=0.44 W m$^{-1}$K$^{-1}$ for Sylgard 170 in FIG. 45 (bottom right panel). These results are consistent with the literature values for these materials[28,29]. We selected sensors with radii of 0.5 mm and 1.5 mm since the small (large) sensor offers greater sensitivity to properties of the top (bottom) layers, as demonstrated in FIG. 55.

Measurements on samples with top layers that have different thicknesses further validate the measurement scheme. FIG. 46 (top panels) shows representative results (R=0.5 mm and 1.5 mm, power q=10 mW mm-2 and 3 mW mm$^{-2}$ respectively) with top layer (Ecoflex) thicknesses between ~300 and 600 μm (spatial variations of +/−10 μm), each with the same type of bottom layer (Sylgard 170). Quasi-steady state temperatures, $T_{ss}$, analyzed using the scheme described previously yield values for the thermal conductivity. The results show consistent results, independent of the top layer thickness, i.e. $k_1$=0.21 W m$^{-1}$K$^{-1}$, $k_2$=0.42 W m$^{-1}$ K$^{-1}$ for h=310 μm; $k_1$=0.21 W m$^{-1}$K$^{-1}$, $k_2$=0.42 W m$^{-1}$K$^{-1}$ for h=410 μm; $k_1$=0.21 W m$^{-1}$K$^{-1}$, $k_2$=0.44 W m$^{-1}$K$^{-1}$ for h=500 μm; $k_1$=0.21 Wm$^{-1}$K$^{-1}$, $k_2$=0.44 W m$^{-1}$K$^{-1}$ for h=600 μm. FIG. 46 (bottom left panel) and the inset in the bottom right panel shows that the repeatability for $T_{ss}$ is ~0.1° C., roughly comparable to fluctuations in the ambient temperature (see supporting information FIG. 51). This value defines uncertainties in the extracted thermal conductivities, as summarized in FIG. 46 (bottom right panel). These uncertainties are consistent with the variations in values observed across samples with different top layer thicknesses, i.e. $k_1$=0.21±0.01 W m$^{-1}$K$^{-1}$ and $k_2$=0.44±0.04 W m$^{-1}$K$^{-1}$.

In many applications, the properties of the nail bed tissues are more important than those of the nail because they vary depending on physiological state. Measurements of changes in the thermal properties of the system are likely to be dominated by those of the tissue, as opposed to the nail. Studies of the sensitivity of the measurement to the bottom layer provide insights in this context. Here, the samples consist of bilayer structures with a fixed top layer (0.3 mm thick, Ecoflex) and various bottom layers (Ecoflex, Sylgard 567, Sylgard 170 and Sylgard 164), as summarized in FIG. 47 (top panels). For both sensors, the Ecoflex/Ecoflex case yields values of $T_{ss}$ that are larger than those of Ecoflex/Sylgard567, Ecoflex/Slygard170 and Ecoflex/Sylgard164. The trends follow the thermal conductivities of the bottom materials (k=0.21±0.01 W m$^{-1}$K$^{-1}$ for Ecoflex, k=0.3±0.02 W m$^{-1}$K$^{-1}$ for Sylgard 567, k=0.44±0.04 W m$^{-1}$K$^{-1}$ for Sylgard 170 and k=0.66±0.01 W m$^{-1}$K$^{-1}$ for Sylgard 164).

FIG. 47 (middle left panel) presents a plot of $T_{ss}$ as a function of $k_2$ for R=1.5 mm, q=3 mW mm$^{-2}$, for two values of $k_1$. The curves clearly depend on $k_1$, which suggests that $k_2$ cannot be determined by using just one sensor/actuator if $k_1$ is unknown. Nevertheless, for physiological monitoring based on measurement of the nail and nail bed tissue, the change in $k_1$ can be assumed to be much smaller than the change in $k_2$. If $\Delta k_2$ and $\Delta T_{ss}$ are the change in $k_2$ and $T_{ss}$, respectively, then we can plot $\Delta T_{ss}/T_{ss}$ as a function of $\Delta k_2/k_2$ for several values of $k_1$ and $k_2$, as in FIG. 47 (panels d and e). Remarkably, the results show that this relationship is only weakly dependent on $k_1$ (panel d) and $k_2$ (panel e) over this physiologically relevant range. As a result, $\Delta k_2/k_2$ can be determined directly from $\Delta T_{ss}/T_{ss}$, independent of the value of $k_1$ and $k_2$. This conclusion is clearly supported by experiments, as shown in FIG. 47 (bottom right panel), for different top-layer materials (Ecoflex and Sylgard567) and bottom-layer materials (Ecoflex, Sylgard567, Sylgard170 and Sylgard164). Here the actuator radius and heating time are the same as those in the FEA.

These studies establish a baseline of understanding that allows interpretation of data from these types of sensors used on human subjects (healthy female, age 29; left middle fingernail with nail thickness of 0.42±0.01 mm measured with a caliper). FIG. 48 shows measurement results from a single subject across 8 days of three repeated measurements performed in the afternoon on each day. To reduce the rates of convective heat transfer, measurements involve a piece of plastic foam to enclose the hand of the subject without touching the fingernail, as shown in FIG. 54. The thermal conductivity of the nail plate varies from 0.27 to 0.29 W m$^{-1}$K$^{-1}$ over the observation period, in a narrow range consistent with values measured using other techniques.[18] The thermal conductivity of the nail bed varies more significantly, from 0.43 to 0.52 W mm$^{-2}$, as might be expected due to normal variations in hydration and surface blood flow, both of which can affect the thermal conductivity[30,31]. For instance, previous reports suggest that variations in blood flow can induce changes in thermal conductivity from 0.25 W m$^{-1}$K$^{-1}$ (null blood flow) to 1 W m$^{-1}$K$^{-1}$ (vasodilation)[32]. These variations likely reflect the physiological changes, as opposed to variations that result from changes in the environment or the sensor response. Results show that repeated measurements on silicone samples over the course of 7 days reveal that variations in $T_{ss}$ are ~0.1° C., consistent with previously reported fluctuations in temperature.

Perfusion behaviors affect the distributions of temperature in living systems, with important purposes in thermoregulation. As such, perfusion is an important index for clinical procedures such as the treatment of tumors[33]. Abnormalities of peripheral microcirculation can play a central role in systemic sclerosis (SSc). Previous studies[10,11,34-36] indicate that the thermal conductivity of tissues can be strongly affected by micro and macrovascular blood flow. FIG. 5b-f illustrate the temporal evolution of the thermal conductivity of the nail bed tissue as a result of changes in blood flow associated with a local, pressure induced occlusion of the blood vessels in the middle left finger of the subject (female, age 29). The measurements used a sensor with R=1.5 mm laminated onto the center of the nail plate for continuous thermal characterization during and after the occlusion. FIG. 48 (panel c) presents the change in temperature of the nail plate of the left middle finger recorded by an infrared camera at the beginning of the period of occlusion. The results show that during the occlusion, the temperature decreases monotonically by >4° C. in the first 2 minutes followed by further reductions but with a reduced rate in the subsequent 7 minutes. The color of the finger turns grey and the pinkish tone of the tissue under the nail plate fades into pale shades. Releasing the occlusion causes an increase and overshoot of the temperature by 9° C. within 100 s, coincident with an increase in blood flow above the initial value and a change in the color of the finger to red. Although the rapid, time dependent variations in temperature and blood flow frustrate precise analysis of the measurements, approximate values of the thermal conductivity of the nail bed tissue can be deduced with $k_1$ fixed to the average value of the measurement in FIG. 48 (panel a). The thermal conductivity of the skin adjacent to the nail plate is measured with the sensor directly mounted on top of the skin, as indicated in the optical image in FIG. 48. Panel e shows that the conductivity decreases with occlusion, from 0.5±0.03 W m$^{-1}$K$^{-1}$ to 0.44±0.02 W m$^{-1}$K$^{-1}$, corresponding to 14% change independent of the specific value of $k_1$ as in Panel f. Similar changes occur in the adjacent skin. Overall, changes in thermal conductivity track those in temperature, as expected in the case that the blood flow affects both temperature and thermal transport. The perfusion resulted in changes in thermal conductivity, as further studied on two subjects (subject 1, previous female; subject 2, male at age 26, nail thickness 0.49±0.01 mm, $k_1$=0.26±0.01 W m$^{-1}$K$^{-1}$) before and after exercise. Thermal conductivity was measured for both subjects at rest before exercise (stationary bike for 15 min) and after, following a rest of 10 min. FIG. 48 (panel f) shows that the thermal conductivity of the nailbed tissue increases after exercise for both subjects. The male subject shows an increase that is larger than that of the female subject, likely corresponding to elevated blood flow.[37]

A second demonstration of measurements on human subjects involves aspects related to thermoregulation. Specifically, changes in the surrounding temperature can alter blood flow in deep tissues.[38] Here, studies involve two healthy subjects (previous female, and another male at age 30, with nail thickness of 0.51±0.01 mm), each with their left middle finger placed on ice bag for 10 minutes. Procedures summarized previously define the thermal conductivity of the nail plate ($k_{nail}$=0.28±0.03 W m$^{-1}$ K$^{-1}$ for female and $k_{nail}$=0.26±0.02 W m$^{-1}$K$^{-1}$ for male); this value is assumed to remain constant. FIG. 49 (panels a, c and e) present measurement results and analysis of data from the female subject. During the cooling period, the thermal conductivity of nail bed tissue decreases by ~12%, likely a result of vasoconstriction induced by cooling. Removing the ice bag, and exercising the finger (rubbing and warm hand wash) for 6 minutes prepares the subject for a second set of measurements. During this process, the thermal conductivity of the nailbed recovers to a value ~7% below the initial state after 6 minutes and only ~2% below after 8 minutes. The results obtained from the male subject in FIG. 49 (panels b, d and f) show similar trends, but with a higher thermal conductivity and a larger change ~30% compared to the female subject. After exercise, the male subject shows an increase of thermal conductivity of the nailbed tissue, the value reaches 5% below the one measured at the room temperature at 6 minutes and 2% above at 8 minutes.

The results establish a general set of materials, device structures, measurement approaches and analysis techniques for non-invasive characterization of the thermal properties of systems comprising a thin layer of material on top of a semi-infinite substrate, specifically modeled after the nail/nailbed structures of the human body. Measurements on a range of synthetic analogs to fingernails highlight the key considerations and define optimized modes of analysis. Evaluations on human subjects illustrate possibilities for tracking changes in perfusion in the nailbed tissue via measurements from the surface of the nail plate. The device is compatible with the addition of other types of sensors, such as optical devices for determining blood oxygenation and capturing photoplethysograms, thereby providing multimodal platforms for tracking physiological health status. Demonstration of device functionality in the context of widely-varying tissues, ranging from soft skin tissue to hard nail surfaces, illustrates the ability to integrate the device with a wide range of tissues, thereby providing a useful platform for a wide range of applications.

Device Fabrication: The process starts with spin casting a thin sacrificial layer of (poly)methyl-methacrylate (PMMA Microchem, Westborough, MA) on a clean silicon wafer. A film of polyimide (PI 2545, Parlin, NJ, 3 μm thick) spin-cast and cured on top of this layer forms the bottom side of the encapsulation. A bilayer of Cr (10 nm)/Au (100 nm) deposited on top of the polyimide by electron beam evaporation and then patterned by photolithography and wet etching forms the conducting traces for the devices. The use of wide interconnect lines minimizes their resistances. A second layer of PI layer formed by spin casting and curing yields the top encapsulation. Photolithography and etching the PI defines the outline of the sensor. Immersing the wafer in acetone removes the underlying PMMA, thereby releasing the sensors from the wafer. Retrieval using a Polyvinyl Alcohol (PVA)-based water soluble tape (3M, Minneapolis, MN) followed by deposition of a thin layer of $SiO_2$ facilitates adhesive bonding to a thin (50 μm) silicone-based substrate (Ecoflex, Smooth-On Inc., Macungie, PA). Removing the PVA by immersion in warm water completes the fabrication.

Measurement Scheme: The sensors connect with a flexible cable to a custom printed circuit board as an interface to the measurement hardware. A precision DC current source (Keithley 6220, USA) supplies a constant current to the sensors and a digital multimeter (DMM, National Instrument, USA) records the voltages. Instrument control and Data acquisition are performed using a custom computer program (LabVIEW, National Instruments, USA) via a GPIB-USB interface.

To evaluate the influence of the thermal diffusivity in the FEA simulations, temperature rise curve of R=1.5 mm sensor is calculated according to different values of thermal diffusivity of top and bottom materials. Calculation results in FIG. 50 reveal the sensitivity of computed results on those two parameters, corresponding to the case of representative data from human nail plate[1] and skin[2]. The study involves systematically increasing the value of $\alpha_1$ (0.10 mm$^2$ s$^{-1}$) by 50%, 100%, and fixing this value and recalculating the data while allowing only $\alpha_2$ to change. For 100% change of thermal diffusivity of top layer material, steady state temperature of the sensor at 40s does not change significantly in FIG. 50 (left panel). Variation of the thermal diffusivity of bottom layer leads to ±3% difference of the steady temperature in FIG. 50 (right panel), suggesting the fitting results has a weak dependence of thermal diffusivity $\alpha$.

FIG. 51 (top left panel) summarizes measurements of the fluctuations in temperature measured from a sensor with R=1.5 mm on Sylgard170. The variations are smaller than 0.1° C. FIG. 51 (top right panel) shows similar measurements but performed with a piece of plastic foam as an enclosure identical to the one used for measurements on human subjects. For the images and data in FIG. 51 (bottom left panel), the infrared camera was focused on the Sylgard170 without the petri dish enclosure and each data point represents a temperature value averaged over the area enclosed by a circle with radius 1.5 mm. The measurements show a 0.5° C. variation in temperature during 15 min. Provided is a summary of data on the long-term stability of the sensor response for measurements on a piece of Ecoflex with a plastic foam enclosure over 7 days. The magnitude of the variations in temperature are 0.1° C., comparable to those shown in (b).

In vivo test on human subjects exhibit more temperature fluctuations compared with the in vitro study with petri dish cover. Those fluctuations in the thermal sensor measurement are shown in FIG. 54. The deviations between the steady state temperature $T_{ss}$ of each curve is generally 0.3-0.5° C., in agreement with other literatures.[8,9] The fitted values of $k_{nail}$ and $k_{tissue}$ reflect influence of the temperature fluctuation. FIG. 54 (bottom right panel) shows the nail surface temperature fluctuation measured by the R=1.5 mm sensor, as result of summated effects of internal heart production and heat transfers between the body and ambient environment. To reduce the rate of convective heat transfer to the ambient, a plastic foam enclosure covered the subjects' hand without contacting the fingernail FIG. 55 summarizes data that reveal the dependence of the response on sensor size. Panels (a) and (c) show that for a fixed top layer, the change of the normalized temperature, $T/T_0$ ($T_0$ is the temperature of each sensor with $k_1(k_2)$=0.1 W m$^{-1}$K$^{-1}$) is larger for the large sensor (R=1.5 mm) than for the small sensor (R=0.5 mm) for both thicknesses of the top layer (h=0.3 mm and 0.5 mm). These results indicate that the larger sensors are more sensitive to the properties of the bottom layer. The small sensors are more sensitive to the top layer as demonstrated in (b) and (d), with bottom layer fixed, the normalized temperature curves show more variation to the top layer thermal conductivity changes for R=0.5 mm than R=1.5 mm sensor

REFERENCES FOR EXAMPLE 5

[1] M. N. Zaiac, A. Walker, *Clin. Dermatol.* 2013, 31, 627.
[2] K. N. Shah, A. I. Rubin, Curr. Probl. Pediatr. Adolesc. Health Care 2012, 42, 204.
[3] R. S. Fawcett, S. Linford, D. L. Stulberg, *Am. Fam. Physician* 2004, 69, 1417.
[4] M. Cutolo, C. Pizzorni, M. E. Secchi, A. Sulli, *Best Pract. Res. Clin. Rheumatol.* 2008, 22, 1093.
[5] L. Thomas, E. G. Zook, E. Haneke, J.-L. Drapé, R. Baran, J. F. Kreusch, In *Baran & Dawber's Diseases of the Nails and their Management*; Wiley-Blackwell, 2012; pp. 637-743.
[6] C. Grover, S. Bansal, *Indian Dermatol. Online J.* 2018, 9, 3.
[7] T. E. Rohrer, B. Leslie, D. J. Grande, *J. Dermatol. Surg. Oncol.* 1994, 20, 19.
[8] R. H. Rice, Y. Xia, R. J. Alvarado, B. S. Phinney, *J. Proteome Res.* 2010, 9, 6752.
[9] S. Yaemsiri, N. Hou, M. M. Slining, K. He, *J. Eur. Acad. Dermatol. Venereol. JEADV* 2010, 24, 420.
[10] R. C. Webb, Y. Ma, S. Krishnan, Y. Li, S. Yoon, X. Guo, X. Feng, Y. Shi, M. Seidel, N. H. Cho, J. Kurniawan, J. Ahad, N. Sheth, J. Kim, J. G. T. Vi, T. Darlington, K. Chang, W. Huang, J. Ayers, A. Gruebele, R. M. Pielak, M. J. Slepian, Y. Huang, A. M. Gorbach, J. A. Rogers, *Sci. Adv.* 2015, 1, e1500701.
[11] R. C. Webb, R. M. Pielak, P. Bastien, J. Ayers, J. Niittynen, J. Kurniawan, M. Manco, A. Lin, N. H. Cho, V. Malyrchuk, G. Balooch, J. A. Rogers, *PLOS ONE* 2015, 10, e0118131.
[12] R. C. Webb, A. P. Bonifas, A. Behnaz, Y. Zhang, K. J. Yu, H. Cheng, M. Shi, Z. Bian, Z. Liu, Y.-S. Kim, W.-H. Yeo, J. S. Park, J. Song, Y. Li, Y. Huang, A. M. Gorbach, J. A. Rogers, *Nat. Mater.* 2013, 12, 938.
[13] S. Amendola, G. Bovesecchi, P. Coppa, G. Marrocco, In 2016 *IEEE International Symposium on Antennas and Propagation (APSURSI)*; 2016; pp. 461-462.
[14] S. E. Gustafsson, *Rev. Sci. Instrum.* 1991, 62, 797.
[15] M. Johnson, S. Shuster, *Br. J. Dermatol.* 1994, 130, 195.
[16] J. B. Hamilton, H. Terada, G. E. Mestler, *J. Gerontol.* 1955, 10, 401.
[17] U. Wollina, M. Berger, K. Karte, *Skin Res. Technol.* 2001, 7, 60.
[18] D. T. Dias, A. Steimacher, A. C. Bento, A. M. Neto, M. L. Baesso, *Photochem. Photobiol.* 2007, 83, 1144.
[19] T. E. Cooper, G. J. Trezek, *Aerosp. Med.* 1971, 42, 24.
[20] T. A. Balasubramaniam, H. F. Bowman, *J. Biomech. Eng.* 1977, 99, 148.
[21] W. J. B. M. van de Staak, A. J. M. Brakkee, H. E. de Rijke-Herweijer, *J. Invest. Dermatol.* 1968, 51, 149.
[22] A. Chanmugam, A. Bhargava, C. Herman, Int. Mech. Eng. Congr. Expo. Proc. Int. Mech. Eng. Congr. Expo. Int. Mech. Eng. Congr. Expo. 2012, 2012, 717.
[23] A. M. Stoll, *J. Invest. Dermatol.* 1977, 69, 328.
[24] A. Sizov, D. Cederkrantz, L. Salmi, A. Rosén, L. Jacobson, S. E. Gustafsson, M. Gustavsson, *Rev. Sci. Instrum.* 2016, 87, 74901.
[25] *Thermal Conductivity: Theory, Properties, and Applications*; Tritt, T. M., Ed.; Physics of Solids and Liquids; Springer US, 2004.
[26] A. R. Moritz, F. C. Henriques, *Am. J. Pathol.* 1947, 23, 695.
[27] J. P. Bull, J. C. Lawrence, *Fire Mater.* 1979, 3, 100.
[28] Dow Corning Sylgard®170 Silicone Elastomer Product Information; Dow Corning, 2017.
[29] L. Tian, Y. Li, R. C. Webb, S. Krishnan, Z. Bian, J. Song, X. Ning, K. Crawford, J. Kurniawan, A. Bonifas, J. Ma, Y. Liu, X. Xie, J. Chen, Y. Liu, Z. Shi, T. Wu, R. Ning, D. Li, S. Sinha, D. G. Cahill, Y. Huang, J. A. Rogers, *Adv. Funct. Mater.* 2017, 27, 1701282.
[30] T. H. Benzinger, A. W. Pratt, C. Kitzinger, *Proc. Natl. Acad. Sci. U.S.A* 1961, 47, 730.
[31] R. Refinetti, *Exp. Physiol.* 2003, 88, 423.
[32] A. Dittmar, T. Pauchard, G. Delhomme, E. Vernet-Maury, *Sens. Actuators* B Chem. 1992, 7, 327.
[33] M. Salcman, E. Moriyama, H. J. Elsner, H. Rossman, R. A. Gettleman, G. Neuberth, G. Corradino, *J. Neurosurg.* 1989, 70, 592.
[34] J. Grayson, *J. Physiol.* 1952, 118, 54.
[35] W. J. B. M. van de Staak, A. J. M. Brakkee, H. E. de Rijke-Herweijer, *J. Invest. Dermatol.* 1968, 51, 149.
[36] R. K. Jain, F. H. Grantham, P. M. Gullino, *J. Nat. Cancer Inst.* 1979, 62, 927.
[37] J. Bangsbo, Y. Hellsten, *Acta Physiol. Scand.* 1998, 162, 305.
[38] H. Barcroft, O. G. Edholm, *J. Physiol.* 1943, 102, 5.

EXAMPLE 5 SUPPLEMENTAL REFERENCES

[1] D. T. Dias, A. Steimacher, A. C. Bento, A. M. Neto, M. L. Baesso, *Photochem. Photobiol.* 2007, 83, 1144.
[2] M. L. Cohen, *J. Invest. Dermatol.* 1977, 69, 333.
[3] SYLGARD® 567 PRIMERLESS SILICONE ENCAPSULANT KIT. Dow Corning, 1999
[4] SYLGARD® 567 PRIMERLESS SILICONE ENCAPSULANT KIT. Dow Corning, 2017
[5] SYLGARD® 170 SILICONE ELASTOMER KIT. Dow Corning, 2017
[6] Dow Corning Sylgard 170 Silicone Encapsulant Black. Dow Corning, 2015
[7] SYLGARD® 164 SILICONE ELASTOMER KIT. Dow Corning, 2015
[8] H. A. M. Daanen, J. Koedam, S. S. Cheung, *Eur. J. Appl. Physiol.* 2012, 112, 2595.
[9] Y. Liu, L. Wang, J. Liu, Y. Di, *J. Therm. Biol.* 2013, 38, 440.

Example 6: Thermal Study of UV Exposure to Skin

Epidermis cells were exposed to UVB, and changes observed. The changes include a color change, becoming more pinkish in appearance, with wrinkles on the surface. Graphical results are displayed in FIG. 56, as measured by a 1 mm sensor of 5 seconds. The sample is a single layer dermis (collagen). The measurements are conducted before UV exposure, immediately following 36 mins of UV exposure, and the next day. Thermal conductivity decreases (e.g., T increases), after UV exposure.

FIG. 57 are histological sections of the skin layers, including stratum corneum, epidermis, and dermis for non-exposed (left images) and UV-exposed (right images). Changes with UV exposure include to the stratum corneum and epidermis, with cell destruction after UV exposure. Color darkens, indicating an acidic pH shift.

FIG. 58 illustrates that sunburn increase thermal conductivity (temperature decrease), opposite of the thermal results from the 3D epidermis cell. Factors contributing to this difference may include: inflammatory reaction after sunburn in the dermis of the living human subject, while in the 3D epidermis cell model, no inflammatory reaction is possible.

STATEMENTS REGARDING INCORPORATION BY REFERENCE AND VARIATIONS

All references, including publications, patent applications, and patents, cited herein are hereby incorporated by reference to the same extent as if each reference were individually and specifically indicated to be incorporated by reference and were set forth in its entirety herein, including to the extent each reference is at least partially not inconsistent with the disclosure in this application (for example, a reference that is partially inconsistent is incorporated by reference except for the partially inconsistent portion of the reference).

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

LIST OF TABLES

TABLE 1

Thermal conductivity values obtained by single point FEA and Scaling Law of 8 separate skin locations from two separate volunteers (Subject 1: 33 year old female; Subject 2: 33 year old male).

| Region | FEA vs Scaling Law | Subject 1 (W/mK) | Subject 2 (W/mK) |
|---|---|---|---|
| Ankle | FEA | 0.36-0.41 | 0.41-0.46 |
|  | SL | 0.37-0.42 | 0.40-0.46 |
| Bicep | FEA | 0.40-0.45 | 0.35-0.40 |
|  | SL | 0.40-0.45 | 0.36-0.41 |
| Cheek | FEA | 0.40-0.46 | 0.39-0.44 |
|  | SL | 0.40-0.45 | 0.39-0.45 |
| Forearm | FEA | 0.42-0.48 | 0.35-0.40 |
|  | SL | 0.42-0.47 | 0.36-0.41 |
| Neck | FEA | 0.42-0.48 | 0.39-0.45 |
|  | SL | 0.41-0.47 | 0.39-0.45 |
| Nose | FEA | 0.40-0.46 | 0.32-0.36 |
|  | SL | 0.40-0.45 | 0.34-0.38 |
| Palm | FEA | 0.35-0.40 | 0.34-0.39 |
|  | SL | 0.36-0.41 | 0.35-0.40 |
| Shoulder | FEA | 0.38-0.43 | 0.42-0.47 |
|  | SL | 0.38-0.43 | 0.41-0.46 |

TABLE 2

Thermal conductivity values obtained by single point FEA compared to thermal conductivity values obtained using the Scaling Law at transient heating times of 2 s, 20 s, and 40 s for 6 synthetic samples: Sylgard 170 (S170), low density polyethylene (LDPE), Ecoflex (EF), Sylgard 184 (S184), polyisobutylene (PIB) and polyacrylic (PA).

|  | FEA vs. SL | t = 2 s; (W/mK) | t = 20 s; (W/mK) | t = 40 s; (W/mK) | Literature (W/mK) |
|---|---|---|---|---|---|
| S170 | FEA | 0.39-0.45 | 0.50-0.54 | 0.54-0.56 | 0.4-0.48 [17, 40] |
|  | SL | 0.38-0.44 | 0.49-0.53 | 0.53-0.55 |  |
| LDPE | FEA | 0.35-0.40 | 0.37-0.39 | 0.38-0.40 | 0.33-0.4 [37] |
|  | SL | 0.36-0.41 | 0.38-0.40 | 0.39-0.41 |  |
| EF | FEA | 0.20-0.24 | 0.21-0.23 | 0.22-0.23 | 0.21 [17] |
|  | SL | 0.23-0.27 | 0.24-0.26 | 0.25-0.26 |  |
| S184 | FEA | 0.19-0.23 | 0.20-0.22 | 0.21-0.22 | 0.18-0.27 [17, 38] |
|  | SL | 0.22-0.26 | 0.23-0.25 | 0.24-0.25 |  |
| PIB | FEA | 0.17-0.21 | 0.17-0.19 | 0.18-0.19 | 0.12-0.19 [17, 39] |
|  | SL | 0.19-0.23 | 0.19-0.21 | 0.20-0.21 |  |
| PA | FEA | 0.20-0.24 | 0.23-0.24 | 0.24-0.25 | 0.19-0.24 [17, 40] |
|  | SL | 0.23-0.27 | 0.28-0.27 | 0.27-0.28 |  |

TABLE 3

Thermal conductivity values deduced from 2D error surfaces deduced from FEA based on experimental data collection as a function of sample type: Sylgard 170 (S170), low density polyethylene (LDPE), Ecoflex (EF), Sylgard 184 (S184), polyisobutylene (PIB), and polyacrylic (PA), heater size: R = 0.5 mm, R = 1.5 mm, and R = 2.0 mm, and transient heating time: 2 s, 20 s, and 40 s.

|  | R (mm) | t = 2 s (W/mK) | t = 20 s (W/mK) | t = 40 s (W/mK) | Lit/3Ω (W/mK) |
|---|---|---|---|---|---|
| S170 | 0.5 | 0.40-0.43 | 0.51-0.52 | 0.53 | 0.4-0.48 [15, 39] |
|  | 1.5 | 0.39-0.45 | 0.50-0.54 | 0.54-0.56 |  |
|  | 2.0 | 0.38-0.45 | 0.49-0.54 | 0.52-0.56 |  |
| LDPE | 0.5 | 0.33-0.35 | 0.36 | 0.37 | 0.33-0.4 [35] |
|  | 1.5 | 0.35-0.40 | 0.37-0.39 | 0.38-0.40 |  |
|  | 2.0 | 0.35-0.41 | 0.40-0.42 | 0.40-0.42 |  |
| EF | 0.5 | 0.19-0.21 | 0.22 | 0.22 | 0.21 [15] |
|  | 1.5 | 0.20-0.24 | 0.21-0.23 | 0.22-0.23 |  |
|  | 2.0 | 0.20-0.24 | 0.22-0.23 | 0.23-0.24 |  |
| S184 | 0.5 | 0.18-0.19 | 0.20 | 0.20 | 0.18-0.27 [15, 36] |
|  | 1.5 | 0.19-0.23 | 0.20-0.22 | 0.21-0.22 |  |
|  | 2.0 | 0.18-0.22 | 0.20-0.22 | 0.21-0.22 |  |
| PIB | 0.5 | 0.17-0.18 | 0.18 | 0.18 | 0.12-0.19 [15, 37] |
|  | 1.5 | 0.17-0.21 | 0.17-0.19 | 0.18-0.19 |  |
|  | 2.0 | 0.16-0.19 | 0.16-0.18 | 0.16-0.18 |  |
| PA | 0.5 | 0.19-0.20 | 0.22 | 0.23 | 0.19-0.22 [15, 38] |
|  | 1.5 | 0.20-0.24 | 0.23-0.24 | 0.24-0.25 |  |
|  | 2.0 | 0.20-0.24 | 0.22-0.24 | 0.24-0.25 |  |

We claim:

1. A wireless electronic device for thermally interfacing with a biological tissue, comprising:
 a flexible substrate;
 at least a first active region and a second active region supported by said flexible substrate, wherein peripheral edges of said first active region and said second active region are spatially separated from each other by a distance such that said first active region and said second active region are not concentrically positioned relative to each other, wherein each of said first active region and said second active region comprises a thermal actuator and a temperature sensor, wherein said thermal actuator is configured to provide a thermal input to said biological tissue, and said temperature sensor is configured to measure a temperature to determine thermal conductivity of said biological tissue, and wherein said temperature sensor and said thermal actuator are formed of a same electrically resistive wire whose resistance varies with temperature to measure temperature and that delivers thermal power to said biological tissue by Joule heating;
- a wireless electronic system in electronic communication with said thermal actuator and said temperature sensor of each of said first active region and said second active region, wherein said wireless electronic system is configured to provide communication with an external controller; and
- an encapsulation layer that isolates said first active region and said second active region,
- wherein said first active region and said second active region are not electrically interconnected to each other.

2. The wireless electronic device of claim 1, wherein said external controller is configured to determine a tissue parameter based on said thermal conductivity.

3. The wireless electronic device of claim 1, configured for long-term interfacing with the biological tissue for a time period that is greater than or equal to 1 day.

4. The wireless electronic device of claim 3, configured to provide a periodically continuous measure of thermal conductivity over a time period that is greater than or equal to 10 minutes.

5. The wireless electronic device of claim 1, wherein the biological tissue comprises skin and the wireless electronic device is an epidermal electronic device that is configured to conformally mount to the skin or a material disposed thereon.

6. The wireless electronic device of claim 1, wherein the biological tissue is a nail tissue.

7. The wireless electronic device of claim 1 that is configured for implantation in a living animal, wherein the biological tissue comprises an internal organ or a subcutaneous tissue.

8. The wireless electronic device of claim 1, wherein the biological tissue is a transplanted tissue, including a transplanted organ.

9. The wireless electronic device of claim 1, wherein said thermal conductivity is used to calculate a tissue parameter that is one or more of tissue responses to treatment, tissue changes due to worsening of disease, tissue changes due to improvement of disease, tissue hydration, inflammation state, tissue oxygenation, tissue perfusion, blood flow, tissue healing, tissue damage, and tissue health.

10. The wireless electronic device of claim 9, wherein the tissue parameter is associated with a sunburn parameter.

11. The wireless electronic device of claim 9, wherein the tissue parameter is personalized for an individual user.

12. The wireless electronic device of claim 1, configured to contact a moisturizer product, wherein the temperature sensor is configured to measure a temperature in the moisturizer product to determine a moisturizer water content.

13. The wireless electronic device of claim 1, for personalized use by an individual user for skin hydration monitoring, evaluation, and treatment thereof.

14. The wireless electronic device of claim 13, configured to obtain a baseline skin hydration value and determine deviation from the baseline skin hydration value indicative of worsening dry skin.

15. The wireless electronic device of claim 13, further comprising a haptic feedback element and/or a visual feedback element to warn the user of a low tissue hydration condition.

16. The wireless electronic device of claim 1, wherein said temperature sensor is configured to measure a temperature change of the biological tissue comprising skin to evaluate excess skin water loss and low skin hydration.

17. The wireless electronic device of claim 16, wherein the excess skin water loss is associated with atopic dermatitis or eczema.

18. The wireless electronic device of claim 1, configured for use in detecting a systemic condition.

19. The wireless electronic device of claim 1, wherein a temperature change of the biological tissue indicates an inflammatory condition or edema.

20. The wireless electronic device of claim 1, wherein resistance of the electrically resistive wire varies with temperature.

21. The wireless electronic device of claim 1, wherein the electrically resistive wire is configured to deliver thermal power to the biological tissue by Joule heating.

22. The wireless electronic device of claim 1, further comprising a plurality of temperature sensors and/or a plurality of thermal actuators.

23. The wireless electronic device of claim 1, wherein said wireless electronic system is configured to power said wireless electronic device from said external controller.

24. The wireless electronic device of claim 1, further comprising a battery to at least partially power said wireless electronic device.

25. The wireless electronic device of claim 1, configured to determine the thermal conductivity at a selected depth from a surface of said biological tissue, ranging to a maximum depth of 8 mm.

26. The wireless electronic device of claim 1, further comprising:
- a first contact pad and a first electrically conductive ribbon that electrically connects the first contact pad to said first active region; and
- a second contact pad and a second electrically conductive ribbon that electrically connects the second contact pad to said second active region,
- wherein said first and second contact pads serve as interfaces to the electronic system for control and data acquisition.

* * * * *